US012752013B2

(12) United States Patent
Weeden et al.

(10) Patent No.: US 12,752,013 B2
(45) Date of Patent: Oct. 6, 2026

(54) MUSCLE TARGETING COMPLEXES AND FORMULATIONS FOR TREATING FACIOSCAPULOHUMERAL MUSCULAR DYSTROPHY

(71) Applicant: Dyne Therapeutics, Inc., Waltham, MA (US)

(72) Inventors: Timothy Weeden, Waltham, MA (US); Nelson Hsia, Waltham, MA (US); Stefano Zanotti, Waltham, MA (US); Oxana Beskrovnaya, Waltham, MA (US); Qifeng Qiu, Waltham, MA (US); Scott Hilderbrand, Waltham, MA (US); Jochen Deckert, Bayreuth (DE); Hans-Peter Vornlocher, Kulmbach (DE); Markus Hossbach, Kulmbach (DE); Kathrin Hultsch, Kulmbach (DE); Nicholas C. Yoder, Brookline, MA (US); Benjamin Vieira, Waltham, MA (US)

(73) Assignee: Dyne Therapeutics, Inc., Waltham, MA (US)

( * ) Notice: Subject to any disclaimer, the term of this patent is extended or adjusted under 35 U.S.C. 154(b) by 0 days.

(21) Appl. No.: 19/382,888

(22) Filed: Nov. 7, 2025

(65) Prior Publication Data

US 2026/0053941 A1 Feb. 26, 2026

Related U.S. Application Data

(63) Continuation of application No. PCT/US2024/061427, filed on Dec. 20, 2024.

(60) Provisional application No. 63/614,024, filed on Dec. 22, 2023.

(51) Int. Cl.
*A61K 47/68* (2017.01)
*A61P 21/00* (2006.01)
*C07K 16/28* (2006.01)

(52) U.S. Cl.
CPC ...... *A61K 47/6807* (2017.08); *A61K 47/6849* (2017.08); *A61K 47/6889* (2017.08); *A61P 21/00* (2018.01); *C07K 16/2881* (2013.01)

(58) Field of Classification Search
None
See application file for complete search history.

(56) References Cited

U.S. PATENT DOCUMENTS 2,631,173 A 3/1953 Hillyer et al.
6,214,345 B1 4/2001 Firestone et al.
7,015,315 B1 3/2006 Cook et al.
7,064,142 B2 6/2006 Sato et al.
7,265,131 B2 9/2007 Johnson et al.
7,442,372 B2 10/2008 Kakkis et al.
7,534,879 B2 5/2009 van Deutekom et al.
7,575,886 B2 8/2009 Venkataraman et al.
7,785,856 B2 8/2010 Lebowitz et al.
7,902,160 B2 3/2011 Matsuo et al.
7,960,541 B2 6/2011 Wilton et al.
7,973,015 B2 7/2011 van Ommen et al.
8,084,601 B2 12/2011 Graham et al.
8,232,384 B2 7/2012 Wilton et al.
8,324,371 B2 12/2012 Popplewell et al.
8,361,979 B2 1/2013 van Ommen et al.
8,409,573 B2 4/2013 Boumsell et al.
8,455,636 B2 6/2013 Fletcher et al.
8,466,340 B2 6/2013 Khanna et al.
8,486,907 B2 7/2013 Wilton et al.
8,524,880 B2 9/2013 Mcclorey et al.
8,580,756 B2 11/2013 Hansen et al.
8,637,483 B2 1/2014 Wilton et al.
8,759,501 B2 6/2014 Zhu et al.
8,759,507 B2 6/2014 van Deutekom et al.
8,785,168 B2 7/2014 Lebowitz et al.
8,802,437 B2 8/2014 Tremblay et al.
8,835,614 B2 9/2014 Avila et al.
8,846,639 B2 9/2014 Swayze et al.
8,859,629 B2 10/2014 van Delft et al.
8,865,883 B2 10/2014 Kole et al.
8,952,147 B2 2/2015 Bouchard et al.
9,018,368 B2 4/2015 Wilton et al.
9,024,007 B2 5/2015 Wilton et al.
9,035,040 B2 5/2015 Wilton et al.
9,044,473 B2 6/2015 Kakkis et al.
9,045,754 B2 6/2015 Bhanot et al.
9,050,333 B2 6/2015 Chen et al.
(Continued)

FOREIGN PATENT DOCUMENTS

CN 102459597 A 11/2010
CN 103443125 A 12/2013
(Continued)

OTHER PUBLICATIONS

Fisher and Spies (PNAS, 1987, vol. 84, pp. 3628-3622) (Year: 1987).*
[No Author Listed] GenBank: AF095738.1. Mus musculus dystrophin gene, exons 22-25 and partial CDs. 2016. Retrieved from the internet Oct. 30, 2019: https://www.ncbi.nlm.nih.gov/nucleotide/AF095738.1?report=genbank&log$=nuclalign&blast_rank=3&RID=VKBMZ9WW014, 5 pages.
[No Author Listed] GenBank: CAE7739414. Unnamed protein product, partial [*Symbiodinium pilosum*]. Feb. 18, 2021. Retrieved from the internet Oct. 12, 2022: https://www.ncbi.nlm.nih.gov/protein/CAE7739414.1.1?report=genbank&log$=prottop&blast_rank=1&RID=MDW2CW3T013, 1 page.
(Continued)

*Primary Examiner* — Karen A. Canella
(74) *Attorney, Agent, or Firm* — Wolf, Greenfield & Sacks, P.C.

(57) ABSTRACT

Aspects of the disclosure relate to complexes and other aspects relate to formulations (e.g., aqueous, lyophilized forms) comprising such complexes comprising an oligonucleotide (e.g., an RNAi oligonucleotide such as an siRNA, useful for targeting DUX4) covalently linked to an antibody (e.g., anti-TfR1 antibody).

28 Claims, 9 Drawing Sheets

Specification includes a Sequence Listing.

(56) References Cited

U.S. PATENT DOCUMENTS

| | | | |
|---|---|---|---|
| 9,078,911 | B2 | 7/2015 | Lu et al. |
| 9,079,934 | B2 | 7/2015 | Takeda et al. |
| 9,186,420 | B2 | 11/2015 | Koeberl et al. |
| 9,217,148 | B2 | 12/2015 | Bestwick et al. |
| 9,222,940 | B2 | 12/2015 | van Delft et al. |
| 9,228,187 | B2 | 1/2016 | Meloni et al. |
| 9,243,245 | B2 | 1/2016 | De Kimpe et al. |
| 9,249,399 | B2 | 2/2016 | Vervecken et al. |
| 9,260,371 | B2 | 2/2016 | Bertozzi et al. |
| 9,416,361 | B2 | 8/2016 | Iversen et al. |
| 9,422,555 | B2 | 8/2016 | Wilton et al. |
| 9,428,534 | B2 | 8/2016 | Christensen et al. |
| 9,447,415 | B2 | 9/2016 | Wilton et al. |
| 9,447,416 | B2 | 9/2016 | Sazani et al. |
| 9,469,850 | B2 | 10/2016 | Zhu et al. |
| 9,469,851 | B2 | 10/2016 | Harper et al. |
| 9,493,498 | B2 | 11/2016 | Avila et al. |
| 9,504,758 | B2 | 11/2016 | van Delft et al. |
| 9,506,058 | B2 | 11/2016 | Kaye |
| 9,512,424 | B2 | 12/2016 | Watanabe et al. |
| 9,528,109 | B2 | 12/2016 | De Kimpe et al. |
| 9,550,834 | B2 | 1/2017 | Shirai et al. |
| 9,550,988 | B2 | 1/2017 | Swayze |
| 9,610,362 | B2 | 4/2017 | Armstrong |
| 9,611,323 | B2 | 4/2017 | Dennis et al. |
| 9,617,540 | B2 | 4/2017 | Bhanot et al. |
| 9,650,632 | B2 | 5/2017 | Popplewell et al. |
| 9,657,049 | B2 | 5/2017 | Koizumi et al. |
| 9,657,050 | B2 | 5/2017 | Koizumi et al. |
| 9,695,418 | B2 | 7/2017 | Seth et al. |
| 9,708,361 | B2 | 7/2017 | Takeda et al. |
| 9,708,406 | B2 | 7/2017 | Zhang et al. |
| 9,708,614 | B2 | 7/2017 | Christensen et al. |
| 9,758,783 | B2 | 9/2017 | Meloni et al. |
| 9,765,338 | B2 | 9/2017 | Bennett et al. |
| 9,840,706 | B2 | 12/2017 | Watanabe et al. |
| 9,850,474 | B2 | 12/2017 | Chen et al. |
| 9,890,381 | B2 | 2/2018 | Watanabe et al. |
| 9,926,557 | B2 | 3/2018 | De Kimpe et al. |
| 9,970,010 | B2 | 5/2018 | Graham et al. |
| 9,988,628 | B2 | 6/2018 | Belayew et al. |
| 9,988,629 | B2 | 6/2018 | Takeda et al. |
| 9,994,851 | B2 | 6/2018 | Wilton et al. |
| 10,098,905 | B2 | 10/2018 | Koeberl et al. |
| 10,100,304 | B2 | 10/2018 | van Deutekom et al. |
| 10,131,682 | B2 | 11/2018 | Zhao |
| 10,144,931 | B2 | 12/2018 | Enya et al. |
| 10,179,912 | B2 | 1/2019 | De Visser et al. |
| 10,190,116 | B2 | 1/2019 | van Deutekom et al. |
| 10,208,299 | B2 | 2/2019 | Gotschall et al. |
| 10,227,577 | B2 | 3/2019 | Do et al. |
| 10,227,590 | B2 | 3/2019 | Wilton et al. |
| 10,238,753 | B2 | 3/2019 | Armstrong |
| 10,239,807 | B2 | 3/2019 | van Delft et al. |
| 10,266,502 | B2 | 4/2019 | van Delft et al. |
| 10,266,827 | B2 | 4/2019 | Wilton et al. |
| 10,287,586 | B2 | 5/2019 | Wilson et al. |
| 10,329,319 | B2 | 6/2019 | Watanabe et al. |
| 10,337,003 | B2 | 7/2019 | Kaye |
| 10,364,431 | B2 | 7/2019 | Kaye |
| 10,385,092 | B2 | 8/2019 | Watanabe et al. |
| 10,407,461 | B2 | 9/2019 | Watanabe et al. |
| 10,421,966 | B2 | 9/2019 | Wilton et al. |
| 10,434,111 | B2 | 10/2019 | Bertozzi et al. |
| 10,450,568 | B2 | 10/2019 | Butler et al. |
| 10,457,944 | B2 | 10/2019 | Popplewell et al. |
| RE47,691 | E | 11/2019 | Wilton et al. |
| 10,464,962 | B2 | 11/2019 | Avila et al. |
| 10,487,106 | B2 | 11/2019 | Watanabe et al. |
| RE47,751 | E | 12/2019 | Wilton et al. |
| 10,493,092 | B2 | 12/2019 | Swayze |
| 10,512,676 | B2 | 12/2019 | Char et al. |
| 10,533,171 | B2 | 1/2020 | van Deutekom et al. |
| 10,533,174 | B2 | 1/2020 | Iversen et al. |
| 10,538,763 | B2 | 1/2020 | Rigo et al. |

| | | | |
|---|---|---|---|
| 10,550,188 | B2 | 2/2020 | Geall et al. |
| 10,647,969 | B2 | 5/2020 | Chen et al. |
| 10,648,044 | B2 | 5/2020 | Vervecken et al. |
| 10,662,217 | B2 | 5/2020 | Watanbe et al. |
| 10,704,060 | B2 | 7/2020 | Gersbach et al. |
| 10,722,559 | B2 | 7/2020 | Concino et al. |
| 10,752,898 | B2 | 8/2020 | Pietri et al. |
| 10,781,448 | B2 | 9/2020 | Watanabe et al. |
| 10,781,450 | B2 | 9/2020 | Wilton et al. |
| 10,781,451 | B2 | 9/2020 | Wilton et al. |
| 10,865,445 | B2 | 12/2020 | van der Maarel et al. |
| 10,876,114 | B2 | 12/2020 | van Deutekom et al. |
| 10,881,743 | B2 | 1/2021 | Geall et al. |
| 10,907,142 | B2 | 2/2021 | Zhu et al. |
| 10,907,157 | B2 | 2/2021 | Belayew et al. |
| 10,913,946 | B2 | 2/2021 | De Visser et al. |
| 10,940,125 | B2 | 3/2021 | Koeberl et al. |
| 10,940,185 | B2 | 3/2021 | Yasukawa et al. |
| 10,961,522 | B2 | 3/2021 | Gotschall et al. |
| 10,968,450 | B2 | 4/2021 | Wilton et al. |
| 10,994,020 | B2 | 5/2021 | Levin et al. |
| 10,995,337 | B2 | 5/2021 | Wilton et al. |
| 11,028,122 | B1 | 6/2021 | Watanabe et al. |
| 11,111,309 | B2 | 9/2021 | Subramanian et al. |
| 11,168,141 | B2 | 11/2021 | Subramanian et al. |
| 11,179,472 | B2 | 11/2021 | Levin et al. |
| 11,208,458 | B2 | 12/2021 | Baik et al. |
| 11,214,782 | B2 | 1/2022 | Chen et al. |
| 11,230,605 | B2 | 1/2022 | Launay et al. |
| 11,248,056 | B1 | 2/2022 | Subramanian et al. |
| 11,253,485 | B2 | 2/2022 | Dodge et al. |
| RE48,960 | E | 3/2022 | Wilton et al. |
| 11,279,725 | B2 | 3/2022 | Avila et al. |
| 11,286,305 | B2 | 3/2022 | Subramanian et al. |
| 11,311,627 | B1 | 4/2022 | Levin et al. |
| 11,339,406 | B2 | 5/2022 | Mingozzi et al. |
| 11,369,689 | B2 | 6/2022 | Subramanian et al. |
| 11,390,682 | B2 | 7/2022 | Subramanian et al. |
| 11,400,163 | B2 | 8/2022 | Levin et al. |
| 11,421,211 | B2 | 8/2022 | Mingozzi et al. |
| 11,491,211 | B2 | 11/2022 | Char et al. |
| 11,497,815 | B2 | 11/2022 | Subramanian et al. |
| 11,518,816 | B2 | 12/2022 | Subramanian et al. |
| 11,525,137 | B2 | 12/2022 | Malecova et al. |
| 11,547,717 | B2 | 1/2023 | Koeberl et al. |
| 11,555,190 | B2 | 1/2023 | Malecova et al. |
| 11,591,583 | B2 | 2/2023 | Gotschall et al. |
| 11,633,496 | B2 | 4/2023 | Subramanian et al. |
| 11,633,498 | B2 | 4/2023 | Subramanian et al. |
| 11,638,761 | B2 | 5/2023 | Subramanian et al. |
| 11,648,318 | B2 | 5/2023 | Subramanian et al. |
| 11,672,872 | B2 | 6/2023 | Subramanian et al. |
| 11,679,161 | B2 | 6/2023 | Subramanian et al. |
| 11,690,812 | B2 | 7/2023 | Koeberl et al. |
| 11,708,569 | B2 | 7/2023 | Kristensen et al. |
| 11,753,632 | B2 | 9/2023 | Gotschall et al. |
| 11,759,525 | B1 | 9/2023 | Subramanian et al. |
| 11,771,776 | B2 | 10/2023 | Subramanian et al. |
| 11,787,869 | B2 | 10/2023 | Subramanian et al. |
| 11,795,233 | B2 | 10/2023 | Subramanian et al. |
| 11,795,234 | B2 | 10/2023 | Subramanian et al. |
| 11,833,217 | B2 | 12/2023 | Subramanian et al. |
| 11,839,660 | B2 | 12/2023 | Subramanian et al. |
| 11,844,843 | B2 | 12/2023 | Subramanian et al. |
| 11,911,484 | B2 | 2/2024 | Subramanian et al. |
| 11,912,779 | B2 | 2/2024 | Malecova et al. |
| 11,931,421 | B2 | 3/2024 | Hilderbrand et al. |
| 11,969,475 | B2 | 4/2024 | Subramanian et al. |
| 11,970,722 | B2 | 4/2024 | Hallows et al. |
| 11,986,537 | B2 | 5/2024 | Subramanian et al. |
| 12,005,124 | B2 | 6/2024 | Subramanian et al. |
| 12,012,460 | B2 | 6/2024 | Subramanian et al. |
| 12,018,087 | B2 | 6/2024 | Subramanian et al. |
| 12,064,483 | B2 | 8/2024 | Levin et al. |
| 12,097,263 | B2 | 9/2024 | Subramanian et al. |
| 12,102,687 | B2 | 10/2024 | Subramanian et al. |
| 12,128,109 | B2 | 10/2024 | Weeden et al. |
| 12,144,867 | B2 | 11/2024 | Subramanian et al. |
| 12,144,868 | B2 | 11/2024 | Subramanian et al. |

(56) References Cited

U.S. PATENT DOCUMENTS 12,173,078 B2 12/2024 Subramanian et al.
12,173,079 B2 12/2024 Subramanian et al.
12,239,716 B2 3/2025 Subramanian et al.
12,239,717 B2 3/2025 Subramanian et al.
12,263,225 B2 4/2025 Subramanian et al.
12,280,122 B2 4/2025 Subramanian et al.
12,319,743 B2 6/2025 Subramanian et al.
12,325,753 B2 6/2025 Subramanian et al.
12,329,824 B1 6/2025 Subramanian et al.
12,329,825 B1 6/2025 Subramanian et al.
12,357,703 B2 7/2025 Subramanian et al.
12,370,264 B1 7/2025 Subramanian et al.
12,397,062 B2 8/2025 Subramanian et al.
12,403,203 B2 9/2025 Subramanian et al.
12,428,487 B2 9/2025 Subramanian et al.
12,440,574 B2 10/2025 Hilderbrand et al.
12,440,575 B2 10/2025 Subramanian et al.
12,460,011 B2 11/2025 Subramanian et al.
12,478,687 B2 11/2025 Subramanian et al.
12,496,352 B2 12/2025 Subramanian et al.
2004/0063654 A1 4/2004 Davis et al.
2004/0191243 A1 9/2004 Chen et al.
2005/0004026 A1 1/2005 Kashibatla et al.
2005/0084906 A1 4/2005 Goetsch et al.
2005/0255487 A1 11/2005 Khvorova et al.
2005/0282252 A1 12/2005 Siegel
2006/0110782 A1 5/2006 Bertozzi et al.
2006/0252107 A1 11/2006 Kubota et al.
2007/0050146 A1 3/2007 Bentwich et al.
2007/0082861 A1 4/2007 Matsuo et al.
2007/0105805 A1 5/2007 Kmiec et al.
2008/0025913 A1 1/2008 Bowdish et al.
2008/0177045 A1 7/2008 Lee et al.
2008/0199960 A1 8/2008 Juliano et al.
2009/0269755 A1 10/2009 Aartsma-Rus et al.
2010/0130591 A1 5/2010 Sazani et al.
2010/0168212 A1 7/2010 Popplewell et al.
2011/0256157 A1 10/2011 Howard et al.
2011/0263682 A1 10/2011 De Kimpe et al.
2012/0059042 A1 3/2012 Platenburg et al.
2012/0077860 A1 3/2012 Garcia et al.
2012/0122801 A1 5/2012 Platenburg
2012/0201809 A1 8/2012 Bhat et al.
2012/0225034 A1 9/2012 Belayew et al.
2012/0270925 A1 10/2012 Wilton et al.
2013/0028891 A1 1/2013 Penichet et al.
2013/0041017 A1 2/2013 Kaplan et al.
2013/0066063 A1 3/2013 Berry et al.
2013/0072541 A1 3/2013 Garcia et al.
2013/0096282 A1 4/2013 Neville
2013/0137763 A1 5/2013 van Delft et al.
2013/0177579 A1 7/2013 Lin et al.
2013/0237585 A1 9/2013 Bennett et al.
2014/0105873 A1 4/2014 Belayew et al.
2014/0105916 A1 4/2014 Brasel et al.
2014/0178383 A1* 6/2014 Brige .................. A61K 47/183
424/135.1
2014/0193436 A1 7/2014 Prudent
2014/0323552 A1 10/2014 Burghes et al.
2014/0336178 A1 11/2014 Kazantsev et al.
2014/0363455 A1 12/2014 Stull et al.
2015/0064181 A1 3/2015 Armstrong
2015/0191725 A1 7/2015 van Deutekom et al.
2015/0196670 A1 7/2015 Dickson et al.
2015/0225722 A1 8/2015 Ozsolak
2015/0247141 A1 9/2015 Uhlmann et al.
2015/0258210 A1 9/2015 van Delft et al.
2015/0266954 A1 9/2015 Davies et al.
2016/0015828 A1 1/2016 Torgov et al.
2016/0032286 A1 2/2016 Montgomery et al.
2016/0053262 A1 2/2016 Platenburg et al.
2016/0090598 A1 3/2016 Oestergaard et al.
2016/0107999 A1 4/2016 Debets et al.
2016/0175460 A1 6/2016 Arathoon et al.
2016/0201064 A1 7/2016 Ozsolak
2016/0235861 A1 8/2016 van Delft et al.
2016/0237157 A1 8/2016 Dennis et al.
2016/0250347 A1 9/2016 van Delft et al.
2016/0264976 A1 9/2016 Laporte et al.
2016/0272973 A1 9/2016 Shehadeh
2016/0304864 A1 10/2016 De Kimpe et al.
2016/0355599 A1 12/2016 Sagert et al.
2017/0002012 A1 1/2017 van Delft et al.
2017/0008858 A1 1/2017 van Delft et al.
2017/0029849 A1 2/2017 Harper et al.
2017/0072068 A1 3/2017 Verkade et al.
2017/0130256 A1 5/2017 van Berkel et al.
2017/0151348 A1 6/2017 Kaspar et al.
2017/0226554 A1 8/2017 Wasiel et al.
2017/0247450 A1 8/2017 Joutel et al.
2017/0281795 A1 10/2017 Geall et al.
2017/0283799 A1 10/2017 Kaye et al.
2017/0348416 A1 12/2017 Hasler et al.
2018/0002433 A1 1/2018 Zhang et al.
2018/0021449 A1 1/2018 Armstrong
2018/0028554 A1 2/2018 De Visser et al.
2018/0094262 A1 4/2018 Montgomery et al.
2018/0111983 A1 4/2018 Hatsell et al.
2018/0134797 A1 5/2018 Zhang et al.
2018/0142245 A1 5/2018 Watanabe et al.
2018/0171333 A1 6/2018 Meloni et al.
2018/0179538 A1 6/2018 Takeda et al.
2018/0216111 A1 8/2018 Wilton et al.
2018/0265859 A1 9/2018 Tremblay et al.
2018/0265870 A1 9/2018 Belayew et al.
2018/0369400 A1 12/2018 Levin et al.
2019/0000986 A1 1/2019 Levin et al.
2019/0008986 A1 1/2019 Butler et al.
2019/0038765 A1 2/2019 van Berkel et al.
2019/0060488 A1 2/2019 Tadin-Strapps et al.
2019/0092833 A1 3/2019 Lin et al.
2019/0092870 A1 3/2019 Launay et al.
2019/0112604 A1 4/2019 De Kimpe et al.
2019/0119383 A1 4/2019 Bruenker et al.
2019/0119679 A1 4/2019 De Kimpe et al.
2019/0127733 A1 5/2019 Butler et al.
2019/0153083 A1 5/2019 Juste et al.
2019/0177723 A1 6/2019 Dickson et al.
2019/0177725 A1 6/2019 De Kimpe et al.
2019/0209604 A1 7/2019 Zhang et al.
2019/0211362 A1 7/2019 Lundberg et al.
2019/0240346 A1 8/2019 Sugo et al.
2019/0249173 A1 8/2019 Vargeese et al.
2019/0270994 A1 9/2019 Wilton et al.
2019/0284556 A1 9/2019 Sazani et al.
2019/0298847 A1 10/2019 Geall et al.
2019/0323010 A1 10/2019 Wilton et al.
2019/0330626 A1 10/2019 Rigo et al.
2019/0336615 A1 11/2019 Thompson et al.
2019/0338043 A1 11/2019 Sonoda et al.
2019/0338311 A1 11/2019 Amoasii et al.
2019/0359982 A1 11/2019 Kaye et al.
2019/0364862 A1 12/2019 Amoasii et al.
2019/0390197 A1 12/2019 Butler et al.
2020/0040337 A1 2/2020 Kaye et al.
2020/0046742 A1 2/2020 Bertozzi et al.
2020/0046854 A1 2/2020 Zhang et al.
2020/0048174 A1 2/2020 van Delft et al.
2020/0123267 A1 4/2020 Zhang et al.
2020/0155702 A1 5/2020 Bacica et al.
2020/0239886 A1 7/2020 De Kimpe et al.
2020/0248179 A1 8/2020 Harper
2020/0282074 A1 9/2020 Levin et al.
2020/0325237 A1 10/2020 Darimont et al.
2020/0385457 A1 12/2020 McNally et al.
2021/0038739 A1 2/2021 Takahashi et al.
2021/0095283 A1 4/2021 Geall et al.
2021/0130486 A1 5/2021 Darimont et al.
2021/0145852 A1 5/2021 Passini et al.
2021/0147576 A1 5/2021 Laurent et al.
2021/0163931 A1 6/2021 Lek et al.
2021/0163941 A1 6/2021 Belayew et al.
2021/0187082 A1 6/2021 Yasukawa et al.
2021/0187116 A1 6/2021 Geall et al.

(56) References Cited

U.S. PATENT DOCUMENTS

| | | | |
|---|---|---|---|
| 2021/0206868 | A1 | 7/2021 | Subramanian et al. |
| 2021/0220479 | A1 | 7/2021 | Subramanian et al. |
| 2021/0228730 | A1 | 7/2021 | Subramanian et al. |
| 2021/0230290 | A1 | 7/2021 | Subramanian et al. |
| 2021/0261680 | A1 | 8/2021 | Subramanian et al. |
| 2021/0308272 | A1 | 10/2021 | Subramanian et al. |
| 2021/0308273 | A1 | 10/2021 | Subramanian et al. |
| 2021/0308274 | A1 | 10/2021 | Subramanian et al. |
| 2021/0317226 | A1 | 10/2021 | Subramanian et al. |
| 2021/0322562 | A1 | 10/2021 | Subramanian et al. |
| 2021/0322563 | A1 | 10/2021 | Subramanian et al. |
| 2021/0324101 | A1 | 10/2021 | Subramanian et al. |
| 2021/0371860 | A1 | 12/2021 | Hagedorn et al. |
| 2021/0380709 | A1 | 12/2021 | Subramanian et al. |
| 2022/0025066 | A1 | 1/2022 | Subramanian et al. |
| 2022/0106592 | A1 | 4/2022 | Harper et al. |
| 2022/0143206 | A1 | 5/2022 | Subramanian et al. |
| 2022/0169743 | A1 | 6/2022 | Subramanian et al. |
| 2022/0193250 | A1 | 6/2022 | Subramanian et al. |
| 2022/0288220 | A1 | 9/2022 | Subramanian et al. |
| 2022/0306685 | A1 | 9/2022 | Weeden et al. |
| 2022/0324992 | A1 | 10/2022 | Subramanian et al. |
| 2022/0378934 | A1 | 12/2022 | Subramanian et al. |
| 2023/0001002 | A1 | 1/2023 | Subramanian et al. |
| 2023/0044278 | A1 | 2/2023 | Subramanian et al. |
| 2023/0045002 | A1 | 2/2023 | Subramanian et al. |
| 2023/0045314 | A1 | 2/2023 | Subramanian et al. |
| 2023/0047754 | A1 | 2/2023 | Geall et al. |
| 2023/0049450 | A1 | 2/2023 | Subramanian et al. |
| 2023/0050911 | A1 | 2/2023 | Subramanian et al. |
| 2023/0051954 | A1 | 2/2023 | Subramanian et al. |
| 2023/0088865 | A1 | 3/2023 | Subramanian et al. |
| 2023/0103793 | A1 | 4/2023 | Subramanian et al. |
| 2023/0111147 | A1 | 4/2023 | Subramanian et al. |
| 2023/0111212 | A1 | 4/2023 | Subramanian et al. |
| 2023/0113823 | A1 | 4/2023 | Subramanian et al. |
| 2023/0117883 | A1 | 4/2023 | Subramanian et al. |
| 2023/0118799 | A1 | 4/2023 | Subramanian et al. |
| 2023/0144436 | A1 | 5/2023 | Subramanian et al. |
| 2023/0203180 | A1 | 6/2023 | Subramanian et al. |
| 2023/0203181 | A1 | 6/2023 | Subramanian et al. |
| 2023/0226212 | A1 | 7/2023 | Subramanian et al. |
| 2023/0227569 | A1 | 7/2023 | Subramanian et al. |
| 2023/0256112 | A1 | 8/2023 | Subramanian et al. |
| 2023/0256113 | A1 | 8/2023 | Subramanian et al. |
| 2023/0270873 | A1 | 8/2023 | Subramanian et al. |
| 2023/0272065 | A1 | 8/2023 | Subramanian et al. |
| 2023/0285582 | A1 | 9/2023 | Subramanian et al. |
| 2023/0285586 | A1 | 9/2023 | Subramanian et al. |
| 2023/0287108 | A1 | 9/2023 | Subramanian et al. |
| 2023/0321264 | A1 | 10/2023 | Subramanian et al. |
| 2023/0330247 | A1 | 10/2023 | Hildebrand et al. |
| 2023/0330562 | A1 | 10/2023 | Weeden et al. |
| 2023/0346966 | A1 | 11/2023 | Subramanian et al. |
| 2023/0346967 | A1 | 11/2023 | Subramanian et al. |
| 2024/0016950 | A1 | 1/2024 | Weeden et al. |
| 2024/0016952 | A1 | 1/2024 | Subramanian et al. |
| 2024/0066139 | A1 | 2/2024 | Subramanian et al. |
| 2024/0066140 | A1 | 2/2024 | Subramanian et al. |
| 2024/0067743 | A1 | 2/2024 | Subramanian et al. |
| 2024/0067744 | A1 | 2/2024 | Subramanian et al. |
| 2024/0100177 | A1 | 3/2024 | Hildebrand et al. |
| 2024/0110184 | A1 | 4/2024 | Brown et al. |
| 2024/0117356 | A1 | 4/2024 | Subramanian et al. |
| 2024/0148891 | A1 | 5/2024 | Subramanian et al. |
| 2024/0197901 | A1 | 6/2024 | Subramanian et al. |
| 2024/0197905 | A1 | 6/2024 | Subramanian et al. |
| 2024/0207430 | A1 | 6/2024 | Subramanian et al. |
| 2024/0209119 | A1 | 6/2024 | Subramanian et al. |
| 2024/0216522 | A1 | 7/2024 | Subramanian et al. |
| 2024/0238435 | A1 | 7/2024 | Subramanian et al. |
| 2024/0252666 | A1 | 8/2024 | Hilderbrand et al. |
| 2024/0287201 | A1 | 8/2024 | Subramanian et al. |
| 2024/0293568 | A1 | 9/2024 | Subramanian et al. |
| 2024/0294921 | A1 | 9/2024 | Subramanian et al. |
| 2024/0301416 | A1 | 9/2024 | Tone et al. |
| 2024/0309107 | A1 | 9/2024 | Subramanian et al. |
| 2024/0318176 | A1 | 9/2024 | Desjardins et al. |
| 2024/0318177 | A1 | 9/2024 | Desjardins et al. |
| 2024/0325558 | A1 | 10/2024 | Zanotti et al. |
| 2024/0368296 | A1 | 11/2024 | Desjardins et al. |
| 2024/0382513 | A1 | 11/2024 | Subramanian et al. |
| 2024/0382609 | A1 | 11/2024 | Desjardins et al. |
| 2024/0398967 | A1 | 12/2024 | Subramanian et al. |
| 2024/0398968 | A1 | 12/2024 | Subramanian et al. |
| 2024/0408227 | A1 | 12/2024 | Subramanian et al. |
| 2025/0018050 | A1 | 1/2025 | Desjardins et al. |
| 2025/0025570 | A1 | 1/2025 | Hsia et al. |
| 2025/0032634 | A1 | 1/2025 | Subramanian et al. |
| 2025/0057972 | A1 | 2/2025 | Subramanian et al. |
| 2025/0066495 | A1 | 2/2025 | Subramanian et al. |
| 2025/0066496 | A1 | 2/2025 | Subramanian et al. |
| 2025/0099603 | A9 | 3/2025 | Subramanian et al. |
| 2025/0152727 | A1 | 5/2025 | Subramanian et al. |
| 2025/0177549 | A1 | 6/2025 | Subramanian et al. |
| 2025/0242042 | A1 | 7/2025 | Subramanian et al. |
| 2025/0249116 | A1 | 8/2025 | Weeden et al. |
| 2025/0249117 | A1 | 8/2025 | Zanotti et al. |
| 2025/0249119 | A1 | 8/2025 | Subramanian et al. |
| 2025/0270340 | A1 | 8/2025 | Subramanian et al. |
| 2025/0276083 | A1 | 9/2025 | Subramanian et al. |
| 2025/0297024 | A1 | 9/2025 | Subramanian et al. |
| 2025/0304710 | A1 | 10/2025 | Subramanian et al. |
| 2025/0339553 | A1 | 11/2025 | Hilderbrand et al. |
| 2025/0360223 | A1 | 11/2025 | Subramanian et al. |
| 2025/0367310 | A1 | 12/2025 | Hilderbrand et al. |
| 2025/0382375 | A1 | 12/2025 | Subramanian et al. |
| 2026/0053941 | A1 | 2/2026 | Weeden et al. |
| 2026/0069704 | A1 | 3/2026 | Hilderbrand et al. |

FOREIGN PATENT DOCUMENTS

| | | | |
|---|---|---|---|
| CN | 103732259 | A | 4/2014 |
| CN | 105142672 | A | 12/2015 |
| CN | 107001473 | A | 8/2017 |
| CN | 107849555 | A | 3/2018 |
| CN | 108220418 | A | 6/2018 |
| CN | 109306375 | A | 2/2019 |
| CN | 110381980 | A | 10/2019 |
| CN | 105358578 | B | 8/2021 |
| EP | 1479771 | A2 | 11/2004 |
| EP | 1619249 | A1 | 1/2006 |
| EP | 2149605 | A2 | 2/2010 |
| EP | 1716232 | B1 | 4/2010 |
| EP | 2203173 | B1 | 7/2010 |
| EP | 2241331 | A2 | 10/2010 |
| EP | 2284264 | A1 | 2/2011 |
| EP | 2410053 | A1 | 1/2012 |
| EP | 2410054 | A1 | 1/2012 |
| EP | 2426203 | A2 | 3/2012 |
| EP | 2121713 | B1 | 6/2013 |
| EP | 2614827 | A2 | 7/2013 |
| EP | 1673104 | B1 | 10/2013 |
| EP | 2801618 | A1 | 11/2014 |
| EP | 2344637 | B1 | 12/2014 |
| EP | 2318037 | B1 | 1/2015 |
| EP | 2465542 | B1 | 1/2015 |
| EP | 2612917 | B1 | 2/2016 |
| EP | 2475376 | B1 | 3/2016 |
| EP | 3031920 | A1 | 6/2016 |
| EP | 2421971 | B1 | 7/2016 |
| EP | 3067421 | A1 | 9/2016 |
| EP | 2027267 | B1 | 11/2016 |
| EP | 2623609 | B1 | 1/2017 |
| EP | 3185889 | A1 | 7/2017 |
| EP | 3192880 | A1 | 7/2017 |
| EP | 2736539 | B1 | 8/2017 |
| EP | 3202905 | A1 | 8/2017 |
| EP | 2457920 | B1 | 10/2017 |
| EP | 3238737 | A1 | 11/2017 |
| EP | 3271453 | A1 | 1/2018 |
| EP | 3315606 | A1 | 5/2018 |
| EP | 1988823 | B1 | 8/2018 |
| EP | 2499249 | B1 | 8/2018 |

(56) References Cited

FOREIGN PATENT DOCUMENTS

| | | | |
|---|---|---|---|
| EP | 2922818 | B1 | 9/2018 |
| EP | 3386534 | A2 | 10/2018 |
| EP | 3436053 | A1 | 2/2019 |
| EP | 3436588 | A1 | 2/2019 |
| EP | 2889043 | B1 | 4/2019 |
| EP | 3473270 | A1 | 4/2019 |
| EP | 3489360 | A2 | 5/2019 |
| EP | 2457919 | B1 | 6/2019 |
| EP | 3510049 | A1 | 7/2019 |
| EP | 3075386 | B1 | 10/2019 |
| EP | 3560958 | A1 | 10/2019 |
| EP | 2825193 | B1 | 11/2019 |
| EP | 3565577 | A1 | 11/2019 |
| EP | 3624831 | A1 | 3/2020 |
| EP | 3135889 | B1 | 7/2020 |
| EP | 3684376 | A1 | 7/2020 |
| EP | 3691657 | A1 | 8/2020 |
| EP | 3720448 | A1 | 10/2020 |
| EP | 3735252 | A2 | 11/2020 |
| EP | 2806900 | B1 | 2/2021 |
| EP | 3018211 | B1 | 6/2021 |
| EP | 3898693 | A1 | 10/2021 |
| EP | 3959319 | A1 | 3/2022 |
| EP | 3980436 | A1 | 4/2022 |
| EP | 3980437 | A1 | 4/2022 |
| EP | 3608330 | B1 | 11/2022 |
| EP | 4121063 | A1 | 1/2023 |
| EP | 4126066 | A1 | 2/2023 |
| EP | 4146229 | A1 | 3/2023 |
| EP | 3563863 | B1 | 7/2023 |
| EP | 3597655 | B1 | 8/2023 |
| EP | 3201320 | B1 | 10/2023 |
| EP | 4291225 | A1 | 12/2023 |
| EP | 3628326 | B1 | 2/2024 |
| EP | 4314298 | A1 | 2/2024 |
| EP | 4122497 | B1 | 4/2024 |
| EP | 4401792 | A1 | 7/2024 |
| IL | 54795 | A | 10/1980 |
| JP | 2002-253259 | A | 9/2002 |
| JP | 2007-104971 | A | 4/2007 |
| JP | 2010-532168 | A | 10/2010 |
| JP | 2013-538560 | A | 1/2012 |
| JP | 2015-532264 | A | 11/2015 |
| JP | 2015-534996 | A | 12/2015 |
| JP | 2016-528258 | A | 9/2016 |
| JP | 2018-503357 | A | 2/2018 |
| JP | 2019-137675 | A | 8/2019 |
| KR | 10-2013-0106811 | A | 9/2013 |
| WO | WO 1989/007970 | A1 | 9/1989 |
| WO | WO 1991/004753 | A1 | 4/1991 |
| WO | WO 2001/083740 | A2 | 11/2001 |
| WO | WO 2003/074654 | A2 | 9/2003 |
| WO | WO 2004/048570 | A1 | 6/2004 |
| WO | WO 2004/069991 | A2 | 8/2004 |
| WO | WO 2005/021064 | A2 | 3/2005 |
| WO | WO 2005/023825 | A2 | 3/2005 |
| WO | WO 2005/078077 | A2 | 8/2005 |
| WO | WO 2006/000057 | A1 | 1/2006 |
| WO | WO 2006/022688 | A1 | 3/2006 |
| WO | WO 2007/089612 | A2 | 8/2007 |
| WO | WO 2007/095056 | A2 | 8/2007 |
| WO | WO 2007/135105 | A1 | 11/2007 |
| WO | WO 2008/018795 | A1 | 2/2008 |
| WO | WO 2008/049085 | A1 | 4/2008 |
| WO | WO 2008/089403 | A2 | 7/2008 |
| WO | WO 2009/054725 | A2 | 4/2009 |
| WO | WO 2009/075815 | A1 | 6/2009 |
| WO | WO 2009/144481 | A2 | 12/2009 |
| WO | WO 2010/005565 | A2 | 1/2010 |
| WO | WO 2010/048586 | A1 | 4/2010 |
| WO | WO 2010/050801 | A1 | 5/2010 |
| WO | WO 2010/050802 | A1 | 5/2010 |
| WO | WO 2010/075010 | A2 | 7/2010 |
| WO | WO 2010/096369 | A1 | 8/2010 |
| WO | WO 2010/123369 | A1 | 10/2010 |

| | | | |
|---|---|---|---|
| WO | WO 2010/129861 | A1 | 11/2010 |
| WO | WO 2010/148253 | A2 | 12/2010 |
| WO | WO 2011/057350 | A1 | 5/2011 |
| WO | WO 2011/078797 | A2 | 6/2011 |
| WO | WO 2011/136645 | A1 | 11/2011 |
| WO | WO 2011/150408 | A2 | 12/2011 |
| WO | WO 2011/154427 | A1 | 12/2011 |
| WO | WO 2012/012443 | A2 | 1/2012 |
| WO | WO 2012/012467 | A2 | 1/2012 |
| WO | WO 2012/024535 | A2 | 2/2012 |
| WO | WO 2012/029986 | A1 | 3/2012 |
| WO | WO 2012/075037 | A1 | 6/2012 |
| WO | WO 2012/087962 | A2 | 6/2012 |
| WO | WO 2012/144906 | A1 | 10/2012 |
| WO | WO 2013/016352 | A1 | 1/2013 |
| WO | WO 2013/019623 | A2 | 2/2013 |
| WO | WO 2013/026832 | A1 | 2/2013 |
| WO | WO 2013/085550 | A2 | 6/2013 |
| WO | WO 2013/100190 | A1 | 7/2013 |
| WO | WO 2013/112053 | A1 | 8/2013 |
| WO | WO 2013/120038 | A2 | 8/2013 |
| WO | WO 2013/136189 | A2 | 9/2013 |
| WO | WO 2013/138662 | A1 | 9/2013 |
| WO | WO 2013/162363 | A1 | 10/2013 |
| WO | WO 2014/007620 | A2 | 1/2014 |
| WO | WO 2014/052276 | A1 | 4/2014 |
| WO | WO 2014/065661 | A1 | 5/2014 |
| WO | WO 2014/144978 | A2 | 9/2014 |
| WO | WO 2014/153220 | A2 | 9/2014 |
| WO | WO 2014/153240 | A2 | 9/2014 |
| WO | WO 2014/189973 | A2 | 11/2014 |
| WO | WO 2015/021457 | A2 | 2/2015 |
| WO | WO 2015/023937 | A1 | 2/2015 |
| WO | WO 2015/023939 | A1 | 2/2015 |
| WO | WO 2015/042581 | A1 | 3/2015 |
| WO | WO 2015/055859 | A1 | 4/2015 |
| WO | WO 2015/070158 | A1 | 5/2015 |
| WO | WO 2015/134365 | A2 | 9/2015 |
| WO | WO 2015/143062 | A1 | 9/2015 |
| WO | WO 2015/179741 | A1 | 11/2015 |
| WO | WO 2016/025519 | A1 | 2/2016 |
| WO | WO 2016/039796 | A2 | 3/2016 |
| WO | WO 2016/054231 | A1 | 4/2016 |
| WO | WO 2016/081643 | A1 | 5/2016 |
| WO | WO 2016/081670 | A2 | 5/2016 |
| WO | WO 2016/094374 | A1 | 6/2016 |
| WO | WO 2016/115490 | A1 | 7/2016 |
| WO | WO 2016/146760 | A1 | 9/2016 |
| WO | WO 2016/187425 | A1 | 11/2016 |
| WO | WO 2016/205641 | A2 | 12/2016 |
| WO | WO 2016/208695 | A1 | 12/2016 |
| WO | WO 2017/047707 | A1 | 3/2017 |
| WO | WO 2017/049157 | A1 | 3/2017 |
| WO | WO 2017/050836 | A1 | 3/2017 |
| WO | WO 2017/062835 | A2 | 4/2017 |
| WO | WO 2017/062862 | A2 | 4/2017 |
| WO | WO 2017/077451 | A1 | 5/2017 |
| WO | WO 2017/100467 | A2 | 6/2017 |
| WO | WO 2017/106643 | A1 | 6/2017 |
| WO | WO 2017/143156 | A1 | 8/2017 |
| WO | WO 2017/173059 | A1 | 10/2017 |
| WO | WO 2017/173060 | A1 | 10/2017 |
| WO | WO 2017/173408 | A1 | 10/2017 |
| WO | WO 2017/173411 | A1 | 10/2017 |
| WO | WO 2017/184529 | A1 | 10/2017 |
| WO | WO 2017/192679 | A1 | 11/2017 |
| WO | WO 2017/205191 | A1 | 11/2017 |
| WO | WO 2017/205513 | A1 | 11/2017 |
| WO | WO 2017/221883 | A1 | 12/2017 |
| WO | WO 2018/007475 | A1 | 1/2018 |
| WO | WO 2018/014042 | A1 | 1/2018 |
| WO | WO 2018/017754 | A1 | 1/2018 |
| WO | WO 2018/046772 | A1 | 3/2018 |
| WO | WO 2018/046774 | A1 | 3/2018 |
| WO | WO 2018/046775 | A1 | 3/2018 |
| WO | WO 2018/057575 | A1 | 3/2018 |
| WO | WO 2018/091544 | A1 | 5/2018 |
| WO | WO 2018/098480 | A1 | 5/2018 |
| WO | WO 2018/100010 | A1 | 6/2018 |

(56) References Cited

FOREIGN PATENT DOCUMENTS

| | | | |
|---|---|---|---|
| WO | WO 2018/107003 | A1 | 6/2018 |
| WO | WO 2018/118627 | A1 | 6/2018 |
| WO | WO 2018/124121 | A1 | 7/2018 |
| WO | WO 2018/124277 | A1 | 7/2018 |
| WO | WO 2018/129296 | A1 | 7/2018 |
| WO | WO 2018/129384 | A1 | 7/2018 |
| WO | WO 2018/213340 | A1 | 11/2018 |
| WO | WO 2018/226861 | A1 | 12/2018 |
| WO | WO 2019/014772 | A1 | 1/2019 |
| WO | WO 2019/023257 | A1 | 1/2019 |
| WO | WO 2019/059973 | A1 | 3/2019 |
| WO | WO 2019/060432 | A2 | 3/2019 |
| WO | WO 2019/060775 | A1 | 3/2019 |
| WO | WO 2019/067975 | A1 | 4/2019 |
| WO | WO 2019/070741 | A1 | 4/2019 |
| WO | WO 2019/071028 | A1 | 4/2019 |
| WO | WO 2019/075417 | A1 | 4/2019 |
| WO | WO 2019/079637 | A2 | 4/2019 |
| WO | WO 2019/092507 | A2 | 5/2019 |
| WO | WO 2019/110725 | A1 | 6/2019 |
| WO | WO 2019/113393 | A1 | 6/2019 |
| WO | WO 2019/126641 | A2 | 6/2019 |
| WO | WO 2019/136180 | A2 | 7/2019 |
| WO | WO 2019/136216 | A1 | 7/2019 |
| WO | WO 2019/151539 | A1 | 8/2019 |
| WO | WO 2019/152609 | A1 | 8/2019 |
| WO | WO 2019/152820 | A1 | 8/2019 |
| WO | WO 2019/157224 | A1 | 8/2019 |
| WO | WO 2019/178532 | A1 | 9/2019 |
| WO | WO 2019/200185 | A1 | 10/2019 |
| WO | WO 2019/209764 | A2 | 10/2019 |
| WO | WO 2019/215175 | A1 | 11/2019 |
| WO | WO 2019/215333 | A1 | 11/2019 |
| WO | WO 2019/217784 | A1 | 11/2019 |
| WO | WO 2019/222411 | A1 | 11/2019 |
| WO | WO 2019/222663 | A1 | 11/2019 |
| WO | WO 2019/229658 | A1 | 12/2019 |
| WO | WO 2019/241385 | A2 | 12/2019 |
| WO | WO 2019/246480 | A1 | 12/2019 |
| WO | WO 2020/028831 | A1 | 2/2020 |
| WO | WO 2020/028832 | A1 | 2/2020 |
| WO | WO 2020/028836 | A1 | 2/2020 |
| WO | WO 2020/028840 | A1 | 2/2020 |
| WO | WO 2020/028841 | A1 | 2/2020 |
| WO | WO 2020/028842 | A1 | 2/2020 |
| WO | WO 2020/028844 | A1 | 2/2020 |
| WO | WO 2020/028857 | A1 | 2/2020 |
| WO | WO 2020/028861 | A1 | 2/2020 |
| WO | WO 2020/028864 | A1 | 2/2020 |
| WO | WO 2020/047282 | A1 | 3/2020 |
| WO | WO 2020/084488 | A1 | 4/2020 |
| WO | WO 2020/094670 | A1 | 5/2020 |
| WO | WO 2020/118246 | A1 | 6/2020 |
| WO | WO 2020/132584 | A1 | 6/2020 |
| WO | WO 2020/142479 | A1 | 7/2020 |
| WO | WO 2020/198268 | A1 | 10/2020 |
| WO | WO 2020/209285 | A1 | 10/2020 |
| WO | WO 2020/214763 | A1 | 10/2020 |
| WO | WO 2020/219820 | A1 | 10/2020 |
| WO | WO 2020/247738 | A1 | 12/2020 |
| WO | WO 2020/247782 | A1 | 12/2020 |
| WO | WO 2020/247818 | A1 | 12/2020 |
| WO | WO 2020/257489 | A1 | 12/2020 |
| WO | WO 2021/003573 | A1 | 1/2021 |
| WO | WO 2021/068761 | A1 | 4/2021 |
| WO | WO 2021/076856 | A1 | 4/2021 |
| WO | WO 2021/108640 | A1 | 6/2021 |
| WO | WO 2021/127457 | A1 | 6/2021 |
| WO | WO 2021/142217 | A1 | 7/2021 |
| WO | WO 2021/142227 | A1 | 7/2021 |
| WO | WO 2021/142234 | A1 | 7/2021 |
| WO | WO 2021/142260 | A1 | 7/2021 |
| WO | WO 2021/142269 | A1 | 7/2021 |
| WO | WO 2021/142275 | A1 | 7/2021 |
| WO | WO 2021/142307 | A1 | 7/2021 |
| WO | WO 2021/142313 | A1 | 7/2021 |
| WO | WO 2021/142331 | A1 | 7/2021 |
| WO | WO 2021/150382 | A1 | 7/2021 |
| WO | WO 2021/154476 | A1 | 8/2021 |
| WO | WO 2021/154477 | A1 | 8/2021 |
| WO | WO 2021/188390 | A1 | 9/2021 |
| WO | WO 2022/020105 | A1 | 1/2022 |
| WO | WO 2022/020106 | A1 | 1/2022 |
| WO | WO 2022/020107 | A1 | 1/2022 |
| WO | WO 2022/020108 | A1 | 1/2022 |
| WO | WO 2022/020109 | A1 | 1/2022 |
| WO | WO 2022/026152 | A1 | 2/2022 |
| WO | WO 2022/051332 | A1 | 3/2022 |
| WO | WO 2022/051665 | A1 | 3/2022 |
| WO | WO 2022/056266 | A2 | 3/2022 |
| WO | WO 2022/115745 | A1 | 6/2022 |
| WO | WO 2022/120132 | A1 | 6/2022 |
| WO | WO 2022/147207 | A1 | 7/2022 |
| WO | WO 2022/147209 | A1 | 7/2022 |
| WO | WO 2022/159712 | A1 | 7/2022 |
| WO | WO 2022/174037 | A1 | 8/2022 |
| WO | WO 2022/212886 | A1 | 10/2022 |
| WO | WO 2022/213118 | A1 | 10/2022 |
| WO | WO 2022/217366 | A1 | 10/2022 |
| WO | WO 2022/232478 | A1 | 11/2022 |
| WO | WO 2022/240758 | A1 | 11/2022 |
| WO | WO 2022/270585 | A1 | 12/2022 |
| WO | WO 2022/271543 | A2 | 12/2022 |
| WO | WO 2022/271549 | A1 | 12/2022 |
| WO | WO 2023/283531 | A2 | 1/2023 |
| WO | WO 2023/283613 | A1 | 1/2023 |
| WO | WO 2023/283614 | A2 | 1/2023 |
| WO | WO 2023/283615 | A1 | 1/2023 |
| WO | WO 2023/283619 | A2 | 1/2023 |
| WO | WO 2023/283620 | A1 | 1/2023 |
| WO | WO 2023/283623 | A1 | 1/2023 |
| WO | WO 2023/283624 | A2 | 1/2023 |
| WO | WO 2023/283629 | A1 | 1/2023 |
| WO | WO 2023/022229 | A1 | 2/2023 |
| WO | WO 2023/026994 | A1 | 3/2023 |
| WO | WO 2023/034818 | A1 | 3/2023 |
| WO | WO 2023/043953 | A1 | 3/2023 |
| WO | WO 2023/044398 | A1 | 3/2023 |
| WO | WO 2023/077120 | A1 | 5/2023 |
| WO | WO 2023/086864 | A1 | 5/2023 |
| WO | WO 2023/121444 | A1 | 6/2023 |
| WO | WO 2023/121445 | A1 | 6/2023 |
| WO | WO 2023/121446 | A1 | 6/2023 |
| WO | WO 2023/141710 | A1 | 8/2023 |
| WO | WO 2023/150623 | A2 | 8/2023 |
| WO | WO 2023/154807 | A2 | 8/2023 |
| WO | WO 2023/168427 | A1 | 9/2023 |
| WO | WO 2023/171820 | A1 | 9/2023 |
| WO | WO 2023/178230 | A1 | 9/2023 |
| WO | WO 2023/196400 | A2 | 10/2023 |
| WO | WO 2023/201318 | A1 | 10/2023 |
| WO | WO 2023/201324 | A1 | 10/2023 |
| WO | WO 2023/201332 | A1 | 10/2023 |
| WO | WO 2024/011135 | A1 | 1/2024 |
| WO | WO 2024/011150 | A1 | 1/2024 |
| WO | WO 2024/064237 | A2 | 3/2024 |
| WO | WO 2024/097644 | A1 | 5/2024 |
| WO | WO 2024/112809 | A2 | 5/2024 |
| WO | WO-2024137767 | A1 * | 6/2024 ............. C12N 15/86 |
| WO | WO 2024/149282 | A1 | 7/2024 |
| WO | WO 2024/182358 | A1 | 9/2024 |
| WO | WO 2025/076486 | A1 | 4/2025 |
| WO | WO 2025/137547 | A1 | 6/2025 |
| WO | WO 2025/147541 | A1 | 7/2025 |
| WO | WO 2025/255283 | A1 | 12/2025 |
| WO | WO 2025/259503 | A1 | 12/2025 |
| WO | WO 2025/265092 | A1 | 12/2025 |

OTHER PUBLICATIONS

[No Author Listed] GenBank: NM_001293798.1. *Homo sapiens* double homeobox 4 (DUX4), transcript variant 2, mRNA. Dec. 31, 2012. Retrieved from the internet May 16, 2024.

(56) References Cited

OTHER PUBLICATIONS

[No Author Listed] GenBank: NM_001306068.2. *Homo sapiens* double homeobox 4 (DUX4), transcript variant 1, mRNA. Jul. 1, 2018. Retrieved from the internet Nov. 6, 2024: «https://www.ncbi.nlm.nih.gov/nuccore/1030311260?sat=46&satkey=163025297». 4 pages.
[No Author Listed] GenBank: NP_001121620. transferrin receptor protein 1 isoform 1 [*Homo sapiens*]. Dec. 28, 2017. Retrieved from the internet Aug. 2, 2023: https://www.ncbi.nlm.nih.gov/protein/NP_001121620.1, 4 pages.
[No Author Listed] GenBank: PKK91089. Hypothetical protein CVV64_04785 [Candidatus Wallbacteria bacterium HGW-Wallbacteria-1]. Oct. 13, 2017. Retrieved from the internet Oct. 12, 2022: https://www.ncbi.nlm.nih.gov/protein/PKK91089.1?report=genbank&log$=prottop&blast_rank=2&RID=MDW2CW3T013, 2 pages.
[No Author Listed] UniProtKB/Swiss-Prot P02786. Transferrin receptor protein 1. Jul. 18, 2018. Retrieved from the Internet Oct. 23, 2019: https://www.uniprot.org/uniprot/P02786.txt?version=225, 20 pages.
[No Author Listed] Wikipedia, Dystrophin, Mar. 9, 2018. Retrieved from the internet Nov. 5, 2019: https://en.wikipedia.org/w/index.php?title=Dystrophin&oldid=829543258, 10 pages.
[No Author Listed] Wikipedia, Mannose 6-phosphate receptor, Mar. 23, 2018. Retrieved from the internet Nov. 6, 2019: https://en.wikipedia.org/w/index.php?title=Mannose_6-phosphate_receptor&oldid=832003836, 8 pages.
[No Author Listed] Wikipedia, Myotonic dystrophy, Sep. 8, 2017. Retrieved from the internet Nov. 5, 2019: https://en.wikipedia.org/w/index.php?title=Myotonic_dystrophy&oldid=799605783, 9 pages.
[No Author Listed], Alessandra Baleyew—Abstract. MDA National Scientific Conference. Neuromuscular Therapeutic Strategies: Overcoming the Barriers from Microscope to Marketplace. Mar. 13-16, 2011. Las Vegas , Nevada. 2 pages.
[No Author Listed], Baliforsen—Ionis Pharmaceuticals Drug Profile. Springer Nature Switzerland AG. Nov. 15, 2016. 9 pages.
[No Author Listed], Building the world's leading muscle disease company. Dyne Company Overview. Jun. 2021. 42 pages.
[No Author Listed], Clinical trial summary NCT000159250 (drisapersen) (Version 2, dated Feb. 19, 2007). 14 pages.
[No Author Listed], Dystrophin—Genomic Sequence. Principle variant—ENST00000357033.9. <https://www.ensembl.org/Homo_sapiens/Transcript/Summary?db=core; g=ENSG0000198947; r=X:31119222-33211549; t=ENST0000357033.> Last accessed Mar. 28, 2023. 1 page.
[No Author Listed], Exondys (eteplirsen): EPAR—Refusal public assessment report and Annex: Scientific conclusions and grounds for refusal. European Medicines Agency. Sep. 20, 2018. 140 pages.
[No Author Listed], FSH Society Facioscapulohumeral Muscular Dystrophy [FSHD] 2010 International Research Consortium & Research Planning Meetings, abstract 8, p. 29.
[No Author Listed], Highlights of prescribing information EXONDYS 51. FDA. <accessdata.fda.gov> Sep. 2016. Retrieved May 22, 2021. 11 pages.
[No Author Listed], *Homo sapiens*transferrin receptor (TFRC), transcript variant X1, mRNA. NCBI Reference Sequence XM_011513112.1. Mar. 12, 2015. 2 pages.
[No Author Listed], IRDye® Peptide Labeling Application Guide. <https://licor.com/documents/nmekjs7iez6sw5p8fv7b7005chbrcog7> Published Apr. 2013. Retrieved Oct. 27, 2021. 8 pages.
[No Author Listed], Morpholino History, Production, and Properties. Gene Tools. Retrieved from https://gene-tools.com/history_production_and_properties. Accessed Jan. 9, 2023. 9 pages.
[No Author Listed], NCBI "NM_004006.2(DMD)". Published Oct. 30, 2020. Accessed from ncbi.nlm.nih.gov on May 21, 2021. 2 pages.
[No Author Listed], STN Database Printout for RN: 2725863-42-1 and 2725863-34-1. CN: Immunoglobulin IgG1 Fab fragment, anti-(human and Macaca fascicularis transferrin receptors type 1) (human-Mus musculus monoclonal F5298 γ-1 chain), disulfide with human-Mus musculus monoclonal F5298.kappa.-chain. Entered into STN Database Nov. 5, 2021. Last accessed Nov. 17, 2021. 2 pages.
[No Author Listed], STN Database Printout for RN: 2767191-74-0. CN: Immunoglobulin G1 Fab fragment, anti (human and Macaca fascicularis transferrin receptors type 1)(human uman-Mus musculus monoclonal F5298 γ-1 chain), disulfide with human-Mus musculus monoclonal F5298.kappa.-chain. Entered into STN Database May 5, 2022. Last accessed May 16, 2022. 4 pages.
[No Author Listed], Transferrin Receptor/CD71 Extracellular Domain (human, recombinant) 2021, retrieved from https://www.caymanchem.com/product/32031/transferrin-receptor-extracellular-domain-(human%2C-recombinant)#:-:text=Cayman's Transferrin Receptor%2FCD71 Extracellular,molecular weight of 103.6 kDa (Year: 2021). 3 pages.
[No_Author_Listed], Dyne Therapeutics Announces Positive Initial Clinical Data from Achieve Trial in DM1 Patients and Deliver Trial in DMD Patients Demonstrating Promise of the FORCE™ Platform in Developing Therapeutics for Rare Muscle Diseases. Press Release. Jan. 3, 2024. Retrieved on Dec. 23, 2024, from: «https://investors.dyne-tx.com/news-releases/news-release-details/dyne-therapeutics-announces-positive-initial-clinical-data». 4 pages.
Aartsma-Rus et al., Antisense-induced multiexon skipping for Duchenne muscular dystrophy makes more sense. Am J Hum Genet. Jan. 2004;74(1):83-92. Epub Dec. 16, 2003.
Aartsma-Rus et al., Antisense-mediated exon skipping: a versatile tool with therapeutic and research applications. RNA. Oct. 2007;13(10):1609-24. doi: 10.1261/rna.653607. Epub Aug. 7, 2007.
Aartsma-Rus et al., Guidelines for antisense oligonucleotide design and insight into splice-modulating mechanisms. Mol Ther. Mar. 2009;17(3):548-53. doi: 10.1038/mt.2008.205. Epub Sep. 23, 2008.
Aartsma-Rus et al., Less is more: therapeutic exon skipping for Duchenne muscular dystrophy. Lancet Neurol. Oct. 2009;8(10):873-5. doi: 10.1016/S1474-4422(09)70229-7. Epub Aug. 25, 2009.
Aartsma-Rus et al., Progress in therapeutic antisense applications for neuromuscular disorders. Eur J Hum Genet. Feb. 2010;18(2):146-53. Epub Oct. 7, 2009.
Aartsma-Rus et al., Targeted exon skipping as a potential gene correction therapy for Duchenne muscular dystrophy. Neuromuscul Disord. Oct. 2002;12 Suppl 1:S71-7. doi: 10.1016/s0960-8966(02)00086-x.
Aartsma-Rus, Antisense-mediated modulation of splicing: therapeutic implications for Duchenne muscular dystrophy. RNA Biol. Jul.-Aug. 2010;7(4):453-61. doi: 10.4161/rna.7.4.12264. Epub Jul. 1, 2010.
Adams et al., Antisense oligonucleotide induced exon skipping and the dystrophin gene transcript: cocktails and chemistries. BMC Mol Biol. Jul. 2, 2007;8:57.
Agard et al., A Comparative Study of Bioorthogonal Reactions with Azides. ACS Chem. Biol. 2006;1(10):644-8. Epub Oct. 20, 2006.
Agard et al., A Strain-Promoted [3 + 2] Azide-Alkyne Cycloaddition for Covalent Modification of Biomolecules in Living Systems. J. Am. Chem. Soc. Nov. 2004;126(46):15046-7.
Alter et al., Systemic delivery of morpholino oligonucleotide restores dystrophin expression bodywide and improves dystrophic pathology. Nat Med. Feb. 2006;12(2):175-7. doi: 10.1038/nm1345. Epub Jan. 29, 2006.
Altshuler et al., Generation of recombinant antibodies and means for increasing their affinity. Biochemistry (Mosc). Dec. 2010:75(13):1584-605.
Anciaux et al., Transition-metal-catalyzed reactions of diazo compounds. 1. Cyclopropanation of double bonds. The Journal of Organic Chemistry. Feb. 1980;45(4):695-702.
Ansseau et al., Antisense Oligonucleotides Used to Target the DUX4 mRNA as Therapeutic Approaches in FaciosScapuloHumeral Muscular Dystrophy (FSHD). Genes (Basel). Mar. 3, 2017;8(3):93. doi: 10.3390/genes8030093.
Ansseau et al., DUX4c is up-regulated in FSHD. It induces the MYF5 protein and human myoblast proliferation. PLoS One. Oct. 15, 2009;4(10):e7482. 11 pages.
Antony-Mayer et al., Bicyclo[6.1.0]nonynes. Chemische Berichte. Nov. 1988;121(11):2013-8.
Aoki et al., Challenges for antisense oligonucleotide-based therapeutics, in particular for exon 51-skipping in Duchenne muscular

(56) References Cited

OTHER PUBLICATIONS dystrophy, 2011 Fourth International Conference on Modeling, Simulation and Applied Optimization, 2011, 1-6, doi: 10.1109/ICMSAO.2011.5775520.
Arechavala-Gomeza et al., Comparative analysis of antisense oligonucleotide sequences for targeted skipping of exon 51 during dystrophin pre-mRNA splicing in human muscle. Hum Gene Ther. Sep. 2007;18(9):798-810. doi: 10.1089/hum.2006.061.
Arnett et al., Therapy for neuromuscular disorders. Curr Opin Genet Dev. Jun. 2009;19(3):290-7. doi: 10.1016/j.gde.2009.03.005. Epub May 4, 2009.
Arzumanov et al., A structure-activity study of the inhibition of HIV-1 Tat-dependent trans-activation by mixmer 2'-O-methyl oligoribonucleotides containing locked nucleic acid (LNA), alpha-L-LNA, or 2'-thio-LNA residues. Oligonucleotides. 2003;13(6):435-53. doi: 10.1089/154545703322860762.
Arzumanov et al., Inhibition of HIV-1 Tat-dependent trans activation by steric block chimeric 2'-O-methyl/LNA oligoribonucleotides. Biochemistry. Dec. 4, 2001;40(48):14645-54. doi: 10.1021/bi011279e.
Ast et al., Estergruppenhaltige Polyalkenylene durch Olefin-Metathese. Die Makromolekulare Chemie. May 1976;177(5):1349-55.
Bao et al, Intractable & Rare Disease Research 5:168-176, 2016.
Barrientos et al., Metabolic Catastrophe in Mice Lacking Transferrin Receptor in Muscle. EBioMedicine. Oct. 4, 2015;2(11):1705-17. doi: 10.1016/j.ebiom.2015.09.041. eCollection Nov. 2015.
Baskin et al., Copper-free click chemistry for dynamic in vivo imaging. PNAS. Oct. 2007;104(43):16793-7.
Baskin et al., Copper-free click chemistry: Bioorthogonal Reagents for Tagging Azides. Aldrichimica Acta. 2010;43(1):15-23.
Behlke, Chemical modification of siRNAs for in vivo use. Oligonucleotides. Dec. 2008;18(4):305-19.
Bennett et al., RNA targeting therapeutics: molecular mechanisms of antisense oligonucleotides as a therapeutic platform. Annu Rev Pharmacol Toxicol. 2010;50:259-93. Epub Oct. 19, 2009.
Beskrovnaya, FORCETM platform delivers exon skipping PMO, leads to durable increases in dystrophin protein in mdx mice and is well tolerated NHPs. Presented at Muscle Study Group Annual Scientific Meeting. Oct. 1, 2021. 29 pages.
Bien-Ly et al., Transferrin receptor (TfR) trafficking determines brain uptake of TfR antibody affinity variants. J Exp Med. Feb. 10, 2014;211(2):233-44. Epub Jan. 27, 2014.
Black, 9.13.4.1.1.3.2 Variation 2: C-Alkylation (and Arylation) by Carbenes and Free Radicals. Science of Synthesis. 2001;9:514.
Böhm et al., Mutation spectrum in the large GTPase dynamin 2, and genotype-phenotype correlation in autosomal dominant centronuclear myopathy. Hum Mutat. Jun. 2012;33(6):949-59. doi: 10.1002/humu.22067. Epub Apr. 4, 2012.
Bortolanza et al., AAV6-mediated systemic shRNA delivery reverses disease in a mouse model of facioscapulohumeral muscular dystrophy. Mol Ther. Nov. 2011;19(11):2055-64. doi: 10.1038/mt.2011.153. Epub Aug. 9, 2011.
Bouwman et al., The prospects of targeting DUX4 in facioscapulohumeral muscular dystrophy. Curr Opin Neurol. Oct. 2020;33(5):635-640.
Brown et al., Tolerance to single, but not multiple, amino acid replacements in antibody VH CDR 2: a means of minimizing B cell wastage from somatic hypermutation? J Immunol. May 1, 1996;156(9):3285-91.
Buntz et al., Quantitative fluorescence imaging determines the absolute number of locked nucleic acid oligonucleotides needed for suppression of target gene expression. Nucleic Acids Res. Jan. 25, 2019;47(2):953-969. doi: 10.1093/nar/gky1158.
Bushby et al., MSG/ENMC FOR DMD Trial Study Group. 145th ENMC International Workshop: planning for an International Trial of Steroid Dosage Regimes in DMD (FOR DMD), Oct. 22-24, 2006, Naarden, The Netherlands. Neuromuscul Disord. May 2007;17(5):423-8. doi: 10.1016/j.nmd.2007.01.006. Epub Apr. 11, 2007.
Bushby et al., Report on the 124th ENMC International Workshop. Treatment of Duchenne muscular dystrophy; defining the gold standards of management in the use of corticosteroids. Apr. 2-4, 2004, Naarden, The Netherlands. Neuromuscul Disord. Sep. 2004;14(8-9):526-34.
Bushby et al., The multidisciplinary management of Duchenne muscular dystrophy. Curr Paed. 2005; 15: 292-300.
Bushel et al., Blood gene expression signatures predict exposure levels. Proc Natl Acad Sci USA. Nov. 13, 2007;104(46):18211-6. doi: 10.1073/pnas.0706987104. Epub Nov. 2, 2007.
Campbell et al., Deflazacort for the treatment of Duchenne Dystrophy: a systematic review. BMC Neurol. Sep. 8, 2003;3:7. doi: 10.1186/1471-2377-3-7. Epub Sep. 8, 2003.
Campbell et al., NuRD and CAF-1-mediated silencing of the D4Z4 array is modulated by DUX4-induced MBD3L proteins. eLife. May 2018;7:e31023. 27 pages.
Candelaria et al., Antibodies Targeting the Transferrin Receptor 1 (TfR1) as Direct Anti-cancer Agents. Front Immunol. Mar. 17, 2021;12:607692.
Carrell et al., Dmpk gene deletion or antisense knockdown does not compromise cardiac or skeletal muscle function in mice. Hum Mol Genet. Oct. 1, 2016;25(19):4328-4338. doi: 10.1093/hmg/ddw266. Epub Aug. 13, 2016.
Casi et al., Antibody-drug conjugates: basic concepts, examples and future perspectives. J Control Release. Jul. 20, 2012;161(2):422-8. doi: 10.1016/j.jconrel.2012.01.026. Epub Jan. 28, 2012.
Cenik et al., Argonaute proteins. Curr Biol. Jun. 21, 2011;21(12):R446-9.
Chamberlain et al., Validity of RNAi-based therapeutics as a treatment for FSHD as demonstrated in a mouse model of muscular dystrophy. MDA National Scientific Conference—Neuromuscular Therapeutic Strategies: Overcoming the Barriers from Microscope to Marketplace (Book of Abstracts) Mar. 13-16, 2011; p. 40. Abstract.
Chen et al., In-depth structural characterization of Kadcyla® (ado-trastuzumab emtansine) and its biosimilar candidate. MAbs. Oct. 2016;8(7):1210-1223. doi: 10.1080/19420862.2016.1204502. Epub Jul. 5, 2016.
Chen et al., Morpholino-mediated Knockdown of DUX4 Toward Facioscapulohumeral Muscular Dystrophy Therapeutics. Mol Ther. Aug. 2016;24(8):1405-11. doi: 10.1038/mt.2016.111. Epub Jun. 3, 2016.
Chernikov et al., Current Development of siRNA Bioconjugates: From Research to the Clinic. Front Pharmacol. Apr. 26, 2019;10:444.
Cho et al., Myotonic dystrophy: emerging mechanisms for DM1 and DM2. Biochim Biophys Acta. Feb. 2007;1772(2):195-204. Epub Jun. 20, 2006.
Chothia et al., Canonical structures for the hypervariable regions of immunoglobulins. J Mol Biol. Aug. 20, 1987;196(4):901-17. doi: 10.1016/0022-2836(87)90412-8.
Cirak et al., Exon skipping and dystrophin restoration in patients with Duchenne muscular dystrophy after systemic phosphorodiamidate morpholino oligomer treatment: an open-label, phase 2, dose-escalation study. Lancet. Aug. 13, 2011;378(9791):595-605. doi: 10.1016/S0140-6736(11)60756-3. Epub Jul. 23, 2011.
Clark et al., Increased brain uptake of targeted nanoparticles by adding an acid-cleavable linkage between transferrin and the nanoparticle core. PNAS. Oct. 2015;112(40):12486-91.
Clayton et al., Antisense Oligonucleotide-mediated Suppression of Muscle Glycogen Synthase 1 Synthesis as an Approach for Substrate Reduction Therapy of Pompe Disease. Mol Ther Nucleic Acids. Oct. 28, 2014;3(10):e206.
Codelli et al., Second-Generation Difluorinated Cyclooctynes for Copper-Free Click Chemistry. J. Am. Chem. Soc. 2008;130(34):11486-11493. Epub Aug. 5, 2008.
Coico et al., Immunology: A short course. 2008 (originally published 2003): 61-2. 8 pages (including English translation).
Crook et al., Enrichment of early fetal-liver hemopoietic stem cells of the rat using monoclonal antibodies against the transferrin receptor, Thy-1, and MRC-OX82. Dev Immunol. 1996;4(4):235-46. doi: 10.1155/1995/85036.
Crooke et al., Antisense research and applications. 1993. p. 15-35.

(56) References Cited

OTHER PUBLICATIONS

Crooke et al., Kinetic characteristics of *Escherichia coli* RNase H1: cleavage of various antisense oligonucleotide—RNA duplexes. Biochem J . Dec. 1, 1995;312(Pt 2):599-608. doi: 10.1042/bj3120599.
Crooke et al., The Effects of 2'-O-Methoxyethyl Oligonucleotides on Renal Function in Humans. Nucleic Acid Ther. Feb. 2018;28(1):10-22. doi: 10.1089/nat.2017.0693. Epub Nov. 29, 2017.
Cuellar et al., Systematic evaluation of antibody-mediated siRNA delivery using an industrial platform of THIOMAB-siRNA conjugates. Nucleic Acids Res. Jan. 2015;43(2):1189-203. Epub Dec. 30, 2014.
Curtius, Ueber die Einwirkung von salpetriger Säure auf salzsauren Glycocolläther. Berichte der deutschen chemischen Gesellschaft. Jul.-Dec. 1883;16(2):2230-1.
Danis et al., Potential therapeutic application of antisense oligonucleotides in the treatment of ocular diseases. Expert Opin Pharmacother. Feb. 2001;2(2):277-91.
Darimont et al., A novel antibody-oligonucleotide conjugate (AOC) platform enables efficient regulation of muscle targets in mice. Abstract. 8-05. J. Cach Sarcopen Musc. 2017; 8:1065-66.
Davis et al., Improved targeting of miRNA with antisense oligonucleotides. Nucleic Acids Res. May 11, 2006;34(8):2294-304. doi: 10.1093/nar/gkl183. Print 2006.
Daxinger et al., Genetic and epigenetic contributors to FSHD. Current Opinion in Genetics & Development. Aug. 2015;33:56-61. Author manuscript. 11 pages.
De Greef et al., Epigenetic mechanisms of facioscapulohumeral muscular dystrophy. Mutat Res. Dec. 1, 2008;647(1-2):94-102. doi: 10.1016/j.mrfmmm.2008.07.011. Epub Aug. 3, 2008.
De Waele et al., Initial Data from the Deliver Trial of DYNE-251 in Males with DMD Mutations Amenable to Exon 51 Skipping. 2024 World Muscle Society Annual Meeting P225. Oct. 9, 2024. Poster.
Debets et al., Bioorthogonal labelling of biomolecules: new functional handles and ligation methods. Org Biomol Chem. Oct. 14, 2013;11(38):6439-55. Epub Aug. 23, 2013.
Demonceau et al., Novel Ruthenium-Based Catalyst Systems for the Ring-Opening Metathesis Polymerization of Low-Strain Cyclic Olefins. Macromolecules. 1997;30(11):3127-36. Epub Jun. 2, 1997.
Desguerre et al.. Endomysial fibrosis in Duchenne muscular dystrophy: a marker of poor outcome associated with macrophage alternative activation. J Neuropathol Exp Neurol. Jul. 2009;68(7):762-73.
Desjardins et al., Building a FORCETM platform-based DMD franchise for the treatment of individuals with mutations amenable to exon skipping. Neuromusc Dis. Oct. 2022; 32: S101-2. Abstract.
Desjardins et al., Building a ForceTM platform-based DMD franchise for the treatment of individuals with mutations amenable to exon skipping. Presented at 27th Int Hybrid Annual Congress of the World Muscle Society. Oct. 11-15, 2022. Poster. 1 page.
Desjardins et al., Enhanced exon skipping and prolonged dystrophin restoration achieved by TfR1-targeted delivery of antisense oligonucleotide using FORCE conjugation in mdx mice. Nucleic Acids Res. Nov. 11, 2022;50(20):11401-11414.
Desjardins et al., Enhanced exon skipping and prolonged dystrophin restoration achieved by TfR1-targeted delivery of antisense oligonucleotide using FORCE conjugation in mdx mice. Nucleic Acids Res. Nov. 11, 2022;50(20):11401-11414. Supplemental Figures and Figure Legends. 34 pages.
Desjardins et al., ForceTM platform achieves robust exon skipping, restores dystrophin at the sarcolemma and halts progression of fibrosis in the severe D2-mdx model of DMD. Abstract. Mar. 2023. 1 page.
Desjardins et al., ForceTM platform achieves robust exon skipping, restores dystrophin at the sarcolemma and halts progression of fibrosis in the severe D2-mdx model of DMD. Poster. Presented at The Muscular Dystrophy Association Clinical and Scientific Conference. Mar. 19-22, 2023. 1 page.
Dixit et al., DUX4, a candidate gene of facioscapulohumeral muscular dystrophy, encodes a transcriptional activator of PITX1. Proc Natl Acad Sci U S A. Nov. 13, 2007;104(46):18157-62. doi: 10.1073/pnas.0708659104. Epub Nov. 5, 2007.
Dmitriev et al., Pearls in the junk: dissecting the molecular pathogenesis of facioscapulohumeral muscular dystrophy. Neuromuscul Disord. Jan. 2009;19(1):17-20. doi: 10.1016/j.nmd.2008.09.004. Epub Oct. 29, 2008.
Dommerholt et al., Readily accessible bicyclononynes for bioorthogonal labeling and three-dimensional imaging of living cells. Angew Chem Int Ed. Dec. 3, 2010;49(49):9422-5.
Dommerholt et al., Strain-Promoted 1,3-Dipolar Cycloaddition of Cycloalkynes and Organic Azides. Top Curr Chem. Apr. 2016;374(2):16. doi: 10.1007/s41061-016-0016-4. Epub Mar. 22, 2016.
Doucet et al., Abstract 150—RNA-based gene therapy for myotonic dystrophy type 1 (DM1). The Ottawa Conference on New Directions in Biology & Disease of Skeletal Muscle. Ottawa, CA. May 5-8, 2010:67. 6 pages total.
Douillard-Guilloux et al., Modulation of glycogen synthesis by RNA interference: towards a new therapeutic approach for glycogenosis type II. Hum Mol Genet. Dec. 15, 2008;17(24):3876-86. doi: 10.1093/hmg/ddn290. Epub Sep. 9, 2008.
Dovgan et al., Antibody-Oligonucleotide Conjugates as Therapeutic, Imaging, and Detection Agents. Bioconjug Chem. Oct. 16, 2019;30(10):2483-2501. doi: 10.1021/acs.bioconjchem.9b00306. Epub Jul. 24, 2019.
Echigoya et al., Effects of systemic multiexon skipping with peptide-conjugated morpholinos in the heart of a dog model of Duchenne muscular dystrophy. Proc Natl Acad Sci U S A. Apr. 18, 2017;114(16):4213-4218. doi: 10.1073/pnas.1613203114. Epub Apr. 3, 2017.
Echigoya et al., Exons 45-55 Skipping Using Mutation-Tailored Cocktails of Antisense Morpholinos in the DMD Gene. Mol Ther. Nov. 6, 2019;27(11):2005-2017. doi: 10.1016/j.ymthe.2019.07.012. Epub Jul. 26, 2019.
Echigoya et al., Quantitative Antisense Screening and Optimization for Exon 51 Skipping in Duchenne Muscular Dystrophy. Mol Ther. Nov. 1, 2017;25(11):2561-2572. doi: 10.1016/j.ymthe.2017.07.014. Epub Jul. 28, 2017.
Efferth et al., Enhancement of cytotoxicity of artemisinins toward cancer cells by ferrous iron. Free Radic Biol Med. Oct. 1, 2004;37(7):998-1009. doi: 10.1016/j.freeradbiomed.2004.06.023.
Egli et al., Re-Engineering RNA Molecules into Therapeutic Agents. Acc Chem Res. Apr. 16, 2019;52(4):1036-1047. doi: 10.1021/acs.accounts.8b00650. Epub Mar. 26, 2019.
Elangkovan et al., Gene Therapy for Duchenne Muscular Dystrophy. J Neuromuscul Dis. 2021;8(s2):S303-S316.
Flanagan et al., Initial data from the Deliver trial of DYNE-251 in males with DMD mutations amenable to exon 51 skipping. 2024 MDA Clinical and Scientific Conference. Abstract M156 + Presentation. Mar. 2024. 15 pages.
Flanagan et al., Initial data from the Deliver trial of DYNE-251 in males with DMD mutations amenable to exon 51 skipping. 2024 MDA Clinical and Scientific Conference. Abstract M156 + Presentation. Mar. 2024. Poster. 3 pages.
Fletcher et al., Morpholino oligomer-mediated exon skipping averts the onset of dystrophic pathology in the mdx mouse. Mol Ther. Sep. 2007;15(9):1587-92. doi: 10.1038/sj.mt.6300245. Epub Jun. 19, 2007.
Fluiter et al., On the in vitro and in vivo properties of four locked nucleic acid nucleotides incorporated into an anti-H-Ras antisense oligonucleotide. Chembiochem. Jun. 2005;6(6):1104-9. doi: 10.1002/cbic.200400419.
Frazier, Antisense oligonucleotide therapies: the promise and the challenges from a toxicologic pathologist's perspective. Toxicol Pathol. Jan. 2015;43(1):78-89. doi: 10.1177/0192623314551840. Epub Nov. 9, 2014.
Freed et al., Pharmacology Review(s) for Application No. 206488Orig1s000. Center for Drug Evaluation and Research (CDER). Published May 25, 2016. Accessed from accessdata.fda.gov on May 21, 2021. 97 pages.
Friden et al., Anti-transferrin receptor antibody and antibody-drug conjugates cross the blood-brain barrier. Proc Natl Acad Sci U S A. Jun. 1, 1991;88(11):4771-5. doi: 10.1073/pnas.88.11.4771.

(56) References Cited

OTHER PUBLICATIONS

Frieden et al., Nuclease stability of LNA oligonucleotides and LNA-DNA chimeras. Nucleosides Nucleotides Nucleic Acids. May-Aug. 2003;22(5-8):1041-3. doi: 10.1081/NCN-120022731.

Furling et al., Abstract R.P.1.01 Therapeutic RNA strategies for myotonic dystrophy with CTG repeats. Neuromuscular Disorders. 2004;14:585. 2 pages total.

Furling et al., Viral vector producing antisense RNA restores myotonic dystrophy myoblast functions. Gene Ther. May 2003; 10(9):795-802.

Gagnon et al., RNAi factors are present and active in human cell nuclei. Cell Rep. Jan. 16, 2014;6(1):211-21. Epub Jan. 2, 2014.

Galderisi et al., Myotonic dystrophy: antisense oligonucleotide inhibition of DMPK gene expression in vitro. Biochem Biophys Res Commun. Apr. 25, 1996;221(3):750-4.

Gao et al., Antisense oligonucleotides: rising stars in eliminating RNA toxicity in myotonic dystrophy. Hum Gene Ther. May 2013;24(5):499-507. doi: 10.1089/hum.2012.212. Epub Jan. 30, 2013.

Geary et al., Pharmacokinetics, biodistribution and cell uptake of antisense oligonucleotides. Adv Drug Deliv Rev. Jun. 29, 2015;87:46-51. doi: 10.1016/j.addr.2015.01.008. Epub Feb. 7, 2015.

Gebski et al., Morpholino antisense oligonucleotide induced dystrophin exon 23 skipping in mdx mouse muscle. Hum Mol Genet. Aug. 1, 2003;12(15):1801-11.

Geng et al., DUX4 activates germline genes, retroelements, and immune mediators: implications for facioscapulohumeral dystrophy. Dev Cell. Jan. 17, 2012;22(1):38-51. doi: 10.1016/j.devcel.2011.11.013. Epub Dec. 29, 2011.

Giles et al., Enhanced RNase H activity with methylphosphonodiester/phosphodiester chimeric antisense oligodeoxynucleotides. Anticancer Drug Des. Feb. 1992;7(1):37-48.

Girones et al. Comparison of the kinetics of cycling of the transferrin receptor in the presence or absence of bound diferric transferrin. Biochem J. Nov. 15, 1989;264(1):35-46.

Goemans et al., Systemic administration of PRO051 in Duchenne's muscular dystrophy. N Engl J Med. Apr. 21, 2011;364(16):1513-22. doi: 10.1056/NEJMoa1011367. Epub Mar. 23, 2011. Erratum in: N Engl J Med. Oct. 6, 2011;365(14):1361.

Gong et al., Simple Method To Prepare Oligonucleotide-Conjugated Antibodies and Its Application in Multiplex Protein Detection in Single Cells. Bioconjug Chem. Jan. 20, 2016;27(1):217-25. doi: 10.1021/acs.bioconjchem.5b00613. Epub Jan. 4, 2016.

Gonzalez-Barriga et al., Intracellular Distribution and Nuclear Activity of Antisense Oligonucleotides After Unassisted Uptake in Myoblasts and Differentiated Myotubes In Vitro. Nucleic Acid Ther. Jun. 2017;27(3):144-158. doi: 10.1089/nat.2016.0641. Epub Apr. 4, 2017.

Gray et al., Combinatorial peptide libraries: mining for cell-binding peptides. Chem Rev. Jan. 22, 2014;114(2):1020-81.

Green et al., A small-molecule inhibitor of sarcomere contractility suppresses hypertrophic cardiomyopathy in mice. Science. Feb. 5, 2016;351(6273):617-21.

Griggs et al., Prednisone in Duchenne dystrophy. A randomized, controlled trial defining the time course and dose response. Clinical Investigation of Duchenne Dystrophy Group. Arch Neurol. Apr. 1991;48(4):383-8. doi: 10.1001/archneur.1991.00530160047012.

Guirguis et al., Disease-drug interaction: Reduced response to propranolol despite increased concentration in the rat with inflammation. J Pharm Sci. May 2003;92(5):1077-84. Abstract.

Haack et al., Toxic rise of clozapine plasma concentrations in relation to inflammation. Eur Neuropsychopharmacol. Oct. 2003;13(5):381-5.

Hammond et al., Antibody-oligonucleotide conjugate achieves CNS delivery in animal models for spinal muscular atrophy. JCI Insight. Dec. 22, 2022;7(24):e154142. doi: 10.1172/jci.insight.154142.

Heemskerk et al., Preclinical PK and PD studies on 2'-O-methyl-phosphorothioate RNA antisense oligonucleotides in the mdx mouse model. Mol Ther. Jun. 2010;18(6):1210-7. doi: 10.1038/mt.2010.72. Epub Apr. 20, 2010.

Hein et al., Click chemistry, a powerful tool for pharmaceutical sciences. Pharm Res. Oct. 2008;25(10):2216-30. doi: 10.1007/s11095-008-9616-1. Epub May 29, 2008.

Helguera et al. An antibody recognizing the apical domain of human transferrin receptor 1 efficiently inhibits the entry of all new world hemorrhagic Fever arenaviruses. J Virol. Apr. 2012;86(7):4024-8. doi: 10.1128/JVI.06397-11. Epub Jan. 25, 2012.

Henry et al., Chemically modified oligonucleotides exhibit decreased immune stimulation in mice. J Pharmacol Exp Ther. Feb. 2000;292(2):468-79.

Iwaki et al., Preparation of Chiral Stationary Phase via Activated Carbamate Intermediate for Liquid Chromatographic Optical Resolution. Chromatographia. Oct. 1987;23:727-30.

Jain et al., Current ADC Linker Chemistry. Pharm Res. Nov. 2015;32(11):3526-40. Epub Mar. 11, 2015.

Jauvin et al., Targeting DMPK with Antisense Oligonucleotide Improves Muscle Strength in Myotonic Dystrophy Type 1 Mice. Mol Ther Nucleic Acids. Jun. 16, 2017;7:465-474. Epub May 17, 2017.

Jearawiriyapaisarn et al., Sustained Dystrophin Expression Induced by Peptide-conjugated Morpholino Oligomers in the Muscles of mdx Mice. Mol Ther. Sep. 2008;16(9):1624-9. doi: 10.1038/mt.2008.120. Epub Jun. 10, 2008.

Jepsen et al., Locked nucleic acid: a potent nucleic acid analog in therapeutics and biotechnology. Oligonucleotides. 2004;14(2):130-46. doi: 10.1089/1545457041526317.

Jirka et al., Cyclic Peptides to Improve Delivery and Exon Skipping of Antisense Oligonucleotides in a Mouse Model for Duchenne Muscular Dystrophy. Mol Ther. Jan. 3, 2018;26(1):132-147. doi: 10.1016/j.ymthe.2017.10.004. Epub Oct. 12, 2017.

Juliano, The delivery of therapeutic oligonucleotides. Nucleic Acids Res. Aug. 19, 2016;44(14):6518-48. doi: 10.1093/nar/gkw236. Epub Apr. 15, 2016.

Kanodia et al., Prospective Design of Anti-Transferrin Receptor Bispecific Antibodies for Optimal Delivery into the Human Brain. CPT Pharmacometrics Syst Pharmacol. May 2016;5(5):283-91. doi: 10.1002/psp4.12081. Epub May 17, 2016.

Khan et al., Silencing Myostatin Using Cholesterol-conjugated siRNAs Induces Muscle Growth. Mol Ther Nucleic Acids. Aug. 2, 2016;5(8):e342. doi: 10.1038/mtna.2016.55.

Khan, Corticosteroid therapy in Duchenne muscular dystrophy. J Neurol Sci. Dec. 1, 1993;120(1):8-14.

Kher et al., Antisense Oligonucleotides and RNA Interference. Challenges in Delivery of Therapeutic Genomics and Proteomics. Aug. 2011:325-86.

Kim et al., Strategies for silencing human disease using RNA interference. Nat Rev Genet. Mar. 2007;8(3):173-84. doi: 10.1038/nrg2006.

Kinali et al., Local restoration of dystrophin expression with the morpholino oligomer AVI-4658 in Duchenne muscular dystrophy: a single-blind, placebo-controlled, dose-escalation, proof-of-concept study. Lancet Neurol. Oct. 2009;8(10):918-28. doi: 10.1016/S1474-4422(09)70211-X. Epub Aug. 25, 2009. Erratum in: Lancet Neurol. Dec. 2009;8(12):1083.

Kline et al., Methods to Make Homogenous Antibody Drug Conjugates. Pharm Res. Nov. 2015;32(11):3480-93. Epub Dec. 16, 2014.

Koshelev et al., Abstract 130—Therapeutic application for a cell culture model of myotonic dystrophy. New Directions in Biology & Disease of Skeletal Muscle. New Orleans, LA. Apr. 27-30, 2008:44. 10 pages total.

Koshelev et al., Heart-specific overexpression of CUGBP1 reproduces functional and molecular abnormalities of myotonic dystrophy type 1. Hum Mol Genet. Mar. 15, 2010;19(6):1066-75. Epub Jan. 5, 2010.

Kumar et al., Antisense RNA: Function and Fate of Duplex RNA in Cells of Higher Eukaryotes. Microbiol Mol Biol Rev. Dec. 1998; 62(4): 1415-34.

Kuran et al., Investigations on the Catalytic Systems Diethylzinc/Di- and Trihydroxybenzenes in the Copolymerization of Carbon Dioxide with Propylene Oxide. Makromol. Chem. 1976;177:1283-92.

(56) References Cited

OTHER PUBLICATIONS

Kurreck et al., Design of antisense oligonucleotides stabilized by locked nucleic acids. Nucleic Acids Res. May 1, 2002;30(9):1911-8. doi: 10.1093/nar/30.9.1911.
Kurreck, Antisense technologies. Improvement through novel chemical modifications. Eur J Biochem. Apr. 2003;270(8):1628-44.
Lai et al., Mechanism of action and spectrum of cell lines sensitive to a doxorubicin-transferrin conjugate. Cancer Chemother Pharmacol. 1998;41(2):155-60. doi: 10.1007/s002800050722.
Lam et al., siRNA Versus miRNA as Therapeutics for Gene Silencing. Mol Ther Nucleic Acids. Sep. 15, 2015;4(9):e252. 20 pages.
Langlois et al., Abstract 831—Ribozyme and Antisense RNA-Based Gene Therapies for Myotonic Dystrophy. Molecular Therapy. May 2003;7(5, Part 2):S320.
Langlois et al., Cytoplasmic and nuclear retained DMPK mRNAs are targets for RNA interference in myotonic dystrophy cells. J Biol Chem. Apr. 29, 2005;280(17):16949-54. Epub Feb. 18, 2005.
Langlois et al., Hammerhead ribozyme-mediated destruction of nuclear foci in myotonic dystrophy myoblasts. Mol Ther. May 2003;7(5 Pt 1):670-80.
Lawrence et al., Crystal structure of the ectodomain of human transferrin receptor. Science. Oct. 22, 1999;286(5440):779-82. doi: 10.1126/science.286.5440.779.
Le Gall et al., Therapeutic Strategies Targeting DUX4 in FSHD. J Clin Med. Sep. 7, 2020;9(9):2886.
Lee et al., Abstract—Targeted Degradation of Toxic RNA in Myotonic Dystrophy. RNA & Oligonucleotide Therapeutics. Cold Spring Harbor Laboratory. Cold Spring Harbor, NY. Apr. 7-10, 2010:35. 19 pages total.
Lee et al., RNase H-mediated degradation of toxic RNA in myotonic dystrophy type 1. Proc Natl Acad Sci U S A. Mar. 13, 2012;109(11):4221-6. doi: 10.1073/pnas.1117019109. Epub Feb. 27, 2012.
Lemmers et al., A unifying genetic model for facioscapulohumeral muscular dystrophy. Science. Sep. 24, 2010;329(5999):1650-3. Epub Aug. 19, 2010.
Lemmers et al., Chromosome 10q-linked FSHD identifies DUX4 as principal disease gene. J Med Genet. Feb. 2022;59(2):180-188. doi: 10.1136/jmedgenet-2020-107041. Epub Jan. 12, 2021.
Lemmers et al., Facioscapulohumeral muscular dystrophy is uniquely associated with one of the two variants of the 4q subtelomere. Nat Genet. Oct. 2002;32(2):235-6.
Lennox et al., Cellular localization of long non-coding RNAs affects silencing by RNAi more than by antisense oligonucleotides. Nucleic Acids Res. Jan. 29, 2016;44(2):863-77. doi: 10.1093/nar/gkv1206. Epub Nov. 17, 2015.
Lesley et al., Selection of cell lines resistant to anti-transferrin receptor antibody: evidence for a mutation in transferrin receptor. Mol Cell Biol. Sep. 1984;4(9):1675-81. doi: 10.1128/mcb.4.9.1675-1681.1984.
Levin, Targeting Therapeutic Oligonucleotides. N Engl J Med. Jan. 5, 2017;376(1):86-88. doi: 10.1056/NEJMcibr1613559.
Li et al., Activation of Frataxin Protein Expression by Antisense Oligonucleotides Targeting the Mutant Expanded Repeat. Nucleic Acid Ther. Feb. 2018;28(1):23-33.
Liang et al., RNase H1-Dependent Antisense Oligonucleotides Are Robustly Active in Directing RNA Cleavage in Both the Cytoplasm and the Nucleus. Mol Ther. Sep. 6, 2017;25(9):2075-2092. Epub Jun. 27, 2017.
Liang et al., Targeted delivery of plasmid DNA to myogenic cells via transferrin-conjugated peptide nucleic acid. Mol Ther. Mar. 2000;1(3):236-43. doi: 10.1006/mthe.2000.0043.
Lim et al., DICER/AGO-dependent epigenetic silencing of D4Z4 repeats enhanced by exogenous siRNA suggests mechanisms and therapies for FSHD. Hum Mol Genet. Sep. 1, 2015;24(17):4817-28. doi: 10.1093/hmg/ddv206. Epub Jun. 3, 2015.
Lima et al., Structural requirements at the catalytic site of the heteroduplex substrate for human RNase H1 catalysis. J Biol Chem. Aug. 27, 2004;279(35):36317-26. doi: 10.1074/jbc.M405035200. Epub Jun. 17, 2004.
Lima et al., The positional influence of the helical geometry of the heteroduplex substrate on human RNase H1 catalysis. Mol Pharmacol. Jan. 2007;71(1):73-82. doi: 10.1124/mol.106.025429. Epub Oct. 6, 2006.
Liu et al. Myostatin antisense RNA-mediated muscle growth in normal and cancer cachexia mice. Gene Ther. Feb. 2008;15(3):155-60. doi: 10.1038/sj.gt.3303016. Epub Nov. 22, 2007.
Liu, Exploring cell type-specific internalizing antibodies for targeted delivery of siRNA. Brief Funct Genomic Proteomic. Jun. 2007;6(2):112-9. doi: 10.1093/bfgp/elm015. Epub Jul. 31, 2007.
Lu et al., Functional amounts of dystrophin produced by skipping the mutated exon in the mdx dystrophic mouse. Nat Med. Aug. 2003;9(8):1009-14. Epub Jul. 6, 2003.
Lu et al., Systemic delivery of antisense oligoribonucleotide restores dystrophin expression in body-wide skeletal muscles. Proc Natl Acad Sci U S A. Jan. 4, 2005;102(1):198-203. doi: 10.1073/pnas.0406700102. Epub Dec. 17, 2004.
Luria-Perez et al., Antibody-mediated targeting of the transferrin receptor in cancer cells. Bol Med Hosp Infant Mex. Nov.-Dec. 2016;73(6):372-379. doi: 10.1016/j.bmhimx.2016.11.004. Epub Dec. 13, 2016.
Malek-Adamian et al., Adjusting the Structure of 2'-Modified Nucleosides and Oligonucleotides via C4'-α-F or C4'-α-OMe Substitution: Synthesis and Conformational Analysis. J Org Chem. Sep. 7, 2018;83(17):9839-9849. doi: 10.1021/acs.joc.8b01329. Epub Jul. 17, 2018.
Mann et al., Antisense-induced exon skipping and synthesis of dystrophin in the mdx mouse. Proc Natl Acad Sci U S A. Jan. 2, 2001;98(1):42-7.
Manzur et al., Update on the management of Duchenne muscular dystrophy. Arch Dis Child. Nov. 2008;93(11):986-90. doi: 10.1136/adc.2007.118141. Epub Jul. 30, 2008.
Marsollier et al., Antisense targeting of 3' end elements involved in DUX4 mRNA processing is an efficient therapeutic strategy for facioscapulohumeral dystrophy: a new gene-silencing approach. Hum Mol Genet. Apr. 15, 2016;25(8):1468-78. doi: 10.1093/hmg/ddw015. Epub Jan. 19, 2016.
Masters et al., Clinical toxicity of antibody drug conjugates: a meta-analysis of payloads. Invest New Drugs. Feb. 2018;36(1):121-135. doi: 10.1007/s10637-017-0520-6. Epub Oct. 13, 2017.
Meeuwissen et al., Cofactor regeneration in polymersome nanoreactors: Enzymatically catalysed Baeyer-Villiger reactions. Journal of Materials Chemistry. Dec. 2011;21(47):18923-6.
Mignon, Update on Ionis-DMPKRX Program. 2018 MDF Annual Conference. Nashville, TN. Sep. 14-15, 2018:22 pages.
Mojsov et al., A Quantitative Evaluation of Methods for Coupling Asparagine. The Journal of Organic Chemistry. Feb. 1980;45(4):555-60.
Monia et al., Evaluation of 2'-modified oligonucleotides containing 2'-deoxy gaps as antisense inhibitors of gene expression. J Biol Chem. Jul. 5, 1993;268(19):14514-22.
Mulders et al., Abstract S8-06—Chemically modified (CAG)n antisense oligonucleotides as molecular tools to silence toxic, expanded DMPK transcripts. 7th International Myotonic Dystrophy Consortium Meeting (IDMC-7). Wuerzburg, Germany. Sep. 9-12, 2009:421-2. 12 pages total.
Mulders et al., Molecular therapy in myotonic dystrophy: focus on RNA gain-of-function. Human Molecular Genetics. 2010;19(1):R90-7. Epub Apr. 20, 2010.
Mulders et al., Triplet-repeat oligonucleotide-mediated reversal of RNA toxicity in myotonic dystrophy. PNAS. Aug. 18, 2009;106(33):13915-20. Supporting information included. 13 pages.
Murray et al., Human Biochemistry. "Mir." Moscow. 1993; 1:34. 5 pages (including English translation).
Nakamura, A. Moving towards successful exon-skipping therapy for Duchenne muscular dystrophy. J Hum Genet. Oct. 2017;62(10):871-876. doi: 10.1038/jhg.2017.57. Epub Jun. 1, 2017.
Natoli et al., The FORCE™ platform achieves robust and durable DUX4 suppression and functional benefit in FSHD mouse models. FHSD International Research Conference, Denver, CO. Jun. 13, 2024. Abstract. 2 pages.

(56) References Cited

OTHER PUBLICATIONS

Natoli et al., The FORCE™ platform achieves robust and durable DUX4 suppression and functional benefit in FSHD mouse models. FHSD International Research Conference, Denver, CO. Jun. 13, 2024. Presentation. 16 pages.
Naylor et al., Deliver, a randomized, double-blind, placebo controlled, multiple ascending dose study of DYNE-251 in boys with DMD amenable to Exon 51 skipping. Poster. Presented at The Muscular Dystrophy Association Clinical and Scientific Conference. Mar. 19-22, 2023. 1 page.
Naylor et al., Deliver, a randomized, double-blind, placebo controlled, multiple ascending dose study of DYNE-251 in boys with DMD amenable to Exon 51 skipping. Abstract. Mar. 2023. 1 page.
Neguembor et al., In junk we trust: repetitive DNA, epigenetics and facioscapulohumeral muscular dystrophy. Epigenomics. Apr. 2010;2(2):271-87.
Nguyen et al., Antisense oligonucleotides for the treatment of cardiomyopathy in Duchenne muscular dystrophy. Am J Transl Res. Mar. 15, 2019;11(3):1202-1218.
Novak et al., Myoblasts and macrophages are required for therapeutic morpholino antisense oligonucleotide delivery to dystrophic muscle. Nat Commun. Oct. 16, 2017;8(1):941. doi: 10.1038/s41467-017-00924-7. Erratum in: Nat Commun. Jan. 15, 2018;9(1):208. Erratum in: Nat Commun. Mar. 23, 2018;9(1):1256.
Nowak et al., Duchenne muscular dystrophy and dystrophin: pathogenesis and opportunities for treatment. EMBO Rep. Sep. 2004;5(9):872-6.
Ochala et al., Novel myosin-based therapies for congenital cardiac and skeletal myopathies. J Med Genet. Oct. 2016;53(10):651-4. doi: 10.1136/jmedgenet-2016-103881. Epub Jul. 13, 2016.
Ohrt et al., In situ fluorescence analysis demonstrates active siRNA exclusion from the nucleus by Exportin 5. Nucleic Acids Res. Mar. 6, 2006;34(5):1369-80. doi: 10.1093/nar/gkl001. Print 2006.
Overby et al., RNA-mediated therapies in myotonic dystrophy. Drug Discov Today. Dec. 2018;23(12):2013-2022. Epub Aug. 4, 2018.
Padlan et al., A possible procedure for reducing the immunogenicity of antibody variable domains while preserving their ligand-binding properties. Molecular Immunology. Apr.-May 1991;28(4-5):489-98.
Pandey et al., Identification and characterization of modified antisense oligonucleotides targeting DMPK in mice and nonhuman primates for the treatment of myotonic dystrophy type 1. J Pharmacol Exp Ther. Nov. 2015;355(2):329-40. doi: 10.1124/jpet.115.226969. Epub Sep. 1, 2015.
Panowski et al., Site-specific antibody drug conjugates for cancer therapy. MAbs. Jan.-Feb. 2014;6(1):34-45.
Picariello et al., Dyne-101 achieves durable knockdown of toxic human nuclear DMPK RNA and correction of splicing in the hTfR1/DMSXL mouse model of DM1. Presented at The Muscular Dystrophy Association Clinical and Scientific Conference. Mar. 13-16, 2022. 1 page.
Picariello et al., The FORCE™ Platform Enables TfR1-mediated Delivery of Enzyme Replacement Therapy to Muscle and Central Nervous System, Resolving Pompe Pathology in Mice. World Muscle Society Annual Meeting. Prague, Czechia. Oct. 9, 2024. Poster.
Picariello et al., The FORCE™ Platform Achieves Robust and Durable DUX4 Suppression and Improves Muscle Function in Facioscapulohumeral Muscular Dystrophy Mouse Model. World Muscle Society Annual Meeting. Prague, Czechia. Oct. 9, 2024. Poster.
Pradeepkumar, Chemically modified oligonucleotides: synthesis, physicochemical and biochemical properties of their duplexes with DNA and RNA. Comprehensive Summaries of Uppsala Disserations from the Faculty of Science and Technology. 2004; 973: 56 pages.
Pradhan et al., Prednisolone in Duchenne muscular dystrophy with imminent loss of ambulation. J Neurol. Oct. 2006;253(10):1309-16. doi: 10.1007/s00415-006-0212-1. Epub Jun. 19, 2006.
Qian et al., Targeted drug delivery via the transferrin receptor-mediated endocytosis pathway. Pharmacol Rev. Dec. 2002;54(4):561-87. doi: 10.1124/pr.54.4.561.
Ramasamy et al., Remarkable enhancement of binding affinity of Heterocycle-modified DNA to DNA and RNA. Synthesis, characterization and biophysical evaluation of N2-imidazolylpropylguanine and N2-imidazolylpropyl-2-aminoadenine modified oligonucleotides. Tetrahedron Let. 1994;35(2):215-18.
Rando et al., Rescue of dystrophin expression in mdx mouse muscle by RNA/DNA oligonucleotides. Proc Natl Acad Sci U S A. May 9, 2000;97(10):5363-8. doi: 10.1073/pnas.97.10.5363.
Richards et al., Facioscapulohumeral muscular dystrophy (FSHD): an enigma unravelled? Hum Genet. Mar. 2012;131(3):325-40. doi: 10.1007/s00439-011-1100-z. Epub Oct. 9, 2011.
Roberts et al., Advances in oligonucleotide drug delivery. Nat Rev Drug Discov. Oct. 2020;19(10):673-694. doi: 10.1038/s41573-020-0075-7. Epub Aug. 11, 2020.
Roberts et al., The Halogenation of Ethylenes. J. Am. Chem. Soc. May 1937;59(5):947-8.
Rodriguez et al. Binding specificity and internalization properties of an antibody-avidin fusion protein targeting the human transferrin receptor. Journal of Controlled Release 124 (2007) 35-42. (2007).
Sahenk et al., The muscular dystrophies: distinct pathogenic mechanisms invite novel therapeutic approaches. Curr Rheumatol Rep. Jun. 2011;13(3):199-207.
Saito et al., Antisense PMO found in dystrophic dog model was effective in cells from exon 7-deleted DMD patient. PLoS One. Aug. 18, 2010;5(8):e12239.
Samoylova et al., Elucidation of muscle-binding peptides by phage display screening. Muscle Nerve. Apr. 1999;22(4):460-6.
Sansone et al., Initial data from the Achieve trial of DYNE-101 in adults with myotonic dystrophy type 1 (DM1). 2024 MDA Clinical and Scientific Conference. Mar. 6, 2024. 19 pages.
Sansone et al., Initial data from the Achieve trial of DYNE-101 in adults with myotonic dystrophy type 1 (DM1). 2024 MDA Clinical and Scientific Conference. Mar. 6, 2024. Poster. 3 pages.
Sazani et al., Safety pharmacology and genotoxicity evaluation of AVI-4658. Int J Toxicol. Mar.-Apr. 2010;29(2):143-56. doi: 10.1177/1091581809359206. Epub Jan. 28, 2010.
Sazani et al., Systemically delivered antisense oligomers upregulate gene expression in mouse tissues. Nat Biotechnol. Dec. 2002;20(12):1228-33. doi: 10.1038/nbt759. Epub Nov. 11, 2002.
Scanlon, Anti-genes: siRNA, ribozymes and antisense. Curr Pharm Biotechnol. Oct. 2004;5(5):415-20.
Scherr et al., Detection of antisense and ribozyme accessible sites on native mRNAs: application to NCOA3 mRNA. Mol Ther. Nov. 2001;4(5):454-60.
Schneider et al., Structural features of the cell surface receptor for transferrin that is recognized by the monoclonal antibody OKT9. J Biol Chem. Jul. 25, 1982;257(14):8516-22.
Schnyder et al., Targeting of skeletal muscle in vitro using biotinylated immunoliposomes. Biochem J. Jan. 1, 2004;377(Pt 1):61-7. doi: 10.1042/BJ20031034.
Setten et al., The current state and future directions of RNAi-based therapeutics. Nat Rev Drug Discov. Jun. 2019;18(6):421-446. doi: 10.1038/s41573-019-0017-4.
Shen et al., Activating frataxin expression by single-stranded siRNAs targeting the GAA repeat expansion. Bioorg Med Chem Lett. Sep. 15, 2018;28(17):2850-2855. doi: 10.1016/j.bmcl.2018.07.033. Epub Jul. 21, 2018.
Shen et al., Chemistry, mechanism and clinical status of antisense oligonucleotides and duplex RNAs. Nucleic Acids Res. Feb. 28, 2018;46(4):1584-1600.
Shieh et al., Initial Data from the Deliver Trial of DYNE-251 in Males with DMD Mutations Amenable to Exon 51 Skipping. American Academy of Neurology (AAN) Annual Meeting. Apr. 15, 2024. Poster.
Shieh et al., Initial Data from the Deliver Trial of DYNE-251 in Males with DMD Mutations Amenable to Exon 51 Skipping. American Academy of Neurology (AAN) Annual Meeting. Apr. 15, 2024. Presentation. 11 pages.

(56) References Cited

OTHER PUBLICATIONS

Shimizu-Motohashi et al., Exon skipping for Duchenne muscular dystrophy: a systematic review and meta-analysis. Orphanet J Rare Dis. Jun. 15, 2018;13(1):93.
Singh et al., Catalytic Enantioselective Cyclopropanation of Olefins Using Carbenoid Chemistry. Synthesis. Feb. 1997;137-49.
Sklar et al., Methylprednisolone increases dystrophin levels by inhibiting myotube death during myogenesis of normal human muscle in vitro. J Neurol Sci. Jan. 1991;101(1):73-81. doi: 10.1016/0022-510x(91)90019-4.
Snider et al., Facioscapulohumeral dystrophy: incomplete suppression of a retrotransposed gene. PLoS Genet. Oct. 28, 2010;6(10):e1001181. 14 pages.
Snider et al., RNA transcripts, miRNA-sized fragments and proteins produced from D4Z4 units: new candidates for the pathophysiology of facioscapulohumeral dystrophy. Hum Mol Genet. Jul. 1, 2009;18(13):2414-30. Epub Apr. 9, 2009.
Stein, The experimental use of antisense oligonucleotides: a guide for the perplexed. J Clin Invest. Sep. 2001;108(5):641-4.
Stocki et al., Blood-brain barrier transport using a high affinity, brain-selective VNAR antibody targeting transferrin receptor 1. FASEB J. Feb. 2021;35(2):e21172. doi: 10.1096/fj.202001787R. Epub Nov. 25, 2020.
Subramanian et al., Abstract 1074. Targeted delivery of oligonucleotide therapeutics to muscle demonstrates potential to treat duchenne muscular dystrophy. Abstract. Mol Ther. 28(4S1): 465. (2020) 1 page.
Subramanian, Splice Correction and Reduction of Toxic DMPK RNA In Vitro and In Vivo Utilizing Novel Antibody Targeted Antisense Oligonucleotides. Presented at ASGST Annual Meeting; May 14, 2021. 19 pages.
Sugo et al., Development of antibody-siRNA conjugate targeted to cardiac and skeletal muscles. J Control Release. Sep. 10, 2016;237:1-13. doi: 10.1016/j.jconrel.2016.06.036. Epub Jun. 29, 2016.
Summerton et al..Morpholino antisense oligomers: design, preparation, and properties. Antisense Nucleic Acid Drug Dev. Jun. 1997;7(3):187-95.
Swayze et al., Antisense oligonucleotides containing locked nucleic acid improve potency but cause significant hepatotoxicity in animals. Nucleic Acids Res. 2007;35(2):687-700. doi: 10.1093/nar/gkl1071. Epub Dec. 19, 2006.
Swayze et al., The medicinal chemistry of oligonucleotides. In: Antisense Drug Technology, Second Edition. 2007. Crooke, Ed. Chapter 6: 143-182.
Takeda et al. Exon-Skipping in Duchenne Muscular Dystrophy. J Neuromuscul Dis. 2021;8(s2):S343-S358. doi: 10.3233/JND-210682.
Tasfaout et al., Single Intramuscular Injection of AAV-shRNA Reduces DNM2 and Prevents Myotubular Myopathy in Mice. Mol Ther. Apr. 4, 2018;26(4):1082-1092. doi: 10.1016/j.ymthe.2018.02.008. Epub Feb. 14, 2018.
Tawil et al., Facioscapulohumeral dystrophy: the path to consensus on pathophysiology. Skelet Muscle. Jun. 10, 2014;4:12.
Thomas et al., Myotonic Dystrophy and Developmental Regulation of RNA Processing. Comprehensive Physiology. Apr. 2018;8(2):509-53. Epub Mar. 25, 2018.
Thornton et al., Abstract—Oligonucleotide Therapeutics in Myotonic Dystrophy. RNA & Oligonucleotide Therapeutics. Cold Spring Harbor Laboratory. Cold Spring Harbor, NY. Apr. 7-10, 2010:31. 19 pages total.
Thornton et al., Myotonic dystrophy: approach to therapy. Curr Opin Genet Dev. Jun. 2017;44:135-140. doi: 10.1016/j.gde.2017.03.007. Epub Apr. 1, 2017.
Trollet et al., Gene therapy for muscular dystrophy: current progress and future prospects. Expert Opin Biol Ther. Jul. 2009;9(7):849-66.
Tron et al., Click chemistry reactions in medicinal chemistry: applications of the 1,3-dipolar cycloaddition between azides and alkynes. Med Res Rev. Mar. 2008;28(2):278-308.
Trowbridge et al., Anti-transferrin receptor monoclonal antibody and toxin-antibody conjugates affect growth of human tumour cells. Nature. Nov. 12, 1981;294(5837):171-3. doi: 10.1038/294171a0.
Van Den Bergen et al., Forty-Five Years of Duchenne Muscular Dystrophy in The Netherlands. J Neuromuscul Dis. 2014;1(1):99-109.
Van Der Maarel et al., Facioscapulohumeral muscular dystrophy and DUX4: breaking the silence. Trends Mol Med. May 2011;17(5):252-8. Epub Feb. 1, 2011.
Van Deutekom et al., Local dystrophin restoration with antisense oligonucleotide PRO051. N Engl J Med. Dec. 27, 2007;357(26):2677-86. doi: 10.1056/NEJMoa073108.
Van Deutekom, Abstract—The Development of RNA-Modulating Therapies. RNA & Oligonucleotide Therapeutics. Cold Spring Harbor Laboratory. Cold Spring Harbor, NY. Apr. 7-10, 2010:3. 19 pages total.
Vanderplanck et al., Abstract Keynote 5—Suppression of DUX4 or DUX4C expression by antisense strategies in a therapeutic approach for FSHD. 7th Australian Gene Therapy Society Meeting. The Journal of Gene Medicine. May 2011;13:414.
Vanderplanck et al., Suppression of DUX4 or DUX4c protein expression by antisense strategies in a therapeutic approach for FSHD. MDA National Scientific Conference—Neuromuscular Therapeutic Strategies: Overcoming the Barriers from Microscope to Marketplace (Book of Abstracts) Mar. 13-16, 2011; p. 8. Abstract.
Vickers et al., Efficient reduction of target RNAs by small interfering RNA and RNase H-dependent antisense agents. A comparative analysis. J Biol Chem. Feb. 28, 2003;278(9):7108-18. Epub Dec. 23, 2002.
Wagner et al., Transferrin-polycation conjugates as carriers for DNA uptake into cells. Proc Natl Acad Sci U S A. May 1990;87(9):3410-4. doi: 10.1073/pnas.87.9.3410.
Walder et al., Role of RNase H in hybrid-arrested translation by antisense oligonucleotides. Proc. Natl. Acad. Sci. Jul. 1988;85:5011-5.
Walker et al., Improved cellular delivery of antisense oligonucleotides using transferrin receptor antibody-oligonucleotide conjugates. Pharm Res. Oct. 1995;12(10):1548-53. doi: 10.1023/a:1016260110049.
Wallace et al., Abstract 387—Developing RNAi Therapy for FSHD. Molecular Therapy. May 2009;17(1):S151.
Wallace et al., RNA interference inhibits DUX4-induced muscle toxicity in vivo: implications for a targeted FSHD therapy. Mol Ther. Jul. 2012;20(7):1417-23. doi: 10.1038/mt.2012.68. Epub Apr. 17, 2012.
Walles et al., ADME and Safety Aspects of Non-cleavable Linkers in Drug Discovery and Development. Curr Top Med Chem. 2017;17(32):3463-3475. doi: 10.2174/1568026618666180118153502.
Weeden et al., FORCE platform overcomes barriers of oligonucleotide delivery to muscle and corrects myotonic dystrophy features in preclinical models. Commun Med (Lond). Jan. 18, 2025;5(1):22.
Wei et al., Therapeutic RNAi for dominant muscle disease. Musc Conn Tissue—Antisense and Stem Cells. Abstract. 2009. S200.
Wheeler et al., Reversal of RNA dominance by displacement of protein sequestered on triplet repeat RNA. Science. Jul. 17, 2009;325(5938):336-9.
Wheeler et al., Targeting nuclear RNA for in vivo correction of myotonic dystrophy. Nature. Aug. 2, 2012;488(7409):111-5. doi: 10.1038/nature11362.
Wheeler, Myotonic dystrophy: therapeutic strategies for the future. Neurotherapeutics. Oct. 2008;5(4):592-600.
Wilton et al., Antisense oligonucleotide-induced exon skipping across the human dystrophin gene transcript. Mol Ther. Jul. 2007;15(7):1288-96. doi: 10.1038/sj.mt.6300095. Epub Feb. 6, 2007.
Wilton et al., Antisense oligonucleotides, exon skipping and the dystrophin gene transcript. Acta Myol. Dec. 2005;24(3):222-9.
Wilton et al., Exon skipping and Duchenne muscular dystrophy: hope, hype and how feasible? Neurol India. Jul.-Sep. 2008;56(3):254-62. doi: 10.4103/0028-3886.43443.
Winkler J. Oligonucleotide conjugates for therapeutic applications. Ther Deliv. Jul. 2013;4(7):791-809. doi: 10.4155/tde.13.47.

(56) References Cited

OTHER PUBLICATIONS

Wolf et al., Achieve trial, a randomized, placebo-controlled, multiple ascending dose study of Dyne-101 in individuals with myotonic dystrophy Type 1 (DM1). Abstract. Mar. 2023. 1 page.
Wolf et al., Achieve trial, a randomized, placebo-controlled, multiple ascending dose study of Dyne-101 in individuals with myotonic dystrophy Type 1 (DM1). Presented at The Muscular Dystrophy Association Clinical and Scientific Conference. Poster. Mar. 19-22, 2023. 1 page.
Wolf et al., Initial Data from the Achieve Trial of DYNE-101 in Adults with Myotonic Dystrophy Type 1 (DM1). 2024 World Muscle Society Annual Meeting P221. Oct. 12-14, 2024. Poster. Prague, Czechia.
Wu et al., Determination of the role of the human RNase H1 in the pharmacology of DNA-like antisense drugs. J Biol Chem. Apr. 23, 2004;279(17):17181-9. Epub Feb. 11, 2004.
Wuebbles et al., Testing the effects of FSHD candidate gene expression in vertebrate muscle development. Int J Clin Exp Pathol. Mar. 28, 2010;3(4):386-400.
Xia et al., Intravenous siRNA of brain cancer with receptor targeting and avidin-biotin technology. Pharm Res. Dec. 2007;24(12):2309-16. doi: 10.1007/s11095-007-9460-8. Epub Oct. 11, 2007.
Yao et al., DUX4-induced gene expression is the major molecular signature in FSHD skeletal muscle. Hum Mol Genet. Oct. 15, 2014; 23(20): 5342-5352. Epub May 26, 2014.
Yao et al., Targeted Delivery of ASOs Demonstrates Potential to Treat Duchenne Muscular Dystrophy. Poster. Presented at ASGCT; May 12, 2020. 1 page.
Ye et al., Generation and functional characterization of the anti-transferrin receptor single-chain antibody-GAL4 (TfRscFv-GAL4) fusion protein. BMC Biotechnol. Nov. 28, 2012;12:91.
Yoshida et al., Evaluation of off-target effects of gapmer antisense oligonucleotides using human cells. Genes Cells. Dec. 2019;24(12):827-835. doi: 10.1111/gtc.12730. Epub Nov. 12, 2019.
Zanotti et al., Abstract 17. Repeat dosing with DYNE-101 is Well Tolerated and Leads to a Sustained Reduction of DMPK RNA expression in key muscles for DM1 pathology in hTfR1/DMSXL mice and NHPs. Abstract. Mol Ther. Apr. 2022; 30(4S1): 9.
Zanotti et al., Abstract 247. The ForceTM platform achieves robust knock down of toxic human nuclear DMPK RNA and foci reduction in DM1 cells and in newly developed hTfR1/DMSXL mouse model. Mol Ther. 29(4S1): 127. Apr. 2021. 1 page.
Zanotti et al., Abstract 82. The ForceTM platform delivers oligonucleotides to the brain in a DM1 mouse model and in NHPs. Mol Ther. Apr. 2023; 31(4S1): 44.
Zanotti et al., Abstract EP.233. The ForceTM platform achieves durable knockdown of toxic human nuclear DMPK RNA and correction of splicing in the hTFR1/DMSXL mouse model. Neuromusc Disord. 2021; 31: S120.
Zanotti et al., DYNE-101 achieves durable knockdown of toxic human nuclear DMPK RNA and correction of splicing in the hTfR1/DMSXL mouse model of DM1. Abstract. Mar. 2022. 1 page.
Zanotti et al., FORCE™ Platform for the Development of Targeted Therapeutics for Rare Muscle Diseases. 2024 New Directions in Biology and Disease of Skeletal Muscle, Ft. Lauderdale, FL. Jun. 23, 2024. Presentation. 22 pages.
Zanotti et al., The ForceTM platform achieves durable knockdown of toxic human nuclear DMPK RNA and correction of splicing in the hTFR1/DMSXL mouse model. Presented at WMS Meeting. Sep. 20-24, 2021. 1 page.
Zanotti, Repeat dosing with DYNE-101 is Well Tolerated and Leads to a Sustained Reduction of DMPK RNA expression in key muscles for DM1 pathology in hTfR1/DMSXL mice and NHPs. Presented at American Society of Gene & Cell Therapy Conference. May 16, 2022. 15 pages.
Zanotti, The ForceTM platform delivers oligonucleotides to the brain in a DM1 mouse model and in NHPs. Presented at American Society of Gene & Cell Therapy Conference. May 17, 2023. 16 pages.
Zanotti, The FORCE™ Platform Achieves Robust Knock Down of Toxic Human Nuclear DMPK RNA and Foci Reduction in DM1 Cells and in Newly Developed hTfR1/DMSXL Mouse Model. Presented at American Society of Gene & Cell Therapy Annual Meeting; May 14, 2021. 13 pages.
Zeng et al., Specific loss of histone H3 lysine 9 trimethylation and HP1gamma/cohesin binding at D4Z4 repeats is associated with facioscapulohumeral dystrophy (FSHD). PLoS Genet. Jul. 2009;5(7):e1000559. doi: 10.1371/journal.pgen.1000559. Epub Jul. 10, 2009.
Zhang et al., Research progress and application prospects for the treatment of Duchenne muscular dystrophy. Chin J Contemp Neurol Neurosurg. Jul. 2018;18(7):480-93. doi: 10.3969/j.issn.1672-6731.2018.07.004.
Brumm et al., "Form S-1 Registration Statement Under The Securities Act Of 1933", Aug. 25, 2020 (Aug. 25, 2020), XP093375478, URL:https://www.sec.gov/Archives/edgar/data/1818794/000119312520230038/d920854ds1.htm.

* cited by examiner

MUSCLE TARGETING COMPLEXES AND FORMULATIONS FOR TREATING FACIOSCAPULOHUMERAL MUSCULAR DYSTROPHY

RELATED APPLICATIONS

This application is a continuation of International Patent Application No. PCT/US2024/061427, filed Dec. 20, 2024, entitled "MUSCLE TARGETING COMPLEXES AND FORMULATIONS FOR TREATING FACIOSCAPULOHUMERAL MUSCULAR DYSTROPHY", which claims the benefit under 35 U.S.C. § 119 (e) to U.S. Provisional Application No. 63/614,024, filed Dec. 22, 2023, entitled "MUSCLE TARGETING COMPLEXES AND FORMULATIONS FOR TREATING FACIOSCAPULOHUMERAL MUSCULAR DYSTROPHY" The contents of these applications each of which are incorporated herein by reference in their entirety.

FIELD OF THE INVENTION

The present application relates to targeting complexes for delivering oligonucleotide molecular payloads to cells, compositions (e.g., formulations) comprising such complexes, and uses thereof, particularly uses relating to treatment of disease.

REFERENCE TO AN ELECTRONIC SEQUENCE LISTING

The contents of the electronic sequence listing (D082470086US01-SEQ-CBD.xml; Size: 37,691 bytes; and Date of Creation: Sep. 18, 2025) is herein incorporated by reference in its entirety.

BACKGROUND

Muscular dystrophies (MDs) are a group of diseases characterized by the progressive weakness and loss of muscle mass. These diseases are caused by mutations in genes which encode proteins needed for healthy muscle tissue. Facioscapulohumeral muscular dystrophy (FSHD) is a dominantly inherited type of MD which primarily affects muscles of the face, shoulder blades, and upper arms. Other symptoms of FSHD include abdominal muscle weakness, retinal abnormalities, hearing loss, and joint pain and inflammation. FSHD is the most prevalent of the nine types of MD affecting both adults and children, with a worldwide incidence of about 1 in 8,300 people. FSHD is caused by aberrant production of double homeobox 4 (DUX4), a protein that regulates gene expression. The DUX4 gene, which encodes the DUX4 protein, is located in the D4Z4 repeat region on chromosome 4 and is typically expressed in adult testes and thymus, and in 2-cell stage embryos, after which it is repressed by hypermethylation of the D4Z4 repeats which surround and compact the DUX4 gene. Two types of FSHD, Type 1 and Type 2 have been described. Type 1, which accounts for about 95% of cases, is associated with deletions of D4Z4 repeats in the subtelomeric region of chromosome 4. Unaffected individuals generally have more than 10 repeats arrayed in the subtelomeric region of chromosome 4, whereas the most common form of FSHD (FSHD1) is caused by a contraction of the array to fewer than 10 repeats, associated with decreased epigenetic repression and variegated expression of DUX4 in skeletal muscle. Two allelic variants of chromosome 4q (4qA and 4qB) exist in the most distal unit of the D4Z4 repeats. 4qA is in cis with a functional polyadenylation consensus site. Contractions on 4qA alleles are pathogenic because the DUX4 transcript is polyadenylated and stable. Type 2 FSHD, which accounts for about 5% of cases, is associated with mutations of the SMCHD1 gene on chromosome 18. Type 2 FSHD may also be associated with the DNMT3B gene or LRIF1 gene. Besides supportive care and treatments to address the symptoms of the disease, there are no effective therapies for FSHD.

SUMMARY

According to some aspects, the present disclosure provides complexes and compositions (e.g., formulations) comprising such complexes that comprise an oligonucleotide covalently linked to an anti-transferrin receptor 1 (TfR1) antibody, wherein the anti-TfR1 antibody comprises: a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14, a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5 or 11, and a light chain complementarity determining region 3 (CDR-L3) comprising a sequence as set forth in SEQ ID NOs: 6 or 16, wherein the oligonucleotide is an RNAi oligonucleotide targeting DUX4, and wherein the complexes are formulated with tris(hydroxymethyl)aminomethane and sucrose.

According to some aspects, the present disclosure provides compositions comprising complexes comprising a structure of formula (I): $[R^1]_{n1}—R^2$, wherein each $R^1$ independently comprises a group of the formula (Ia):

(Ia)

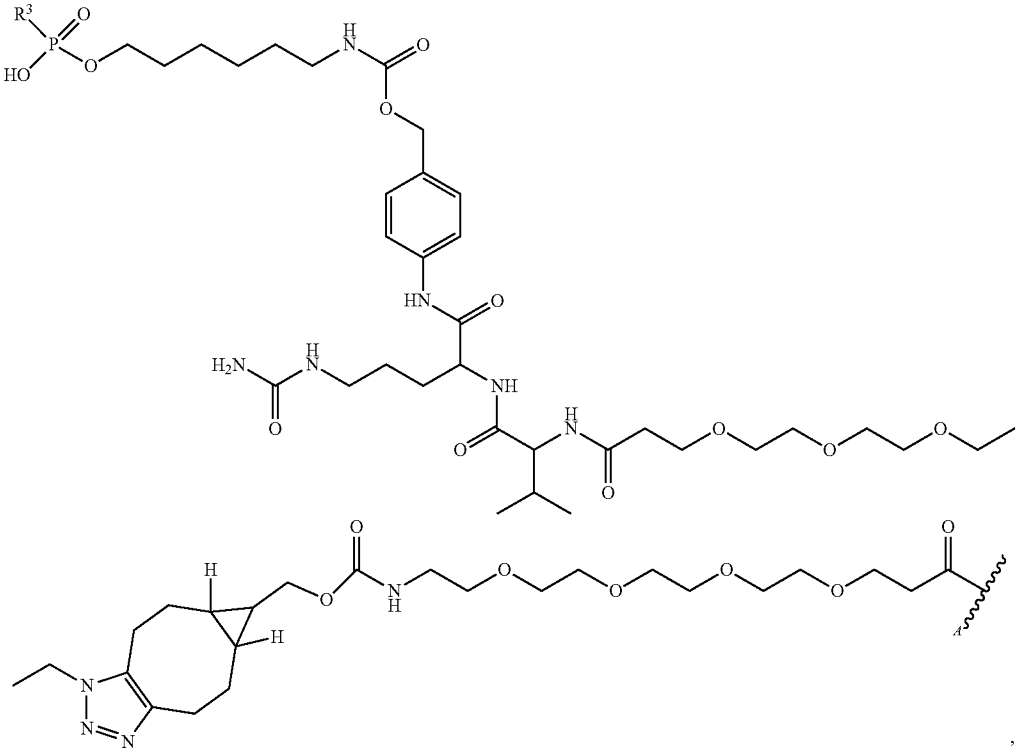

, or a pharmaceutically acceptable salt thereof,
wherein $R^2$ comprises an antibody, and $R^3$ comprises an RNAi oligonucleotide;

wherein $R^1$ is covalently linked to $R^2$ at attachment point A; and wherein n1 is an integer representing the number of instances of $R^1$, wherein each instance of $R^1$ is covalently linked to a different amino acid residue of the antibody;

wherein the complexes are formulated with tris(hydroxymethyl)aminomethane and sucrose.

In some embodiments, each different amino acid residue is a lysine.

In some embodiments, the antibody is an anti-TfR1 antibody.

In some embodiments, the antibody comprises: a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14, a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5 or 11, and a light chain complementarity determining region 3 (CDR-L3) comprising a sequence as set forth in SEQ ID NOs: 6 or 16.

In some embodiments, the formulation is in a lyophilized form, a frozen solid form, or in an aqueous solution. In some embodiments, the formulation is in a lyophilized form. In some embodiments, the formulation is in a frozen solid form. In some embodiments, the formulation is in an aqueous solution.

In some embodiments, the formulation is in an aqueous solution and wherein the tris(hydroxymethyl)aminomethane is present in the aqueous solution at a concentration in the range of 5 mM to 50 mM.

In some embodiments, the formulation is in an aqueous solution and wherein the sucrose is present in the aqueous solution at a concentration in the range of 5% to 15% weight per volume (w/v %).

In some embodiments, the formulation is in an aqueous solution and wherein the aqueous solution has a pH in the range of 6.5 to 8.5.

In some embodiments, the formulation is in an aqueous solution and wherein the tris(hydroxymethyl)aminomethane is present in the aqueous solution at a concentration of 25 mM and/or the sucrose is present in the aqueous solution at a concentration of 10 w/v % and/or the aqueous solution is at a pH of 7.5.

In some embodiments, the antibody is a Fab fragment, a full-length IgG, a Fab' fragment, a $F(ab')_2$ fragment, an scFv, or an Fv.

In some embodiments, the antibody is a Fab fragment.

In some embodiments, the antibody comprises a heavy chain variable region (VH) comprising an amino acid sequence at least 85% identical to SEQ ID NO: 17; and/or wherein the antibody comprises a light chain variable region (VL) comprising an amino acid sequence at least 85% identical to SEQ ID NO: 18.

In some embodiments, the antibody comprises a VH comprising the amino acid sequence of SEQ ID NO: 17 and/or a VL comprising the amino acid sequence of SEQ ID NO: 18.

In some embodiments, the antibody comprises a heavy chain comprising an amino acid sequence at least 85% identical to SEQ ID NO: 19; and/or wherein the antibody comprises a light chain comprising an amino acid sequence at least 85% identical to SEQ ID NO: 20.

In some embodiments, the antibody comprises a heavy chain comprising the amino acid sequence of SEQ ID NO: 19 and/or a light chain comprising the amino acid sequence of SEQ ID NO: 20.

In some embodiments, the VH comprises an N-terminal pyroglutamate.

In some embodiments, the RNAi oligonucleotide comprises an antisense strand of 18-25 nucleosides in length.

In some embodiments, the antisense strand comprises a region of complementarity of at least 16 consecutive nucleosides in length to a nucleobase sequence as set forth in SEQ ID NO: 24.

In some embodiments, the region of complementarity is 22 consecutive nucleosides in length.

In some embodiments, the antisense strand comprises a region of complementarity of at least 16 consecutive nucleosides in length to a nucleobase sequence as set forth in SEQ ID NO: 28.

In some embodiments, the region of complementarity is 22 consecutive nucleosides in length.

In some embodiments, the RNAi oligonucleotide comprises an antisense strand comprising at least 15 consecutive nucleosides of a nucleobase sequence as set forth in SEQ ID NO: 22.

In some embodiments, the antisense strand comprises the nucleobase sequence of SEQ ID NO: 22.

In some embodiments, the RNAi oligonucleotide further comprises a sense strand comprising at least 15 consecutive nucleosides complementary to the antisense strand.

In some embodiments, the sense strand comprises at least 15 consecutive nucleosides of a nucleobase sequence as set forth in SEQ ID NO: 21.

In some embodiments, the sense strand comprises the nucleobase sequence of SEQ ID NO: 21.

In some embodiments, the RNAi oligonucleotide comprises one or more modified nucleosides.

In some embodiments, the RNAi oligonucleotide further comprises one or more phosphorothioate internucleoside linkages.

In some embodiments, the one or more modified nucleosides are 2' modified nucleosides.

In some embodiments, wherein each 2' modified nucleoside is 2'-O-methyl (2'-O-Me) or 2'-fluoro (2'-F).

In some embodiments, the antisense strand further comprises a 5'-(E)-vinylphosphonate.

In some embodiments, each $R^1$ comprises a group of the formula (Ib):

(Ib)

3′-mA*mC*mAmAmGmAmAmGmGfCmAmCmUmUmUmAmAmGmAmCmC*fG*mU-5′-VP Antisense (SEQ ID NO: 22)
5′-mU*mU*mCmUfUmCmCmGfUfGfAmAmAfUmUmCmUmGfG*mC*mA-3′ Sense (SEQ ID NO: 21)

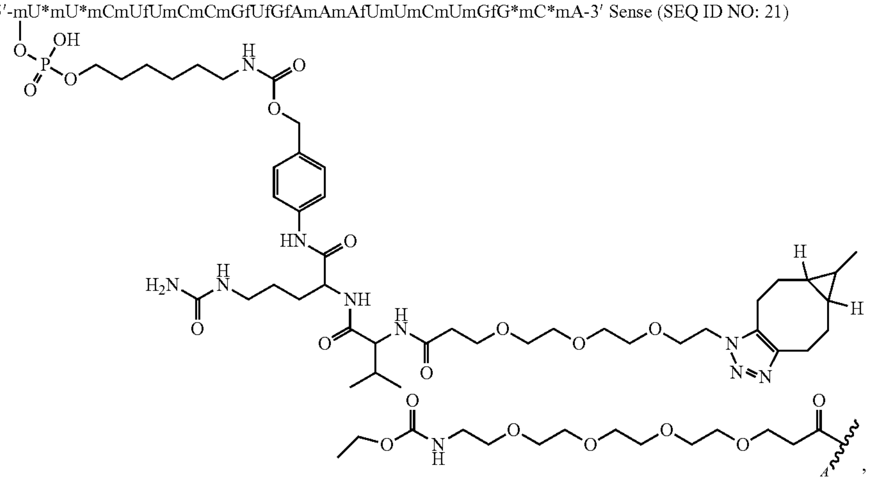

or a pharmaceutically acceptable salt thereof, wherein: mA, mC, mG, and mU are 2'-O-methyl adenosine, 2'-O-methyl cytidine, 2'-O-methyl guanosine, and 2'-O-methyl uridine, respectively;

fA, fC, fG, and fU are 2'-fluoro adenosine, 2'-fluoro cytidine, 2'-fluoro guanosine, and 2'-fluoro uridine, respectively; * between two nucleosides represents a phosphorothioate linkage; the absence of "*" between two nucleosides represents a phosphodiester internucleoside linkage; and "VP" represents 5'-(E)-Vinylphosphonate, such that the RNAi oligonucleotide comprises an antisense strand comprising a nucleobase sequence of UGCCAGAAUUUCACGGAAGAACA (SEQ ID NO: 22) and a sense strand comprising a nucleobase sequence of UUCUUCCGUGAAAUUCUGGCA (SEQ ID NO: 21).

In some embodiments, each $R^1$ comprises a group of the formula (Ic), in which the antisense strand and the sense strand form a double stranded oligonucleotide:

(Ic)
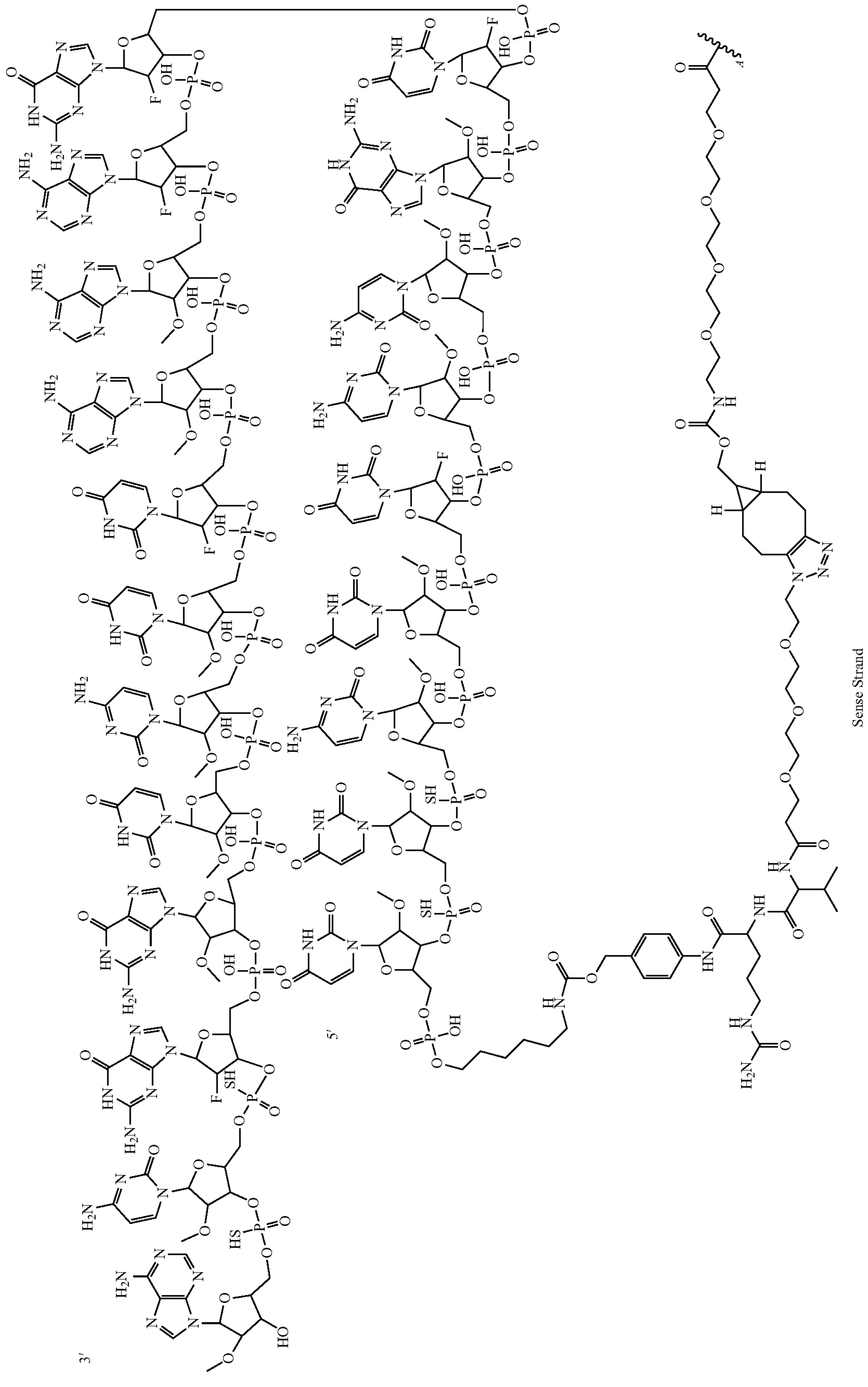

-continued
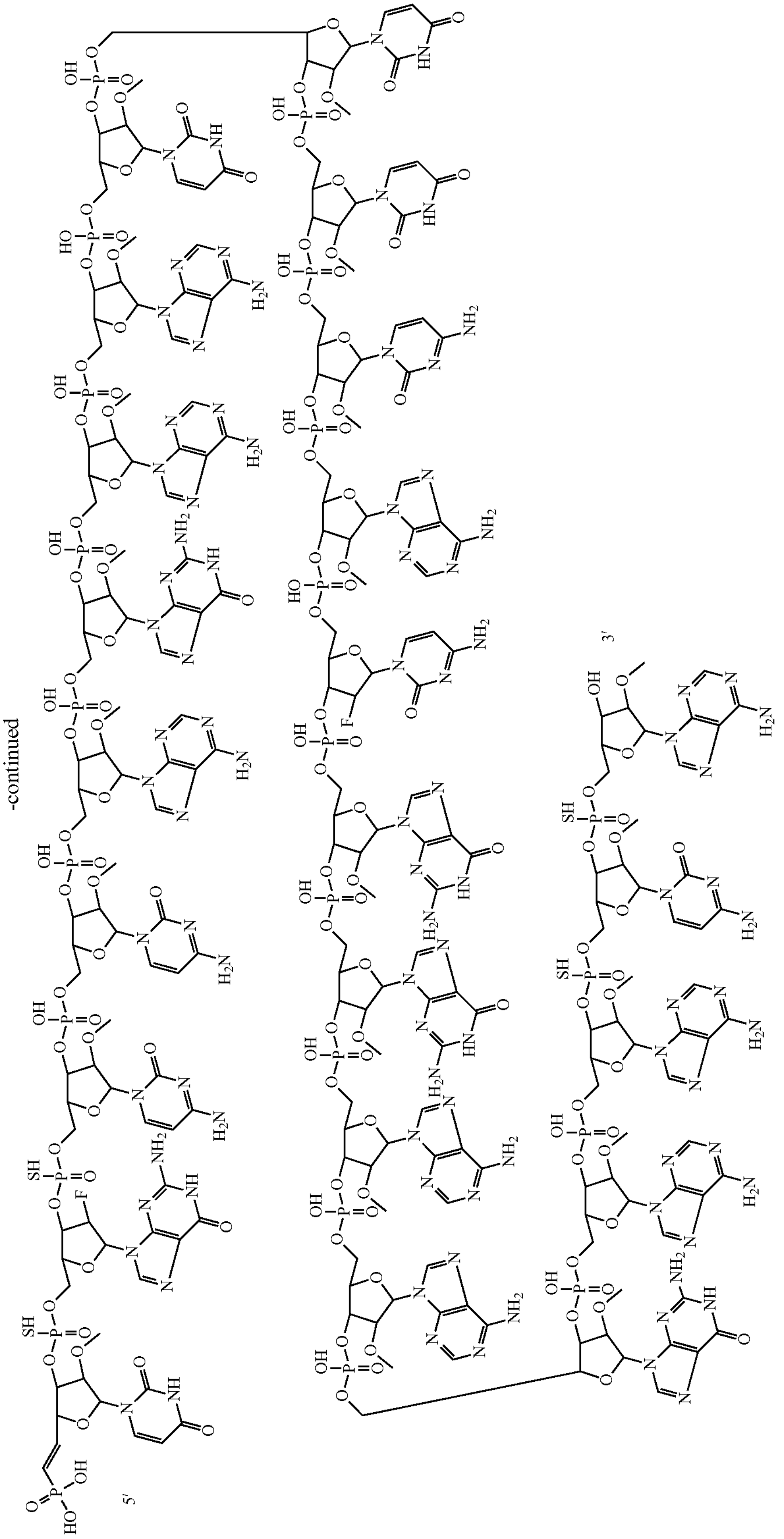
Antisense Strand or a pharmaceutically acceptable salt thereof.

In some embodiments, the complexes are present in the composition at a concentration in the range of 10 mg/mL to 200 mg/mL.

In some embodiments, the compositions further comprise one or more antibodies that are not covalently linked to an oligonucleotide.

In some embodiments, the average value of n1 of complexes in the composition is in the range of 0.5 to 5.

In some embodiments, the average value of n1 of complexes in the composition is 1.

Further provided herein are methods of reducing DUX4 expression in a subject, the method comprising administering to the subject an effective amount of the compositions provided herein.

Further provided herein are methods of treating facioscapulohumeral muscular dystrophy (FSHD) in a subject, the method comprising administering to the subject an effective amount of the composition provided herein.

In some embodiments, the subject has aberrant production of DUX4 protein.

In some embodiments, the complexes reduce DUX4 expression in the subject.

In some embodiments, reducing DUX4 expression comprises reducing DUX4 protein and/or mRNA levels.

In some embodiments, the antibody comprises a VH that comprises an N-terminal pyroglutamate.

According to some aspects, the present disclosure provides complexes comprising a structure of formula (I): $[R^1]_{n1}$—$R^2$, wherein each $R^1$ comprises a group of the formula (Ia):

(Ia)

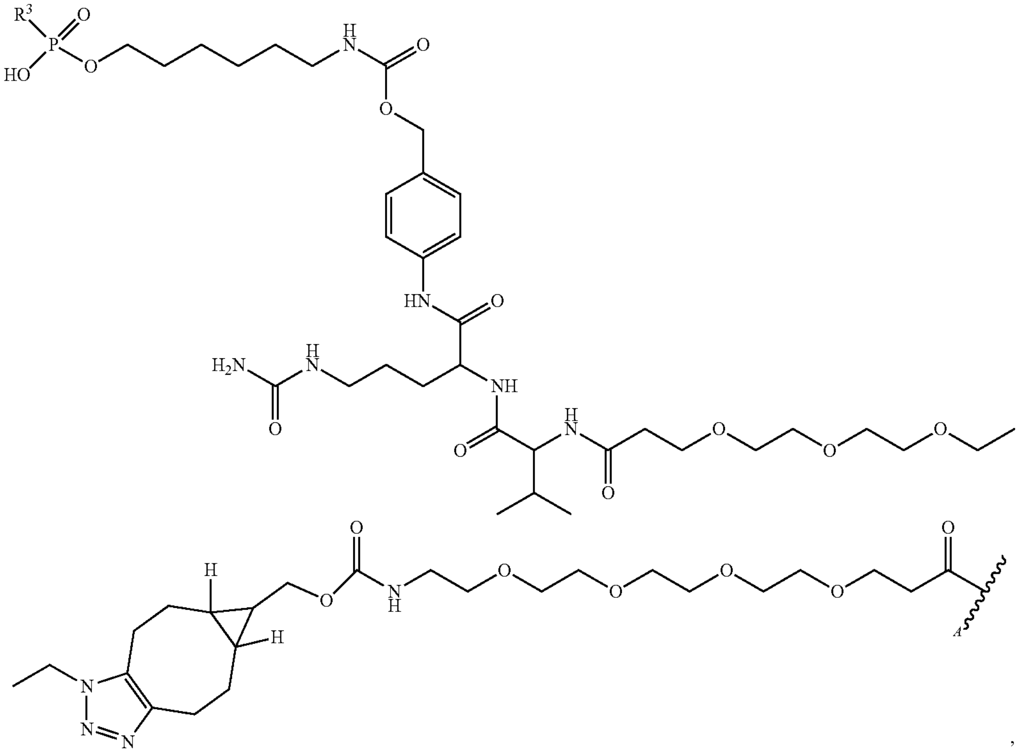

, or a pharmaceutically acceptable salt thereof, wherein $R^3$ comprises an RNAi oligonucleotide comprising an antisense strand comprising a nucleobase sequence of SEQ ID NO: 22 and a structure (5'→3') of VP-mU*fG*mCmCmAmGmAmAmUmUmUmCmAfCmGmGmAmAmGmAmA*mC*mA, and a sense strand comprising a nucleobase sequence of SEQ ID NO: 21 and a structure (5'→3') of mU*mU*mCmUfUmCmCmGfUfGfAmAmAfUmUmCmUmGfG*mC*mA, wherein: mA, mC, mG, and mU are 2'-O-methyl adenosine, 2'-O-methyl cytidine, 2'-O-methyl guanosine, and 2'-O-methyl uridine, respectively; fA, fC, fG, and fU are 2'-fluoro adenosine, 2'-fluoro cytidine, 2'-fluoro guanosine, and 2'-fluoro uridine, respectively; * between two nucleosides represents a phosphorothioate linkage; the absence of "*" between two nucleosides represents a phosphodiester internucleoside linkage; and "VP" represents 5'-(E)-Vinylphosphonate;

wherein $R^2$ comprises a Fab, and wherein the Fab comprises a CDR-H1, a CDR-H2, a CDR-H3, a CDR-L1, a CDR-L2, and a CDR-L3 selected from Table 2.

In some embodiments, the Fab comprises a VH comprising the amino acid sequence of SEQ ID NO: 17 and a VL comprising the amino acid sequence of SEQ ID NO: 18.

In some embodiments, the Fab comprises a VH comprising an N-terminal pyroglutamate.

In some embodiments, the Fab comprises a heavy chain comprising the amino acid sequence of SEQ ID NO: 19 and a light chain comprising the amino acid sequence of SEQ ID NO: 20; wherein $R^1$ is covalently linked to $R^2$ at attachment point A; and wherein n1 is an integer representing the number of instances of $R^1$, wherein each instance of $R^1$ is covalently linked to a different amino acid residue of the Fab.

In some embodiments, each different amino acid residue is a lysine.

According to some aspects, the present disclosure provides complexes comprising a structure of formula (I): $[R^1]_{n1}$—$R^2$, wherein each $R^1$ comprises a group of the formula (Ib):

(Ib)

3′-mA*mC*mAmAmGmAmAmGmGfCmAmCmUmUmUmAmAmGmAmCmC*fG*mU-5′-VP Antisense (SEQ ID NO: 22)

5′-mU*mU*mCmUfUmCmCmGfUfGfAmAmAfUmUmCmUmGfG*mC*mA-3′ Sense (SEQ ID NO: 21)

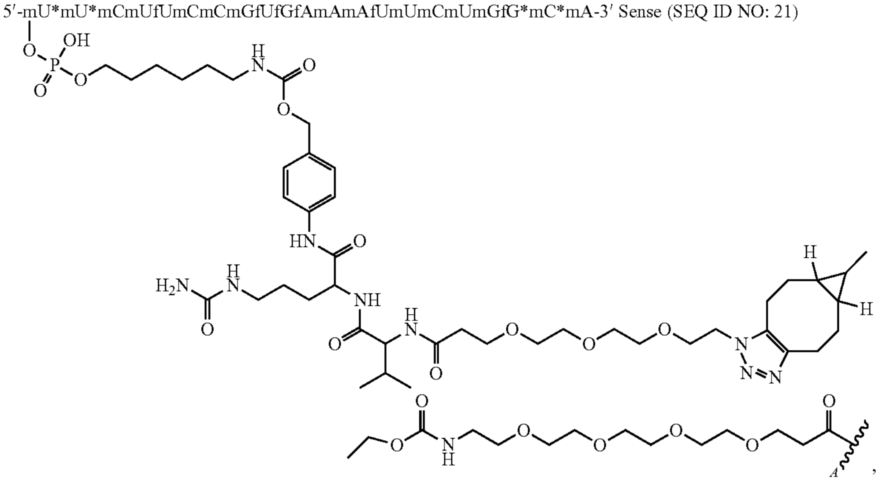

or a pharmaceutically acceptable salt thereof, wherein: mA, mC, mG, and mU are 2'-O-methyl adenosine, 2'-O-methyl cytidine, 2'-O-methyl guanosine, and 2'-O-methyl uridine, respectively; fA, fC, fG, and fU are 2'-fluoro adenosine, 2'-fluoro cytidine, 2'-fluoro guanosine, and 2'-fluoro uridine, respectively; * between two nucleosides represents a phosphorothioate linkage; the absence of "*" between two nucleosides represents a phosphodiester internucleoside linkage; and "VP" represents 5'-(E)-Vinylphosphonate, such that the oligonucleotide is an RNAi oligonucleotide comprising an antisense strand comprising a nucleobase sequence of UGCCAGAAUUUCACGGAAGAACA (SEQ ID NO: 22) and a sense strand comprising a nucleobase sequence of UUCUUCCGUGAAAUUCUGGCA (SEQ ID NO: 21);

wherein $R^2$ comprises a Fab, and wherein the Fab comprises a CDR-H1, a CDR-H2, a CDR-H3, a CDR-L1, a CDR-L2, and a CDR-L3 selected from Table 2.

In some embodiments, the Fab comprises a VH comprising the amino acid sequence of SEQ ID NO: 17 and a VL comprising the amino acid sequence of SEQ ID NO: 18.

In some embodiments, the Fab comprises a VH comprising an N-terminal pyroglutamate.

In some embodiments, the Fab comprises a heavy chain comprising the amino acid sequence of SEQ ID NO: 19 and a light chain comprising the amino acid sequence of SEQ ID NO: 20;

wherein $R^1$ is covalently linked to $R^2$ at attachment point A; and wherein n1 is an integer representing the number of instances of $R^1$, wherein each instance of $R^1$ is covalently linked to a different amino acid residue of the Fab.

In some embodiments, each different amino acid residue is a lysine.

According to some aspects, the present disclosure provides complexes comprising a structure of formula (I): $[R^1]_{n1}$—$R^2$, wherein $R^1$ comprises a group of the formula (Ic), in which the antisense strand and the sense strand form a double stranded oligonucleotide:

(Ic)
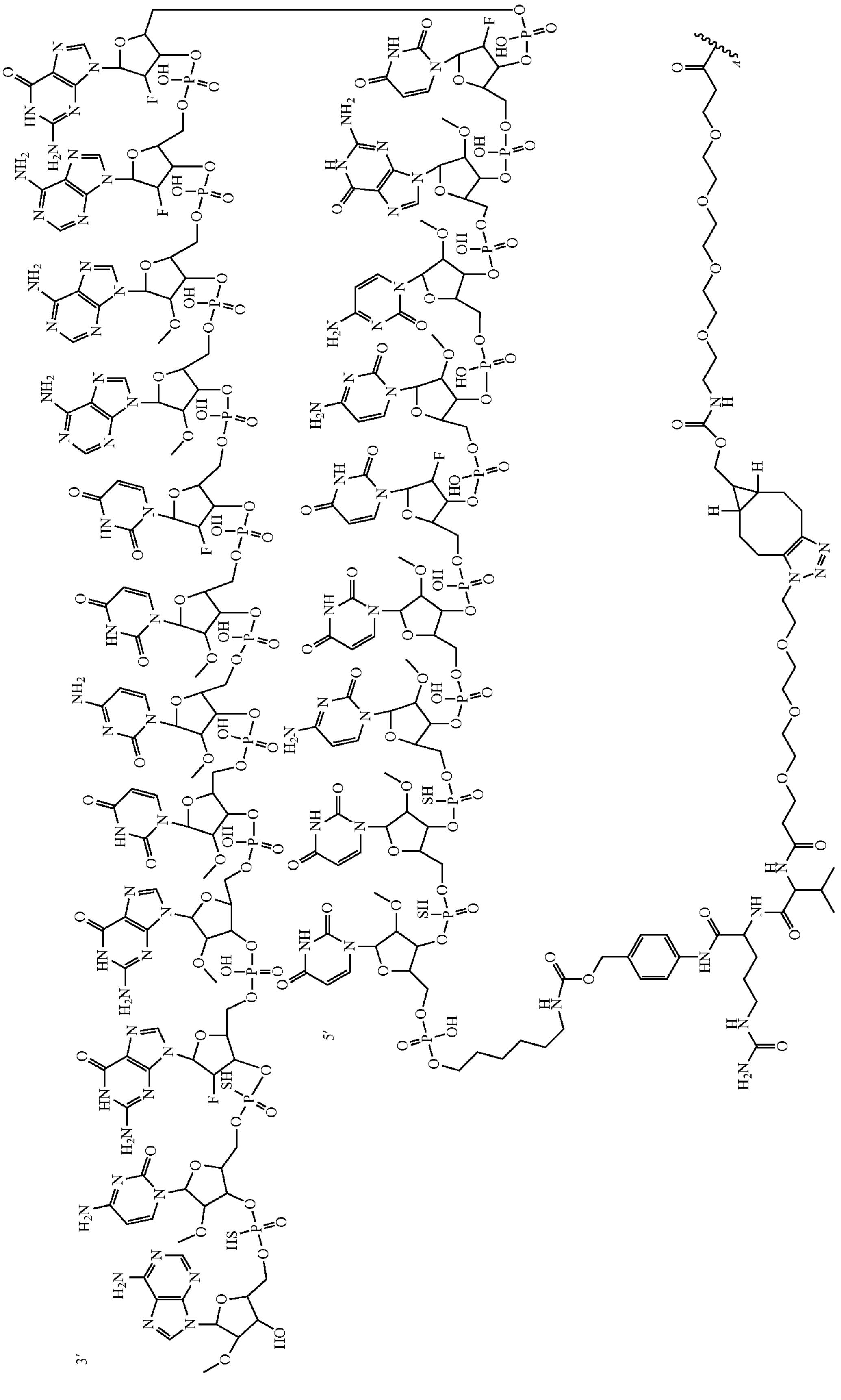
Sense Strand

-continued
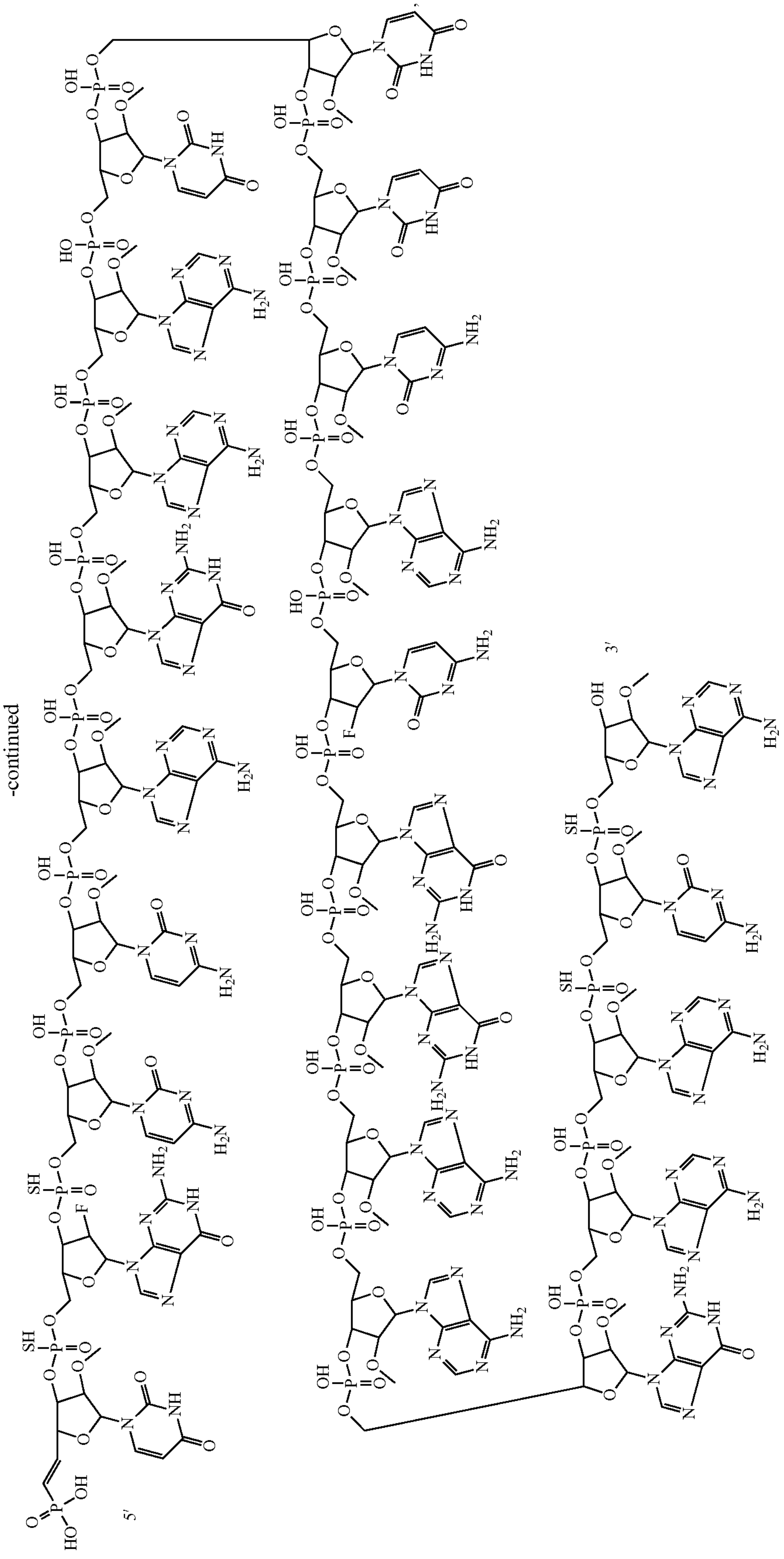
Antisense Strand or a pharmaceutically acceptable salt thereof, wherein $R^2$ comprises a Fab comprising a CDR-H1, a CDR-H2, a CDR-H3, a CDR-L1, a CDR-L2, and a CDR-L3 selected from Table 2.

In some embodiments, the Fab comprises a VH comprising the amino acid sequence of SEQ ID NO: 17 and a VL comprising the amino acid sequence of SEQ ID NO: 18.

In some embodiments the Fab comprises a VH comprising an N-terminal pyroglutamate.

In some embodiments the Fab comprises a heavy chain comprising the amino acid sequence of SEQ ID NO: 19 and a light chain comprising the amino acid sequence of SEQ ID NO: 20; wherein $R^1$ is covalently linked to $R^2$ at attachment point A;

wherein n1 is an integer representing the number of instances of $R^1$, wherein each instance of $R^1$ is covalently linked to a different amino acid residue of the Fab.

In some embodiments, each different amino acid residue is a lysine.

According to some aspects, the present disclosure provides complexes comprising a structure of the formula (Id):

(Id)
3′-mA*mC*mAmAmGmAmAmGmGfCmAmCmUmUmUmAmAmGmAmCmC*fG*mU-5′-VP Antisense (SEQ ID NO: 22)
5′-mU*mU*mCmUfUmCmCmGfUfGfAmAmAfUmUmCmUmGfG*mC*mA-3′ Sense (SEQ ID NO: 21)
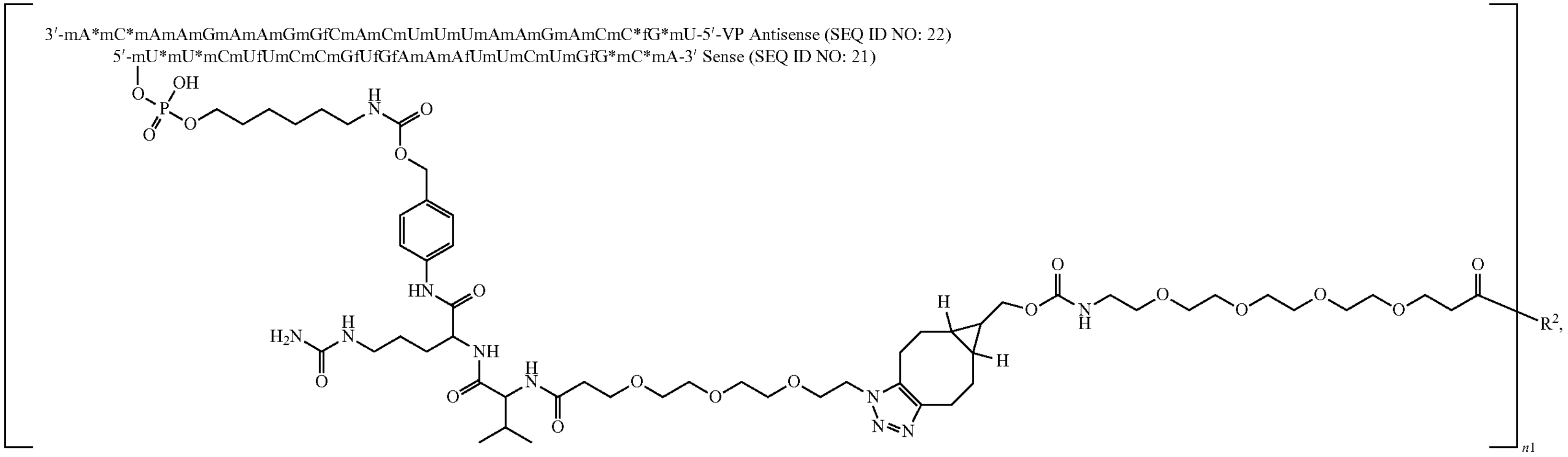

or a pharmaceutically acceptable salt thereof, wherein: mA, mC, mG, and mU are 2'-O-methyl adenosine, 2'-O-methyl cytidine, 2'-O-methyl guanosine, and 2'-O-methyl uridine, respectively;

fA, fC, fG, and fU are 2'-fluoro adenosine, 2'-fluoro cytidine, 2'-fluoro guanosine, and 2'-fluoro uridine, respectively; * between two nucleosides represents a phosphorothioate linkage; the absence of "*" between two nucleosides represents a phosphodiester internucleoside linkage; and "VP" represents 5'-(E)-Vinylphosphonate, such that the oligonucleotide is an RNAi oligonucleotide comprising an antisense strand comprising a nucleobase sequence of UGCCAGAAUUUCACGGAAGAACA (SEQ ID NO: 22) and a sense strand comprising a nucleobase sequence of UUCUUCCGUGAAAUUCUGGCA (SEQ ID NO: 21;

wherein $R^2$ comprises a Fab, and wherein the Fab comprises a CDR-H1, a CDR-H2, a CDR-H3, a CDR-L1, a CDR-L2, and a CDR-L3 selected from Table 2.

In some embodiments, the Fab comprises a VH comprising the amino acid sequence of SEQ ID NO: 17 and a VL comprising the amino acid sequence of SEQ ID NO: 18.

In some embodiments, the Fab comprises a VH comprising an N-terminal pyroglutamate.

In some embodiments, the Fab comprises a heavy chain comprising the amino acid sequence of SEQ ID NO: 19 and a light chain comprising the amino acid sequence of SEQ ID NO: 20;

wherein n1 is an integer representing the number of instances of the group enclosed by square brackets, wherein each instance of the group enclosed by square brackets is covalently linked to a different amino acid residue of the Fab.

In some embodiments, each different amino acid residue is a lysine.

According to some aspects, provided herein are formulations comprising a plurality of complexes of provided herein, and tris(hydroxymethyl)aminomethane at a concentration of 5 to 50 mM, and sucrose at a concentration of 2 w/v % to 15 w/v %, wherein the formulation is an aqueous solution and is at a pH of 6.5 to 8.5. In some embodiments, the plurality of complexes are at a concentration of 10 mg/mL to 200 mg/mL.

According to some aspects, provided herein are formulations comprising a plurality of complexes provided herein, and tris(hydroxymethyl)aminomethane at a concentration of 5 to 50 mM, and sucrose at a concentration of 3 w/v % to 10 w/v %, wherein the formulation is an aqueous solution and is at a pH of 6.5 to 8.5. In some embodiments, the plurality of complexes are at a concentration of 10 mg/mL to 200 mg/mL.

According to some aspects, provided herein are formulations comprising a plurality of complexes provided herein, and tris(hydroxymethyl)aminomethane at a concentration of 25 mM, and sucrose at a concentration of 10 w/v %, wherein the formulation is an aqueous solution and is at a pH of 7.5. In some embodiments, the plurality of complexes are at a concentration of 10 mg/mL to 200 mg/mL.

In some embodiments, the formulations further comprise one or more antibodies that are not covalently linked to an oligonucleotide.

In some embodiments, the average value of n1 of complexes in the formulation is in the range of 0.5 to 5.

In some embodiments, the average value of n1 of complexes in the formulation is 1.

According to some aspects, a lyophilized form of a formulation provided herein is disclosed.

According to some aspects, a product produced by a process comprising lyophilizing a formulation provided herein is disclosed.

According to some aspects, a frozen form of a formulation provided herein is disclosed.

According to some aspects, a product produced by a process comprising freezing a formulation provided herein is disclosed.

According to some aspects, a lyophilized cake comprising a plurality of complexes provided herein, tris(hydroxymethyl)aminomethane, and sucrose is disclosed.

DETAILED DESCRIPTION OF INVENTION

Figure 1:
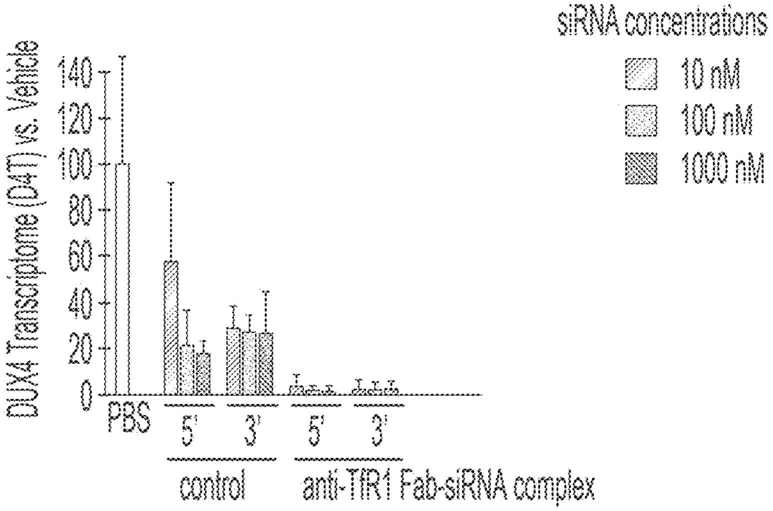
FIG. 1 shows a composite score of the mRNA levels of three DUX4 transcriptome (D4T) markers (MBD3L2, TRIM43, and ZSCAN4) in FSHD patient-derived C6 myotubes, following treatment with siRNA-antibody complexes at a concentration of 10 nM, 100 nM, or 1000 nM. The siRNA-antibody complexes contained an anti-TfR1 antibody provided in Table 2 covalently linked to a DUX4-targeting siRNA. An exon 1 targeting siRNA was used as a positive control.

According to some aspects, the present disclosure provides complexes and compositions (e.g., formulations) comprising such complexes. In some embodiments, the complexes are formulated with tris(hydroxymethyl) aminomethane and sucrose. In some embodiments, the complexes are formulated as aqueous or lyophilized (e.g., lyophilized powder) forms. In some embodiments, a complex comprises an oligonucleotide (e.g., an RNAi oligonucleotide) covalently linked to an antibody. In some embodiments, a complex comprises a muscle-targeting complex comprising an oligonucleotide (e.g., an RNAi oligonucleotide) covalently linked to an anti-transferrin receptor 1 (TfR1) antibody. In some embodiments, a complex comprises a muscle-targeting complex comprising an oligonucleotide (e.g., an RNAi oligonucleotide) covalently linked to the anti-transferrin receptor 1 (TfR1) antibody provided in Table 2. In some embodiments, a complex comprises a muscle-targeting complex comprising an oligonucleotide (e.g., an RNAi oligonucleotide) targeting DUX4 covalently linked to the anti-transferrin receptor 1 (TfR1) antibody provided in Table 2. Also provided are methods of using the complexes and compositions (e.g., formulations) described herein for treating a subject having facioscapulohumeral muscular dystrophy (FSHD) and/or methods of reducing the expression or activity of DUX4 (e.g., DUX4 protein and/or mRNA) in a cell.

Further aspects of the disclosure, including a description of defined terms, are provided below.

Definitions

Administering: As used herein, the terms “administering” or “administration” means to provide a complex to a subject in a manner that is physiologically and/or (e.g., and) pharmacologically useful (e.g., to treat a condition in the subject).

Approximately: As used herein, the term “approximately” or “about,” as applied to one or more values of interest, refers to a value that is similar to a stated reference value. In certain embodiments, the term “approximately” or “about” refers to a range of values that fall within 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Antibody: As used herein, the term “antibody” refers to a polypeptide that includes at least one immunoglobulin variable domain or at least one antigenic determinant, e.g., paratope that specifically binds to an antigen. In some embodiments, an antibody is a full-length antibody. In some embodiments, an antibody is a chimeric antibody. In some embodiments, an antibody is a humanized antibody. However, in some embodiments, an antibody is a Fab fragment, a Fab' fragment, a $F(ab')_2$ fragment, a Fv fragment or a scFv fragment. In some embodiments, an antibody is a nanobody derived from a camelid antibody or a nanobody derived from shark antibody. In some embodiments, an antibody is a diabody. In some embodiments, an antibody comprises a framework having a human germline sequence. In another embodiment, an antibody comprises a heavy chain constant domain selected from the group consisting of IgG, IgG1, IgG2, IgG2A, IgG2B, IgG2C, IgG3, IgG4, IgA1, IgA2, IgD, IgM, and IgE constant domains. In some embodiments, an antibody comprises a heavy (H) chain variable region (abbreviated herein as VH), and/or (e.g., and) a light (L) chain variable region (abbreviated herein as VL). In some embodiments, an antibody comprises a constant domain, e.g., an Fc region. An immunoglobulin constant domain refers to a heavy or light chain constant domain. Human IgG heavy chain and light chain constant domain amino acid sequences and their functional variations are known. With respect to the heavy chain, in some embodiments, the heavy chain of an antibody described herein can be an alpha (α), delta (Δ), epsilon (ε), gamma (γ) or mu (μ) heavy chain. In some embodiments, the heavy chain of an antibody described herein can comprise a human alpha (α), delta (Δ), epsilon (ε), gamma (γ) or mu (μ) heavy chain. In a particular embodiment, an antibody described herein comprises a human gamma 1 CH1, CH2, and/or (e.g., and) CH3 domain. In some embodiments, the amino acid sequence of the VH domain comprises the amino acid sequence of a human gamma (γ) heavy chain constant region, such as any known in the art. Non-limiting examples of human constant region sequences have been described in the art, e.g., see U.S. Pat. No. 5,693,780 and Kabat E A et al., (1991) supra. In some embodiments, the VH domain comprises an amino acid sequence that is at least 70%, 75%, 80%, 85%, 90%, 95%, 98%, or at least 99% identical to any of the variable chain constant regions provided herein. In some embodiments, an antibody is modified, e.g., modified via glycosylation, phosphorylation, sumoylation, and/or (e.g., and) methylation. In some embodiments, an antibody is a glycosylated antibody, which is conjugated to one or more sugar or carbohydrate molecules. In some embodiments, the one or more sugar or carbohydrate molecule are conjugated to the antibody via N-glycosylation, O-glycosylation, C-glycosylation, glypiation (GPI anchor attachment), and/or (e.g., and) phosphoglycosylation. In some embodiments, the one or more sugar or carbohydrate molecule are monosaccharides, disaccharides, oligosaccharides, or glycans. In some embodiments, the one or more sugar or carbohydrate molecule is a branched oligosaccharide or a branched glycan. In some embodiments, the one or more sugar or carbohydrate molecule includes a mannose unit, a glucose unit, an N-acetylglucosamine unit, an N-acetylgalactosamine unit, a galactose unit, a fucose unit, or a phospholipid unit. In some embodiments, an antibody is a construct that comprises a polypeptide comprising one or more antigen binding fragments of the disclosure linked to a linker polypeptide or an immunoglobulin constant domain. Linker polypeptides comprise two or more amino acid residues joined by peptide bonds and are used to link one or more antigen binding portions. Examples of linker polypeptides have been reported (see e.g., Holliger, P., et al. (1993) Proc. Natl. Acad. Sci. USA 90:64446448; Poljak, R. J., et al. (1994) Structure 2:1121-1123). Still further, an antibody may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058).

CDR: As used herein, the term "CDR" refers to the complementarity determining region within antibody variable sequences. A typical antibody molecule comprises a heavy chain variable region (VH) and a light chain variable region (VL), which are usually involved in antigen binding. The VH and VL regions can be further subdivided into regions of hypervariability, also known as "complementarity determining regions" ("CDR"), interspersed with regions that are more conserved, which are known as "framework regions" ("FR"). Each VH and VL is typically composed of three CDRs and four FRs, arranged from amino-terminus to carboxy-terminus in the following order: FR1, CDR1, FR2, CDR2, FR3, CDR3, FR4. The extent of the framework region and CDRs can be precisely identified using methodology known in the art, for example, by the Kabat definition, the IMGT definition, the Chothia definition, the AbM definition, and/or (e.g., and) the contact definition, all of which are well known in the art. See, e.g., Kabat, E. A., et al. (1991) Sequences of Proteins of Immunological Interest, Fifth Edition, U.S. Department of Health and Human Services, NIH Publication No. 91-3242; IMGT®, the international ImMunoGeneTics information System® http://www.imgt.org, Lefranc, M.-P. et al., Nucleic Acids Res., 27:209-212 (1999); Ruiz, M. et al., Nucleic Acids Res., 28:219-221 (2000); Lefranc, M.-P., Nucleic Acids Res., 29:207-209 (2001); Lefranc, M.-P., Nucleic Acids Res., 31:307-310 (2003); Lefranc, M.-P. et al., In Silico Biol., 5, 0006 (2004) [Epub], 5:45-60 (2005); Lefranc, M.-P. et al., Nucleic Acids Res., 33:D593-597 (2005); Lefranc, M.-P. et al., Nucleic Acids Res., 37:D1006-1012 (2009); Lefranc, M.-P. et al., Nucleic Acids Res., 43:D413-422 (2015); Chothia et al., (1989) Nature 342:877; Chothia, C. et al. (1987) J. Mol. Biol. 196:901-917, Al-lazikani et al (1997) J. Molec. Biol. 273:927-948; and Almagro, J. Mol. Recognit. 17:132-143 (2004). See also hgmp.mrc.ac.uk and bioinf.org.uk/abs. As used herein, a CDR may refer to the CDR defined by any method known in the art. Two antibodies having the same CDR means that the two antibodies have the same amino acid sequence of that CDR as determined by the same method, for example, the IMGT definition.

There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Sub-portions of CDRs may be designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems. Examples of CDR definition systems are provided in Table 1.

TABLE 1

| CDR Definitions | | | |
|---|---|---|---|
| | IMGT[1] | Kabat[2] | Chothia[3] |
| CDR-H1 | 27-38 | 31-35 | 26-32 |
| CDR-H2 | 56-65 | 50-65 | 53-55 |
| CDR-H3 | 105-116/117 | 95-102 | 96-101 |
| CDR-L1 | 27-38 | 24-34 | 26-32 |
| CDR-L2 | 56-65 | 50-56 | 50-52 |
| CDR-L3 | 105-116/117 | 89-97 | 91-96 |

[1]IGMT ®, the international ImMunoGeneTics information system ®, imgt.org, Lefranc, M.-P. et al., Nucleic Acids Res., 27: 209-212 (1999)
[2]Kabat et al. (1991) Sequences of Proteins of Immunological Interest, Fifth Edition, U.S. Department of Health and Human Services, NIH Publication No. 91-3242
[3]Chothia et al., J. Mol. Biol. 196: 901-917 (1987))

Chimeric antibody: The term "chimeric antibody" refers to antibodies which comprise heavy and light chain variable region sequences from one species and constant region sequences from another species, such as antibodies having murine heavy and light chain variable regions linked to human constant regions.

Complementary: As used herein, the term "complementary" refers to the capacity for precise pairing between two nucleotides or nucleosides or two sets of nucleotides or nucleosides. In particular, complementary is a term that characterizes an extent of hydrogen bond pairing that brings about binding between two nucleotides or nucleosides or two sets of nucleotides or nucleosides. For example, if a base at one position of an oligonucleotide is capable of hydrogen bonding with a base at the corresponding position of a target nucleic acid (e.g., an mRNA), then the bases are considered to be complementary to each other at that position. Base pairings may include both canonical Watson-Crick base pairing and non-Watson-Crick base pairing (e.g., Wobble base pairing and Hoogsteen base pairing). For example, in some embodiments, for complementary base pairings, adenosine-type bases (A) are complementary to thymidine-type bases (T) or uracil-type bases (U), that cytosine-type bases (C) are complementary to guanosine-type bases (G), and that universal bases such as 3-nitropyrrole or 5-nitroindole can hybridize to and are considered complementary to any A, C, U, or T. Inosine (I) has also been considered in the art to be a universal base and is considered complementary to any A, C, U or T.

Covalently linked: As used herein, the term "covalently linked" refers to a characteristic of two or more molecules being linked together via at least one covalent bond. In some embodiments, two molecules can be covalently linked together by a single bond, e.g., a disulfide bond or disulfide bridge, that serves as a linker between the molecules. However, in some embodiments, two or more molecules can be covalently linked together via a molecule that serves as a linker that joins the two or more molecules together through multiple covalent bonds. In some embodiments, a linker may be a cleavable linker. However, in some embodiments, a linker may be a non-cleavable linker.

DUX4: As used herein, the term "DUX4" refers to a gene that encodes double homeobox 4, a protein which is generally expressed during fetal development and in the testes of adult males. In some embodiments, DUX4 may be a human (Gene ID: 100288687), non-human primate (e.g., Gene ID: 750891, Gene ID: 100405864), or rodent gene (e.g., Gene ID: 306226). In humans, expression of the DUX4 gene outside of fetal development and the testes is associated with facioscapulohumeral muscular dystrophy. In addition, multiple human transcript variants (e.g., as annotated under GenBank RefSeq Accession Numbers: NM_001293798.2, NM_001306068.3, NM_001363820.1) have been characterized that encode different protein isoforms.

Facioscapulohumeral muscular dystrophy (FSHD): As used herein, the term "facioscapulohumeral muscular dystrophy (FSHD)" refers to a genetic disease caused by mutations in the DUX4 gene, SMCHD1 gene, DNMT3B gene, or LRIF1 gene that is characterized by muscle mass loss and muscle atrophy, primarily in the muscles of the face, shoulder blades, and upper arms. Two types of the disease, Type 1 and Type 2, have been described. Type 1 is associated with deletions in D4Z4 repeat regions on chromosome 4 which contains the DUX4 gene. In some embodiments, Type 1 is associated with deletions in D4Z4 repeat regions on chromosome 4 allelic variant 4qA which contains the DUX4 gene. Type 2 is associated with mutations in the SMCHD1 gene, DNMT3B gene, or LRIF1 gene (see, e.g. Jia et al., "Facioscapulohumeral muscular dystrophy type 2: an update on the clinical, genetic, and molecular findings" Neuromuscul Disord. (2021), 31(11): 1101-1112. Both Type 1 and Type 2 FSHD are characterized by aberrant production of the DUX4 protein after fetal development outside of the testes. Facioscapulohumeral dystrophy, the genetic basis for the disease, and related symptoms are described in the art (see, e.g. Campbell, A. E., et al., "Facioscapulohumeral dystrophy: Activating an early embryonic transcriptional program in human skeletal muscle" Human Mol Genet. (2018); and Tawil, R. "Facioscapulohumeral muscular dystrophy" Handbook Clin. Neurol. (2018), 148: 541-548.) FSHD Type 1 is associated with Online Mendelian Inheritance in Man (OMIM) Entry #158900. FSHD Type 2 is associated with OMIM Entry #158901.

Framework: As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, CDR-L2, and CDR-L3 of light chain and CDR-H1, CDR-H2, and CDR-H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FRs within the variable region of a single, naturally occurring immunoglobulin chain. As used herein, a FR represents one of the four sub-regions, and FRs represents two or more of the four sub-regions constituting a framework region. Human heavy chain and light chain acceptor sequences are known in the art. In one embodiment, the acceptor sequences known in the art may be used in the antibodies disclosed herein.

Human antibody: The term "human antibody", as used herein, is intended to include antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

Humanized antibody: The term "humanized antibody" refers to antibodies which comprise heavy and light chain variable region sequences from a non-human species (e.g., a mouse) but in which at least a portion of the VH and/or (e.g., and) VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences. In one embodiment, humanized anti-transferrin receptor antibodies and antigen binding portions are provided. Such antibodies may be generated by obtaining murine anti-transferrin receptor monoclonal antibodies using traditional hybridoma technology followed by humanization using in vitro genetic engineering, such as those disclosed in Kasaian et al PCT publication No. WO 2005/123126 A2.

Internalizing cell surface receptor: As used herein, the term, "internalizing cell surface receptor" refers to a cell surface receptor that is internalized by cells, e.g., upon external stimulation, e.g., ligand binding to the receptor. In some embodiments, an internalizing cell surface receptor is internalized by endocytosis. In some embodiments, an internalizing cell surface receptor is internalized by clathrin-mediated endocytosis. However, in some embodiments, an internalizing cell surface receptor is internalized by a clathrin-independent pathway, such as, for example, phagocytosis, macropinocytosis, caveolae- and raft-mediated uptake or constitutive clathrin-independent endocytosis. In some embodiments, the internalizing cell surface receptor comprises an intracellular domain, a transmembrane domain, and/or (e.g., and) an extracellular domain, which may optionally further comprise a ligand-binding domain. In some embodiments, a cell surface receptor becomes internalized by a cell after ligand binding. In some embodiments, a ligand may be a muscle-targeting agent or a muscle-targeting antibody. In some embodiments, an internalizing cell surface receptor is a transferrin receptor.

Kabat numbering: The terms "Kabat numbering", "Kabat definitions and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof (Kabat et al. (1971) Ann. NY Acad, Sci. 190:382-391 and, Kabat, E. A., et al. (1991) Sequences of Proteins of Immunological Interest, Fifth Edition, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

Molecular payload: As used herein, the term "molecular payload" refers to a molecule or species that functions to modulate a biological outcome. In some embodiments, a molecular payload is linked to, or otherwise associated with a muscle-targeting agent. In some embodiments, the molecular payload is a small molecule, a protein, a peptide, a nucleic acid, or an oligonucleotide. In some embodiments, the molecular payload functions to modulate the transcription of a DNA sequence, to modulate the expression of a protein, or to modulate the activity of a protein. In some embodiments, the molecular payload is an oligonucleotide that comprises a strand having a region of complementarity to a target gene.

Oligonucleotide: As used herein, the term "oligonucleotide" refers to an oligomeric nucleic acid compound of up to 200 nucleotides in length. Examples of oligonucleotides include, but are not limited to, RNAi oligonucleotides (e.g., siRNAs, shRNAs), microRNAs, gapmers, mixmers, phosphorodiamidate morpholinos, peptide nucleic acids, aptamers, guide nucleic acids (e.g., Cas9 guide RNAs), etc. Oligonucleotides may be single-stranded or double-stranded. In some embodiments, an oligonucleotide may comprise one or more modified nucleosides (e.g., 2'-O-methyl sugar modifications, purine or pyrimidine modifications). In some embodiments, an oligonucleotide may comprise one or more modified internucleoside linkage. In some embodiments, an oligonucleotide may comprise one or more phosphorothioate linkages, which may be in the Rp or Sp stereochemical conformation.

Pharmaceutically acceptable salt: As used herein, the term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences,* 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions, such as halide, hydroxide, carboxylate, sulfate, phosphate, nitrate, lower alkyl sulfonate, and aryl sulfonate.

Region of complementarity: As used herein, the term "region of complementarity" refers to a nucleotide sequence, e.g., of an oligonucleotide, that is sufficiently complementary to a cognate nucleotide sequence, e.g., of a target nucleic acid, such that the two nucleotide sequences are capable of annealing to one another under physiological conditions (e.g., in a cell). In some embodiments, a region of complementarity is fully complementary to a cognate nucleotide sequence of target nucleic acid. However, in some embodiments, a region of complementarity is partially complementary to a cognate nucleotide sequence of target nucleic acid (e.g., at least 80%, 90%, 95% or 99% complementarity). In some embodiments, a region of complementarity contains 1, 2, 3, or 4 mismatches compared with a cognate nucleotide sequence of a target nucleic acid.

Specifically binds: As used herein, the term "specifically binds" refers to the ability of a molecule to bind to a binding partner with a degree of affinity or avidity that enables the molecule to be used to distinguish the binding partner from an appropriate control in a binding assay or other binding context. With respect to an antibody, the term, "specifically binds", refers to the ability of the antibody to bind to a specific antigen with a degree of affinity or avidity, compared with an appropriate reference antigen or antigens, that enables the antibody to be used to distinguish the specific antigen from others, e.g., to an extent that permits preferential targeting to certain cells, e.g., muscle cells, through binding to the antigen, as described herein. In some embodiments, an antibody specifically binds to a target if the antibody has a $K_D$ for binding the target of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, $10^{-13}$ M, or less. In some embodiments, an antibody specifically binds to the transferrin receptor, e.g., an epitope of the apical domain of transferrin receptor.

Subject: As used herein, the term "subject" refers to a mammal. In some embodiments, a subject is non-human primate, or rodent. In some embodiments, a subject is a human. In some embodiments, a subject is a patient, e.g., a human patient that has or is suspected of having a disease. In some embodiments, the subject is a human patient who has or is suspected of having FSHD.

Transferrin receptor: As used herein, the term, "transferrin receptor" (also known as TFRC, CD71, p90, TFR, or TFR1) refers to an internalizing cell surface receptor that binds transferrin to facilitate iron uptake by endocytosis. In some embodiments, a transferrin receptor may be of human (NCBI Gene ID 7037), non-human primate (e.g., NCBI Gene ID 711568 or NCBI Gene ID 102136007), or rodent (e.g., NCBI Gene ID 22042) origin. In addition, multiple human transcript variants have been characterized that encoded different isoforms of the receptor (e.g., as annotated under GenBank RefSeq Accession Numbers: NP_001121620.1, NP_003225.2, NP_001300894.1, and NP_001300895.1).

2'-modified nucleoside: As used herein, the terms "2'-modified nucleoside" and "2'-modified ribonucleoside" are used interchangeably and refer to a nucleoside having a sugar moiety modified at the 2' position. In some embodiments, the 2'-modified nucleoside is a 2'→4' bicyclic nucleoside, where the 2' and 4' positions of the sugar are bridged (e.g., via a methylene, an ethylene, or a (S)-constrained ethyl bridge). In some embodiments, the 2'-modified nucleoside is a non-bicyclic 2'-modified nucleoside, e.g., where the 2' position of the sugar moiety is substituted. Non-limiting examples of 2'-modified nucleosides include: 2'-deoxy, 2'-fluoro (2'-F), 2'-O-methyl (2'-O-Me), 2'-O-methoxyethyl (2'-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), 2'-O—N-methylacetamido (2'-O-NMA), locked nucleic acid (LNA, methylene-bridged nucleic acid), ethylene-bridged nucleic acid (ENA), and (S)-constrained ethyl-bridged nucleic acid (cEt). In some embodiments, the 2'-modified nucleosides described herein are high-affinity modified nucleosides and oligonucleotides comprising the 2'-modified nucleosides have increased affinity to a target sequences, relative to an unmodified oligonucleotide. Examples of structures of 2'-modified nucleosides are provided below:

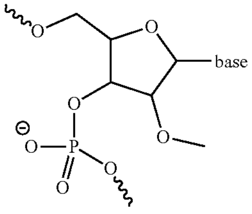

2′-O-methyl

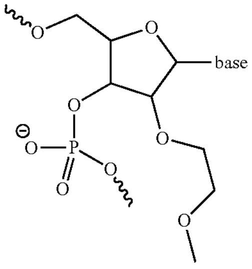

2′-O-methoxyethyl
(MOE)

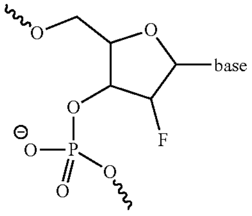

2′-fluoro

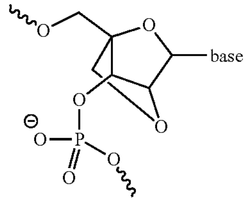

locked nucleic acid
(LNA)

-continued

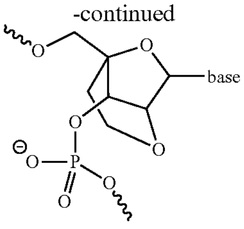

ethylene-bridged
nucleic acid (ENA)

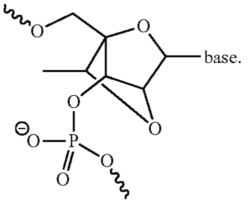

(S)-constrained
ethyl (cEt)

These examples are shown with phosphate groups, but any internucleoside linkages are contemplated between 2'-modified nucleosides. In certain embodiments, the internucleoside phosphate groups are as depicted, i.e., deprotonated in salt form. In certain embodiments, the internucleoside phosphate groups are protonated. The extent to which the phosphate groups are protonated or deprotonated will vary depending on the chemical environment of the nucleosides (e.g., pH, presence of basic media, etc.).

Ranges: All ranges provided in the present disclosure are inclusive of the end points.

Complexes

Provided herein are complexes that comprise a targeting agent, e.g., an antibody, covalently linked to an oligonucleotide. In some embodiments, a complex comprises a muscle-targeting antibody (e.g., an anti-TfR1 antibody) covalently linked to one or more oligonucleotides. In some embodiments, the oligonucleotide is an RNAi oligonucleotide (e.g., siRNA) that targets a DUX4 RNA to reduce expression or activity of DUX4 (e.g., to reduce DUX4 protein and/or mRNA levels).

Complexes described herein generally comprise a linker that covalently links an antibody (e.g., an anti-TfR1 antibody) described herein to an oligonucleotide (e.g., an RNAi oligonucleotide). A linker comprises at least one covalent bond.

In some embodiments, complexes described herein comprise a structure of formula (I): $[R_1]_{n1}$—$R^2$, in which each $R^1$ independently comprises a compound comprising an oligonucleotide (e.g., an RNAi oligonucleotide) and $R^2$ comprises an antibody (e.g., an anti-TfR1 antibody), and wherein in each complex n1 is independently an integer (e.g., one or greater) representing the number of instances of $R^1$ in each complex. In some embodiments, each $R^1$ independently comprises a group comprising an oligonucleotide. In some embodiments, each $R^1$ independently comprises a group that comprises additional elements in addition to an oligonucleotide. In some embodiments, $R^2$ comprises an antibody (e.g., an anti-TfR1 antibody) comprising a heavy chain comprising a heavy chain variable region (VH) and a heavy chain constant region, and a light chain comprising a light chain variable region (VL) and a light chain constant region. In some embodiments, each $R^1$ of a complex is independently covalently linked to a different amino acid residue (e.g., lysine or cysteine) of $R^2$.

In some embodiments, in each complex n1 is independently an integer (e.g., one or greater). In some embodiments, the antibody comprises a sequence as set forth in Table 2. For example, in some embodiments, the antibody comprises a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14; and/or comprises a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5 or 11, and a light chain complementarity determining region 3 (CDR-L3) comprising a sequence as set forth in SEQ ID NO: 6 or 16. In some embodiments, the antibody comprises a heavy chain variable region (VH) comprising an amino acid sequence at least 85% (e.g., at least 95%) identical to SEQ ID NO: 17 and/or comprises a light chain variable region (VL) comprising an amino acid sequence at least 85% (e.g., at least 95%) identical to SEQ ID NO: 18. In some embodiments, the antibody comprises a VH comprising the amino acid sequence of SEQ ID NO: 17 and/or comprises a VL comprising the amino acid sequence of SEQ ID NO: 18. In some embodiments, the antibody comprises a heavy chain comprising an amino acid sequence at least 85% (e.g., at least 95%) identical to SEQ ID NO: 19 and/or comprises a light chain comprising an amino acid sequence at least 85% (e.g., at least 95%) identical to SEQ ID NO: 20. In some embodiments, the antibody comprises a heavy chain comprising the amino acid sequence of SEQ ID NO: 19 and/or comprises a light chain comprising the amino acid sequence of SEQ ID NO: 20. In some embodiments, the antibody is a Fab fragment, a full-length IgG, a Fab' fragment, a $F(ab')_2$ fragment, an scFv, or an Fv. In some embodiments, the antibody is a Fab fragment.

In some embodiments, the value of n1 of each or any complex (e.g., any complex in any of the compositions or formulations disclosed herein) is an integer up to the number of amino acid residues in the antibody to which conjugation is desired or targeted (e.g., the number of lysine residues). In some embodiments, in each complex the value of n1 is independently selected from 1, 2, 3, 4, 5, 6, 7, 8, 9, 10, 11, 12, 13, 14, 15, 16, 17, 18, 19, 20, 21, 22, 23, 24, 25, 26, and 27. In some embodiments, in each complex the value of n1 is independently selected from 1, 2, 3, 4, 5, 6, 7, 8, 9, 10, 11, 12, 13, 14, 15, 16, 17, 18, 19, 20, 21, 22, 23, 24, 25 and 26. In some embodiments, in each complex the value of n1 is 1. In some embodiments, in each complex the value of n1 is independently in the range of 1-27, 1-26, 1-10, 1-5, or 1-3. In some embodiments, the average value of n1 of complexes of the composition is in the range of 1 to 5 (e.g., 1-5, 1-4, 1-3, 3-5, or 1-2). In some embodiments, compositions described herein comprise complexes that comprise a structure of formula (I): $[R^1]_{n1}$—$R^2$, wherein n1 is 0. In some embodiments, the average value of n1 of complexes of the composition is in the range of 0.5 to 5 (e.g., 0.5-5, 1-5, 1-4, 1-3, 3-5, 0.5-4, 0.5-3, 0.5-2, 0.5-1.5, 0.5-1, 0.7-1.5, 1-1.6, 1-1.5, 1-1.4, 1-1.3, 1-1.2, 1.1-1.5, 0.8-2, 0.8-1.5, 0.8-1.3, 0.8-1.2, 0.8-1.1, 0.9-3, 0.9-2, 0.9-1.8, 0.9-1.6, 0.9-1.5, 0.9-1.4, 0.9-1.3, or 0.9-1.2). In some embodiments, the average value of n1 of complexes of the composition is 1. In some embodiments, in each complex type n1 is independently an integer of one or greater representing the number of instances of $R^1$ in each complex of the complex type, and in which the different complex types of the composition are characterized by having different n1 values (e.g., n1 values in the range of 1-27, 1-26, 1-25, 1-20, 1-15, 1-10, 1-5, or 1-3).

In some embodiments, compositions are provided (e.g., formulations comprising tris(hydroxymethyl)aminomethane and/or sucrose, as described herein) that comprise a plurality of different complexes. In some embodiments, the plurality of different complexes comprise a common targeting agent (e.g. an antibody) and a common oligonucleotide (e.g., an RNAi oligonucleotide, such as a DUX4-targeting RNAi oligonucleotide). In such embodiments, different complex types are characterized by having different numbers of oligonucleotides covalently linked to an antibody. For example, in some embodiments, compositions are provided that comprise a plurality of complexes comprising a structure of formula (I): $[R^1]_{n1}$—$R^2$, in which each $R^1$ independently comprises a compound comprising an oligonucleotide (e.g., a DUX4-targeting RNAi oligonucleotide) and $R^2$ comprises an antibody (e.g., anti-TfR1 antibody), and in which n1 is an integer representing the number of instances of $R^1$ in a complex, and in which different complexes of the composition may have different n1 values (e.g., n1 values in the range of 1-27, 1-26, 1-10, 1-5, or 1-3). In some embodiments, in complexes of a composition n1 is independently an integer. In some embodiments, in complexes of a composition n1 is 1. In some embodiments, the average value of n1 of complexes of the composition is in the range of 0.5 to 5 (e.g., 0.5-5, 1-5, 1-4, 1-3, 3-5, 0.5-4, 0.5-3, 0.5-2, 0.5-1.5, 0.5-1, 0.7-1.5, 1-1.6, 1-1.5, 1-1.4, 1-1.3, 1-1.2, 1.1-1.5, 0.8-2, 0.8-1.5, 0.8-1.3, 0.8-1.2, 0.8-1.1, 0.9-3, 0.9-2, 0.9-1.8, 0.9-1.6, 0.9-1.5, 0.9-1.4, 0.9-1.3, or 0.9-1.2). In some embodiments, the average value of n1 of complexes of the composition is 1. In some embodiments, compositions described herein comprise complexes in which n1 is 0.

In some embodiments, a composition described herein comprises an antibody that is not conjugated to an oligonucleotide (e.g., in trace amounts) and an antibody conjugated to one or more oligonucleotides. In some embodiments, the antibody that is not conjugated to an oligonucleotide may be referred to as a compound comprising a structure of formula (I): $[R^1]_{n1}$—$R^2$, for which n1 is zero. Accordingly, in some embodiments, a composition for administration to a subject in the methods described herein comprises compounds (e.g., complexes) comprising a structure of formula (I): $[R^1]_{n1}$—$R^2$, for which each $R^1$ independently comprises a group comprising an oligonucleotide, $R^2$ comprises an antibody and n1 is independently an integer of zero or greater that reflects the number of instances of $R^1$ in each compound (e.g., complex). In some embodiments, the fraction of compounds comprising a structure of formula (I): $[R^1]_{n1}$—$R^2$, in a composition, for which n1 is zero, compared with all compounds of that structure in the composition for which n1 is one or greater, is less than 10%, less than 5%, less than 1% less than 0.5%, less than 0.1%, less than 0.05%, or less than 0.01%. As such, in some embodiments, the average value of n1 of complexes in a composition disclosed herein is in the range of 0.5 to 5 (e.g., 0.5-5, 1-5, 1-4, 1-3, 3-5, 0.5-4, 0.5-3, 0.5-2, 0.5-1.5, 0.5-1, 0.7-1.5, 1-1.6, 1-1.5, 1-1.4, 1-1.3, 1-1.2, 1.1-1.5, 0.8-2, 0.8-1.5, 0.8-1.3, 0.8-1.2, 0.8-1.1, 0.9-3, 0.9-2, 0.9-1.8, 0.9-1.6, 0.9-1.5, 0.9-1.4, 0.9-1.3, or 0.9-1.2). In some embodiments, the average value of n1 of complexes of the composition is 1.

In some embodiments, each instance of $R^1$ in a complex is covalently linked to a different amino acid residue of the antibody. In some embodiments, an amino acid to which $R^1$ is covalently linked comprises an ε-amino group (e.g., lysine, arginine). In some embodiments, an amino acid to which $R^1$ is covalently linked is a lysine. In some embodiments, an amino acid to which $R^1$ is covalently linked is a cysteine. In some embodiments, $R^1$ is directly covalently linked to an amino acid residue of the antibody. However, in some embodiments, $R^1$ is indirectly covalently linked to an amino acid of the antibody, e.g., covalently linked to a glycosylation site on the amino acid. In some embodiments, $R^1$ is not covalently linked to an amino acid residue residing in a CDR region of the antibody.

In some embodiments, complexes provided herein (e.g., in compositions or formulations described herein) comprise a structure of formula (I): $[R^1]_{n1}$—$R^2$, in which each instance of $R^1$ independently comprises a group of the formula (Ia):

(Ia)

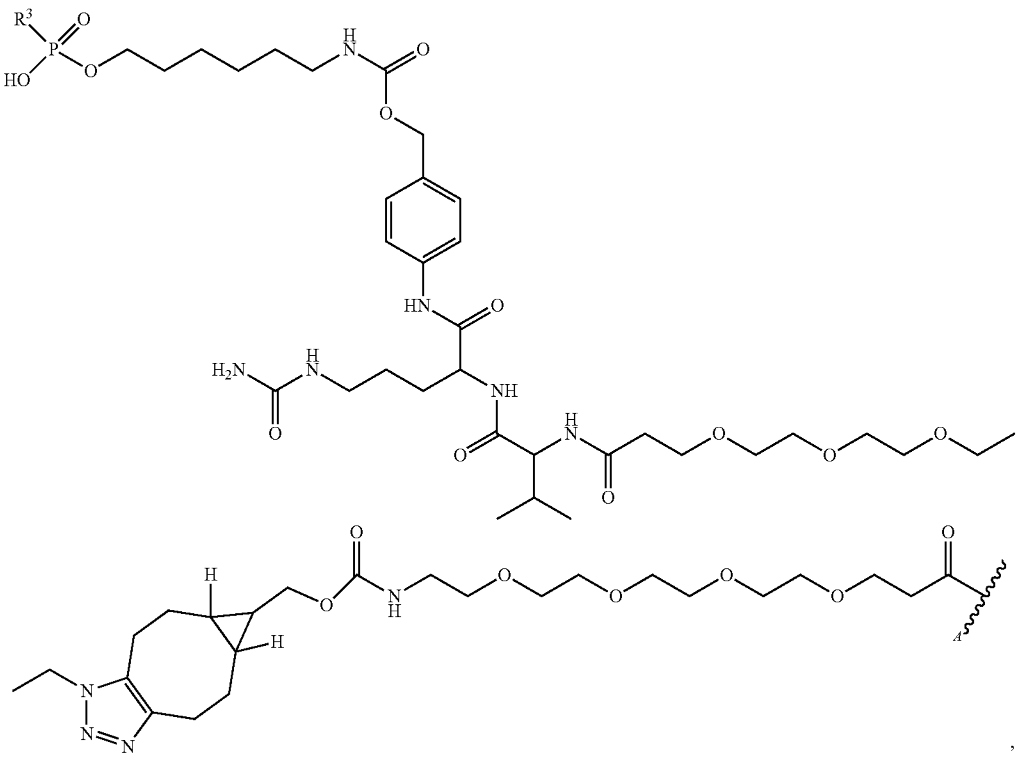

, or a pharmaceutically acceptable salt thereof, in which $R^3$ comprises an oligonucleotide, e.g., an RNAi oligonucleotide; and $R^1$ is covalently linked (e.g., indirectly or directly linked, e.g., directly linked) to $R^2$ at attachment point A. In some embodiments, $R^2$ comprises an antibody comprising a sequence as set forth in Table 2. For example, in some embodiments, $R^2$ comprises an antibody comprising a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14; and/or comprising a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5, or 11, and a light chain complementarity determining region 3 (CDR-L3) comprising a sequence as set forth in SEQ ID NO: 6 or 16. In some embodiments, $R^2$ comprises an antibody comprising a heavy chain variable region (VH) comprising an amino acid sequence at least 85% (e.g., at least 95%) identical to SEQ ID NO: 17 and/or comprising a light chain variable region (VL) comprising an amino acid sequence at least 85% (e.g., at least 95%) identical to SEQ ID NO: 18. In some embodiments, $R^2$ comprises an antibody comprising a VH comprising the amino acid sequence of SEQ ID NO: 17 and/or comprising a VL comprising the amino acid sequence of SEQ ID NO: 18. In some embodiments, $R^2$ comprises an antibody comprising a heavy chain comprising an amino acid sequence at least 85% (e.g., at least 95%) identical to SEQ ID NO: 19 and/or comprising a light chain comprising an amino acid sequence at least 85% (e.g., at least 95%) identical to SEQ ID NO: 20. In some embodiments, $R^2$ comprises an antibody comprising a heavy chain comprising the amino acid sequence of SEQ ID NO: 19 and/or comprising a light chain comprising the amino acid sequence of SEQ ID NO: 20. In some embodiments, $R^2$ comprises an antibody that is a Fab fragment, a full-length IgG, a Fab' fragment, a $F(ab')_2$ fragment, an scFv, or an Fv. In some embodiments, $R^2$ comprises an antibody that is a Fab fragment. In some embodiments, $R^3$ comprises an RNAi oligonucleotide (e.g., an siRNA) comprising an antisense strand comprising a nucleobase sequence of SEQ ID NO: 22 and a structure (5'→3') of VP-mU*fG*mCmCmAmGmAmAmUmUmUmCmAfCm GmGmAmAmGmAmA*mC*mA, and a sense strand comprising a nucleobase sequence of SEQ ID NO: 21 and a structure (5'→3') of mU*mU*mCmUfUmCmCmGfUfGfAmAmAfUmUmCm UmGfG*mC*mA, wherein: mA, mC, mG, and mU are 2'-O-methyl adenosine, 2'-O-methyl cytidine, 2'-O-methyl guanosine, and 2'-O-methyl uridine, respectively; fA, fC, fG, and fU are 2'-fluoro adenosine, 2'-fluoro cytidine, 2'-fluoro guanosine, and 2'-fluoro uridine, respectively; * between two nucleosides represents a phosphorothioate linkage; the absence of "*" between two nucleosides represents a phosphodiester internucleoside linkage; and "VP" represents 5'-(E)-Vinylphosphonate. In some embodiments, in each complex n1 is independently an integer (e.g., one or greater). In some embodiments, in each complex n1 is 1.

In some embodiments, complexes provided herein (e.g., in compositions or formulations described herein) comprise a structure of formula (I): $[R^1]_{n1}$—$R^2$, in which each $R^1$ comprises a group of the formula (Ib):

(Ib)

3′-mA*mC*mAmAmGmAmAmGmGfCmAmCmUmUmUmAmAmGmAmCmC*fG*mU-5′-VP Antisense (SEQ ID NO: 22)

5′-mU*mU*mCmUfUmCmCmGfUfGfAmAmAfUmUmCmUmGfG*mC*mA-3′ Sense (SEQ ID NO: 21)

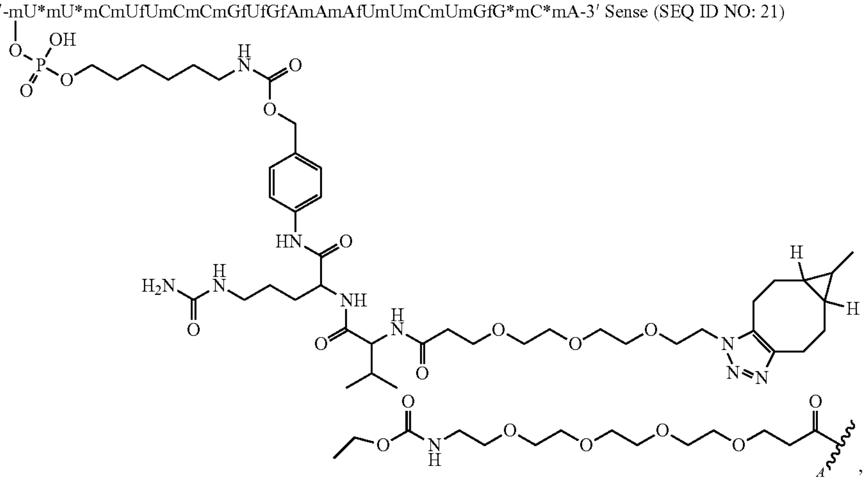

, or a pharmaceutically acceptable salt thereof, wherein: mA, mC, mG, and mU are 2'-O-methyl adenosine, 2'-O-methyl cytidine, 2'-O-methyl guanosine, and 2'-O-methyl uridine, respectively;

fA, fC, fG, and fU are 2'-fluoro adenosine, 2'-fluoro cytidine, 2'-fluoro guanosine, and 2'-fluoro uridine, respectively; * between two nucleosides represents a phosphorothioate linkage; the absence of "*" between two nucleosides represents a phosphodiester internucleoside linkage; and "VP" represents 5'-(E)-Vinylphosphonate; and wherein the oligonucleotide is an RNAi oligonucleotide (e.g., siRNA) comprising an antisense strand comprising a nucleobase sequence of UGCCAGAAUUUCACGGAAGAACA (SEQ ID NO: 22) and a sense strand comprising a nucleobase sequence of UUCUUCCGUGAAAUUCUGGCA (SEQ ID NO: 21); wherein n1 is an integer (e.g., one or greater) representing the number of instances of $R^1$ in each complex, and each $R^1$ is covalently linked to $R^2$ at attachment point A. In some embodiments, $R^2$ comprises an antibody comprising a sequence as set forth in Table 2. For example, in some embodiments, $R^2$ comprises an antibody comprising a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14; and/or comprising a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5, or 11, and a light chain complementarity determining region 3 (CDR-L3) comprising a sequence as set forth in SEQ ID NO: 6 or 16. In some embodiments, $R^2$ comprises an antibody comprising a heavy chain variable region (VH) comprising an amino acid sequence at least 85% (e.g., at least 95%) identical to SEQ ID NO: 17 and/or comprising a light chain variable region (VL) comprising an amino acid sequence at least 85% (e.g., at least 95%) identical to SEQ ID NO: 18. In some embodiments, $R^2$ comprises an antibody comprising a VH comprising the amino acid sequence of SEQ ID NO: 17 and/or comprising a VL comprising the amino acid sequence of SEQ ID NO: 18. In some embodiments, $R^2$ comprises an antibody comprising a heavy chain comprising an amino acid sequence at least 85% (e.g., at least 95%) identical to SEQ ID NO: 19 and/or comprising a light chain comprising an amino acid sequence at least 85% (e.g., at least 95%) identical to SEQ ID NO: 20. In some embodiments, $R^2$ comprises an antibody comprising a heavy chain comprising the amino acid sequence of SEQ ID NO: 19 and/or comprising a light chain comprising the amino acid sequence of SEQ ID NO: 20. In some embodiments, $R^2$ comprises an antibody that is a Fab fragment, a full-length IgG, a Fab' fragment, a $F(ab')_2$ fragment, an scFv, or an Fv. In some embodiments, $R^2$ comprises an antibody that is a Fab fragment.

In some embodiments, complexes provided herein (e.g., in compositions or formulations described herein) comprise a structure of formula (I): $[R^1]_{n1}$—$R^2$, in which each $R^1$ comprises a group of the formula (Ic), in which the antisense strand and the sense strand form a double stranded oligonucleotide:

(Ic)
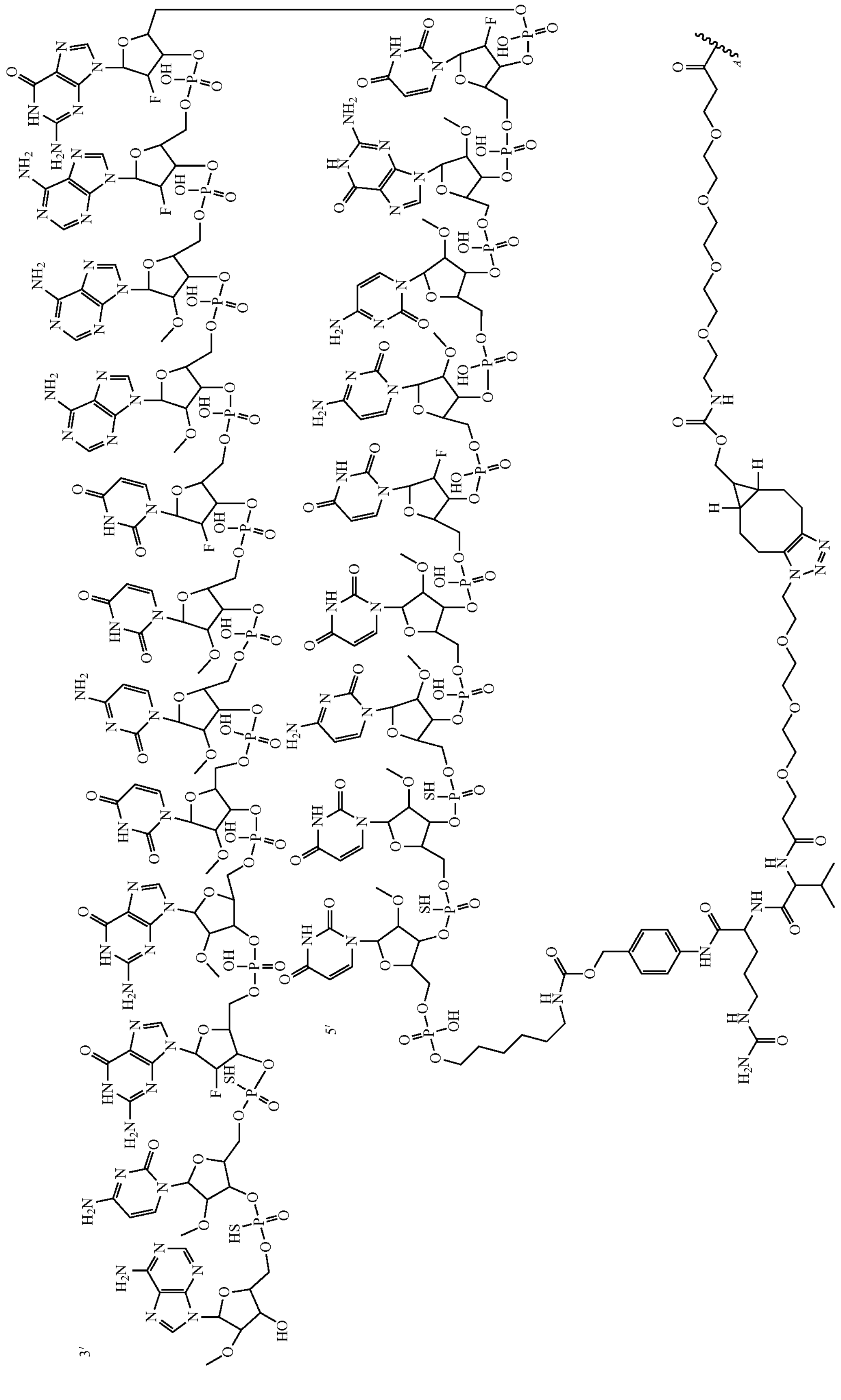
Sense Strand

-continued
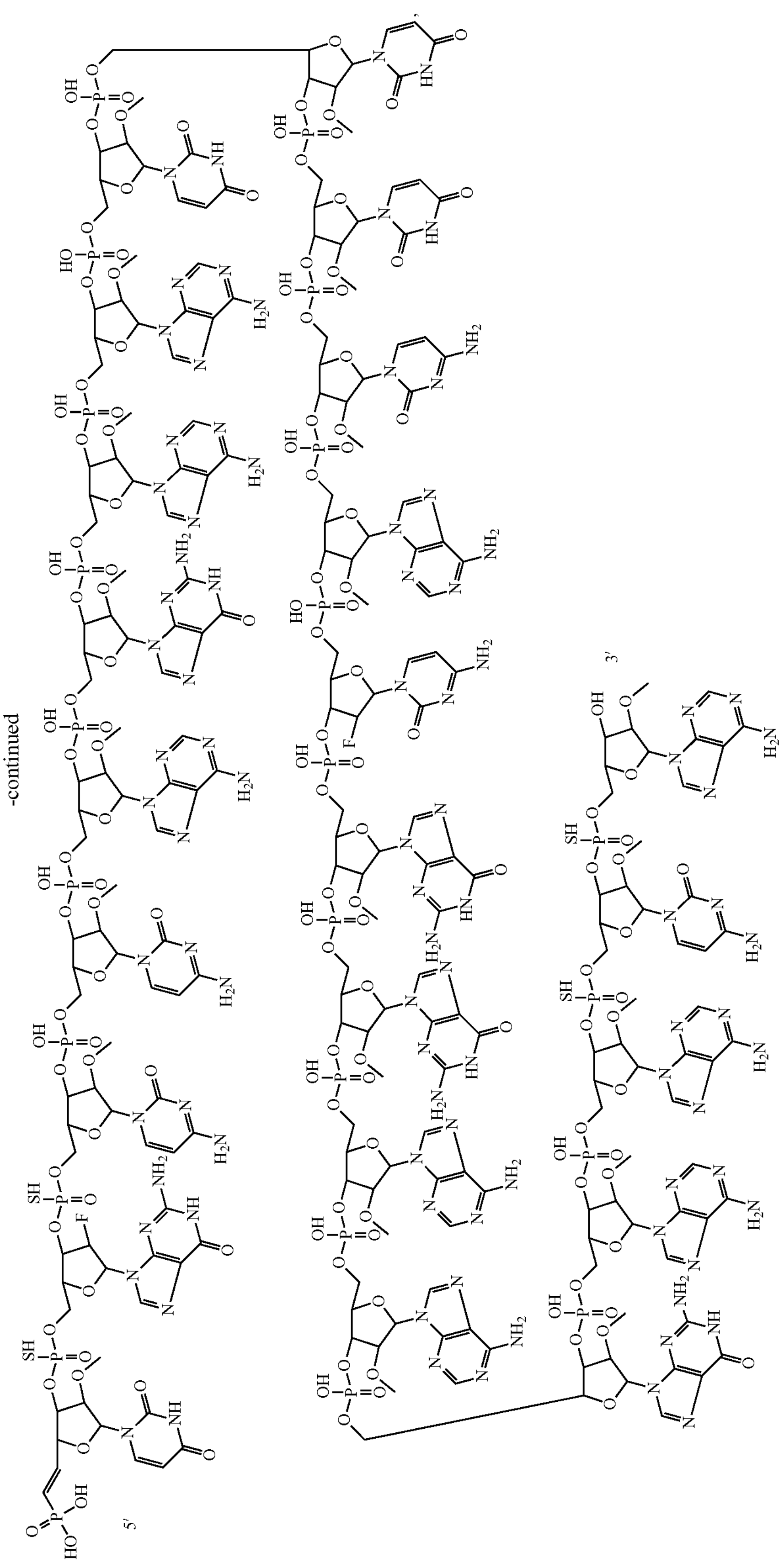
5′
3′
Antisense Strand or a pharmaceutically acceptable salt thereof, wherein $R^1$ is covalently linked to $R^2$ at attachment point A. In some embodiments, n1 is an integer (e.g., one or greater) representing the number of instances of $R^1$ in each complex. In some embodiments, $R^2$ comprises an antibody comprising a sequence as set forth in Table 2. For example, in some embodiments, $R^2$ comprises an antibody comprising a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14; and/or comprising a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5, or 11, and a light chain complementarity determining region 3 (CDR-L3) comprising a sequence as set forth in SEQ ID NO: 6 or 16. In some embodiments, $R^2$ comprises an antibody comprising a heavy chain variable region (VH) comprising an amino acid sequence at least 85% (e.g., at least 95%) identical to SEQ ID NO: 17 and/or comprising a light chain variable region (VL) comprising an amino acid sequence at least 85% (e.g., at least 95%) identical to SEQ ID NO: 18. In some embodiments, $R^2$ comprises an antibody comprising a VH comprising the amino acid sequence of SEQ ID NO: 17 and/or comprising a VL comprising the amino acid sequence of SEQ ID NO: 18. In some embodiments, $R^2$ comprises an antibody comprising a heavy chain comprising an amino acid sequence at least 85% (e.g., at least 95%) identical to SEQ ID NO: 19 and/or comprising a light chain comprising an amino acid sequence at least 85% (e.g., at least 95%) identical to SEQ ID NO: 20. In some embodiments, $R^2$ comprises an antibody comprising a heavy chain comprising the amino acid sequence of SEQ ID NO: 19 and/or comprising a light chain comprising the amino acid sequence of SEQ ID NO: 20. In some embodiments, $R^2$ comprises an antibody that is a Fab fragment, a full-length IgG, a Fab' fragment, a $F(ab')_2$ fragment, an scFv, or an Fv. In some embodiments, $R^2$ comprises an antibody that is a Fab fragment.

In some embodiments, complexes provided herein (e.g., in compositions or formulations described herein) comprise a structure of the formula (Id):

(Id)
3′-mA*mC*mAmAmGmAmAmGmGfCmAmCmUmUmUmAmAmGmAmCmC*fG*mU-5′-VP Antisense (SEQ ID NO: 22)
5′-mU*mU*mCmUfUmCmCmGfUfGfAmAmAfUmUmCmUmGfG*mC*mA-3′ Sense (SEQ ID NO: 21)
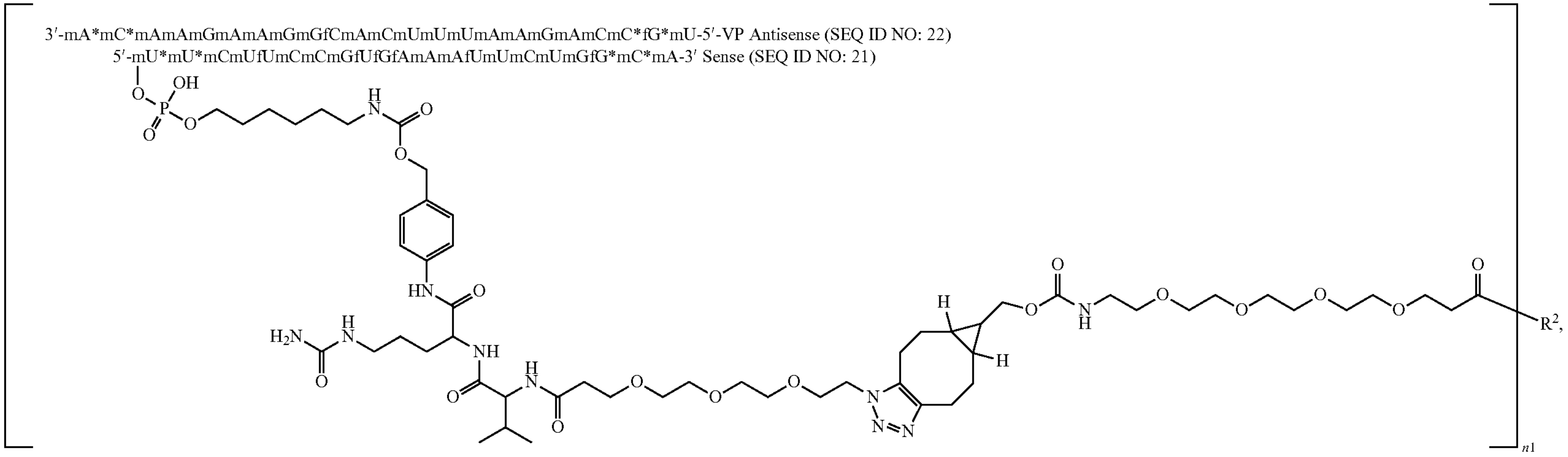

or a pharmaceutically acceptable salt thereof, wherein: mA, mC, mG, and mU are 2'-O-methyl adenosine, 2'-O-methyl cytidine, 2'-O-methyl guanosine, and 2'-O-methyl uridine, respectively;

fA, fC, fG, and fU are 2'-fluoro adenosine, 2'-fluoro cytidine, 2'-fluoro guanosine, and 2'-fluoro uridine, respectively; * between two nucleosides represents a phosphorothioate linkage; the absence of "*" between two nucleosides represents a phosphodiester internucleoside linkage; and "VP" represents 5'-(E)-Vinylphosphonate; and wherein the oligonucleotide is an RNAi oligonucleotide (e.g., siRNA) comprising an antisense strand comprising a nucleobase sequence of UGCCAGAAUUUCACGGAAGAACA (SEQ ID NO: 22) and a sense strand comprising a nucleobase sequence of UUCUUCCGUGAAAUUCUGGCA (SEQ ID NO: 21);

wherein $R^2$ comprises an antibody comprising a sequence as set forth in Table 2; wherein n1 is an integer (e.g., one or greater) representing the number of instances of the group enclosed by square brackets, wherein each instance of the group enclosed by square brackets is covalently linked to a different amino acid residue of the antibody, optionally wherein each different amino acid residue is a lysine. In some embodiments, $R^2$ comprises an antibody comprising a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14; and/or comprising a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5, or 11, and a light chain complementarity determining region 3 (CDR-L3) comprising a sequence as set forth in SEQ ID NO: 6 or 16. In some embodiments, $R^2$ 12030680.1 comprises an antibody comprising a heavy chain variable region (VH) comprising an amino acid sequence at least 85% (e.g., at least 95%) identical to SEQ ID NO: 17 and/or comprising a light chain variable region (VL) comprising an amino acid sequence at least 85% (e.g., at least 95%) identical to SEQ ID NO: 18. In some embodiments, $R^2$ comprises an antibody comprising a VH comprising the amino acid sequence of SEQ ID NO: 17 and/or comprising a VL comprising the amino acid sequence of SEQ ID NO: 18. In some embodiments, $R^2$ comprises an antibody comprising a heavy chain comprising an amino acid sequence at least 85% (e.g., at least 95%) identical to SEQ ID NO: 19 and/or comprising a light chain comprising an amino acid sequence at least 85% (e.g., at least 95%) identical to SEQ ID NO: 20. In some embodiments, $R^2$ comprises an antibody comprising a heavy chain comprising the amino acid sequence of SEQ ID NO: 19 and/or comprising a light chain comprising the amino acid sequence of SEQ ID NO: 20. In some embodiments, $R^2$ comprises an antibody that is a Fab fragment, a full-length IgG, a Fab' fragment, a $F(ab')_2$ fragment, an scFv, or an Fv. In some embodiments, $R^2$ comprises an antibody that is a Fab fragment.

Each of formula (Ia), formula (Ib), formula (Ic) and formula (Id), as depicted herein, include one or more phosphorous containing groups (e.g., phosphate group, phosphorothioate group, phosphodiester group) that are protonated. In certain embodiments, the phosphorous containing groups (e.g., phosphate group, phosphorothioate group, phosphodiester group) are as depicted, i.e., protonated. In certain embodiments, the phosphorous containing groups (e.g., phosphate group, phosphorothioate group, phosphodiester group) groups are deprotonated, i.e., in salt form. The extent to which the phosphorous containing groups are protonated or deprotonated will vary depending on the chemical environment of the complexes (e.g., pH, presence of basic media, etc.). For example, in a composition (e.g., formulation) described herein that has a pH of about 7.5, or at a physiological pH, complexes comprising a structure of formula (Ia), formula (Ib), formula (Ic) and formula (Id) may comprise one or more deprotonated phosphorous containing groups (e.g., a phosphate group, a phosphorothioate group, a phosphodiester group).

In some embodiments, complexes described herein comprise a structure of formula (A):

(A)

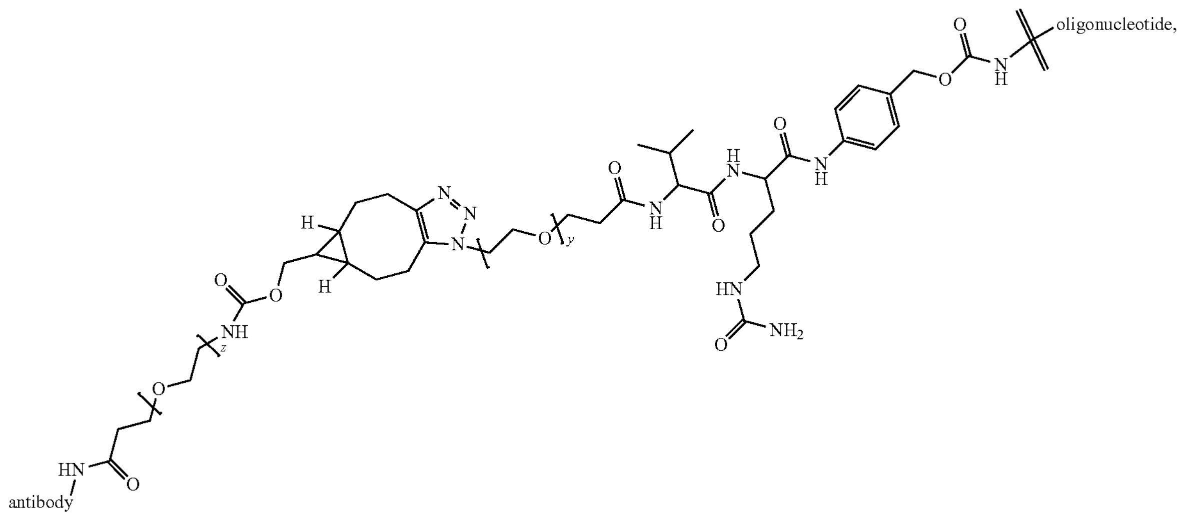

wherein y is 0-15 (e.g., 3), z is 0-15 (e.g., 4), and wherein

represents an indirect or direct linkage. In some embodiments, the amide shown adjacent the antibody (e.g., anti-TfR1 antibody) in the structure (A) results from a reaction with an amine of the antibody, such as a lysine epsilon amine. In some embodiments, a complex described herein comprises an anti-TfR1 antibody (e.g., an anti-TfR1 Fab) covalently linked via a lysine of the antibody to the 5' end of an oligonucleotide (e.g., an RNAi oligonucleotide). In some embodiments, the antibody comprises a sequence as set forth in Table 2. For example, in some embodiments, the antibody comprises a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14; and/or comprises a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5, or 11, and a light chain complementarity determining region 3 (CDR-L3) comprising a sequence as set forth in SEQ ID NO: 6 or 16. In some embodiments, the antibody comprises a heavy chain variable region (VH) comprising an amino acid sequence at least 85% (e.g., at least 95%) identical to SEQ ID NO: 17 and/or comprises a light chain variable region (VL) comprising an amino acid sequence at least 85% (e.g., at least 95%) identical to SEQ ID NO: 18. In some embodiments, the antibody comprises a VH comprising the amino acid sequence of SEQ ID NO: 17 and/or comprises a VL comprising the amino acid sequence of SEQ ID NO: 18. In some embodiments, the antibody comprises a heavy chain comprising an amino acid sequence at least 85% (e.g., at least 95%) identical to SEQ ID NO: 19 and/or comprises a light chain comprising an amino acid sequence at least 85% (e.g., at least 95%) identical to SEQ ID NO: 20. In some embodiments, the antibody comprises a heavy chain comprising the amino acid sequence of SEQ ID NO: 19 and/or comprises a light chain comprising the amino acid sequence of SEQ ID NO: 20. In some embodiments, the antibody is a Fab fragment, a full-length IgG, a Fab' fragment, a $F(ab')_2$ fragment, an scFv, or an Fv. In some embodiments, the antibody is a Fab fragment.

Antibodies

In some embodiments, complexes described herein comprise an antibody that binds human transferrin receptor 1 (TfR1). An example human TfR1 amino acid sequence, corresponding to NCBI sequence NP_003225.2 (transferrin receptor protein 1 isoform 1, *Homo sapiens*) is as follows:

(SEQ ID NO: 23)

```
MMDQARSAFSNLFGGEPLSYTRFSLARQVDGDNSHVEMKLAVDEEENADN
NTKANVTKPKRCSGSICYGTIAVIVFFLIGFMIGYLGYCKGVEPKTECER
LAGTESPVREEPGEDFPAARRLYWDDLKRKLSEKLDSTDFTGTIKLLNEN
SYVPREAGSQKDENLALYVENQFREFKLSKVWRDQHFVKIQVKDSAQNSV
IIVDKNGRLVYLVENPGGYVAYSKAATVTGKLVHANFGTKKDFEDLYTPV
NGSIVIVRAGKITFAEKVANAESLNAIGVLIYMDQTKFPIVNAELSFFGH
AHLGTGDPYTPGFPSFNHTQFPPSRSSGLPNIPVQTISRAAAEKLFGNME
GDCPSDWKTDSTCRMVTSESKNVKLTVSNVLKEIKILNIFGVIKGFVEPD
HYVVVGAQRDAWGPGAAKSGVGTALLLKLAQMFSDMVLKDGFQPSRSIIF
ASWSAGDFGSVGATEWLEGYLSSLHLKAFTYINLDKAVLGTSNFKVSASP
LLYTLIEKTMQNVKHPVTGQFLYQDSNWASKVEKLTLDNAAFPFLAYSGI
PAVSFCFCEDTDYPYLGTTMDTYKELIERIPELNKVARAAAEVAGQFVIK
LTHDVELNLDYERYNSQLLSFVRDLNQYRADIKEMGLSLQWLYSARGDFF
RATSRLTTDFGNAEKTDRFVMKKLNDRVMRVEYHFLSPYVSPKESPFRHV
```

-continued

FWGSGSHTLPALLENLKLRKQNNGAFNETLFRNQLALATWTIQGAANALS

GDVWDIDNEF.

Table 2 provides examples of sequences of an anti-TfR1 antibody useful in the complexes provided herein.

TABLE 2

Examples of anti-TfR1 antibody sequences

| Feature | IMGT | Kabat | Chothia |
|---|---|---|---|
| CDR-H1 | GYSITSGYY (SEQ ID NO: 1) | SGYYWN (SEQ ID NO: 7) | GYSITSGY (SEQ ID NO: 12) |
| CDR-H2 | ITFDGAN (SEQ ID NO: 2) | YITFDGANNYNPSLKN (SEQ ID NO: 8) | FDG (SEQ ID NO: 13) |
| CDR-H3 | TRSSYDYDVL DY (SEQ ID NO: 3) | SSYDYDVLDY (SEQ ID NO: 9) | SYDYDVLD (SEQ ID NO: 14) |
| CDR-L1 | QDISNF (SEQ ID NO: 4) | RASQDISNFLN (SEQ ID NO: 10) | SQDISNF (SEQ ID NO: 15) |
| CDR-L2 | YTS (SEQ ID NO: 5) | YTSRLHS (SEQ ID NO: 11) | YTS (SEQ ID NO: 5) |
| CDR-L3 | QQGHTLPYT (SEQ ID NO: 6) | QQGHTLPYT (SEQ ID NO: 6) | GHTLPY (SEQ ID NO: 16) |
| VH | QVQLQESGPGLVKPSQTLSLTCTVTGYSITSGYYWNWIRQPPGKGLEWI GYITFDGANNYNPSLKNRVSISRDTSKNQFSLKLSSVTAEDTATYYCTR SSYDYDVLDYWGQGTTVTVSS (SEQ ID NO: 17) | | |
| VL | DIQMTQSPSSLSASVGDRVTITCRASQDISNFLNWYQQKPGQPVKLLIY YTSRLHSGVPSRFSGSGSGTDFTLTISSLQPEDFATYYCQQGHTLPYTFG QGTKLEIK (SEQ ID NO: 18) | | |
| Fab HC | QVQLQESGPGLVKPSQTLSLTCTVTGYSITSGYYWNWIRQPPGKGLEWI GYITFDGANNYNPSLKNRVSISRDTSKNQFSLKLSSVTAEDTATYYCTR SSYDYDVLDYWGQGTTVTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKKVEPKSCDKTHT (SEQ ID NO: 19) | | |
| Fab LC | DIQMTQSPSSLSASVGDRVTITCRASQDISNFLNWYQQKPGQPVKLLIY YTSRLHSGVPSRFSGSGSGTDFTLTISSLQPEDFATYYCQQGHTLPYTFG QGTKLEIKRTVAAPSVFIFPPSDEQLKSGTASVVCLLNNFYPREAKVQW KVDNALQSGNSQESVTEQDSKDSTYSLSSTLTLSKADYEKHKVYACEV THQGLSSPVTKSFNRGEC (SEQ ID NO: 20) | | |

In some embodiments, the anti-TfR1 antibody of the present disclosure comprises a heavy chain complementarity determining region 1 (CDR-H1) of SEQ ID NO: 1 (according to the IMGT definition system), a heavy chain complementarity determining region 2 (CDR-H2) of SEQ ID NO: 2 (according to the IMGT definition system), a heavy chain complementarity determining region 3 (CDR-H3) of SEQ ID NO: 3 (according to the IMGT definition system), a light chain complementarity determining region 1 (CDR-L1) of SEQ ID NO: 4 (according to the IMGT definition system), a light chain complementarity determining region 2 (CDR-L2) of SEQ ID NO: 5 (according to the IMGT definition system), and a light chain complementarity determining region 3 (CDR-L3) of SEQ ID NO: 6 (according to the IMGT definition system).

In some embodiments, the anti-TfR1 antibody of the present disclosure comprises a heavy chain complementarity determining region 1 (CDR-H1) of SEQ ID NO: 7 (according to the Kabat definition system), a heavy chain complementarity determining region 2 (CDR-H2) of SEQ ID NO: 8 (according to the Kabat definition system), a heavy chain complementarity determining region 3 (CDR-H3) of SEQ ID NO: 9 (according to the Kabat definition system), a light chain complementarity determining region 1 (CDR-L1) of SEQ ID NO: 10 (according to the Kabat definition system), a light chain complementarity determining region 2 (CDR-L2) of SEQ ID NO: 11 (according to the Kabat definition system), and a light chain complementarity determining region 3 (CDR-L3) of SEQ ID NO: 6 (according to the Kabat definition system).

In some embodiments, the anti-TfR1 antibody of the present disclosure comprises a heavy chain complementarity determining region 1 (CDR-H1) of SEQ ID NO: 12 (according to the Chothia definition system), a heavy chain complementarity determining region 2 (CDR-H2) of SEQ ID NO: 13 (according to the Chothia definition system), a heavy chain complementarity determining region 3 (CDR-H3) of SEQ ID NO: 14 (according to the Chothia definition system), a light chain complementarity determining region 1 (CDR-L1) of SEQ ID NO: 15 (according to the Chothia definition system), a light chain complementarity determining region 2 (CDR-L2) of SEQ ID NO: 5 (according to the Chothia definition system), and a light chain complementarity determining region 3 (CDR-L3) of SEQ ID NO: 16 (according to the Chothia definition system).

In some embodiments, the anti-TfR1 antibody of the present disclosure comprises a heavy chain variable region (VH) containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VH comprising the amino acid sequence of SEQ ID NO: 17. Alternatively or in addition (e.g., in addition), the anti-TfR1 antibody of the present disclosure comprises a light chain variable region (VL) containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VL comprising the amino acid sequence of SEQ ID NO: 18.

In some embodiments, the anti-TfR1 antibody of the present disclosure comprises a VH comprising an amino acid sequence that is at least 75% (e.g., 75%, 80%, 85%, 90%, 95%, 98%, or 99%) identical in the framework regions to the VH comprising the amino acid sequence of SEQ ID NO: 17. Alternatively or in addition (e.g., in addition), in some embodiments, the anti-TfR1 antibody of the present disclosure comprises a VL comprising an amino acid sequence that is at least 75% (e.g., 75%, 80%, 85%, 90%, 95%, 98%, or 99%) identical in the framework regions to the VL comprising the amino acid sequence of SEQ ID NO: 18.

In some embodiments, the anti-TfR1 antibody of the present disclosure comprises a VH comprising the amino acid sequence of SEQ ID NO: 17. Alternatively or in addition (e.g., in addition), in some embodiments, the anti-TfR1 antibody of the present disclosure comprises a VL comprising the amino acid sequence of SEQ ID NO: 18.

In some embodiments, the anti-TfR1 antibody of the present disclosure comprises a heavy chain comprising an amino acid sequence least 75% (e.g., 75%, 80%, 85%, 90%, 95%, 98%, or 99%) identical to the amino acid sequence of SEQ ID NO: 19. Alternatively or in addition (e.g., in addition), the anti-TfR1 antibody of the present disclosure comprises a light chain comprising an amino acid sequence least 75% (e.g., 75%, 80%, 85%, 90%, 95%, 98%, or 99%) identical to the amino acid sequence of SEQ ID NO: 20. In some embodiments, the anti-TfR1 antibody of the present disclosure is a Fab that comprises a heavy chain comprising an amino acid sequence least 75% (e.g., 75%, 80%, 85%, 90%, 95%, 98%, or 99%) identical to the amino acid sequence of SEQ ID NO: 19. Alternatively or in addition (e.g., in addition), the anti-TfR1 antibody of the present disclosure is a Fab that comprises a light chain comprising an amino acid sequence least 75% (e.g., 75%, 80%, 85%, 90%, 95%, 98%, or 99%) identical to the amino acid sequence of SEQ ID NO: 20.

In some embodiments, the anti-TfR1 antibody of the present disclosure comprises a heavy chain comprising the amino acid sequence of SEQ ID NO: 19. Alternatively or in addition (e.g., in addition), the anti-TfR1 antibody of the present disclosure comprises a light chain comprising the amino acid sequence of SEQ ID NO: 20. In some embodiments, the anti-TfR1 antibody of the present disclosure is a Fab that comprises a heavy chain comprising an amino acid sequence of SEQ ID NO: 19. Alternatively or in addition (e.g., in addition), the anti-TfR1 antibody of the present disclosure is a Fab that comprises a light chain comprising the amino acid sequence of SEQ ID NO: 20.

In some embodiments, the anti-TfR1 antibody provided herein may have one or more post-translational modifications. In some embodiments, N-terminal cyclization, also called pyroglutamate formation (pyro-Glu), may occur in the antibody at N-terminal Glutamate (Glu) and/or Glutamine (Gln) residues during production. As such, it should be appreciated that an antibody specified as having a sequence comprising an N-terminal glutamate or glutamine residue encompasses antibodies that have undergone pyroglutamate formation resulting from a post-translational modification. In some embodiments, pyroglutamate formation occurs in a heavy chain sequence. In some embodiments, pyroglutamate formation occurs in a light chain sequence.

Oligonucleotides

In some embodiments, the oligonucleotides provided herein are useful for targeting DUX4 (e.g., for reducing expression or activity of DUX4, such as the level of DUX4 protein and/or mRNA). In some embodiments, the oligonucleotides are designed to cause RNAi mediated degradation of DUX4 mRNA. In some embodiments, the oligonucleotide is an RNAi oligonucleotide. In some embodiments, the oligonucleotide provided herein comprises an antisense strand that comprises a region of complementarity to a DUX4 RNA. In some embodiments, the oligonucleotide provided herein further comprises a sense strand that forms a double-stranded oligonucleotide (e.g., siRNA). In some embodiments, the oligonucleotide is designed to have desirable bioavailability and/or serum-stability properties. In some embodiments, the oligonucleotide is designed to have desirable binding affinity properties. In some embodiments, the oligonucleotide is designed to have desirable toxicity profiles. In some embodiments, the oligonucleotide is designed to have low-complement activation and/or cytokine induction properties. In some embodiments, the oligonucleotide is designed to have reduced off-target effects, e.g., compared to other known DUX4-targeting siRNAs.

Examples of oligonucleotides useful for targeting DUX4 are provided in U.S. Pat. No. 9,988,628, published on Feb. 2, 2017, entitled "AGENTS USEFUL IN TREATING FACIOSCAPULOHUMERAL MUSCULAR DYSTROPHY"; U.S. Pat. No. 9,469,851, published Oct. 30, 2014, entitled "RECOMBINANT VIRUS PRODUCTS AND METHODS FOR INHIBITING EXPRESSION OF DUX4"; US Patent Application Publication 20120225034, published on Sep. 6, 2012, entitled "AGENTS USEFUL IN TREATING FACIOSCAPULOHUMERAL MUSCULAR DYSTROPHY"; PCT Patent Application Publication Number WO 2013/120038, published on Aug. 15, 2013, entitled "MORPHOLINO TARGETING DUX4 FOR TREATING FSHD"; Chen et al., "Morpholino-mediated Knockdown of DUX4 Toward Facioscapulohumeral Muscular Dystrophy Therapeutics," Molecular Therapy, 2016, 24:8, 1405-1411; and Ansseau et al., "Antisense Oligonucleotides Used to Target the DUX4 mRNA as Therapeutic Approaches in Facioscapulohumeral Muscular Dystrophy (FSHD)," Genes, 2017, 8, 93; the contents of each of which are incorporated herein in their entireties. In some embodiments, oligonucleotides may comprise a region of complementarity to a sequence as set forth as: Human DUX4, corresponding to NCBI sequence NM_001293798.2 (SEQ ID NO: 25) or NCBI Sequence: NM_001306068.3 (SEQ ID NO: 26) as below and/or (e.g., and) Mouse DUX4, corresponding to NCBI sequence NM_001081954.1 (SEQ ID NO: 27), as below. Other non-limiting exemplary human DUX4 RNA include NCBI Sequence: NM_033178, GenBank accession numbers FJ439133, AF117653, HM101229, HM101230, HM101232, HM101233, HM101234, HM101235, HM101240, HM101241, HM101242, HM101243, HM101244, HM101245, HM101246, HM101247, HM101248, HM101249, HM101250, HM101251 and HM190160, HM190161, HM190162, HM190163, HM190164, HM190165, HM190166, HM190167, HM190168, HM190169, HM190170, HM190171, HM190172, HM190173, HM190174, HM190175, HM190176, HM190177, HM190178, HM190179, HM190180, HM190181, HM190182, HM190183, HM190184, HM190185, HM190186, HM190187, HM190188, HM190189, HM190190, HM190191, HM190192, HM190193, HM190194, HM190195, HM190196, each of which is incorporated herein by reference. In some embodiments, the oligonucleotide may have a region of complementarity to a hypomethylated, contracted D4Z4 repeat, as in Daxinger, et al., "Genetic and Epigenetic Contributors to FSHD," published in Curr Opin Genet Dev in 2015, Lim J-W, et al., DICER/AGO-dependent epigenetic silencing of D4Z4 repeats enhanced by exogenous siRNA suggests mechanisms and therapies for FSHD Hum Mol Genet. 2015 Sep. 1; 24(17): 4817-4828, the contents of each of which are incorporated in their entireties.

In some embodiments, oligonucleotides may comprise a region of complementarity to a sequence set forth as follows, which is an example human DUX4 gene sequence (NM_001293798.2) (SEQ ID NO: 25):

```
ATGGCCCTCCCGACACCCTCGGACAGCACCCTCCCCGCGGAAGCCCGGGG
ACGAGGACGGCGACGGAGACTCGTTTGGACCCCGAGCCAAAGCGAGGCCC
TGCGAGCCTGCTTTGAGCGGAACCCGTACCCGGGCATCGCCACCAGAGAA
CGGCTGGCCCAGGCCATCGGCATTCCGGAGCCCAGGGTCCAGATTTGGTT
TCAGAATGAGAGGTCACGCCAGCTGAGGCAGCACCGGCGGGAATCTCGGC
CCTGGCCCGGGAGACGCGGCCCGCCAGAAGGCCGGCGAAAGCGGACCGCC
GTCACCGGATCCCAGACCGCCCTGCTCCTCCGAGCCTTTGAGAAGGATCG
CTTTCCAGGCATCGCCGCCCGGGAGGAGCTGGCCAGAGAGACGGGCCTCC
CGGAGTCCAGGATTCAGATCTGGTTTCAGAATCGAAGGGCCAGGCACCCG
GGACAGGGTGGCAGGGCGCCCGCGCAGGCAGGCGGCCTGTGCAGCGCGGC
CCCCGGCGGGGGTCACCCTGCTCCCTCGTGGGTCGCCTTCGCCCACACCG
GCGCGTGGGGAACGGGGCTTCCCGCACCCCACGTGCCCTGCGCGCCTGGG
GCTCTCCCACAGGGGGCTTTCGTGAGCCAGGCAGCGAGGGCCGCCCCCGC
GCTGCAGCCCAGCCAGGCCGCGCCGGCAGAGGGGATCTCCCAACCTGCCC
CGGCGCGCGGGGATTTCGCCTACGCCGCCCCGGCTCCTCCGGACGGGGCG
CTCTCCCACCCTCAGGCTCCTCGCTGGCCTCCGCACCCGGGCAAAAGCCG
GGAGGACCGGGACCCGCAGCGCGACGGCCTGCCGGGCCCCTGCGCGGTGG
CACAGCCTGGGCCCGCTCAAGCGGGGCCGCAGGGCCAAGGGGTGCTTGCG
CCACCCACGTCCCAGGGGAGTCCGTGGTGGGGCTGGGGCCGGGGTCCCCA
GGTCGCCGGGGCGGCGTGGGAACCCCAAGCCGGGGCAGCTCCACCTCCCC
AGCCCGCGCCCCCGGACGCCTCCGCCTCCGCGCGGCAGGGGCAGATGCAA
GGCATCCCGGCGCCCTCCCAGGCGCTCCAGGAGCCGGCGCCCTGGTCTGC
ACTCCCCTGCGGCCTGCTGCTGGATGAGCTCCTGGCGAGCCCGGAGTTTC
TGCAGCAGGCGCAACCTCTCCTAGAAACGGAGGCCCCGGGGGAGCTGGAG
GCCTCGGAAGAGGCCGCCTCGCTGGAAGCACCCCTCAGCGAGGAAGAATA
CCGGGCTCTGCTGGAGGAGCTTTAGGACGCGGGGTCTAGGCCCGGTGAGA
GACTCCACACCGCGGAGAACTGCCATTCTTTCCTGGGCATCCCGGGGATC
CCAGAGCCGGCCCAGGTACCAGCAGACCTGCGCGCAGTGCGCACCCCGGC
```

-continued

```
TGACGTGCAAGGGAGCTCGCTGGCCTCTCTGTGCCCTTGTTCTTCCGTGA
AATTCTGGCTGAATGTCTCCCCCCACCTTCCGACGCTGTCTAGGCAAACC
TGGATTAGAGTTACATCTCCTGGATGATTAGTTCAGAGATATATTAAAAT
GCCCCCTCCCTGTGGATCCTATAG
```

In some embodiments, oligonucleotides may comprise a region of complementarity to a sequence set forth as follows, which is an example human DUX4 gene sequence (NM_001306068.3) (SEQ ID NO: 26):

```
ATGGCCCTCCCGACACCCTCGGACAGCACCCTCCCCGCGGAAGCCCGGGG
ACGAGGACGGCGACGGAGACTCGTTTGGACCCCGAGCCAAAGCGAGGCCC
TGCGAGCCTGCTTTGAGCGGAACCCGTACCCGGGCATCGCCACCAGAGAA
CGGCTGGCCCAGGCCATCGGCATTCCGGAGCCCAGGGTCCAGATTTGGTT
TCAGAATGAGAGGTCACGCCAGCTGAGGCAGCACCGGCGGGAATCTCGGC
CCTGGCCCGGGAGACGCGGCCCGCCAGAAGGCCGGCGAAAGCGGACCGCC
GTCACCGGATCCCAGACCGCCCTGCTCCTCCGAGCCTTTGAGAAGGATCG
CTTTCCAGGCATCGCCGCCCGGGAGGAGCTGGCCAGAGAGACGGGCCTCC
CGGAGTCCAGGATTCAGATCTGGTTTCAGAATCGAAGGGCCAGGCACCCG
GGACAGGGTGGCAGGGCGCCCGCGCAGGCAGGCGGCCTGTGCAGCGCGGC
CCCCGGCGGGGGTCACCCTGCTCCCTCGTGGGTCGCCTTCGCCCACACCG
GCGCGTGGGGAACGGGGCTTCCCGCACCCCACGTGCCCTGCGCGCCTGGG
GCTCTCCCACAGGGGGCTTTCGTGAGCCAGGCAGCGAGGGCCGCCCCCGC
GCTGCAGCCCAGCCAGGCCGCGCCGGCAGAGGGGATCTCCCAACCTGCCC
CGGCGCGCGGGGATTTCGCCTACGCCGCCCCGGCTCCTCCGGACGGGGCG
CTCTCCCACCCTCAGGCTCCTCGGTGGCCTCCGCACCCGGGCAAAAGCCG
GGAGGACCGGGACCCGCAGCGCGACGGCCTGCCGGGCCCCTGCGCGGTGG
CACAGCCTGGGCCCGCTCAAGCGGGGCCGCAGGGCCAAGGGGTGCTTGCG
CCACCCACGTCCCAGGGGAGTCCGTGGTGGGGCTGGGGCCGGGGTCCCCA
GGTCGCCGGGGCGGCGTGGGAACCCCAAGCCGGGGCAGCTCCACCTCCCC
AGCCCGCGCCCCCGGACGCCTCCGCCTCCGCGCGGCAGGGGCAGATGCAA
GGCATCCCGGCGCCCTCCCAGGCGCTCCAGGAGCCGGCGCCCTGGTCTGC
ACTCCCCTGCGGCCTGCTGCTGGATGAGCTCCTGGCGAGCCCGGAGTTTC
TGCAGCAGGCGCAACCTCTCCTAGAAACGGAGGCCCCGGGGGAGCTGGAG
GCCTCGGAAGAGGCCGCCTCGCTGGAAGCACCCCTCAGCGAGGAAGAATA
CCGGGCTCTGCTGGAGGAGCTTTAGGACGCGGGGTTGGGACGGGGTCGGG
TGGTTCGGGGCAGGGCGGTGGCCTCTCTTTCGCGGGGAACACCTGGCTGG
CTACGGAGGGGCGTGTCTCCGCCCCGCCCCCTCCACCGGGCTGACCGGCC
TGGGATTCCTGCCTTCTAGGTCTAGGCCCGGTGAGAGACTCCACTCCGCG
GAGAACTGCCTTTCTTTCCTGGGCATCCCGGGGATCCCAGAGCCGGCCCA
GGTACCAGCAGACCTGCGCGCAGTGCGCACCCCGGCTGACGTGCAAGGGA
GCTCGCTGGCCTCTCTGTGCCCTTGTTCTTCCGTGAAATTCTGGCTGAAT
GTCTCCCCCCACCTTCCGACGCTGTCTAGGCAAACCTGGATTAGAGTTAC
```

-continued

ATCTCCTGGATGATTAGTTCAGAGATATATTAAAATGCCCCCTCCCTGTG

GATCCTATAG

In some embodiments, oligonucleotides may comprise a region of complementarity to a sequence set forth as follows, which is an example mouse DUX4 gene sequence (SEQ ID NO: 27) (NM_001081954.1):

ATGGCAGAAGCTGGCAGCCCTGTTGGTGGCAGTGGTGTGGCACGGGAATC

CCGGCGGCGCAGGAAGACGGTTTGGCAGGCCTGGCAAGAGCAGGCCCTGC

TATCAACTTTCAAGAAGAAGAGATACCTGAGCTTCAAGGAGAGGAAGGAG

CTGGCCAAGCGAATGGGGGTCTCAGATTGCCGCATCCGCGTGTGGTTTCA

GAACCGCAGGAATCGCAGTGGAGAGGAGGGGCATGCCTCAAAGAGGTCCA

TCAGAGGCTCCAGGCGGCTAGCCTCGCCACAGCTCCAGGAAGAGCTTGGA

TCCAGGCCACAGGGTAGAGGCATGCGCTCATCTGGCAGAAGGCCTCGCAC

TCGACTCACCTCGCTACAGCTCAGGATCCTAGGGCAAGCCTTTGAGAGGA

ACCCACGACCAGGCTTTGCTACCAGGGAGGAGCTGGCGCGTGACACAGGG

TTGCCCGAGGACACGATCCACATATGGTTTCAAAACCGAAGAGCTCGGCG

GCGCCACAGGAGGGGCAGGCCCACAGCTCAAGATCAAGACTTGCTGGCGT

CACAAGGGTCGGATGGGGCCCCTGCAGGTCCGGAAGGCAGAGAGCGTGAA

GGTGCCCAGGAGAACTTGTTGCCACAGGAAGAAGCAGGAAGTACGGGCAT

GGATACCTCGAGCCCTAGCGACTTGCCCTCCTTCTGCGGAGAGTCCCAGC

CTTTCCAAGTGGCACAGCCCCGTGGAGCAGGCCAACAAGAGGCCCCCACT

CGAGCAGGCAACGCAGGCTCTCTGGAACCCCTCCTTGATCAGCTGCTGGA

TGAAGTCCAAGTAGAAGAGCCTGCTCCAGCCCCTCTGAATTTGGATGGAG

ACCCTGGTGGCAGGGTGCATGAAGGTTCCCAGGAGAGCTTTTGGCCACAG

GAAGAAGCAGGAAGTACAGGCATGGATACTTCTAGCCCCAGCGACTCAAA

CTCCTTCTGCAGAGAGTCCCAGCCTTCCCAAGTGGCACAGCCCTGTGGAG

CGGGCCAAGAAGATGCCCGCACTCAAGCAGACAGCACAGGCCCTCTGGAA

CTCCTCCTCCTTGATCAACTGCTGGACGAAGTCCAAAAGGAAGAGCATGT

GCCAGTCCCACTGGATTGGGGTAGAAATCCTGGCAGCAGGGAGCATGAAG

GTTCCCAGGACAGCTTACTGCCCCTGGAGGAAGCAGTAAATTCGGGCATG

GATACCTCGATCCCTAGCATCTGGCCAACCTTCTGCAGAGAATCCCAGCC

TCCCCAAGTGGCACAGCCCTCTGGACCAGGCCAAGCACAGGCCCCCACTC

AAGGTGGGAACACGGACCCCCTGGAGCTCTTCCTCTATCAACTGTTGGAT

GAAGTCCAAGTAGAAGAGCATGCTCCAGCCCCTCTGAATTGGGATGTAGA

TCCTGGTGGCAGGGTGCATGAAGGTTCGTGGGAGAGCTTTTGGCCACAGG

AAGAAGCAGGAAGTACAGGCCTGGATACTTCAAGCCCCAGCGACTCAAAC

TCCTTCTTCAGAGAGTCCAAGCCTTCCCAAGTGGCACAGCGCCGTGGAGC

GGGCCAAGAAGATGCCCGCACTCAAGCAGACAGCACAGGCCCTCTGGAAC

TCCTCCTCTTTGATCAACTGCTGGACGAAGTCCAAAAGGAAGAGCATGTG

CCAGCCCCACTGGATTGGGGTAGAAATCCTGGCAGCATGGAGCATGAAGG

TTCCCAGGACAGCTTACTGCCCCTGGAGGAAGCAGCAAATTCGGGCAGGG

-continued

ATACCTCGATCCCTAGCATCTGGCCAGCCTTCTGCAGAAAATCCCAGCCT

CCCCAAGTGGCACAGCCCTCTGGACCAGGCCAAGCACAGGCCCCCATTCA

AGGTGGGAACACGGACCCCCTGGAGCTCTTCCTTGATCAACTGCTGACCG

AAGTCCAACTTGAGGAGCAGGGGCCTGCCCCTGTGAATGTGGAGGAAACA

TGGGAGCAAATGGACACAACACCTATCTGCCTCTCACTTCAGAAGAATAT

CAGACTCTTCTAGATATGCTCTGA

In some embodiments, an oligonucleotide may comprise a region of complementarity to DUX4 sequences of multiple species, e.g., selected from human, mouse and non-human species (e.g., cynomolgus monkey).

In some embodiments, an oligonucleotide provided herein is a double-stranded RNAi oligonucleotide (e.g., siRNA) targeting DUX4. In some embodiments, a DUX4-targeting RNAi oligonucleotide is 7, 8, 9, 10, 11, 12, 13, 14, 15, 16, 17, 18, 19, 20, 21, 22, 23, 24, 25, 26, 27, 28, 29, 30, 35, 40, 45, 50, or more base pairs in length. In some embodiments, a DUX4-targeting RNAi oligonucleotide is 8 to 30 base pairs in length, 10 to 15 base pairs in length, 10 to 20 base pairs in length, 15 to 25 base pairs in length, 19 to 21 base pairs in length, 21 to 23 base pairs in length.

In some embodiments, an oligonucleotide described herein is a double stranded RNAi oligonucleotide (e.g., an siRNA) comprising an antisense strand and a sense strand. In some embodiments, the antisense strand is 18-25 (e.g., 18, 19, 20, 21, 22, 23, 24, or 25) nucleosides in length. In some embodiments, the antisense strand is 23 nucleosides in length. In some embodiments, the sense strand is 18-25 (e.g., 18, 19, 20, 21, 22, 23, 24, or 25) nucleosides in length. In some embodiments, the sense strand is 21 nucleosides in length.

In some embodiments, an oligonucleotide described herein is a double stranded RNAi oligonucleotide (e.g., an siRNA) comprising an antisense strand comprising a region of complementarity of at least 16 (e.g., 16, 17, 18, 19, 20, or more) consecutive nucleosides to a DUX4 sequence as set forth in SEQ ID NO: 25, 26, and/or 27. In some embodiments, the antisense strand comprises a region of complementarity of at least 16 (e.g., 16, 17, 18, 19, 20, or more) consecutive nucleosides to a target sequence as set forth in SEQ ID NO: 24 or 21. In some embodiments, the antisense strand comprises a region of complementarity of at least 16 (e.g., 16, 17, 18, 19, 20, or more) consecutive nucleosides to a target sequence as set forth in SEQ ID NO: 28.

In some embodiments, an oligonucleotide described herein is a double stranded RNAi oligonucleotide (e.g., an siRNA) comprising an antisense strand that is 18-25 nucleosides (e.g., 18, 19, 20, 21, 22, 23, 24, or 25 nucleosides) in length and comprising a region of complementarity to a target sequence as set forth in SEQ ID NO: 24 (UGUUC-UUCCGUGAAAUUCUGGCA), wherein the region of complementarity is at least 16 nucleosides (e.g., 16, 17, 18, 19, 20, 21, or 22 nucleosides) in length. In some embodiments, the antisense strand is 23 nucleosides in length and comprises a region of complementarity to a target sequence as set forth in SEQ ID NO: 24 (UGUUC-UUCCGUGAAAUUCUGGCA), wherein the region of complementarity is at least 20 nucleosides (e.g., 20, 21, or 22 nucleosides) in length. In some embodiments, an oligonucleotide described herein is a double stranded RNAi oligonucleotide (e.g., an siRNA) comprising an antisense strand that is 18-25 nucleosides (e.g., 18, 19, 20, 21, 22, 23, 24, or 25 nucleosides) in length and comprising a region of complementarity to a target sequence as set forth in SEQ ID NO: 28 (UGUUCUUCCGUGAAAUUCUGGCU), wherein the region of complementarity is at least 16 nucleosides (e.g., 16, 17, 18, 19, 20, 21, or 22 nucleosides) in length. In some embodiments, the antisense strand is 23 nucleosides in length and comprises a region of complementarity to a target sequence as set forth in SEQ ID NO: 28 (UGUUCUUCCGUGAAAUUCUGGCU), wherein the region of complementarity is at least 20 nucleosides (e.g., 20, 21, or 22 nucleosides) in length. In some embodiments, the region of complementarity is fully complementarity with all or a portion of its target sequence. In some embodiments, the region of complementarity includes 1, 2, 3 or more mismatches.

In some embodiments, an oligonucleotide described herein is a double stranded RNAi oligonucleotide (e.g., an siRNA) comprising an antisense strand that comprises at least 15 consecutive nucleosides of (e.g., at least 15, at least 16, at least 17, at least 18, at least 19, or at least 20) the nucleobase sequence of SEQ ID NO: 22 (UGCCAGAAUUUCACGGAAGAACA). In some embodiments, the oligonucleotide further comprises a sense strand comprising at least 15 (e.g., 15, 16, 17, 18, 19, 20, or more) consecutive nucleosides complementary to the antisense strand. In some embodiments, the oligonucleotide further comprises a sense strand that comprises at least 15 consecutive nucleosides of (e.g., at least 15, at least 16, at least 17, at least 18, at least 19, or at least 20) the nucleobase sequence of SEQ ID NO: 21 (UUCUUCCGUGAAAUUCUGGCA).

In some embodiments, an oligonucleotide described herein is a double stranded RNAi oligonucleotide (e.g., an siRNA) comprising an antisense strand that comprises the nucleobase sequence of SEQ ID NO: 22 (UGCCAGAAUUUCACGGAAGAACA). In some embodiments, the oligonucleotide further comprises a sense strand that comprises the nucleobase sequence of SEQ ID NO: 21 (UUCUUCCGUGAAAUUCUGGCA).

In some embodiments, an oligonucleotide described herein is a double stranded RNAi oligonucleotide (e.g., an siRNA) comprising an antisense strand that comprises the nucleobase sequence of SEQ ID NO: 22 (UGCCAGAAUUUCACGGAAGAACA) and a sense strand that hybridizes to the antisense strand and comprises the nucleobase sequence of SEQ ID NO: 21 (UUCUUCCGUGAAAUUCUGGCA), wherein the antisense strand and/or (e.g., and) the sense strand comprises one or more modified nucleosides (e.g., 2'-modified nucleosides). In some embodiment, the one or more modified nucleosides are selected from 2'-O-Me and 2'-F modified nucleosides. In some embodiments, the antisense strand further comprises a 5'-(E)-vinylphosphonate.

In some embodiments, an oligonucleotide described herein is a double stranded RNAi oligonucleotide (e.g., an siRNA) comprising an antisense strand that comprises the nucleobase sequence of SEQ ID NO: 22 (UGCCAGAAUUUCACGGAAGAACA) and a sense strand that hybridizes to the antisense strand and comprises the nucleobase sequence of SEQ ID NO: 21 (UUCUUCCGUGAAAUUCUGGCA), wherein each nucleoside in the antisense strand and/or (e.g., and) each nucleoside in the sense strand is a 2'-modified nucleoside selected from 2'-O-Me and 2'-F modified nucleosides. In some embodiments, nucleosides at three consecutive positions of the sense strand are 2'-F modified nucleosides and the nucleosides at three consecutive positions of the antisense strand are 2'-O-Me modified nucleosides. In some embodiments, the antisense strand further comprises a 5'-(E)-vinylphosphonate.

In some embodiments, an oligonucleotide described herein is a double stranded RNAi oligonucleotide (e.g., an siRNA) comprising an antisense strand that comprises the nucleobase sequence of SEQ ID NO: 22 (UGCCAGAAUUUCACGGAAGAACA) and a sense strand that hybridizes to the antisense strand and comprises the nucleobase sequence of SEQ ID NO: 21 (UUCUUCCGUGAAAUUCUGGCA), wherein each nucleoside in the antisense strand and each nucleoside in the sense strand is a 2'-modified nucleoside selected from 2'-O-Me and 2'-F modified nucleosides, wherein the nucleosides at three consecutive positions of the sense strand are 2'-F modified nucleosides and the nucleosides at three consecutive positions of the antisense strand are 2'-O-Me modified nucleosides, and wherein the antisense strand and/or (e.g., and) the sense strand each comprises one or more phosphorothioate internucleoside linkages. In some embodiments, the antisense strand further comprises a 5'-(E)-vinylphosphonate.

In some embodiments, the sense strand does not comprise any phosphorothioate internucleoside linkages (all the internucleoside linkages in the sense strand are phosphodiester internucleoside linkages), and the antisense strand comprises 1, 2, or 3 phosphorothioate internucleoside linkages. In some embodiments, the sense strand comprises 2 phosphorothioate internucleoside linkages, and the antisense strand comprises 4 phosphorothioate internucleoside linkages. In some embodiments, the sense strand comprises 4 phosphorothioate internucleoside linkages, and the antisense strand comprises 4 phosphorothioate internucleoside linkages.

In some embodiments, the antisense strand comprises 2 phosphorothioate internucleoside linkages, optionally wherein the two internucleoside linkages at the 3' end of the antisense strand are phosphorothioate internucleoside linkages and the rest of the internucleoside linkages in the antisense strand are phosphodiester internucleoside linkages. In some embodiments, the antisense strand comprises 4 phosphorothioate internucleoside linkages, optionally wherein the two internucleoside linkages at the 3' end and the two internucleoside linkage at the 5' end of the antisense strand are phosphorothioate internucleoside linkages and the rest of the internucleoside linkages in the antisense strand are phosphodiester internucleoside linkages. In some embodiments, the sense strand comprises 2 phosphorothioate internucleoside linkages, optionally wherein the two internucleoside linkages at the 5' end of the sense strand are phosphorothioate internucleoside linkages and the rest of the internucleoside linkages in the sense strand are phosphodiester internucleoside linkages. In some embodiments, the sense strand comprises 4 phosphorothioate internucleoside linkages. In some embodiments, the two internucleoside linkages at the 5' end and the two internucleoside linkages at the 3' end of the sense strand are phosphorothioate internucleoside linkages, and the rest of the internucleoside linkages in the sense strand are phosphodiester internucleoside linkages.

In some embodiments, the antisense strand of the oligonucleotide described herein comprises a structure of (5' to 3'; referred to herein as "MAS7"): mN*fN*mNmNmNmNmNmNmNmNmNmNmNfNmNmNmNmNmNmNmNmN*mN*mN, wherein "mN" indicates 2'-O-methyl (2'-O-Me) modified nucleoside; "fN" indicates 2'-fluoro (2'-F) modified nucleoside; "*" represents phosphorothioate internucleoside linkage; and the absence of "*" between two nucleosides represents phosphodiester internucleoside linkage.

In some embodiments, the MAS7 structure further comprises a 5' vinylphosphonate (e.g., 5'-(E)-vinylphosphonate) modification (5' to 3'; referred to herein as "VP-MAS7"): VP-mN*fN*mNmNmNmNmNmNmNmNmNmNmNmNfNm NmNmNmNmNmNmNmN*mN*mN, wherein "mN" indicates 2'-O-methyl (2'-O-Me) modified nucleoside; "fN" indicates 2'-fluoro (2'-F) modified nucleoside; "*" represents phosphorothioate internucleoside linkage; the absence of "*" between two nucleosides represents phosphodiester internucleoside linkage; and VP represents 5'-(E)-vinylphosphonate.

In some embodiments, the sense strand of the oligonucleotide described herein comprises a structure of (5' to 3'; referred to herein as "MS8"): mN*mN*mNmNfNmNmNmNmNfNfNfNmNmNfNmNmNm NmNfN*mN*mN, wherein "mN" indicates 2'-O-methyl (2'-O-Me) modified nucleoside; "fN" indicates 2'-fluoro (2'-F) modified nucleoside; "*" represents phosphorothioate internucleoside linkage; and the absence of "*" between two nucleosides represents phosphodiester internucleoside linkage.

In some embodiments, the oligonucleotide described herein comprises an antisense strand comprising a structure of (5' to 3'; VP-MAS7): VP-mN*fN*mNmNmNmNmNmNmNmNmNmNmNmNfNm NmNmNmNmNmNmNmN*mN*mN, and a sense strand comprising a structure of (5' to 3'; MS8): mN*mN*mNmNfNmNmNmNmNfNfNfNmNmNfNmNmNm NmNfN*mN*mN, wherein "mN" indicates 2'-O-methyl (2'-O-Me) modified nucleoside; "fN" indicates 2'-fluoro (2'-F) modified nucleoside; "*" represents phosphorothioate internucleoside linkage; and the absence of "*" between two nucleosides represents phosphodiester internucleoside linkage; and VP represents 5'-(E)-vinylphosphonate.

In some embodiments, an oligonucleotide described herein (e.g., a DUX4 targeting RNAi oligonucleotide described herein) comprises an antisense strand comprising a nucleobase sequence of SEQ ID NO: 22 and a structure (5'→3') of VP-mU*fG*mCmCmAmGmAmAmUmUmUmCmAfCm GmGmAmAmGmAmA*mC*mA, and a sense strand comprising a nucleobase sequence of SEQ ID NO: 21 and a structure (5'→3') of mU*mU*mCmUfUmCmCmGfUfGfAmAmAfUmUmCm UmGfG*mC*mA, wherein: mA, mC, mG, and mU are 2'-O-methyl adenosine, 2'-O-methyl cytidine, 2'-O-methyl guanosine, and 2'-O-methyl uridine, respectively; fA, fC, fG, and fU are 2'-fluoro adenosine, 2'-fluoro cytidine, 2'-fluoro guanosine, and 2'-fluoro uridine, respectively; * between two nucleosides represents a phosphorothioate linkage; the absence of "*" between two nucleosides represents a phosphodiester internucleoside linkage; and "VP" represents 5'-(E)-Vinylphosphonate.

In some embodiments, an oligonucleotide described herein (e.g., a DUX4 targeting RNAi oligonucleotide described herein) comprises a structure of the formula (Ie), in which the antisense strand and the sense strand form a double stranded oligonucleotide:

(Ie)
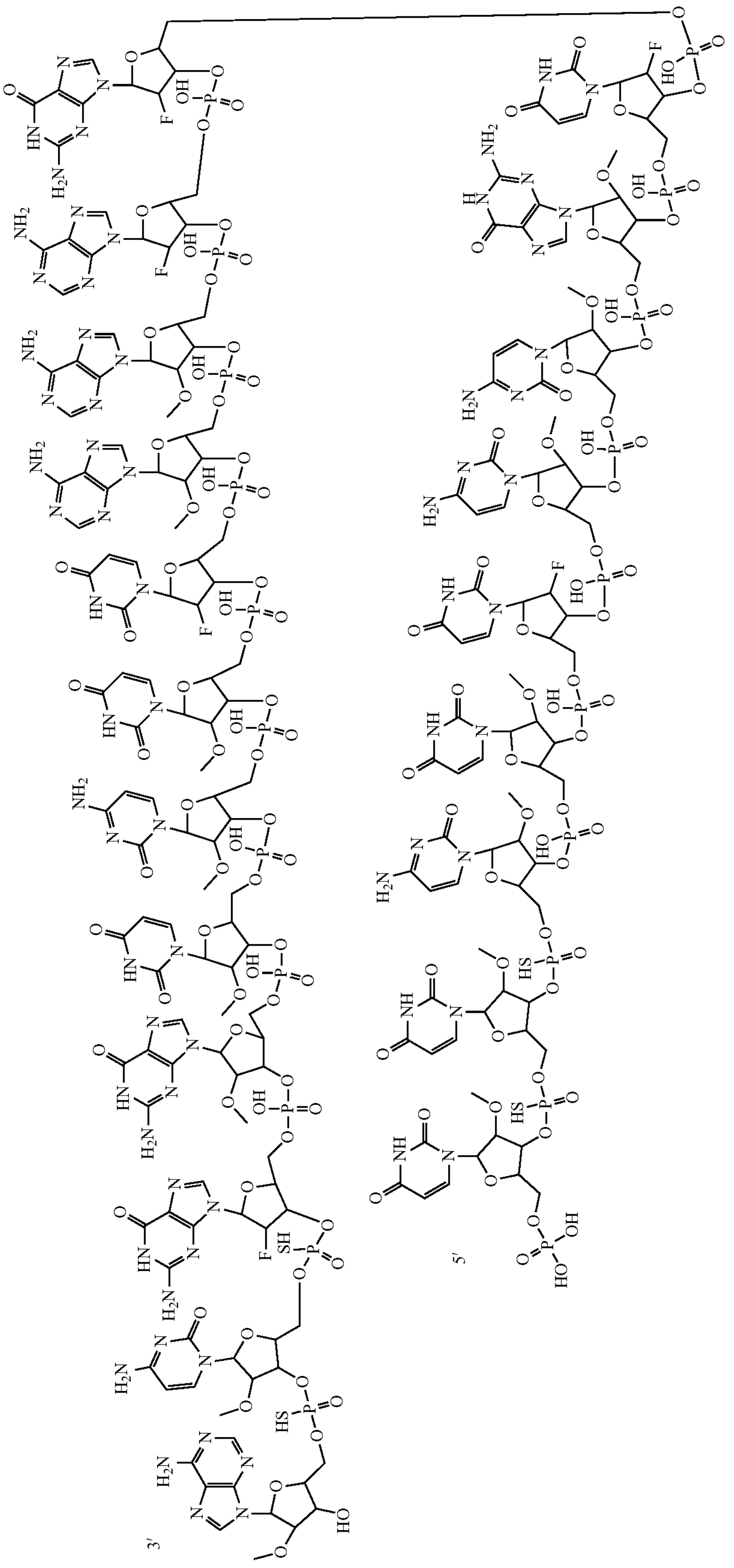
Sense Strand

-continued
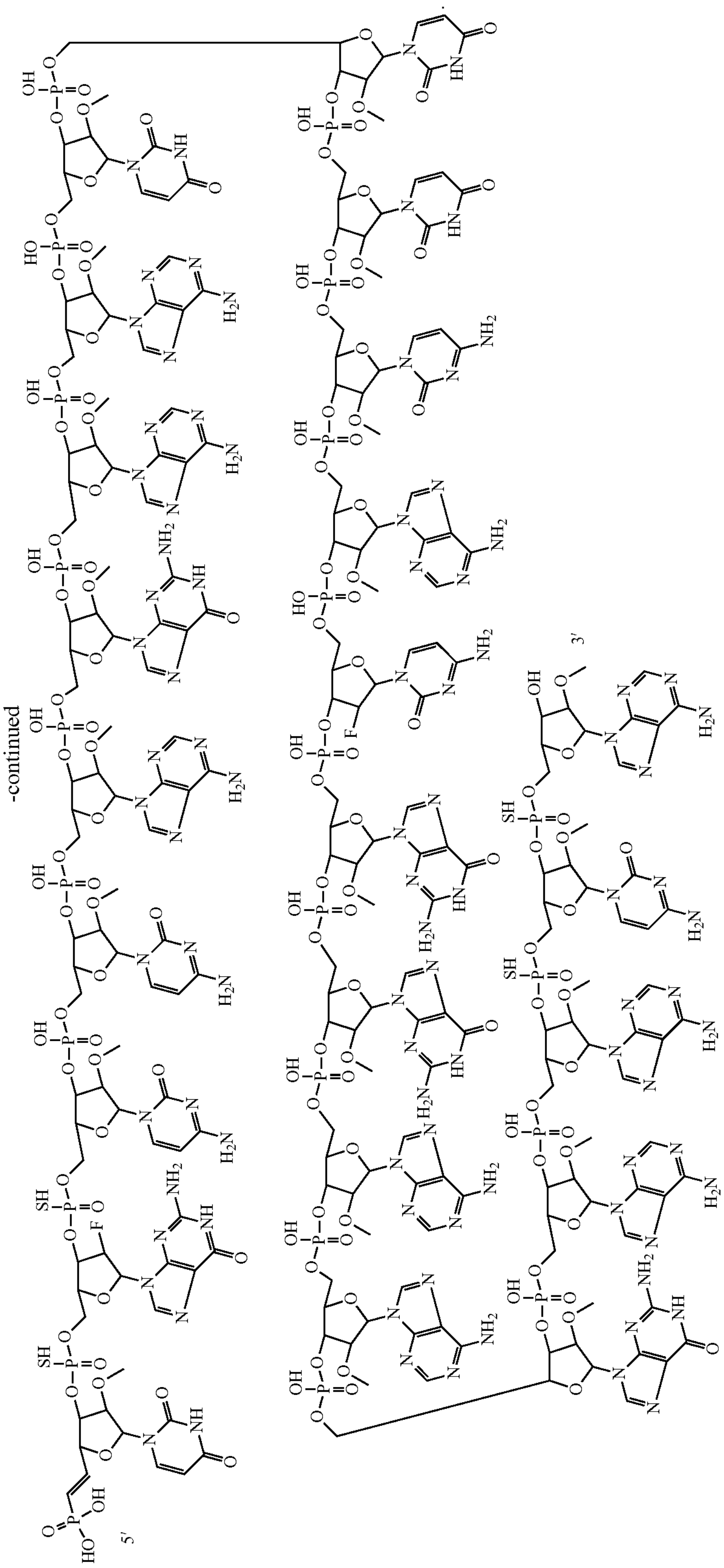
Antisense Strand

In some embodiments, an oligonucleotide described herein (e.g., a DUX4 targeting RNAi oligonucleotide described herein) can be in salt form, e.g., as sodium, potassium, or magnesium salts.

In some embodiments, the 5' or 3' nucleoside (e.g., terminal nucleoside) of an oligonucleotide described herein (e.g., a DUX4-targeting RNAi oligonucleotide) is conjugated to an amine group, optionally via a spacer. In some embodiments, the spacer comprises an aliphatic moiety. In some embodiments, the spacer comprises a polyethylene glycol moiety. In some embodiments, a phosphodiester linkage is present between the spacer and the 5' or 3' nucleoside of the oligonucleotide. In some embodiments, the 5' or 3' nucleoside (e.g., terminal nucleoside) of an oligonucleotide described herein is covalently linked to a spacer that is a substituted or unsubstituted aliphatic, substituted or unsubstituted heteroaliphatic, substituted or unsubstituted carbocyclylene, substituted or unsubstituted heterocyclylene, substituted or unsubstituted arylene, substituted or unsubstituted heteroarylene, —O—, —N($R^A$)—, —S—, —C(═O)—, —C(═O)O—, —C(═O)N$R^A$—, —N$R^A$C(═O)—, —N$R^A$C(═O)$R^A$—, —C(═O)$R^A$—, —N$R^A$C(═O)O—, —N$R^A$C(═O)N($R^A$)—, —OC(═O)—, —OC(═O)O—, —OC(═O)N($R^A$)—, —S(O)$_2$N$R^A$—, —N$R^A$S(O)$_2$—, or a combination thereof; each $R^A$ is independently hydrogen or substituted or unsubstituted alkyl. In certain embodiments, the spacer is a substituted or unsubstituted alkylene, substituted or unsubstituted heterocyclylene, substituted or unsubstituted heteroarylene, —O—, —N($R^A$)—, or —C(═O)N($R^A$)$_2$, or a combination thereof.

In some embodiments, the 5' or 3' nucleoside of the oligonucleotide is conjugated to a compound of the formula —$NH_2$—$(CH_2)_n$—, wherein n is an integer from 1 to 12. In some embodiments, n is 6, 7, 8, 9, 10, 11, or 12. In particular embodiments, n is 6. In some embodiments, a phosphodiester linkage is present between the compound of the formula $NH_2$—$(CH_2)_n$— and the 5' or 3' nucleoside of the oligonucleotide, wherein n is an integer from 1 to 12. In some embodiments, n is 6, 7, 8, 9, 10, 11, or 12. In particular embodiments, n is 6.

In some embodiments, the 5' nucleoside of the sense strand of the oligonucleotide is conjugated to a compound of the formula —$NH_2$—$(CH_2)_n$—, wherein n is an integer from 1 to 12 (e.g., 6). In some embodiments, the 3' nucleoside of the sense strand of the oligonucleotide is conjugated to a compound of the formula —$NH_2$—$(CH_2)_n$—, wherein n is an integer from 1 to 12 (e.g., 6).

In some embodiments, a compound of the formula $NH_2$—$(CH_2)_6$— is conjugated to the oligonucleotide via a reaction between 6-amino-1-hexanol ($NH_2$—$(CH_2)_6$—OH) and the 5' phosphate of the oligonucleotide. In some embodiments, a compound of the formula $NH_2$—$(CH_2)_6$— is conjugated to the oligonucleotide via a reaction between 6-amino-1-hexanol ($NH_2$—$(CH_2)_6$—OH) and the 5' phosphate of the sense strand of the oligonucleotide. In some embodiments, a compound of the formula $NH_2$—$(CH_2)_6$— is conjugated to the oligonucleotide via a reaction between 6-amino-1-hexanol ($NH_2$—$(CH_2)_6$—OH) and the 5' phosphate of the antisense strand of the oligonucleotide.

In some embodiments, a compound of the formula $NH_2$—$(CH_2)_6$— is conjugated to the oligonucleotide via a reaction between 6-amino-1-hexanol ($NH_2$—$(CH_2)_6$—OH) and the 3' phosphate of the oligonucleotide. In some embodiments, a compound of the formula $NH_2$—$(CH_2)_6$— is conjugated to the oligonucleotide via a reaction between 6-amino-1-hexanol ($NH_2$—$(CH_2)_6$—OH) and the 3' phosphate of the sense strand of an oligonucleotide. In some embodiments, a compound of the formula $NH_2$—$(CH_2)_6$— is conjugated to the oligonucleotide via a reaction between 6-amino-1-hexanol ($NH_2$—$(CH_2)_6$—OH) and the 3' phosphate of the antisense strand of the oligonucleotide.

In some embodiments, an oligonucleotide described herein (e.g., a DUX4 targeting RNAi oligonucleotide described herein) conjugated to the formula $NH_2$—$(CH_2)_6$— comprises a structure of the formula (If), in which the antisense strand and the sense strand form a double stranded oligonucleotide:

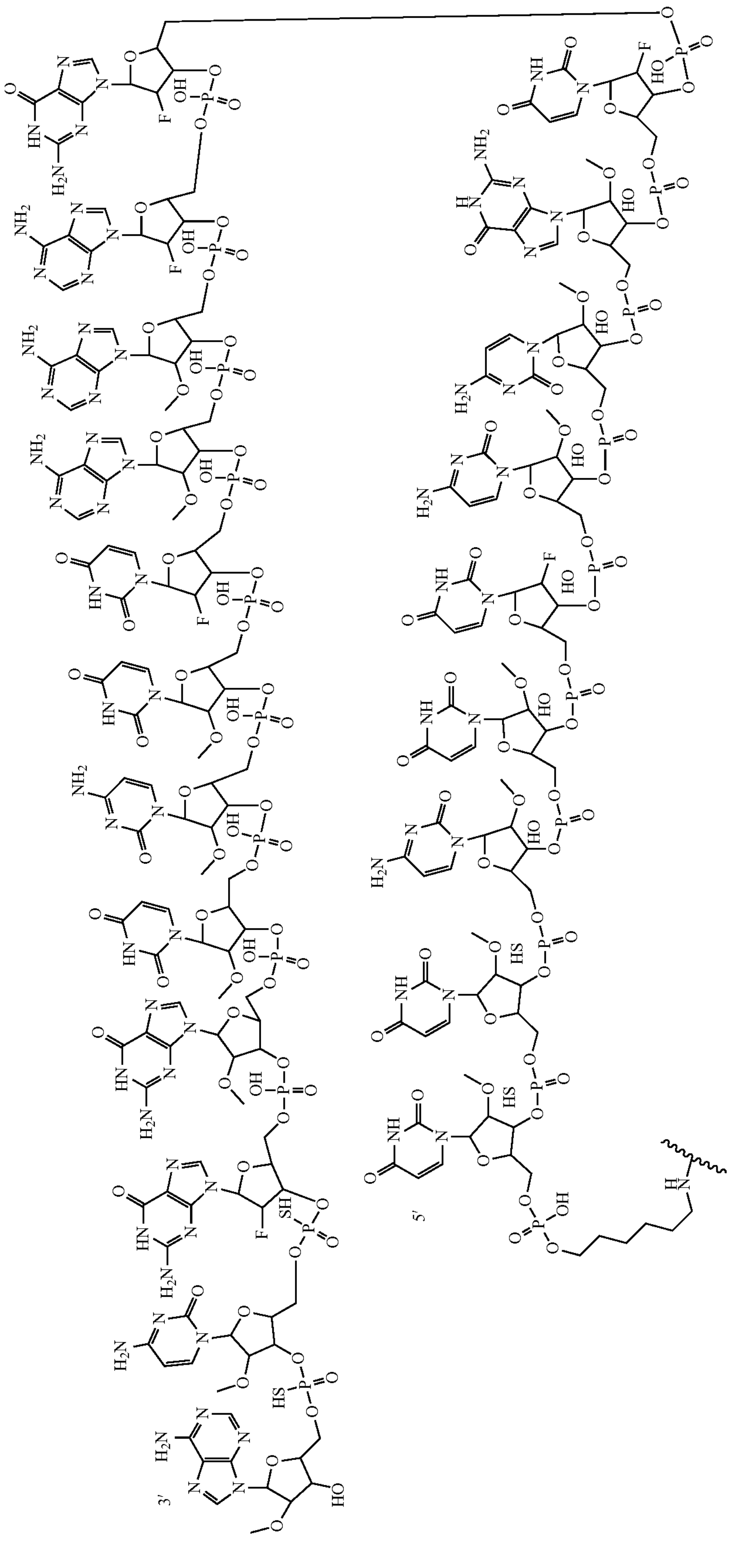
Sense Strand

-continued
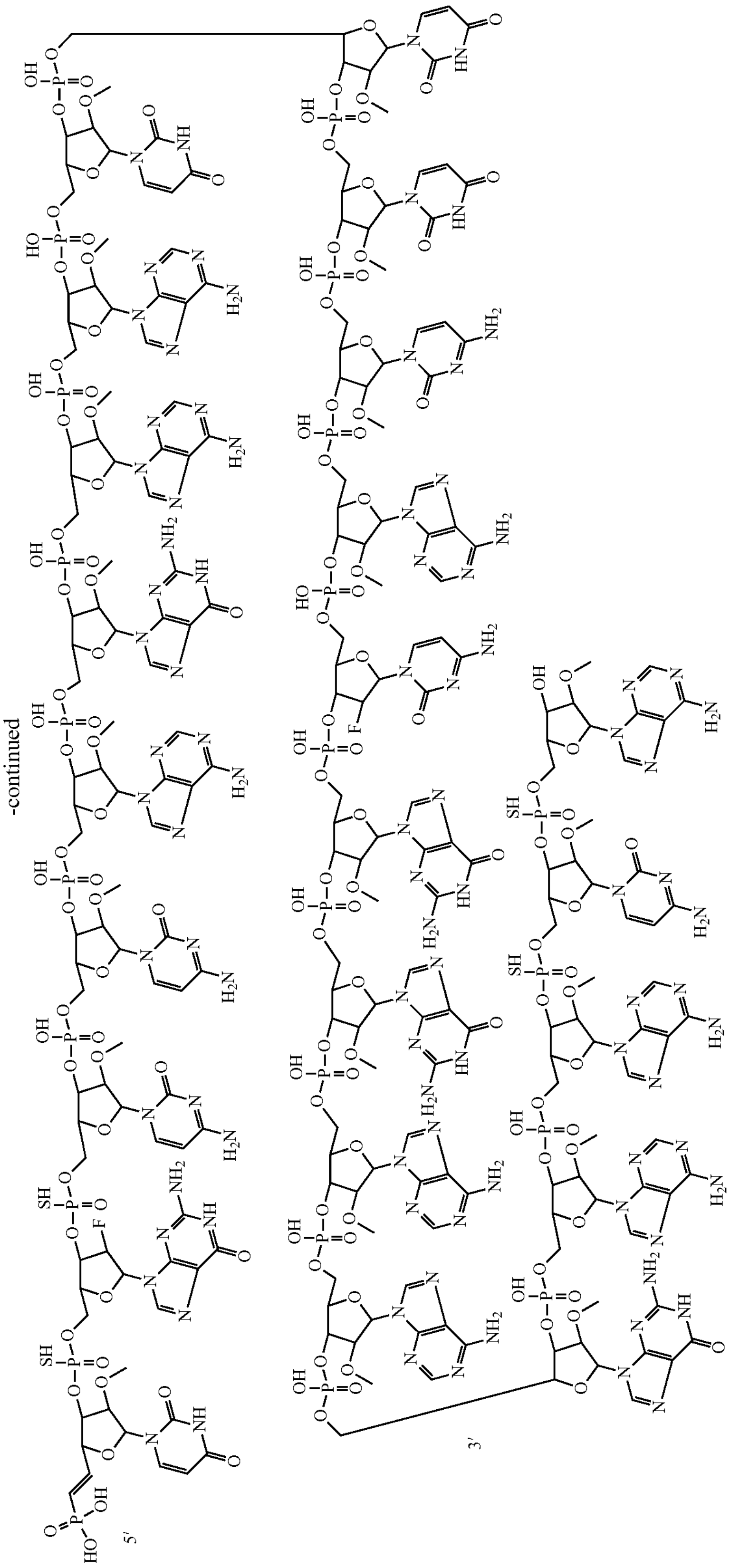
Antisense Strand

In some embodiments, the oligonucleotide is conjugated to a targeting agent, e.g., a muscle targeting agent such as an anti-TfR1 antibody, e.g., via an amine group of a lysine of the targeting agent.

In some embodiments, it should be appreciated that methylation of the nucleobase uracil at the C5 position forms thymine. Thus, in some embodiments, a nucleotide or nucleoside having a C5 methylated uracil (or 5-methyl-uracil) may be equivalently identified as a thymine nucleotide or nucleoside.

In some embodiments, any one or more of the thymine bases (T's) in any one of the oligonucleotides and/or target sequences provided herein may independently and optionally be uracil bases (U's), and/or any one or more of the U's in any one of the oligonucleotides or target sequences provided herein (e.g., a DUX4-targeting RNAi oligonucleotide) may independently and optionally be T's.

Compositions

In some embodiments, compositions described herein comprise complexes (i.e., a plurality of complexes), each of which complex comprises an antibody (e.g., anti-TFR1 antibody) covalently linked to one or more oligonucleotides (e.g., a DUX4-targeting RNAi oligonucleotide described herein), wherein the antibody comprises a heavy chain comprising a heavy chain variable region (VH) and a heavy chain constant region, and a light chain comprising a light chain variable region (VL) and a light chain constant region. In some embodiments, the antibody of such complexes comprises a CDR-H1, CDR-H2, CDR-H3, CDR-L1, CDR-L2, and CDR-L3 as set forth in Table 2. Complexes of a composition described herein can comprise any structure provided herein, e.g., a structure of formula (I) (e.g., comprising a group of the formula (Ia), formula (Ib), formula (Ic), formula (Id), or formula (A)).

In some embodiments, compositions described herein comprise complexes (i.e., a plurality of complexes) wherein each complex comprises a structure of formula (I): $[R^1]_{n1}$—$R^2$, in which each $R^1$ independently comprises a compound comprising an oligonucleotide (e.g., a DUX4-targeting RNAi oligonucleotide described herein) and is covalently linked to $R^2$, wherein $R^2$ comprises an antibody (e.g., anti-TfR1 antibody) comprising a heavy chain comprising a heavy chain variable region (VH) and a heavy chain constant region, and a light chain comprising a light chain variable region (VL) and a light chain constant region. In some embodiments, each $R^1$ of a complex is independently covalently linked to a different amino acid residue (e.g., lysine or cysteine) of $R^2$.

In some embodiments, the value of n1 of complexes in the composition is independently and optionally an integer from one up to the number of amino acid residues to which conjugation is desired or targeted (e.g., the number of lysine residues) in the antibody (e.g., an antibody comprised within $R^2$). In some embodiments, the value of n1 of each complex in the composition is independently and optionally selected from 1, 2, 3, 4, 5, 6, 7, 8, 9, 10, 11, 12, 13, 14, 15, 16, 17, 18, 19, 20, 21, 22, 23, 24, 25, 26, and 27. In some embodiments, the value of n1 of each complex in the composition is independently and optionally selected from 1, 2, 3, 4, 5, 6, 7, 8, 9, 10, 11, 12, 13, 14, 15, 16, 17, 18, 19, 20, 21, 22, 23, 24, 25 and 26. In some embodiments, the value of n1 of each complex in the composition is 1. In some embodiments, the value of n1 of each complex in the composition is independently selected and optionally from an integer in the range of 1 to 27, 1 to 26, 1 to 10, 1 to 5, or 1 to 3. In some embodiments, the average value of n1 of complexes of the composition is in the range of 1 to 2, 1 to 3, 1 to 5, 1 to 10, 1 to 26, or 1 to 27. In some embodiments, compositions described herein comprise complexes in which the value of n1 is 0. In some embodiments, the average value of n1 of complexes of the composition is in the range of 0.5 to 5 (e.g., 0.5-5, 1-5, 1-4, 1-3, 3-5, 0.5-4, 0.5-3, 0.5-2, 0.5-1.5, 0.5-1, 0.7-1.5, 1-1.6, 1-1.5, 1-1.4, 1-1.3, 1-1.2, 1.1-1.5, 0.8-2, 0.8-1.5, 0.8-1.3, 0.8-1.2, 0.8-1.1, 0.9-3, 0.9-2, 0.9-1.8, 0.9-1.6, 0.9-1.5, 0.9-1.4, 0.9-1.3, or 0.9-1.2). In some embodiments, the average value of n1 of complexes of the composition is 1.

In some embodiments, a composition described herein comprises an antibody that is not conjugated to an oligonucleotide (e.g., in trace amounts) and an antibody conjugated to one or more oligonucleotides. In some embodiments, the antibody that is not conjugated to an oligonucleotide may be referred to as a compound comprising a structure of formula (I): $[R^1]_{n1}$—$R^2$, for which n1 is zero. Accordingly, in some embodiments, a composition for administration to a subject in the methods described herein comprises compounds (e.g., complexes) comprising a structure of formula (I): $[R^1]_{n1}$—$R^2$, for which each $R^1$ independently comprises a group comprising an oligonucleotide, $R^2$ comprises an antibody and n1 is independently an integer of zero or greater that reflects the number of instances of $R^1$ in each compound (e.g., complex). In some embodiments, the fraction of compounds comprising a structure of formula (I): $[R^1]_{n1}$—$R^2$, in a composition, for which n1 is zero, compared with all compounds of that structure in the composition for which n1 is one or greater, is less than 10%, less than 5%, less than 1% less than 0.5%, less than 0.1%, less than 0.05%, or less than 0.01%. As such, in some embodiments, the average value of n1 of complexes in a composition disclosed herein is in the range of 0.5 to 5 (e.g., 0.5-5, 1-5, 1-4, 1-3, 3-5, 0.5-4, 0.5-3, 0.5-2, 0.5-1.5, 0.5-1, 0.7-1.5, 1-1.6, 1-1.5, 1-1.4, 1-1.3, 1-1.2, 1.1-1.5, 0.8-2, 0.8-1.5, 0.8-1.3, 0.8-1.2, 0.8-1.1, 0.9-3, 0.9-2, 0.9-1.8, 0.9-1.6, 0.9-1.5, 0.9-1.4, 0.9-1.3, or 0.9-1.2). In some embodiments, the average value of n1 of complexes of the composition is 1.

Formulations

Complexes provided herein are formulated in a manner suitable for pharmaceutical use. In some embodiments, complexes can be delivered to a subject using a formulation that minimizes degradation, facilitates delivery and/or (e.g., and) uptake, or provides another beneficial property to complexes in the formulation. Accordingly, in some embodiments, it has been found that formulating complexes (e.g., complexes comprising an oligonucleotide covalently linked with a Fab) with tris(hydroxymethyl)aminomethane (also known as tromethamine or THAM) and/or sucrose is particularly advantageous for pharmaceutical use, e.g., as described herein. Thus, in some embodiments, provided herein are formulations (e.g., aqueous solutions, lyophilized forms, or frozen forms) comprising complexes together with tris(hydroxymethyl)aminomethane and/or sucrose. Such formulations can be suitably prepared such that when administered to a subject, either into the immediate environment of a target cell or systemically, a sufficient amount of the complexes enter target muscle cells.

In some embodiments, formulations are provided herein that comprise complexes (i.e., a plurality of complexes) that comprise an oligonucleotide (e.g., an RNAi oligonucleotide) covalently linked to an antibody. In some embodiments, provided herein is a formulation comprising complexes, in which each complex comprises an oligonucleotide (e.g., an RNAi oligonucleotide) covalently linked to an anti-TfR1 antibody, optionally wherein the antibody of such complexes comprises a CDR-H1, CDR-H2, CDR-H3, CDR-L1, CDR-L2, and CDR-L3 as set forth in Table 2, and further, in some embodiments, wherein the complexes are formulated with tris(hydroxymethyl)aminomethane and sucrose. In some embodiments, the antibody is an anti-TfR1 antibody.

In some embodiments, formulations are provided that comprise complexes comprising a structure of formula (I): $[R^1]_{n1}$—$R^2$, in which each $R^1$ independently comprises a compound comprising an oligonucleotide (e.g., an RNAi oligonucleotide) and $R^2$ comprises an antibody (e.g., anti-TfR1 antibody), and in which n1 is an integer representing the number of instances of $R^1$ in the complex.

In some embodiments, formulations described herein comprise complexes comprising an antibody that comprises a CDR-H1, CDR-H2, CDR-H3, CDR-L1, CDR-L2, and CDR-L3 as set forth in Table 2. In some embodiments, the antibody comprises a VH comprising the amino acid sequence of SEQ ID NO: 17 and a VL comprising the amino acid sequence of SEQ ID NO: 18. In some embodiments, the antibody is a Fab and comprises a heavy chain comprising the amino acid sequence of SEQ ID NO: 19 and a light chain comprising the amino acid sequence of SEQ ID NO: 20.

In some embodiments, a formulation described herein comprises complexes described herein at a concentration of between 1-200 mg of the complex per mL of the formulation. In some embodiments, a formulation described herein comprises complexes at a concentration of 10-200 mg/mL (e.g., 10-200 mg/mL, 10-100 mg/mL, 10-50 mg/mL, 10-30 mg/mL, 10-20 mg/mL, 15-200 mg/mL, 15-150 mg/mL, 15-100 mg/mL, 15-45 mg/mL, 20-40 mg/mL, 25-35 mg/mL, 25.5-34.5 mg/mL, 26-34 mg/mL, 27-33 mg/mL, 28-32 mg/mL, 29-31 mg/mL, 29.5-30.5 mg/mL, 10-40 mg/mL, 15-35 mg/mL, 20-30 mg/mL, 21-29 mg/mL, 21.2-28.8 mg/mL, 22-28 mg/mL, 23-27 mg/mL, 24-26 mg/mL, 24.5-25.5 mg/mL, 50-200 mg/mL, 100-200 mg/mL, 150-200 mg/mL, 175-200 mg/mL, 20-150 mg/mL, 30-150 mg/mL, 50-150 mg/mL, 100-150 mg/mL, 75-150 mg/mL, or 40-100 mg/mL). In some embodiments, the concentration of complexes in a formulation may vary by up to 20% (e.g., +/−up to 20%, +/−up to 15%, +/−up to 10%, or +/−up to 5%) of a set value.

In some embodiments, any one or a plurality of the complexes described herein is formulated with tris(hydroxymethyl)aminomethane and sucrose in an aqueous solution. In some embodiments, the tris(hydroxymethyl)aminomethane is present in the aqueous solution at a concentration in the range of 5-50 mM (e.g., 5-40 mM, 5-35 mM, 5-30 mM, 10-50 mM, 15-45 mM, 10-40 mM, 20-40 mM, 20-35 mM, 20-30 mM, 21-29 mM, 22-28 mM, 23-27 mM, 24-26 mM). In some embodiments, the tris(hydroxymethyl)aminomethane is present in the aqueous solution at a concentration of approximately 25 mM (e.g., 25 mM). In some embodiments, the sucrose is present in the aqueous solution at a concentration in the range of 2% to 15% weight per volume (w/v %), for example, 3-10 w/v %, 5-10 w/v %, 5-15 w/v %, 7-13 w/v %, 8-15% w/v %, 9-15% w/v %, 9-11% w/v %, 9.5-11% w/v %, or for example, in the range of 9-10 w/v %, 10-11 w/v %, 10-12 w/v %, or 8-12 w/v %. In some embodiments, the sucrose is present in the aqueous solution at a concentration of approximately 3 w/v % (e.g., 3 w/v %). In some embodiments, the sucrose is present in the aqueous solution at a concentration of approximately 6 w/v % (e.g., 6 w/v %). In some embodiments, the sucrose is present in the aqueous solution at a concentration in the range of 7-13 w/v %, 8-12 w/v %, or 9-11 w/v %. In some embodiments, the sucrose is present in the aqueous solution at a concentration of approximately 10 w/v % (e.g., 10 w/v %). In some embodiments, the aqueous solution has a pH in the range of 6.5 to 8.5, for example, 6.5-6.5, 6.7-6.9, 6.9-7.1, 7.1-7.3, 7.2-7.8, 7.3-7.5, 7.4-7.5, 7.4-7.6, 7.5-7.6; for example, 7.0-8.0, or for example, in the pH range of 7.0-7.3, 7.2-7.8, 7.3-7.5, 7.4-7.6, 7.5-7.6, 7.5-7.7, 7.7-7.9, 7.9-8.0, 8.0-8.2, 8.2-8.4, 8.3-8.4, 8.4-8.5, 8.5-8.6, or 7.3-7.7. In some embodiments, the aqueous solution has a pH in the range of 7.0-8.0 (e.g., 7.0-7.8, 7.1-7.8, 7.2-7.8, 7.3-7.7, 7.3-7.5, 7.3-7.6, 7.4-7.6, or 7.4-7.8). In some embodiments, the aqueous solution has a pH of approximately 7.5 (e.g., 7.5). In some embodiments, the aqueous solution has a pH in the range of 7.4-7.7. In some embodiments, the aqueous solution has a pH in the range of 7.4-7.6 (e.g., 7.5, or about 7.5).

In some embodiments, any one of the formulations described herein is an aqueous solution, wherein tris(hydroxymethyl)aminomethane is present in the aqueous solution at a concentration of approximately 25 mM (e.g., 25 mM), wherein sucrose is present in the aqueous solution at a concentration of approximately 3 w/v % (e.g., 3 w/v %), and wherein the aqueous solution is at a pH of approximately 7.5 (e.g., 7.5).

In some embodiments, any one of the formulations described herein is an aqueous solution, wherein tris(hydroxymethyl)aminomethane is present in the aqueous solution at a concentration of approximately 25 mM (e.g., 25 mM), wherein sucrose is present in the aqueous solution at a concentration of approximately 3 w/v % (e.g., 3 w/v %), wherein complexes are present in the aqueous solution at a concentration of approximately 10-200 mg/ml and wherein the aqueous solution is at a pH of approximately 7.5 (e.g., 7.5).

In some embodiments, any one of the formulations described herein is an aqueous solution, wherein tris(hydroxymethyl)aminomethane is present in the aqueous solution at a concentration of approximately 25 mM (e.g., 25 mM), wherein sucrose is present in the aqueous solution at a concentration of approximately 6 w/v % (e.g., 6 w/v %), and wherein the aqueous solution is at a pH of approximately 7.5 (e.g., 7.5).

In some embodiments, any one of the formulations described herein is an aqueous solution, wherein tris(hydroxymethyl)aminomethane is present in the aqueous solution at a concentration of approximately 25 mM (e.g., 25 mM), wherein sucrose is present in the aqueous solution at a concentration of approximately 6 w/v % (e.g., 6 w/v %), wherein complexes are present in the aqueous solution at a concentration of approximately 10-200 mg/ml and wherein the aqueous solution is at a pH of approximately 7.5 (e.g., 7.5).

In some embodiments, any one of the formulations described herein is an aqueous solution, wherein tris(hydroxymethyl)aminomethane is present in the aqueous solution at a concentration of approximately 25 mM (e.g., 25 mM), wherein sucrose is present in the aqueous solution at a concentration of approximately 10 w/v % (e.g., 10 w/v %), and wherein the aqueous solution is at a pH of approximately 7.5 (e.g., 7.5).

In some embodiments, any one of the formulations described herein is an aqueous solution, wherein tris(hydroxymethyl)aminomethane is present in the aqueous solution at a concentration of approximately 25 mM (e.g., 25 mM), wherein sucrose is present in the aqueous solution at a concentration of approximately 10 w/v % (e.g., 10 w/v %), wherein complexes are present in the aqueous solution at a concentration of approximately 10-200 mg/ml and wherein the aqueous solution is at a pH of approximately 7.5 (e.g., 7.5).

In some embodiments, any one or a plurality of the complexes described herein is formulated with tris(hydroxymethyl)aminomethane and sucrose in a lyophilized form (e.g., lyophilized powder). In some embodiments, the lyophilized form (e.g., lyophilized powder) is obtained by lyophilization of any one of the aqueous solutions described herein.

In some embodiments, a lyophilized form is a lyophilized cake. In some embodiments, a lyophilized cake comprises a plurality of complexes provided herein, tris(hydroxymethyl) aminomethane, and sucrose.

In some embodiments, any one or a plurality of the complexes described herein is formulated with tris(hydroxymethyl)aminomethane and sucrose in a frozen form (e.g., a frozen aqueous solid). In some embodiments, the frozen form (e.g., frozen aqueous solid) is obtained by freezing of any one of the aqueous solutions described herein. A frozen form may be frozen to a temperature of less than −20° C. (e.g., less than −20° C., less than −30° C., less than −40° C., less than −50° C., less than −60° C., less than −70° C., less than −80° C., or lower).

In some embodiments, the value of n1 of each complex in the formulation is independently and optionally an integer from zero up to the number of amino acid residues to which conjugation is desired or targeted (e.g., the number of lysine residues) in the antibody ($R^2$). In some embodiments, the value of n1 of each complex in the formulation is independently and optionally selected from 0, 1, 2, 3, 4, 5, 6, 7, 8, 9, 10, 11, 12, 13, 14, 15, 16, 17, 18, 19, 20, 21, 22, 23, 24, 25, 26, and 27. In some embodiments, the value of n1 of each complex in the formulation is independently and optionally selected from 0, 1, 2, 3, 4, 5, 6, 7, 8, 9, 10, 11, 12, 13, 14, 15, 16, 17, 18, 19, 20, 21, 22, 23, 24, 25 and 26. In some embodiments, the value of n1 of each complex in the formulation is 1. In some embodiments, the value of n1 of each complex in the formulation is independently selected and optionally from an integer in the range of 1 to 27, 1 to 26, 1 to 10, 1 to 5, or 1 to 3. In some embodiments, the average value of n1 of complexes in the formulation is in the range of 1 to 2, 1 to 3, 1 to 5, 1 to 10, 1 to 26 or 1 to 27. In some embodiments, formulations described herein comprise complexes that comprise a structure of formula (I): $[R^1]_{n1}$—$R^2$, wherein n1 is 0. In some embodiments, the average value of n1 of complexes of the formulation is in the range of 0.5 to 5 (e.g., 0.5-5, 1-5, 1-4, 1-3, 3-5, 0.5-4, 0.5-3, 0.5-2, 0.5-1.5, 0.5-1, 0.7-1.5, 1-1.6, 1-1.5, 1-1.4, 1-1.3, 1-1.2, 1.1-1.5, 0.8-2, 0.8-1.5, 0.8-1.3, 0.8-1.2, 0.8-1.1, 0.9-3, 0.9-2, 0.9-1.8, 0.9-1.6, 0.9-1.5, 0.9-1.4, 0.9-1.3, or 0.9-1.2). In some embodiments, the average value of n1 of complexes of the formulation is 1.

In some embodiments, each instance of $R^1$ in a complex herein (e.g., a complex of a formulation provided herein) is conjugated to a different amino acid residue of the antibody. In some embodiments, each different amino acid comprises an ε-amino group (e.g., lysine, arginine). However, in some embodiments, each different amino acid to which $R^1$ is covalently linked is a cysteine. In some embodiments, $R^1$ is directly covalently linked to an amino acid residue of the antibody. However, in some embodiments, $R^1$ is indirectly covalently linked to an amino acid of the antibody, e.g., covalently linked to a glycosylation site on the amino acid. In some embodiments, formulations are provided in which complexes for which $R^1$ is covalently linked to an amino acid residue residing in a CDR region of the antibody are present in only trace amounts, or in undetectable amount, or not at all. In some embodiments, formulations are provided in which complexes for which $R^1$ is covalently linked to an amino acid residue residing in a CDR region of the antibody are not detectable in the formulation using standard detection techniques.

In some embodiments, formulations provided herein comprise complexes that comprise a structure of formula (I): $[R^1]_{n1}$—$R^2$, in which each instance of $R^1$ independently comprises a group of the formula (Ia):

(Ia)

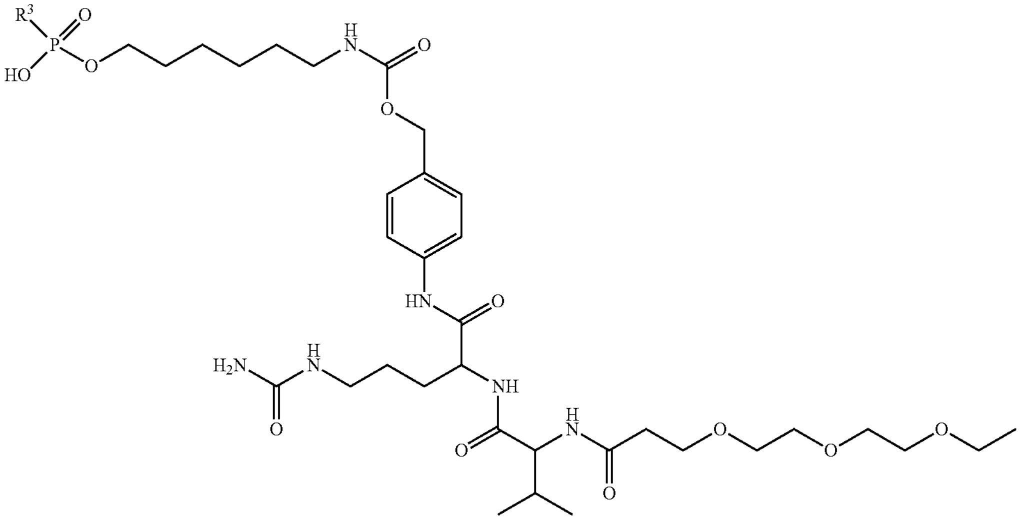

-continued

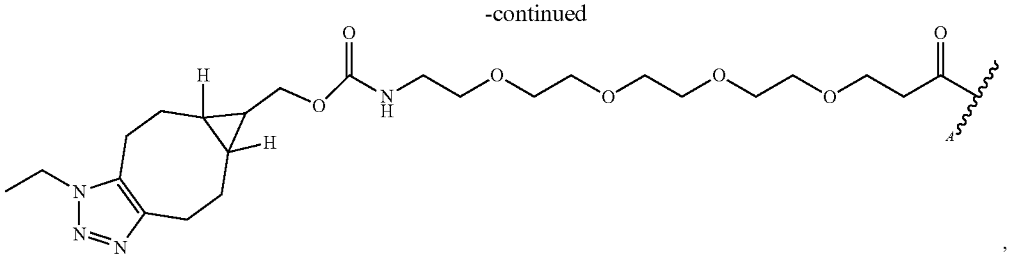

, or a pharmaceutically acceptable salt thereof, in which $R^3$ comprises an oligonucleotide, e.g., an RNAi oligonucleotide; and $R^1$ is covalently linked to $R^2$ at attachment point A. In some embodiments, $R^2$ comprises an antibody comprising a sequence as set forth in Table 2. For example, in some embodiments, $R^2$ comprises an antibody comprising a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14; and/or comprising a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5, or 11, and a light chain complementarity determining region 3 (CDR-L3) comprising a sequence as set forth in SEQ ID NO: 6 or 16. In some embodiments, $R^2$ comprises an antibody comprising a heavy chain variable region (VH) comprising an amino acid sequence at least 85% (e.g., at least 95%) identical to SEQ ID NO: 17 and/or comprising a light chain variable region (VL) comprising an amino acid sequence at least 85% (e.g., at least 95%) identical to SEQ ID NO: 18. In some embodiments, $R^2$ comprises an antibody comprising a VH comprising the amino acid sequence of SEQ ID NO: 17 and/or comprising a VL comprising the amino acid sequence of SEQ ID NO: 18. In some embodiments, $R^2$ comprises an antibody comprising a heavy chain comprising an amino acid sequence at least 85% (e.g., at least 95%) identical to SEQ ID NO: 19 and/or comprising a light chain comprising an amino acid sequence at least 85% (e.g., at least 95%) identical to SEQ ID NO: 20. In some embodiments, $R^2$ comprises an antibody comprising a heavy chain comprising the amino acid sequence of SEQ ID NO: 19 and/or comprising a light chain comprising the amino acid sequence of SEQ ID NO: 20. In some embodiments, $R^2$ comprises an antibody that is a Fab fragment, a full-length IgG, a Fab' fragment, a $F(ab')_2$ fragment, an scFv, or an Fv. In some embodiments, $R^2$ comprises an antibody that is a Fab fragment. In some embodiments, $R^3$ comprises an RNAi oligonucleotide comprising an antisense strand comprising a nucleobase sequence of SEQ ID NO: 22 and a structure (5'→3') of VP-mU*fG*mCmCmAmGmAmAmUmUmUmCm AfCmGmGmAmAmGmAmA*mC*mA, and a sense strand comprising a nucleobase sequence of SEQ ID NO: 21 and a structure (5'→3') of mU*mU*mCmUfUmCmCmGfUfGfAmAmAfUmUm CmUmGfG*mC*mA, wherein: mA, mC, mG, and mU are 2'-O-methyl adenosine, 2'-O-methyl cytidine, 2'-O-methyl guanosine, and 2'-O-methyl uridine, respectively; fA, fC, fG, and fU are 2'-fluoro adenosine, 2'-fluoro cytidine, 2'-fluoro guanosine, and 2'-fluoro uridine, respectively; * between two nucleosides represents a phosphorothioate linkage; the absence of "*" between two nucleosides represents a phosphodiester internucleoside linkage; and "VP" represents 5'-(E)-Vinylphosphonate. In some embodiments, in each complex n1 is independently an integer (e.g., an integer in the range of 1-27, 1-26, 1-10, 1-5, or 1-3). In some embodiments, in each complex n1 is 1. In some embodiments, formulations described herein further comprise complexes that comprise a structure of formula (I): $[R^1]_{n1}$—$R^2$, wherein n1 is 0. In some embodiments, the average value of n1 of complexes of the composition is in the range of 0.5 to 5 (e.g., 0.5-5, 1-5, 1-4, 1-3, 3-5, 0.5-4, 0.5-3, 0.5-2, 0.5-1.5, 0.5-1, 0.7-1.5, 1-1.6, 1-1.5, 1-1.4, 1-1.3, 1-1.2, 1.1-1.5, 0.8-2, 0.8-1.5, 0.8-1.3, 0.8-1.2, 0.8-1.1, 0.9-3, 0.9-2, 0.9-1.8, 0.9-1.6, 0.9-1.5, 0.9-1.4, 0.9-1.3, or 0.9-1.2). In some embodiments, the average value of n1 of complexes of the composition is 1. In some embodiments, formulations further comprise tris(hydroxymethyl)aminomethane and sucrose. In some embodiments, formulations comprise tris(hydroxymethyl)aminomethane at a concentration of 25 mM and/or (e.g., and) sucrose at a concentration of 10 w/v %, optionally wherein the formulation has a pH of 7.5. In some embodiments, formulations comprise complexes at a concentration of 30 mg/mL.

In some embodiments, formulations provided herein comprise complexes that comprise a structure of formula (I): $[R^1]_{n1}$—$R^2$, in which each instance of $R^1$ in a complex of a formulation provided herein comprises a group of the formula (Ib):

(Ib)

3′-mA*mC*mAmAmGmAmAmGmGfCmAmCmUmUmUmAmAmGmAmCmC*fG*mU-5′-VP Antisense (SEQ ID NO: 22)
5′-mU*mU*mCmUfUmCmCmGfUfGfAmAmAfUmUmCmUmGfG*mC*mA-3′ Sense (SEQ ID NO: 21)

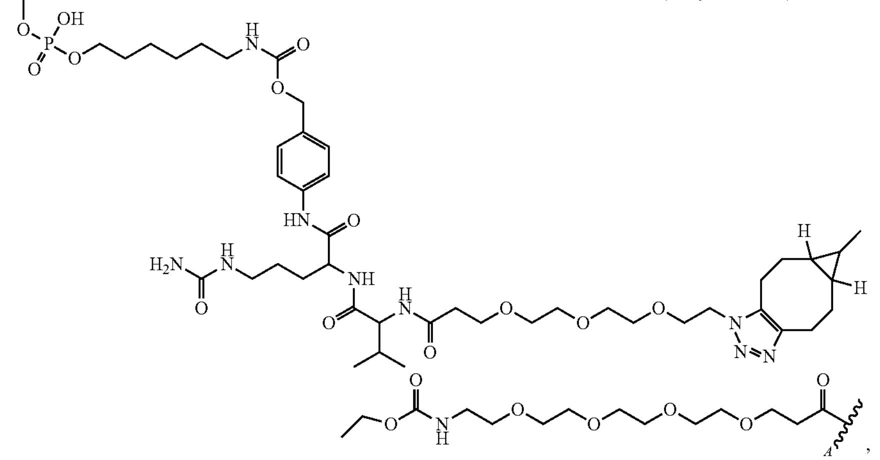

, or a pharmaceutically acceptable salt thereof, wherein: mA, mC, mG, and mU are 2'-O-methyl adenosine, 2'-O-methyl cytidine, 2'-O-methyl guanosine, and 2'-O-methyl uridine, respectively; fA, fC, fG, and fU are 2'-fluoro adenosine, 2'-fluoro cytidine, 2'-fluoro guanosine, and 2'-fluoro uridine, respectively; * between two nucleosides represents a phosphorothioate linkage; the absence of "*" between two nucleosides represents a phosphodiester internucleoside linkage; and "VP" represents 5'-(E)-Vinylphosphonate; and wherein the oligonucleotide is an RNAi oligonucleotide (e.g., siRNA) comprising an antisense strand comprising a nucleobase sequence of UGCCAGAAUUUCACGGAAGAACA (SEQ ID NO: 22) and a sense strand comprising a nucleobase sequence of UUCUUCCGUGAAAUUCUGGCA (SEQ ID NO: 21); wherein n1 is an integer (e.g., one or greater) representing the number of instances of $R^1$ in each complex, and each $R^1$ is covalently linked to $R^2$ at attachment point A. In some embodiments, $R^2$ comprises an antibody comprising a sequence as set forth in Table 2. For example, in some embodiments, $R^2$ comprises an antibody comprising a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14; and/or comprising a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5, or 11, and a light chain complementarity determining region 3 (CDR-L3) comprising a sequence as set forth in SEQ ID NO: 6 or 16. In some embodiments, $R^2$ comprises an antibody comprising a heavy chain variable region (VH) comprising an amino acid sequence at least 85% (e.g., at least 95%) identical to SEQ ID NO: 17 and/or comprising a light chain variable region (VL) comprising an amino acid sequence at least 85% (e.g., at least 95%) identical to SEQ ID NO: 18. In some embodiments, $R^2$ comprises an antibody comprising a VH comprising the amino acid sequence of SEQ ID NO: 17 and/or comprising a VL comprising the amino acid sequence of SEQ ID NO: 18. In some embodiments, $R^2$ comprises an antibody comprising a heavy chain comprising an amino acid sequence at least 85% (e.g., at least 95%) identical to SEQ ID NO: 19 and/or comprising a light chain comprising an amino acid sequence at least 85% (e.g., at least 95%) identical to SEQ ID NO: 20. In some embodiments, $R^2$ comprises an antibody comprising a heavy chain comprising the amino acid sequence of SEQ ID NO: 19 and/or comprising a light chain comprising the amino acid sequence of SEQ ID NO: 20. In some embodiments, $R^2$ comprises an antibody that is a Fab fragment, a full-length IgG, a Fab' fragment, a $F(ab')_2$ fragment, an scFv, or an Fv. In some embodiments, $R^2$ comprises an antibody that is a Fab fragment. In some embodiments, formulations described herein further comprise complexes that comprise a structure of formula (I): $[R^1]_{n1}$—$R^2$, wherein n1 is 0. In some embodiments, the average value of n1 of complexes of the formulation is in the range of 0.5 to 5 (e.g., 0.5-5, 1-5, 1-4, 1-3, 3-5, 0.5-4, 0.5-3, 0.5-2, 0.5-1.5, 0.5-1, 0.7-1.5, 1-1.6, 1-1.5, 1-1.4, 1-1.3, 1-1.2, 1.1-1.5, 0.8-2, 0.8-1.5, 0.8-1.3, 0.8-1.2, 0.8-1.1, 0.9-3, 0.9-2, 0.9-1.8, 0.9-1.6, 0.9-1.5, 0.9-1.4, 0.9-1.3, or 0.9-1.2). In some embodiments, the average value of n1 of complexes of the formulation is 1. In some embodiments, formulations further comprise tris(hydroxymethyl)aminomethane and sucrose. In some embodiments, formulations comprise tris(hydroxymethyl)aminomethane at a concentration of 25 mM and/or (e.g., and) sucrose at a concentration of 10 w/v %, optionally wherein the formulation has a pH of 7.5. In some embodiments, formulations comprise complexes at a concentration of 30 mg/mL.

In some embodiments, formulations provided herein comprise complexes that comprise a structure of formula (I): $[R^1]_{n1}$—$R^2$, in which each $R^1$ comprises a group of the formula (Ic), in which the antisense strand and the sense strand form a double stranded oligonucleotide:

(Ic)
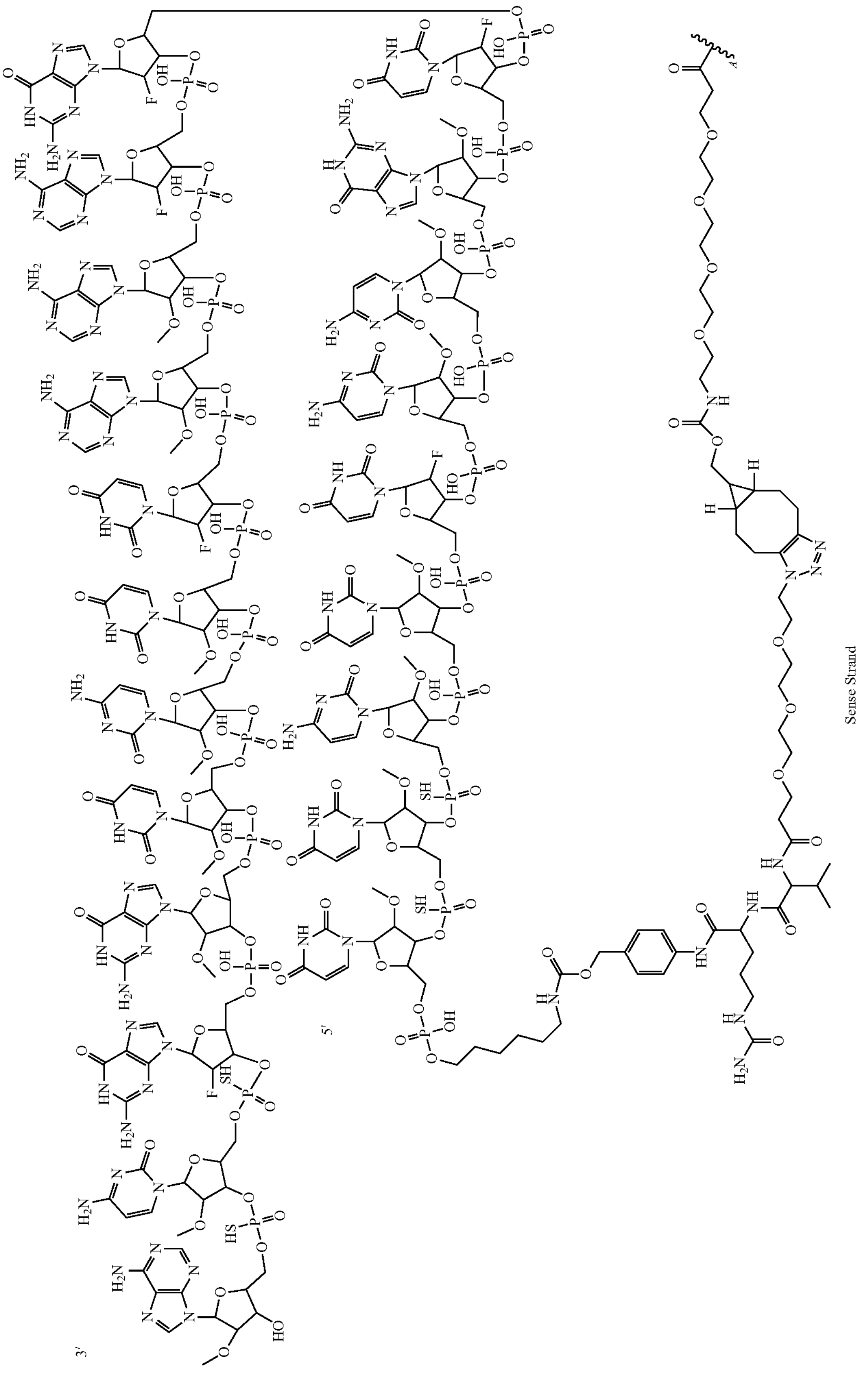

-continued
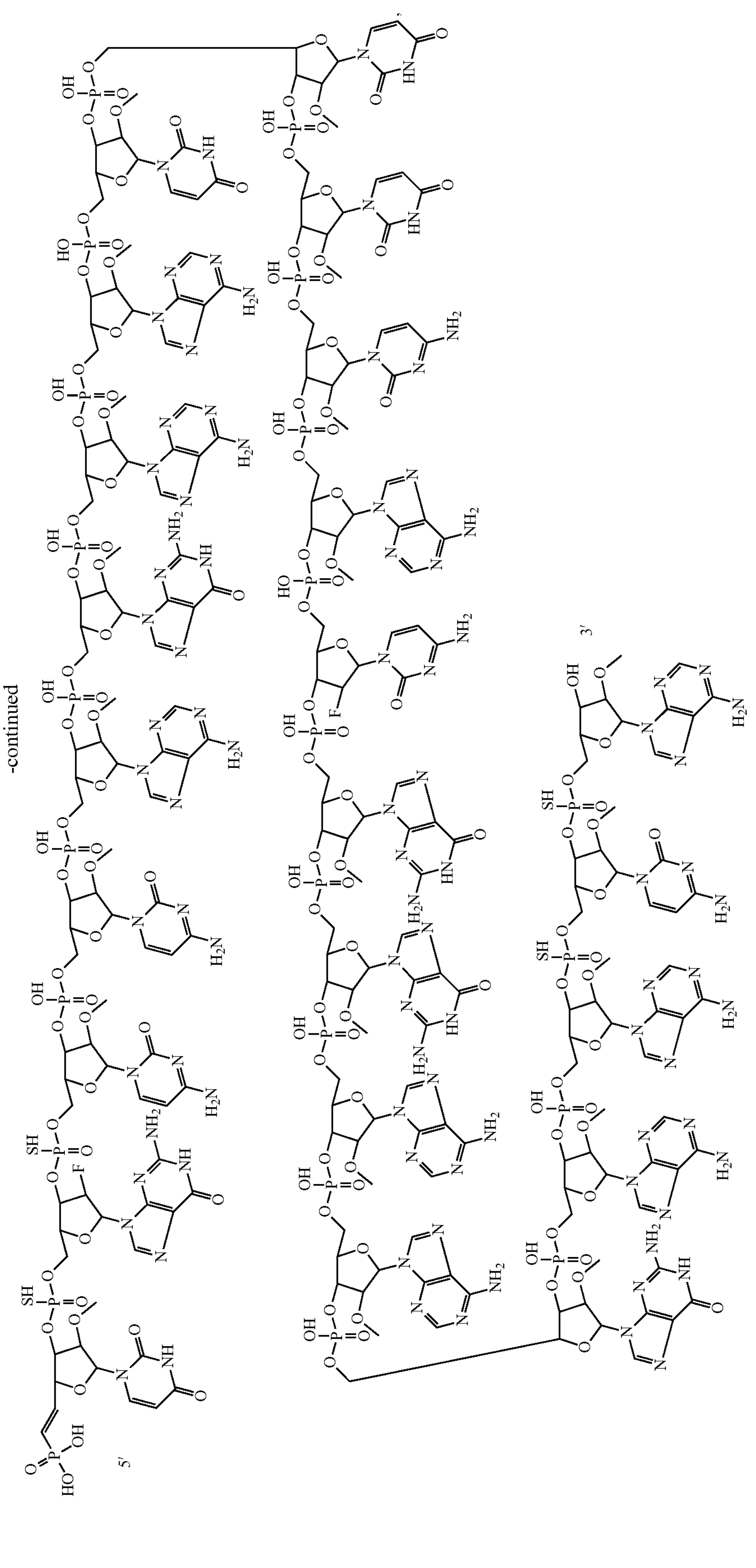
Antisense Strand or a pharmaceutically acceptable salt thereof, wherein $R^1$ is covalently linked to $R^2$ at attachment point A. In some embodiments, n1 is an integer (e.g., one or greater) representing the number of instances of $R^1$ in each complex. In some embodiments, $R^2$ comprises an antibody comprising a sequence as set forth in Table 2. For example, in some embodiments, $R^2$ comprises an antibody comprising a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14; and/or comprising a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5, or 11, and a light chain complementarity determining region 3 (CDR-L3) comprising a sequence as set forth in SEQ ID NO: 6 or 16. In some embodiments, $R^2$ comprises an antibody comprising a heavy chain variable region (VH) comprising an amino acid sequence at least 85% (e.g., at least 95%) identical to SEQ ID NO: 17 and/or comprising a light chain variable region (VL) comprising an amino acid sequence at least 85% (e.g., at least 95%) identical to SEQ ID NO: 18. In some embodiments, $R^2$ comprises an antibody comprising a VH comprising the amino acid sequence of SEQ ID NO: 17 and/or comprising a VL comprising the amino acid sequence of SEQ ID NO: 18. In some embodiments, $R^2$ comprises an antibody comprising a heavy chain comprising an amino acid sequence at least 85% (e.g., at least 95%) identical to SEQ ID NO: 19 and/or comprising a light chain comprising an amino acid sequence at least 85% (e.g., at least 95%) identical to SEQ ID NO: 20. In some embodiments, $R^2$ comprises an antibody comprising a heavy chain comprising the amino acid sequence of SEQ ID NO: 19 and/or comprising a light chain comprising the amino acid sequence of SEQ ID NO: 20. In some embodiments, $R^2$ comprises an antibody that is a Fab fragment, a full-length IgG, a Fab' fragment, a $F(ab')_2$ fragment, an scFv, or an Fv. In some embodiments, $R^2$ comprises an antibody that is a Fab fragment. In some embodiments, formulations described herein further comprise complexes that comprise a structure of formula (I): $[R^1]_{n1}—R^2$, wherein n1 is 0. In some embodiments, the average value of n1 of complexes of the formulation is in the range of 0.5 to 5 (e.g., 0.5-5, 1-5, 1-4, 1-3, 3-5, 0.5-4, 0.5-3, 0.5-2, 0.5-1.5, 0.5-1, 0.7-1.5, 1-1.6, 1-1.5, 1-1.4, 1-1.3, 1-1.2, 1.1-1.5, 0.8-2, 0.8-1.5, 0.8-1.3, 0.8-1.2, 0.8-1.1, 0.9-3, 0.9-2, 0.9-1.8, 0.9-1.6, 0.9-1.5, 0.9-1.4, 0.9-1.3, or 0.9-1.2). In some embodiments, the average value of n1 of complexes of the formulation is 1. In some embodiments, formulations further comprise tris(hydroxymethyl)aminomethane and sucrose. In some embodiments, formulations comprise tris(hydroxymethyl)aminomethane at a concentration of 25 mM and/or (e.g., and) sucrose at a concentration of 10 w/v %, optionally wherein the formulation has a pH of 7.5. In some embodiments, formulations comprise complexes at a concentration of 30 mg/mL.

In some embodiments, formulations provided herein comprise complexes that comprise a structure of the formula (Id):

(Id)
3′-mA*mC*mAmAmGmAmAmGmGfCmAmCmUmUmUmAmAmGmAmCmC*fG*mU-5′-VP Antisense (SEQ ID NO: 22)
5′-mU*mU*mCmUfUmCmCmGfUfGfAmAmAfUmUmCmUmGfG*mC*mA-3′ Sense (SEQ ID NO: 21)
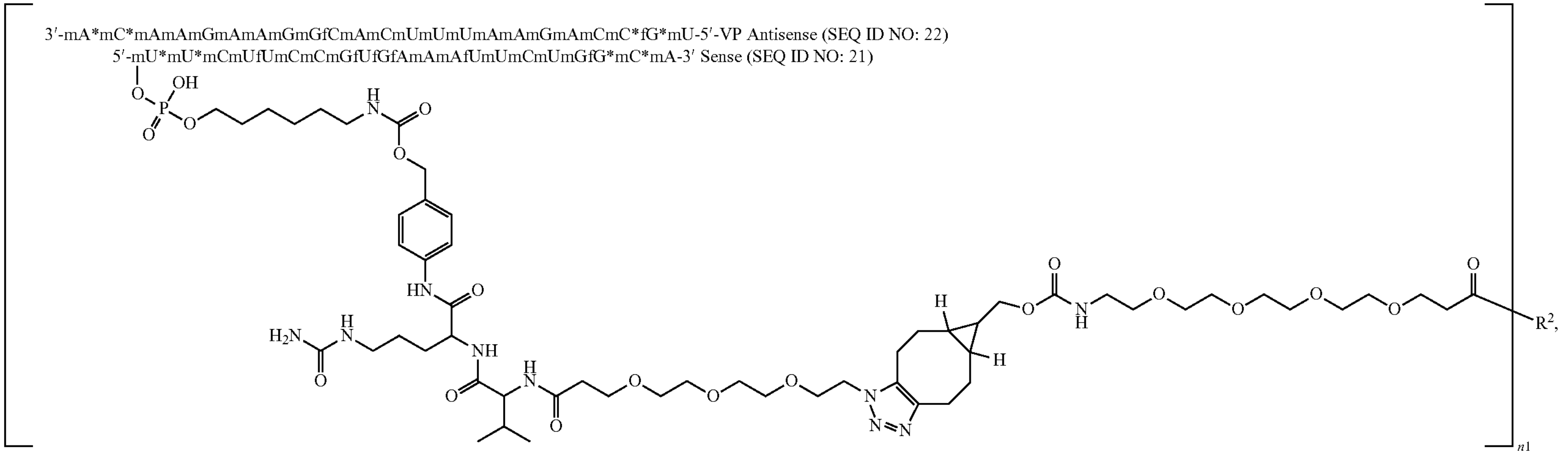

or a pharmaceutically acceptable salt thereof, wherein: mA, mC, mG, and mU are 2'-O-methyl adenosine, 2'-O-methyl cytidine, 2'-O-methyl guanosine, and 2'-O-methyl uridine, respectively; fA, fC, fG, and fU are 2'-fluoro adenosine, 2'-fluoro cytidine, 2'-fluoro guanosine, and 2'-fluoro uridine, respectively; * between two nucleosides represents a phosphorothioate linkage; the absence of "*" between two nucleosides represents a phosphodiester internucleoside linkage; and "VP" represents 5'-(E)-Vinylphosphonate; and wherein the oligonucleotide is an RNAi oligonucleotide (e.g., siRNA) comprising an antisense strand comprising a nucleobase sequence of UGCCAGAAUUUCACGGAAGAACA (SEQ ID NO: 22) and a sense strand comprising a nucleobase sequence of UUCUUCCGUGAAAUUCUGGCA (SEQ ID NO: 21); wherein $R^2$ comprises an antibody comprising a sequence as set forth in Table 2; wherein n1 is an integer (e.g., one or greater) representing the number of instances of the group enclosed by square brackets, wherein each instance of the group enclosed by square brackets is covalently linked to a different amino acid residue of the antibody, optionally wherein each different amino acid residue is a lysine. In some embodiments, $R^2$ comprises an antibody comprising a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14; and/or comprising a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5, or 11, and a light chain complementarity determining region 3 (CDR-L3) comprising a sequence as set forth in SEQ ID NO: 6 or 16. In some embodiments, $R^2$ comprises an antibody comprising a heavy chain variable region (VH) comprising an amino acid sequence at least 85% (e.g., at least 95%) identical to SEQ ID NO: 17 and/or comprising a light chain variable region (VL) comprising an amino acid sequence at least 85% (e.g., at least 95%) identical to SEQ ID NO: 18. In some embodiments, $R^2$ comprises an antibody comprising a VH comprising the amino acid sequence of SEQ ID NO: 17 and/or comprising a VL comprising the amino acid sequence of SEQ ID NO: 18. In some embodiments, $R^2$ comprises an antibody comprising a heavy chain comprising an amino acid sequence at least 85% (e.g., at least 95%) identical to SEQ ID NO: 19 and/or comprising a light chain comprising an amino acid sequence at least 85% (e.g., at least 95%) identical to SEQ ID NO: 20. In some embodiments, $R^2$ comprises an antibody comprising a heavy chain comprising the amino acid sequence of SEQ ID NO: 19 and/or comprising a light chain comprising the amino acid sequence of SEQ ID NO: 20. In some embodiments, $R^2$ comprises an antibody that is a Fab fragment, a full-length IgG, a Fab' fragment, a $F(ab')_2$ fragment, an scFv, or an Fv. In some embodiments, $R^2$ comprises an antibody that is a Fab fragment. In some embodiments, formulations described herein further comprise complexes in which n1 is 0. In some embodiments, the average value of n1 of complexes of the formulation is in the range of 0.5 to 5 (e.g., 0.5-5, 1-5, 1-4, 1-3, 3-5, 0.5-4, 0.5-3, 0.5-2, 0.5-1.5, 0.5-1, 0.7-1.5, 1-1.6, 1-1.5, 1-1.4, 1-1.3, 1-1.2, 1.1-1.5, 0.8-2, 0.8-1.5, 0.8-1.3, 0.8-1.2, 0.8-1.1, 0.9-3, 0.9-2, 0.9-1.8, 0.9-1.6, 0.9-1.5, 0.9-1.4, 0.9-1.3, or 0.9-1.2). In some embodiments, the average value of n1 of complexes of the formulation is 1. In some embodiments, formulations further comprise tris(hydroxymethyl)aminomethane and sucrose. In some embodiments, formulations comprise tris(hydroxymethyl)aminomethane at a concentration of 25 mM and/or (e.g., and) sucrose at a concentration of 10 w/v %, optionally wherein the formulation has a pH of 7.5. In some embodiments, formulations comprise complexes at a concentration of 30 mg/mL.

In some embodiments, complexes provided in the formulations described herein comprise a structure of formula (A):

(A)

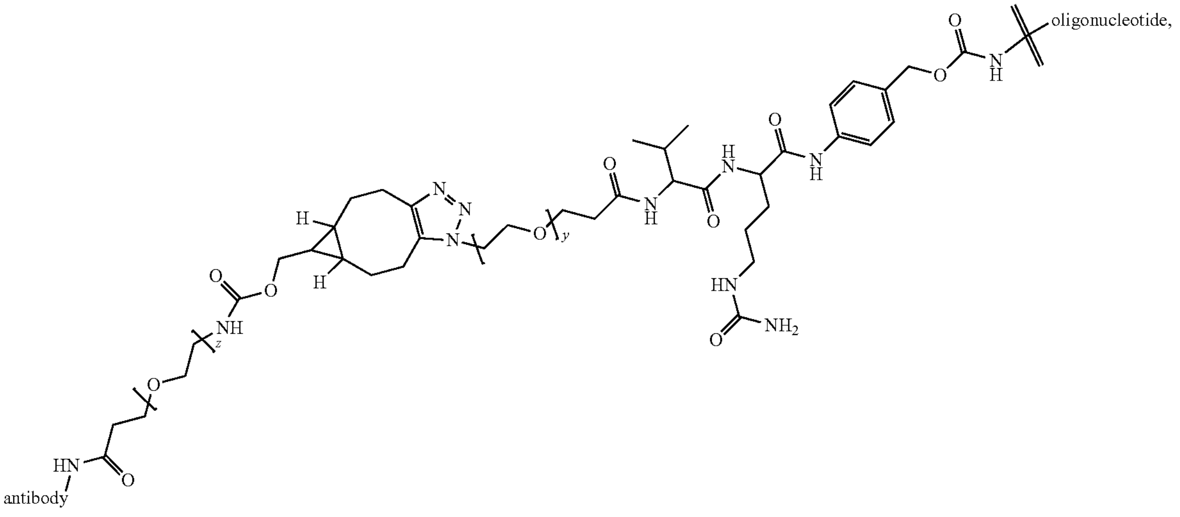

wherein y is 0-15 (e.g., 3) and z is 0-15 (e.g., 4), and wherein

represents an indirect or direct linkage. In some embodiments, the amide shown adjacent the antibody (e.g., anti-TfR1 antibody) in the structure (A) results from a reaction with an amine of the antibody, such as a lysine epsilon amine. In some embodiments, a complex described herein comprises an anti-TfR1 antibody (e.g., an anti-TfR1 Fab) covalently linked via a lysine of the antibody to the 5' end of an oligonucleotide (e.g., an RNAi oligonucleotide). In some embodiments, the antibody comprises a sequence as set forth in Table 2. For example, in some embodiments, the antibody comprises a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14; and/or comprises a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5, or 11, and a light chain complementarity determining region 3 (CDR-L3) comprising a sequence as set forth in SEQ ID NO: 6 or 16. In some embodiments, the antibody comprises a heavy chain variable region (VH) comprising an amino acid sequence at least 85% (e.g., at least 95%) identical to SEQ ID NO: 17 and/or comprises a light chain variable region (VL) comprising an amino acid sequence at least 85% (e.g., at least 95%) identical to SEQ ID NO: 18. In some embodiments, the antibody comprises a VH comprising the amino acid sequence of SEQ ID NO: 17 and/or comprises a VL comprising the amino acid sequence of SEQ ID NO: 18. In some embodiments, the antibody comprises a heavy chain comprising an amino acid sequence at least 85% (e.g., at least 95%) identical to SEQ ID NO: 19 and/or comprises a light chain comprising an amino acid sequence at least 85% (e.g., at least 95%) identical to SEQ ID NO: 20. In some embodiments, the antibody comprises a heavy chain comprising the amino acid sequence of SEQ ID NO: 19 and/or comprises a light chain comprising the amino acid sequence of SEQ ID NO: 20. In some embodiments, the antibody is a Fab fragment, a full-length IgG, a Fab' fragment, a $F(ab')_2$ fragment, an scFv, or an Fv. In some embodiments, the antibody is a Fab fragment. In some embodiments, formulations further comprise tris(hydroxymethyl)aminomethane and sucrose. In some embodiments, formulations comprise tris(hydroxymethyl)aminomethane at a concentration of 25 mM and/or (e.g., and) sucrose at a concentration of 10 w/v %, optionally wherein the formulation has a pH of 7.5. In some embodiments, formulations comprise complexes at a concentration of 30 mg/mL.

As described herein, in some embodiments, formulations provided herein comprise sucrose. In some embodiments, sucrose serves at least in part as a lyoprotectant. In some embodiments, the sucrose is from a plant, e.g., grass, fruit, or vegetable (e.g., root vegetable) source (e.g., beet (e.g., sugar beet, for example, *Saccharum* spp.)), sugarcane (e.g., *Beta vulgaris*), dates, sugar maple, sweet sorghum, apples, oranges, carrots, molasses, maple syrup, corn sweeteners) or animal product (e.g., honey). In some embodiments, the sucrose is from beet or sugarcane (e.g., beet sucrose, sugarcane sucrose). In some embodiments, a lyoprotectant other than sucrose may be used, e.g., trehalose, mannitol, lactose, polyethylene glycol, or polyvinyl pyrrolidone. However, in some embodiments, a collapse temperature modifier (e.g., dextran, ficoll, or gelatin) may be provided in a formulation.

In some embodiments, provided is a product (e.g., lyophilized formulation described herein), produced by a process comprising lyophilizing an aqueous solution of a formulation (e.g., aqueous form) described herein.

In some embodiments, a pharmaceutical composition is formulated to be compatible with its intended route of administration. Examples of routes of administration include parenteral, e.g., intravenous, intradermal, subcutaneous, administration. Typically, the route of administration is intravenous or subcutaneous.

Methods of Use/Treatment

Complexes comprising a muscle-targeting agent (e.g., an anti-TfR1 antibody) covalently linked to a molecular payload (e.g., an RNAi oligonucleotide) as described herein are effective in treating FSHD. In some embodiments, complexes are effective in treating Type 1 FSHD. In some embodiments, complexes are effective in treating Type 2 FSHD. In some embodiments, FSHD is associated with deletions in D4Z4 repeat regions on chromosome 4 which contain the DUX4 gene. In some embodiments, FSHD is associated with mutations in the SMCHD1 gene. In some embodiments, FSHD is associated with mutations in the DNMT3B gene. In some embodiments, FSHD is associated with mutations in the LRIF1 gene. In some embodiments, a subject may be a human subject, a non-human primate subject, a rodent subject, or any suitable mammalian subject. In some embodiments, a subject may have myotonic dystrophy. In some embodiments, a subject has elevated expression of the DUX4 gene outside of fetal development and the testes. In some embodiments, the subject has facioscapulohumeral muscular dystrophy of Type 1 or Type 2. In some embodiments, the subject having FSHD has mutations in the SMCHD1 gene. In some embodiments, the subject having FSHD has mutations in the DNMT3B gene. In some embodiments, the subject having FSHD has mutations in the LRIF1 gene. In some embodiments, the subject having FSHD has deletion mutations in D4Z4 repeat regions on chromosome 4.

An aspect of the disclosure includes methods involving administering to a subject a composition (e.g., a formulation) comprising an effective amount of complex(es) as described herein. In some embodiments, an effective amount of a pharmaceutical composition that comprises complex (es) comprising an antibody (e.g., Fab) described herein covalently linked to an oligonucleotide (e.g., a DUX4 targeting RNAi oligonucleotide) described herein can be administered to a subject in need of treatment. In some embodiments, a pharmaceutical composition comprising complex(es) as described herein may be administered by a suitable route, which may include intravenous administration, e.g., as a bolus or by continuous infusion over a period of time. In some embodiments, a pharmaceutical composition comprising complex(es) as described herein may be administered by a suitable route, which may include subcutaneous administration. In some embodiments, administration may be performed by intravenous, intramuscular, intraperitoneal, intracerebrospinal, subcutaneous, intra-articular, intrasynovial, or intrathecal routes. In some embodiments, a pharmaceutical composition may be in solid form, aqueous form, or a liquid form. In some embodiments, an aqueous or liquid form may be nebulized or lyophilized. In some embodiments, a lyophilized form may be reconstituted with an aqueous or liquid solution.

In some embodiments, provided are methods of and/or uses for treating a subject having aberrant (e.g., increased) expression of DUX4 RNA and/or protein in muscle comprising administering to the subject a composition (e.g., a formulation) described herein that comprises an effective amount of complex(es) described herein. In some embodiments, provided are methods of and/or uses for reducing the expression or activity of DUX4 (e.g., reducing levels of DUX4 RNA and/or protein) in a cell (e.g., a muscle cell), the methods comprising contacting the cell with a formulation described herein comprising an effective amount of complex (es) described herein. In some embodiments, the method comprises administering a lyophilized form (e.g., lyophilized powder) of the formulation described herein, comprising reconstituting a lyophilized form of the formulation in an aqueous solution, and administering the aqueous solution of the formulation to a subject in need thereof. For example, in some embodiments, a lyophilized form of the formulation is shipped and/or stored in the lyophilized form, reconstituted at a location for administering the aqueous solution of the formulation (e.g., healthcare provider location), and administered in the reconstituted form (e.g., as an aqueous solution) by injection or intravenously, e.g., by infusion.

In some embodiments, a pharmaceutical composition is administered via site-specific or local delivery techniques. Examples of these techniques include implantable depot sources of the complex, local delivery catheters, site specific carriers, direct injection, or direct application.

In some embodiments, a pharmaceutical composition that comprises a complex comprising a an anti-TfR1 antibody (e.g., a fab) covalently linked to a molecular payload (e.g., a DUX4 targeting RNAi oligonucleotide) is administered at an effective concentration that confers therapeutic effect on a subject. Effective amounts vary, as recognized by those skilled in the art, depending on the severity of the disease, unique characteristics of the subject being treated, e.g. age, physical conditions, health, or weight, the duration of the treatment, the nature of any concurrent therapies, the route of administration and related factors. These related factors are known to those in the art and may be addressed with no more than routine experimentation. In some embodiments, an effective concentration is the maximum dose that is considered to be safe for the patient. In some embodiments, an effective concentration will be the lowest possible concentration that provides maximum efficacy.

Empirical considerations, e.g. the half-life of the complex (es) in a subject, generally will contribute to determination of the concentration of pharmaceutical composition that is used for treatment. The frequency of administration may be empirically determined and adjusted to maximize the efficacy of the treatment.

The efficacy of treatment may be assessed using any suitable methods. In some embodiments, the efficacy of treatment may be assessed by evaluation of observation of symptoms associated with FSHD including muscle mass loss and muscle atrophy, primarily in the muscles of the face, shoulder blades, and upper arms.

In some embodiments, a pharmaceutical composition that comprises a complex comprising a muscle-targeting agent (e.g., an anti-TfR1 antibody) covalently linked to a molecular payload (e.g., an RNAi oligonucleotide) described herein is administered to a subject at an effective concentration sufficient to modulate activity or expression of a target gene by at least 10%, at least 20%, at least 30%, at least 40%, at least 50%, at least 60%, at least 70%, at least 80%, at least 90% or at least 95% relative to a control, e.g. baseline level of gene expression prior to treatment.

EXAMPLES

Example 1: Activities of Anti-TfR1 Fab-siRNA Complexes in FSHD Patient Myotubes Activities of complexes containing an anti-TfR1 antibody provided in Table 2 covalently linked via a linker to a DUX4-targeting siRNA were tested in AB1080 immortalized FSHD patient-derived myotubes. The DUX4-targeting siRNA comprises an antisense strand comprising a nucleobase sequence of SEQ ID NO: 22 and a structure (5'→3') of VP-mU*fG*mCmCmAmGmAmAmUmUmUmCmAfCm GmGmAmAmGmAmA*mC*mA and a sense strand comprising a nucleobase sequence of SEQ ID NO: 21 and a structure (5'→3') of mU*mU*mCmUfUmCmCmGfUfGfAmAmAfUmUmCm UmGfG*mC*mA, wherein: mA, mC, mG, and mU are 2'-O-methyl adenosine, 2'-O-methyl cytidine, 2'-O-methyl guanosine, and 2'-O-methyl uridine, respectively; fA, fC, fG, and fU are 2'-fluoro adenosine, 2'-fluoro cytidine, 2'-fluoro guanosine, and 2'-fluoro uridine, respectively; * between two nucleosides represents a phosphorothioate linkage; the absence of "*" between two nucleosides represents a phosphodiester internucleoside linkage; and "VP" represents 5'-(E)-Vinylphosphonate.

Two versions of the anti-TfR1 Fab-siRNA complex were tested, one in which the anti-TfR1 Fab was covalently linked to the 3' end of the sense strand of the siRNA and one in which the anti-TfR1 Fab was covalently linked to the 5' end of the sense strand of each siRNA. A complex containing an anti-TfR1 antibody provided in Table 2 covalently linked via a linker to an exon 1 targeting siRNA was used as a positive control.

AB1080 (C6) immortalized FSHD patient-derived myotubes were treated with the siRNA complexes at a concentration equivalent to 10 nM, 100 nM, or 1000 nM for 10 days. cDNA was obtained from cells with the TaqMan Fast Advanced Cells-to-Ct Kit (Thermo Fisher Scientific), and levels of three DUX4 transcriptome markers MBD3L2 (Hs00544743_m1), TRIM43 (Hs00299174_m1), ZSCAN4 (Hs00537549_m1), and RPL13A(Hs04194366_g1) were analyzed via qPCR with specific TaqMan assays (Thermo Fisher Scientific). Two-step amplification reactions and fluorescence measurements for determination of cycle threshold (Ct) were conducted on a QuantStudio 7 instrument (Thermo Fisher Scientific). Composite scores calculated using the average mRNA level of three DUX4 transcriptome markers MBD3L2, TRIM43, and ZSCAN4 in FSHD patient-derived C6 myotubes are shown in FIG. 1.

Results show that the tested anti-TfR1 Fab-siRNA complexes achieved significant level of knockdown of the tested DUX4 transcriptome markers in FSHD patient-derived C6 myotubes compared to the positive control.

Example 2: Activities of an Anti-TfR1 Fab-siRNA Complex in FSHD Patient-Derived Primary Cells Activities of a complex containing an anti-TfR1 antibody provided in Table 2 covalently linked to a DUX4-targeting siRNA, were tested in FSHD1 primary cells (MB010, MB015, MB016, MB018 and MB020). In the complex, the anti-TfR1 Fab is covalently linked to the 5' end of the sense strand of each siRNA via a linker, and the corresponding antisense strand is annealed to the sense strand. The anti-TfR1 Fab-siRNA complex comprises a structure of formula (Id):

(Id)
3′-mA*mC*mAmAmGmAmAmGmGfCmAmCmUmUmUmAmAmGmAmCmC*fG*mU-5′-VP Antisense (SEQ ID NO: 22)
5′-mU*mU*mCmUfUmCmCmGfUfGfAmAmAfUmUmCmUmGfG*mC*mA-3′ Sense (SEQ ID NO: 21)
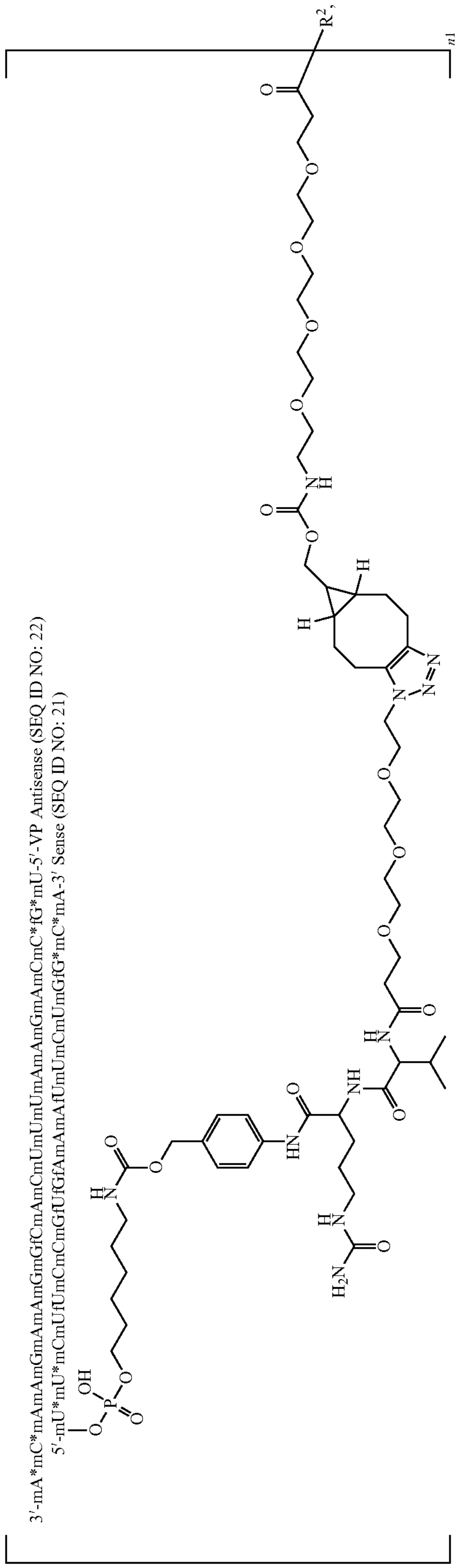

or a pharmaceutically acceptable salt thereof, wherein: mA, mC, mG, and mU are 2'-O-methyl adenosine, 2'-O-methyl cytidine, 2'-O-methyl guanosine, and 2'-O-methyl uridine, respectively; fA, fC, fG, and fU are 2'-fluoro adenosine, 2'-fluoro cytidine, 2'-fluoro guanosine, and 2'-fluoro uridine, respectively; * between two nucleosides represents a phosphorothioate linkage; the absence of "*" between two nucleosides represents a phosphodiester internucleoside linkage; and "VP" represents 5'-(E)-Vinylphosphonate; wherein the oligonucleotide is an RNAi oligonucleotide (e.g., siRNA) comprising an antisense strand comprising a nucleobase sequence of UGCCAGAAUUUCACGGAAGAACA (SEQ ID NO: 22) and a sense strand comprising a nucleobase sequence of UUCUUCCGUGAAAUUCUGGCA (SEQ ID NO: 21); wherein $R^2$ comprises an antibody comprising a sequence as set forth in Table 2, and wherein in each complex, n1 is 1.

The primary cells were treated with the anti-TfR1 Fab-siRNA complex at a concentration equivalent of 100 nM of siRNA for 7 days. cDNA was obtained from cells with the TaqMan Fast Advanced Cells-to-Ct Kit (Thermo Fisher Scientific), and levels of three DUX4 transcriptome markers MBD3L2 (Hs00544743_m1), TRIM43 (Hs00299174_m1), ZSCAN4 (Hs00537549_m1), and RPL13A (Hs04194366_g1) were analyzed via qPCR with specific TaqMan assays (Thermo Fisher Scientific). Two-step amplification reactions and fluorescence measurements for determination of cycle threshold (Ct) were conducted on a QuantStudio 7 instrument (Thermo Fisher Scientific).

Results (see Table 3) show that the anti-TfR1 Fab-siRNA complex achieved significant reduction of the tested DUX4 transcriptome markers in FSHD patient-derived primary cells.

TABLE 3

| | DUX4 transcriptomics (% control) | |
|---|---|---|
| FSHD cells | Average | SD |
| MB010 | 60.3 | 20.7 |
| MB015 | 33.7 | 12.0 |
| MB016 | 37.6 | 10.9 |
| MB018 | 34.5 | 13.4 |
| MB020 | 2.7 | 1.2 |

Example 3: Activities of Anti-TfR1 Fab-siRNA Complexes in Mouse Muscle Tissues

Activities of the complexes described in Example 1, containing an anti-TfR1 antibody provided in Table 2 covalently linked via a linker to a DUX4-targeting siRNA, were tested in eight- to nine-week-old hTfR1/FLExDUX4/ACTA mice. hTfR1/FLExDUX4/ACTA mice are transgenic mice that carry a transgene encoding human hTfR1 protein, a Cre recombinase-activatable DUX4 expression vector, and a muscle-specific tamoxifen-inducible Cre recombinase expression vector. This system allows low level, spontaneous DUX4 activation in skeletal muscle in the absence of tamoxifen, or acute induction of DUX4 expression following tamoxifen administration. DUX4 activation in this mouse model causes expression of the DUX4 transcriptome (D4T). D4T activation therefore provides an indirect measurement of DUX4 levels, which is itself extremely difficult to detect.

Two versions of the anti-TfR1 Fab-siRNA complex were tested, one in which the anti-TfR1 Fab was covalently linked to the 3' end of the sense strand of the siRNA and one in which the anti-TfR1 Fab was covalently linked to the 5' end of the sense strand of each siRNA.

The hTfR1/FLExDUX4/ACTA mice were intravenously injected with a single dose of a vehicle control (phosphate-buffered saline) or an siRNA complex at a concentration equivalent to 10 mg/kg of siRNA. Each experimental condition was replicated in three to fifteen individual hTfR1/FLExDUX4/ACTA mice. Following twenty-eight days after injection, the mice were euthanized. Gastrocnemius and quadricep muscles were collected and snap frozen in RNAlater™ Stabilization Solution (Thermo Fisher Scientific). Total miRNA was isolated from gastrocnemius and quadricep muscles with the Maxwell® RSC miRNA tissue kit (Promega) and real-time quantitative RT-PCR was performed.

Figure 2A:
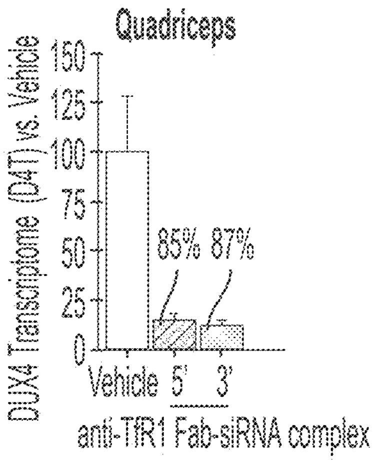
FIGS. 2A-2B show a composite score of the mRNA levels of three DUX4 mouse transcriptome (D4T) markers (Wfdc3, Sord, Serpinb6c) in mouse muscle quadriceps (FIG. 2A) and gastrocnemius (FIG. 2B) muscles relative to vehicle-treated controls. Tissues were collected 4 weeks after a single intravenous injection of DUX4-targeting siRNA complexes covalently linked to anti-TfR1 antibody provided in Table 2 at a dose of 10 mg/kg of siRNA.
Figure 2B:
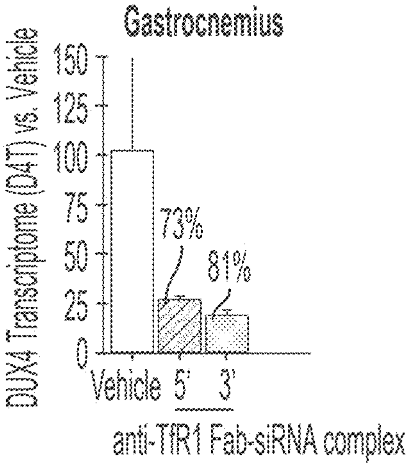

Three murine downstream DUX4 transcriptome markers Wfdc3 (Mm01243777_m1), Sord (Mm00455377_g1), Serpinb6c (Mm00655242_m1), and Rp137A (Mm00782745_s1) were analyzed via qPCR with specific TaqMan assays (Thermo Fisher Scientific). Two-step amplification reactions and fluorescence measurements for determination of cycle threshold (Ct) were conducted on a QuantStudio 7 instrument (Thermo Fisher Scientific). FSHD composite scores were calculated using the three DUX4 transcriptome markers (Wfdc3, Sord, Serpinb6c) where ΔCt=(Average Ct of 3 DUX4 markers)−(Average Ct of Rpl37A), ΔΔCt=ΔCt (Treated)−ΔCt (Vehicle), FSHD Composite=2−ΔΔCT*100(%) (see Table 4, FIGS. 2A and 2B).

Results show that the anti-TfR1 Fab-siRNA complexes achieved significant reduction of the tested DUX4 mouse transcriptome markers in the gastrocnemius and quadriceps of hTfR1/FLExDUX4/ACTA mice.

TABLE 4

| | DUX4 transcriptome knockdown (% knockdown vs vehicle) | |
|---|---|---|
| antiTfR1-siRNA | Quadriceps | Gastrocnemius |
| siRNA - 5' | 85 | 73 |
| siRNA - 3' | 87 | 81 |

Example 4: Stability and Binding Affinity of Anti-TfR1 Fab-siRNA Complexes in Exemplary Formulations A formulation comprising complexes of formula (Id), or a pharmaceutically acceptable salt thereof, as described in Example 2, containing an anti-TfR1 antibody provided in Table 2 covalently linked to a DUX4-targeting siRNA was prepared. The anti-TfR1 Fab-siRNA complexes were formulated in a buffer at a Fab concentration of approximately 16 mg/mL. The buffer conditions were as follows: 25 mM tris(hydroxymethyl)aminomethane, 10% (w/v) sucrose, pH 7.5.

Heat stability of the complex formulated in the formulation buffer was tested by size exclusion chromatography (SEC). The formulation was incubated at room temperature for 4 weeks, and the samples were analyzed using analytical UPLC-SEC (Waters Xbridge Protein BEH SEC 2.5 um, 4.6×30 mm, 0.3 mL/min, in PBS) (see FIG. 3A). The monomer percentage of the DAR1 peak was measured to determine if the complex remained stable and intact (see FIG. 3B). The peak area was also measured to assess if the complex precipitated during the incubation period (see FIG. 3C).

Figure 3A:
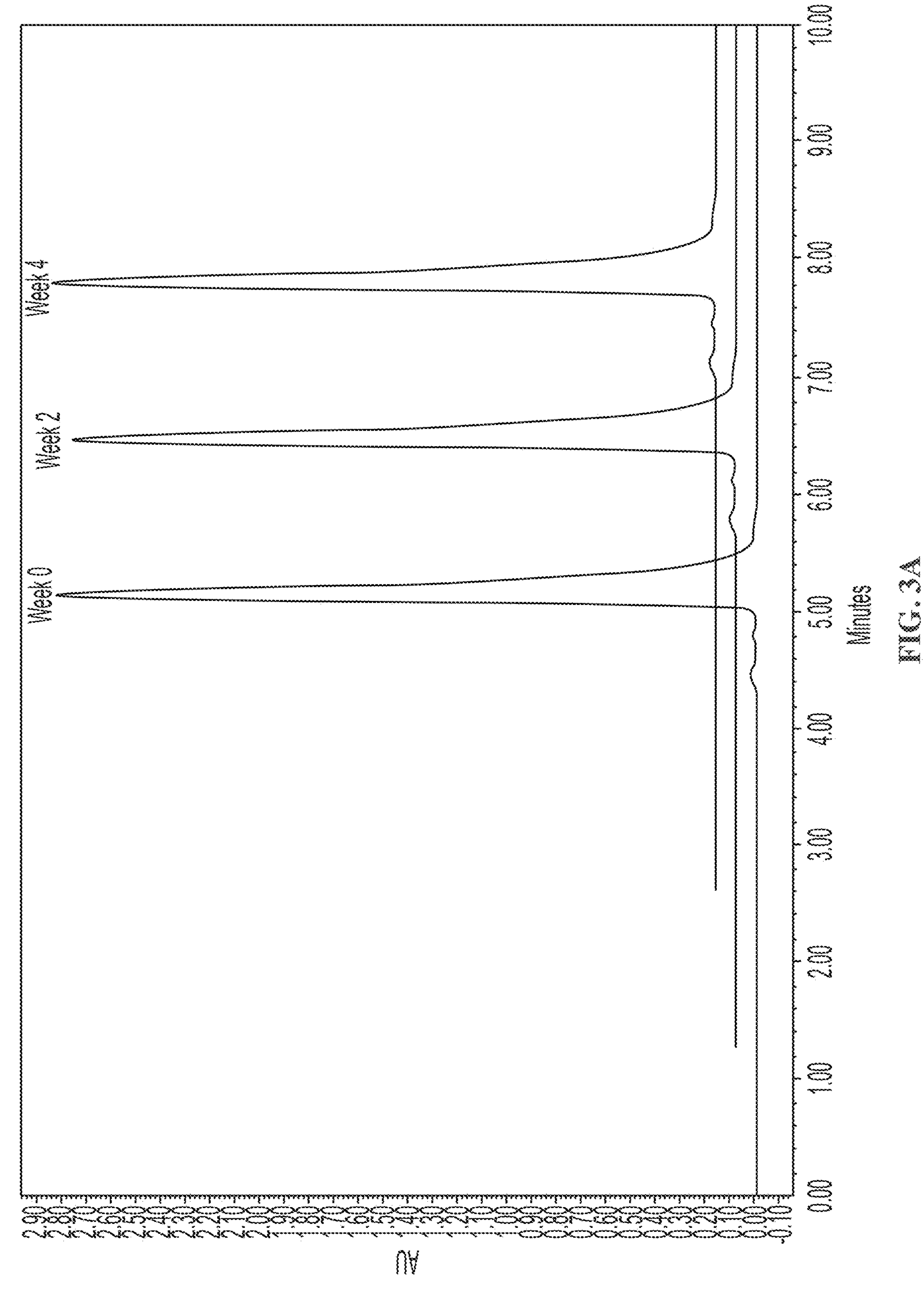
FIGS. 3A-3C show heat stability of complexes of formula (Id), comprising an anti-TfR1 antibody provided in Table 2 covalently linked to a DUX4-targeting siRNA in a formulation containing 25 mM tris(hydroxymethyl)aminomethane, 10% (w/v) sucrose, at a pH of 7.5. The complex was incubated at room temperature for 4 weeks, and the samples were analyzed using analytical ultra-high performance liquid chromatography-size exclusion chromatography (UPLC-SEC) (FIG. 3A). The x-axis corresponds to the Week 0 trace only with the other timepoints offset for clarity. SEC monomer percentage results are shown in FIG. 3B. SEC peak area results are shown in FIG. 3C.
Figure 3B:
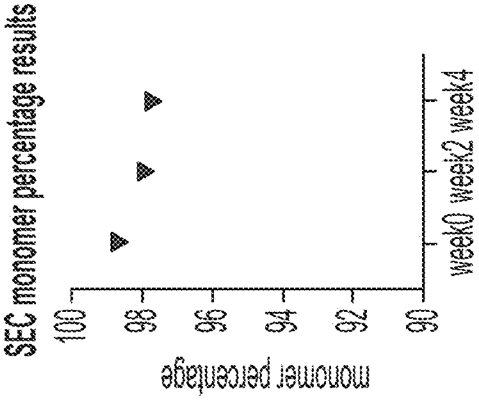
Figure 3C:
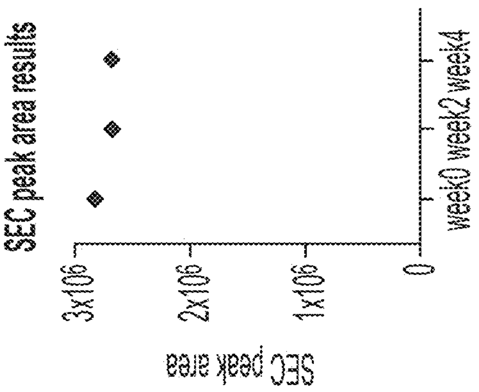

The results in FIGS. 3A-3C showed that the complexes remained stable, with only slight changes observed in the monomer percentage and peak area. No changes occurred when the samples were kept at −20° C. and −80° C.

Figure 4A:
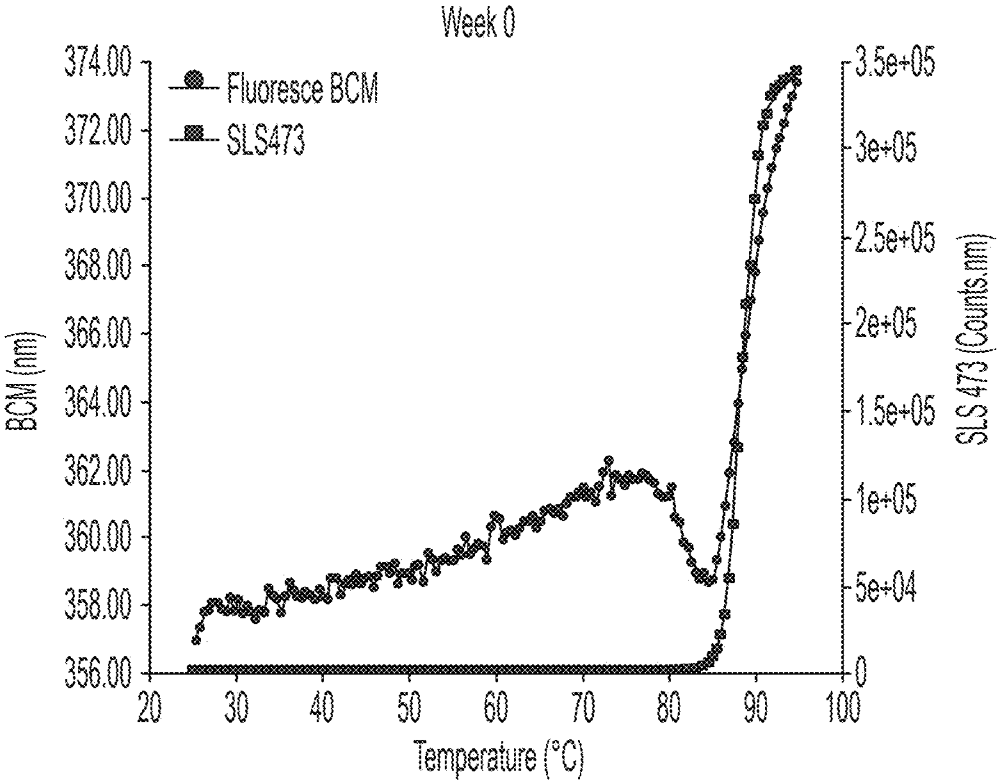
FIGS. 4A-4B show heat stability of complexes of formula (Id), comprising an anti-TfR1 antibody provided in Table 2 covalently linked to a DUX4-targeting siRNA in a formulation containing 25 mM tris(hydroxymethyl)aminomethane, 10% (w/v) sucrose, at a pH of 7.5. The complex was analyzed using UNcle stability screening platform (Unchained Labs) and specifically, by the UNcle $T_m/T_{agg}$ method, using BCM (barycentric mean) and SLS473 (static light scattering) analyses. The complex was analyzed at two different time points: week 0 (FIG. 4A) and week 4 (FIG. 4B) after incubation at room temperature.
Figure 4B:
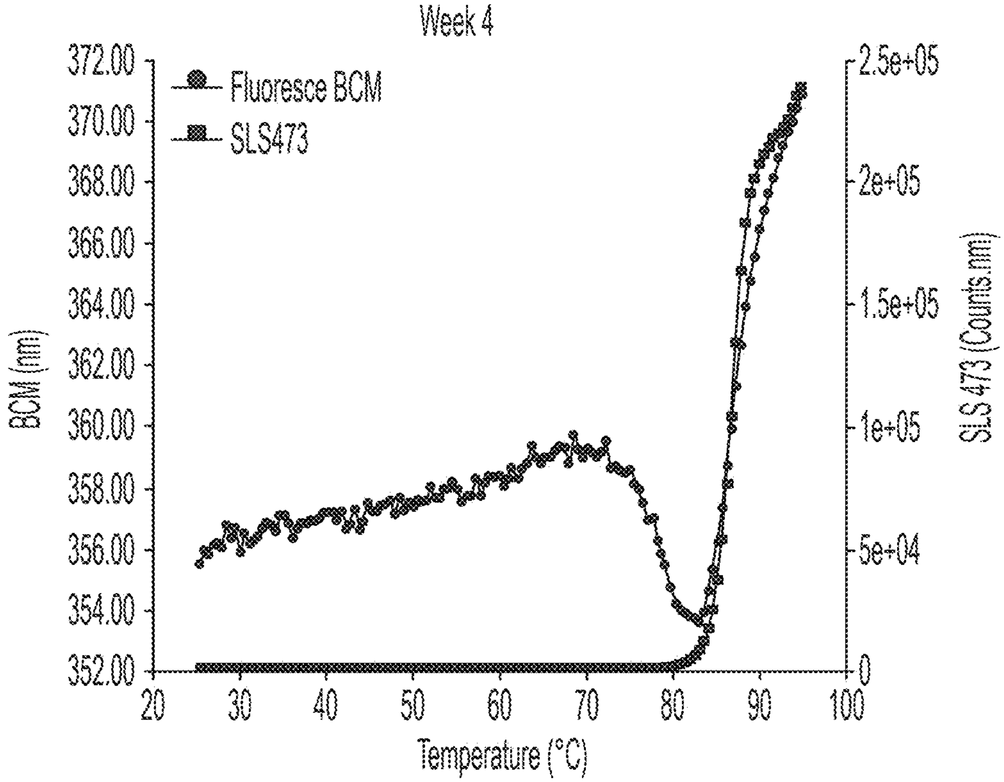

Additionally, heat stability of the complex formulated in the formulation buffer was measured by UNcle stability screening platform (Unchained Labs). UNcle combines full-spectrum fluorescence, Static Light Scattering (SLS) and Dynamic Light Scattering (DLS) measurement modes. Heat stability of the complex was measured by the UNcle $T_m/T_{agg}$ method (9 ul of 10 mg/ml sample loaded in UNcle sample cartridge) (see FIGS. 4A-4B). FIGS. 4A and 4B show the results of BCM and SLS473 analyses for the complex at two different time points: week 0 and week 4 after incubation at room temperature. The BCM method analyzes the intrinsic protein fluorescence of the conjugate complex to characterize protein unfolding and determine the melting temperature ($T_m$) of the protein complex. The $T_m$ values measured by BCM for the week 0 and week 4 samples are 86.8° C. and 86.5° C., respectively. SLS (s"atic light scatter"ng) uses "elastic scattering" to measure the scattering intensity of the protein complex, with intensity increasing as proteins aggregate. SLS473 provides the $T_{agg}$ value, which represents the aggregation tendency of the protein complex. The $T_{agg}$ values measured by SLS473 for the week 0 and week 4 samples are 82.4° C. and 82.8° C., respectively.

The results show that after incubation at room temperature for 4 weeks, the heat stability of the complex did not change.

Figure 5:
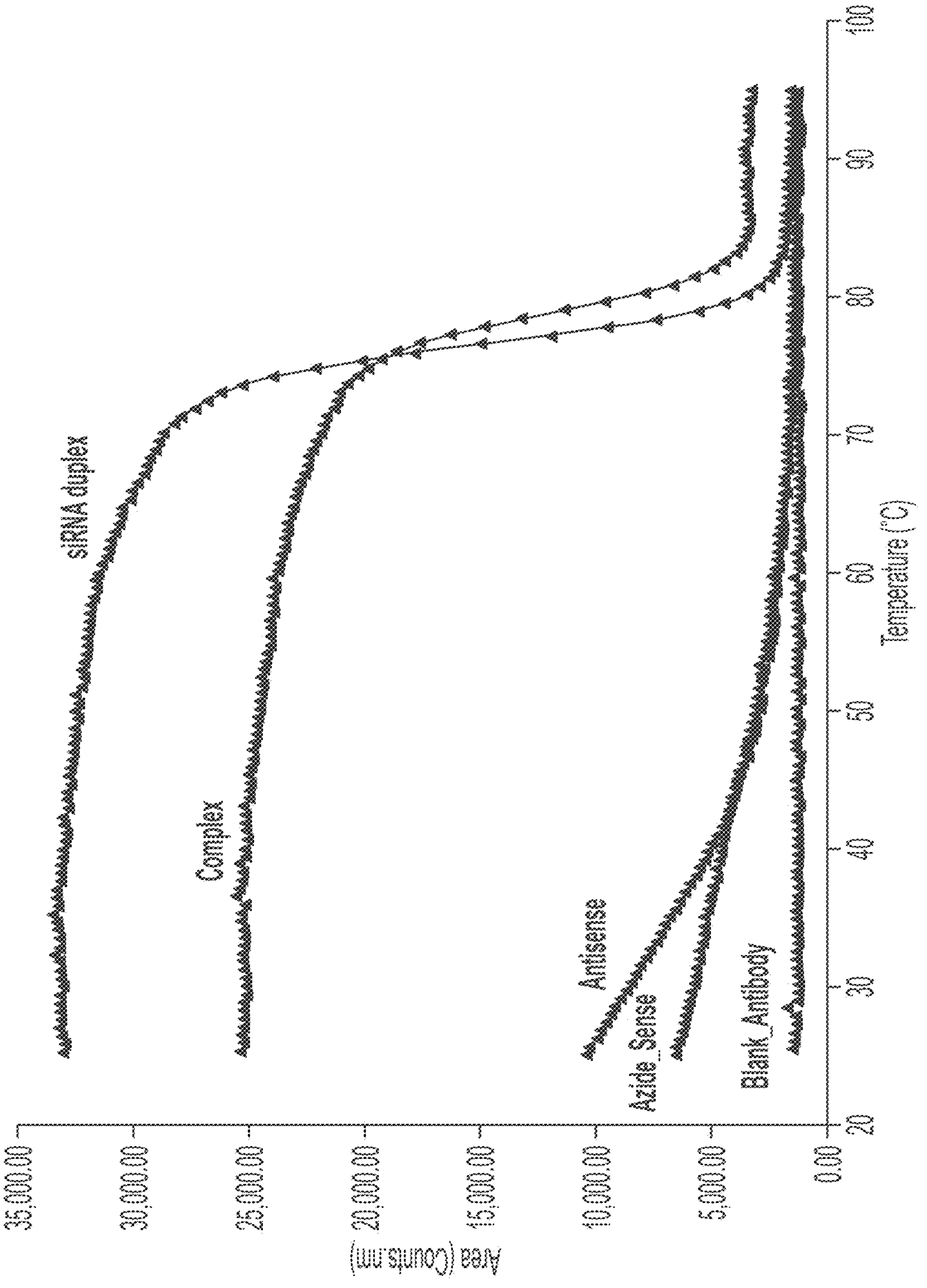
FIG. 5 shows heat stability of the complexes of formula (Id), comprising an anti-TfR1 antibody provided in Table 2 covalently linked to a DUX4-targeting siRNA in comparison with the unconjugated DUX4-targeting siRNA duplex. Differential scanning fluorimetry (DSF) was used to measure heat stability of the complexes.

Differential scanning fluorimetry (DSF), an assay used to monitor the heat stability of RNA, was also run on UNcle. DSF measures the melting temperature (Tm) of siRNAs in their naked duplex form as well as when they are in the complex. The anti-TfR1 Fab-siRNA complex or the anti-TfR1 Fab were buffer exchanged into TE buffer and concentrated to 0.21 mM. They were then mixed with a diluted RiboGreen dye in TE buffer at a ratio of 1:1, with the RiboGreen dye being diluted 2000 times. DSF was run on UNcle using a pre-set program called "Tm by Sypro". The fluorescence signals at 473 nm were applied to generate DSF profiles. The results are shown in FIG. 5 and demonstrate that both the naked siRNA duplex and the siRNA complex exhibit similar heat stability. The siRNA duplex was stable when the complex was kept at room temperature for four weeks. Melting temperatures measured at weeks 0, 2, and 4 were 78.3° C., 78.5° C., and 78.5° C., respectively.

Figure 6:
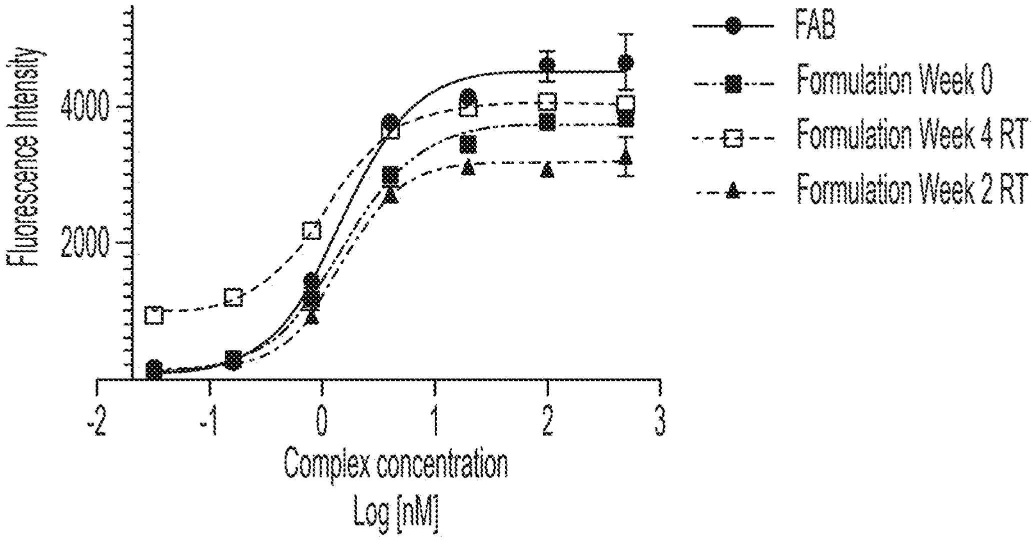
FIG. 6 shows binding affinity of complexes of formula (Id), containing an anti-TfR1 antibody provided in Table 2 covalently linked to a DUX4-targeting siRNA in a formulation containing 25 mM tris(hydroxymethyl)aminometh-ane, 10% (w/v) sucrose, at a pH of 7.5. The complexes were incubated at room temperature for four weeks and the binding affinity was analyzed by enzyme-linked immunosorbent assay (ELISA).

Binding affinity of the complex formulated in the formulation buffer was also tested by enzyme-linked immunosorbent assay (ELISA). The formulation was incubated at room temperature for four weeks. As shown in FIG. 6, the complex maintained its binding affinity to TfR1 after four weeks.

In addition to the above-discussed complexes in a formulation buffer comprising 25 mM tris(hydroxymethyl)aminomethane and 10% (w/v) sucrose, with a pH of 7.5, two alternative formulations were also tested. The buffer conditions in each of the alternative formulations were as follows:

Alternative Formulation a: 25 mM Tris, 3% (w/v) sucrose, pH 7.5.

Alternative Formulation b: 25 mM Tris, 6% (w/v) sucrose+50 mM NaCl, pH 7.5.

Figure 7A:
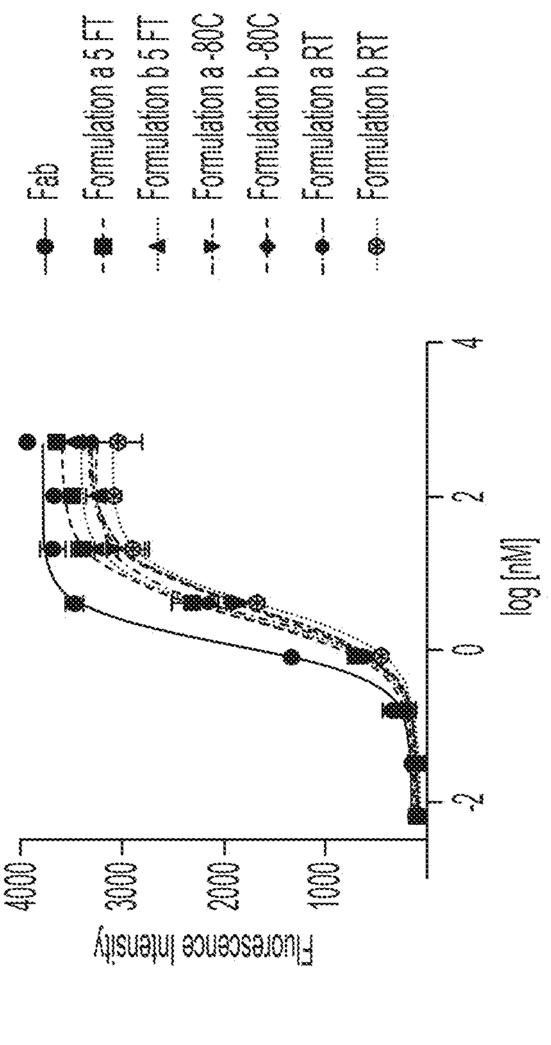
FIGS. 7A-7C show binding affinity (FIG. 7A) and stability (FIG. 7B and FIG. 7C) of complexes of formula (Id), containing an anti-TfR1 antibody provided in Table 2 covalently linked to a DUX4-targeting siRNA in two additional formulations. Formulation a contains 25 mM Tris, 3% (w/v) sucrose, at a pH of 7.5. Formulation b contains 25 mM Tris, 6% (w/v) sucrose+50 mM NaCl, at a pH of 7.5.
Figure 7B:
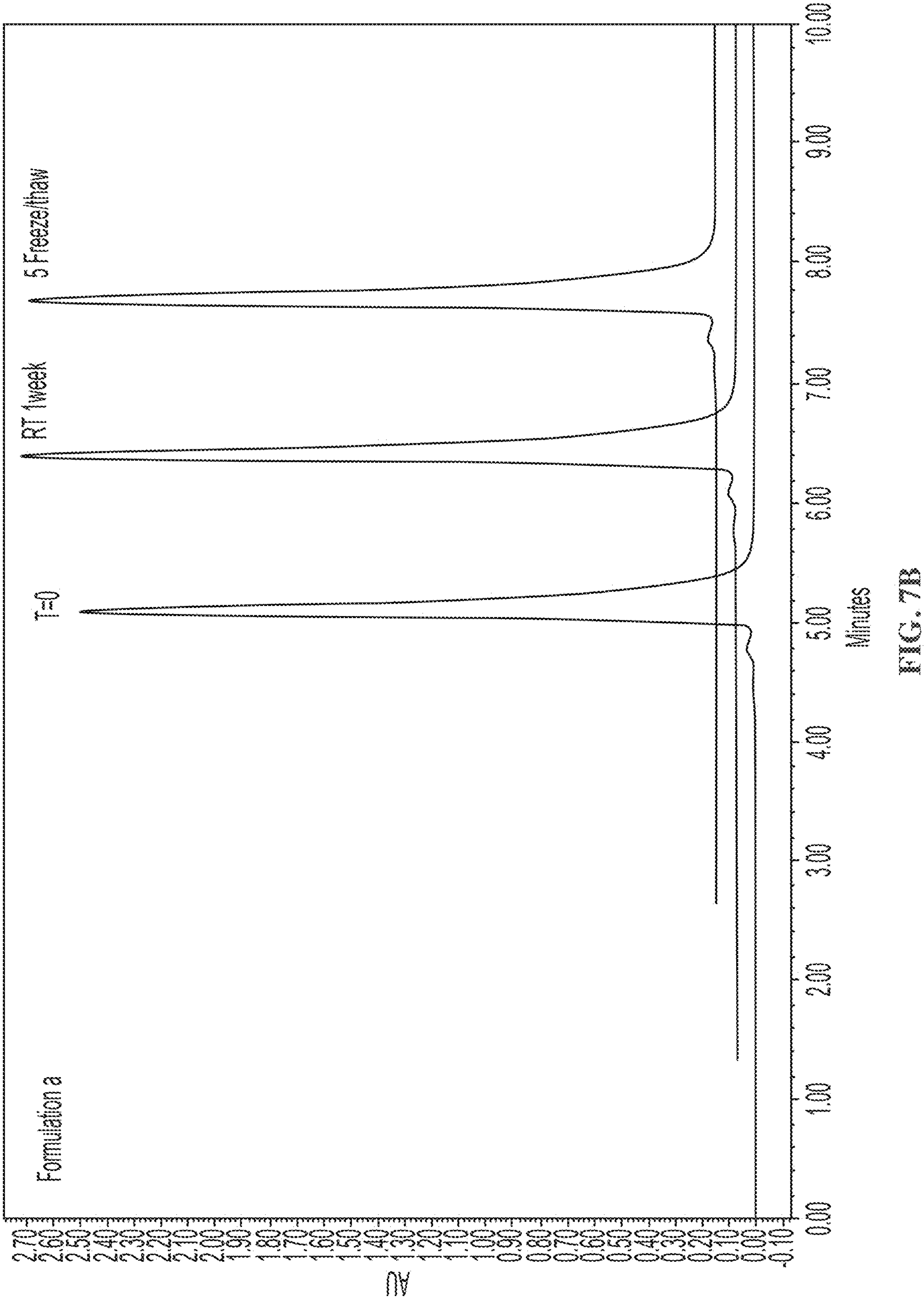
Figure 7C:
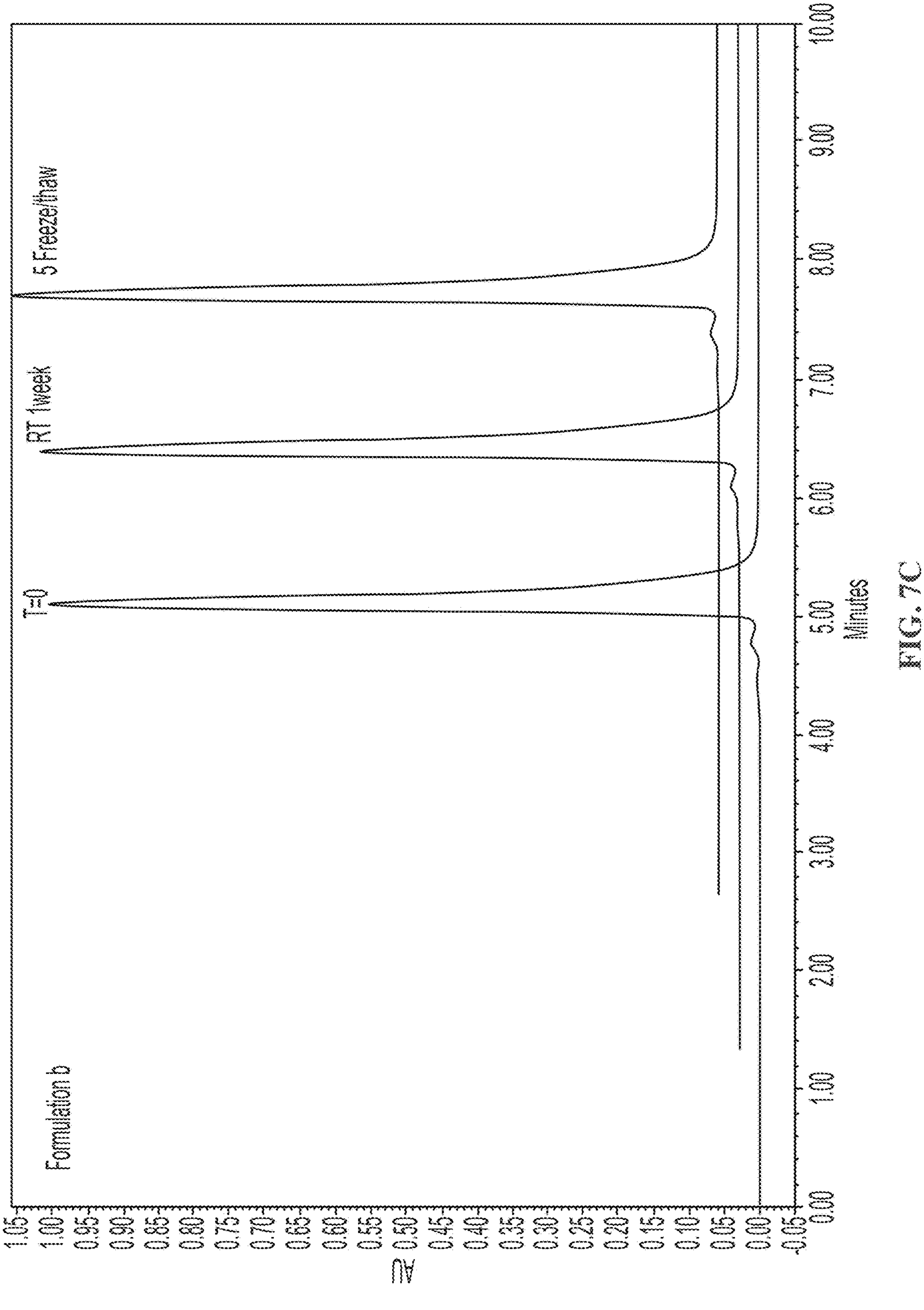

The formulated samples were stored at −80° C. and room temperature (RT) for one week, and no changes were observed when the samples were tested using SEC, ELISA, DLS, and DSF (see FIGS. 7A-7C).

Additionally, the anti-TfR1 Fab-siRNA complexes formulated in the three formulation buffers were subjected to five freeze/thaw cycles, and no changes in stability were found (FIG. 7C).

The DUX4-targeting siRNAs described herein were also tested for stability in human serum and human liver lysate and were confirmed to be stable in human serum and human liver lysate. Immunostimulatory properties of the DUX4-targeting siRNAs were also evaluated in human peripheral blood mononuclear cells (PBMCs) and did not show strong immunogenicity. Lastly, an off-target assessment in human primary hepatocytes was conducted and the DUX4-targeting siRNAs showed reduced off-target effects compared to other known DUX4-targeting siRNAs.

Additional Embodiments

1. A composition comprising complexes that comprise an oligonucleotide covalently linked to an anti-transferrin receptor 1 (TfR1) antibody, wherein the anti-TfR1 antibody comprises: a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14, a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5 or 11, and a light chain complementarity determining region 3 (CDR-L3) comprising a sequence as set forth in SEQ ID NOs: 6 or 16, wherein the oligonucleotide is an RNAi oligonucleotide.

2. A composition comprising complexes comprising a structure of formula (I): $[R^1]_{n1}—R^2$, wherein each $R^1$ independently comprises a group of the formula (Ia):

(Ia)

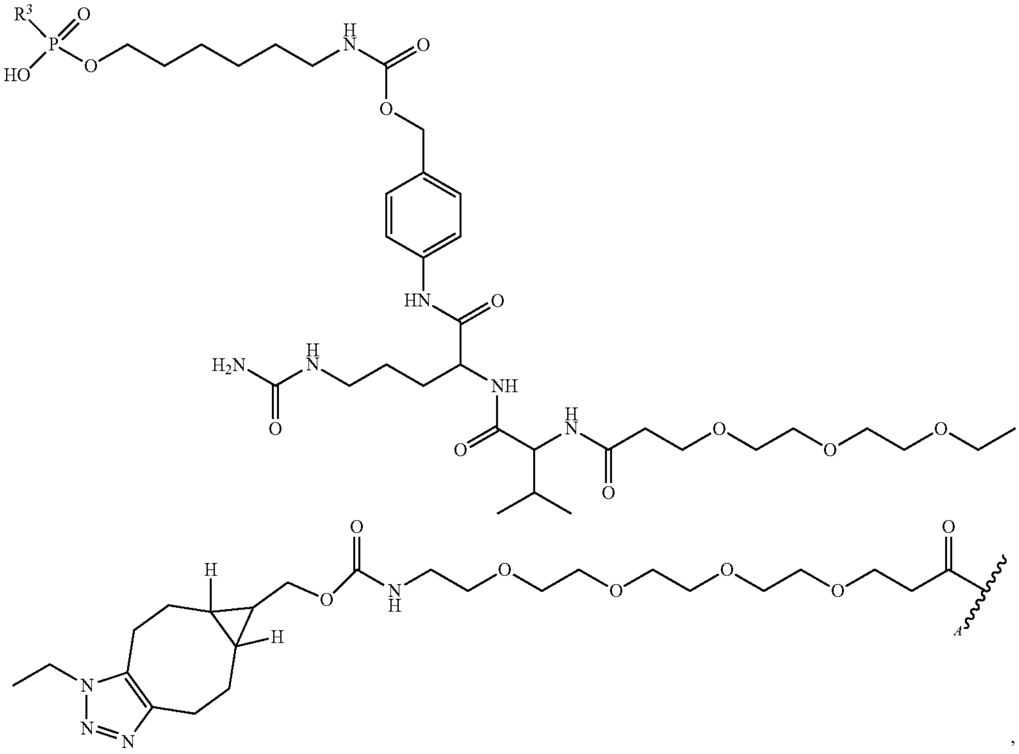

, or a pharmaceutically acceptable salt thereof, wherein $R^2$ comprises an antibody, and $R^3$ comprises an RNAi oligonucleotide;

wherein $R^1$ is covalently linked to $R^2$ at attachment point A; and wherein n1 is an integer representing the number of instances of $R^1$, wherein each instance of $R^1$ is covalently linked to a different amino acid residue of the antibody, optionally wherein each different amino acid residue is a lysine;

optionally wherein the antibody is an anti-TfR1 antibody.

3. The composition of embodiment 2, wherein the antibody comprises:

a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14, a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5 or 11, and a light chain complementarity determining region 3 (CDR-L3) comprising a sequence as set forth in SEQ ID NOs: 6 or 16.

4. The composition of any one of embodiments 1 to 3, wherein the composition is a formulation comprising tris (hydroxymethyl)aminomethane and sucrose.

5. The composition of embodiment 4, wherein the formulation is in a lyophilized form.

6. The composition of embodiment 4, wherein the formulation is in a frozen solid form.

7. The composition of embodiment 4, wherein the formulation is in an aqueous solution.

8. The composition of embodiment 7, wherein the tris (hydroxymethyl)aminomethane is present in the aqueous solution at a concentration in the range of 5 mM to 50 mM.

9. The composition of embodiment 7 or 8, wherein the sucrose is present in the aqueous solution at a concentration in the range of 5% to 15% weight per volume (w/v %).

10. The composition of any one of embodiments 7 to 9, wherein the aqueous solution has a pH in the range of 6.5 to 8.5.

11. The composition of any one of embodiments 7 to 10, wherein the tris(hydroxymethyl)aminomethane is present in the aqueous solution at a concentration of 25 mM and/or the sucrose is present in the aqueous solution at a concentration of 10 w/v % and/or the aqueous solution is at a pH of 7.5.

12. The composition of any one of embodiments 1-11, wherein the antibody is a Fab fragment, a full-length IgG, a Fab' fragment, a $F(ab')_2$ fragment, an scFv, or an Fv.

13. The composition of embodiment 12, wherein the antibody is a Fab fragment.

14. The composition of any one of embodiments 1-13, wherein the antibody comprises a heavy chain variable region (VH) comprising an amino acid sequence at least 85% identical to SEQ ID NO: 17; and/or wherein the antibody comprises a light chain variable region (VL) comprising an amino acid sequence at least 85% identical to SEQ ID NO: 18, optionally wherein the antibody comprises a VH comprising the amino acid sequence of SEQ ID NO: 17 and/or a VL comprising the amino acid sequence of SEQ ID NO: 18.

15. The composition of embodiment 14, wherein the VH comprises an N-terminal pyroglutamate.

16. The composition of any one of embodiments 1-14, wherein the antibody comprises a heavy chain comprising an amino acid sequence at least 85% identical to SEQ ID NO: 19; and/or wherein the antibody comprises a light chain comprising an amino acid sequence at least 85% identical to SEQ ID NO: 20, optionally wherein the antibody comprises a heavy chain comprising the amino acid sequence of SEQ ID NO: 19 and/or a light chain comprising the amino acid sequence of SEQ ID NO: 20.

17. The composition of any one of embodiments 1-16, wherein the RNAi oligonucleotide comprises an antisense strand of 18-25 nucleosides in length.

18. The composition of any one of embodiments 1-17, wherein the RNAi oligonucleotide comprises an antisense strand comprising a region of complementarity of at least 16 consecutive nucleosides in length to a nucleobase sequence as set forth in SEQ ID NO: 24, optionally wherein the region of complementarity is 22 consecutive nucleosides in length.

19. The composition of any one of embodiments 1-18, wherein the RNAi oligonucleotide comprises an antisense strand comprising at least 15 consecutive nucleosides of a nucleobase sequence as set forth in SEQ ID NO: 22, optionally wherein the antisense strand comprises the nucleobase sequence of SEQ ID NO: 22.

20. The composition of any one of embodiments 1-19, wherein the RNAi oligonucleotide further comprises a sense strand comprising at least 15 consecutive nucleosides complementary to the antisense strand.

21. The composition of any one of embodiments 1-20, wherein the sense strand comprises at least 15 consecutive nucleosides of a nucleobase sequence as set forth in SEQ ID NO: 21, optionally wherein the sense strand comprises the nucleobase sequence of SEQ ID NO: 21.

22. The composition of any one of embodiments 1-21, wherein the RNAi oligonucleotide comprises one or more modified nucleosides.

23. The composition of embodiment 22, wherein the one or more modified nucleosides are 2' modified nucleosides, optionally, wherein each 2' modified nucleoside is 2'-O-methyl (2'-O-Me) or 2'-fluoro (2'-F).

24. The composition of any one of embodiments 1-23, wherein the antisense strand further comprises a 5'-(E)-vinylphosphonate.

25. The composition of any one of embodiments 1-24, wherein the RNAi oligonucleotide comprises one or more phosphorothioate internucleoside linkages.

26. The composition of any one of embodiments 2-25, wherein each $R^1$ comprises a group of the formula (Ib):

(Ib)

3'-mA*mC*mAmAmGmAmAmGmGfCmAmCmUmUmUmAmAmGmAmCmC*fG*mU-5'-VP Antisense (SEQ ID NO: 22)

5'-mU*mU*mCmUfUmCmCmGfUfGfAmAmAfUmUmCmUmGfG*mC*mA-3' Sense (SEQ ID NO: 21)

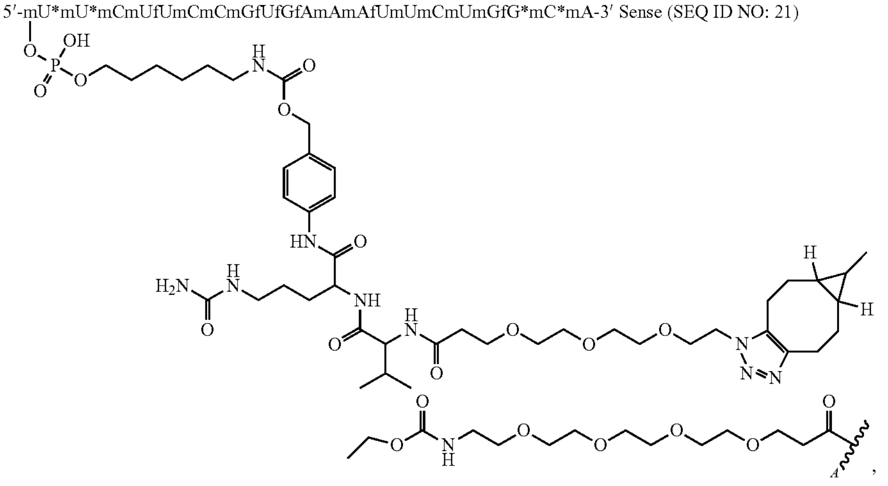

or a pharmaceutically acceptable salt thereof, wherein: mA, mC, mG, and mU are 2'-O-methyl adenosine, 2'-O-methyl cytidine, 2'-O-methyl guanosine, and 2'-O-methyl uridine, respectively;

fA, fC, fG, and fU are 2'-fluoro adenosine, 2'-fluoro cytidine, 2'-fluoro guanosine, and 2'-fluoro uridine, respectively; * between two nucleosides represents a phosphorothioate linkage; the absence of "*" between two nucleosides represents a phosphodiester internucleoside linkage; and "VP" represents 5'-(E)-Vinylphosphonate, such that the RNAi oligonucleotide comprises an antisense strand comprising a nucleobase sequence of UGCCAGAAUUUCACGGAAGAACA (SEQ ID NO: 22) and a sense strand comprising a nucleobase sequence of UUCUUCCGUGAAAUUCUGGCA (SEQ ID NO: 21).

27. The composition of any one of embodiments 2-25, wherein each $R^1$ comprises a group of the formula (Ic), in which the antisense strand and the sense strand form a double stranded oligonucleotide:

(Ic)
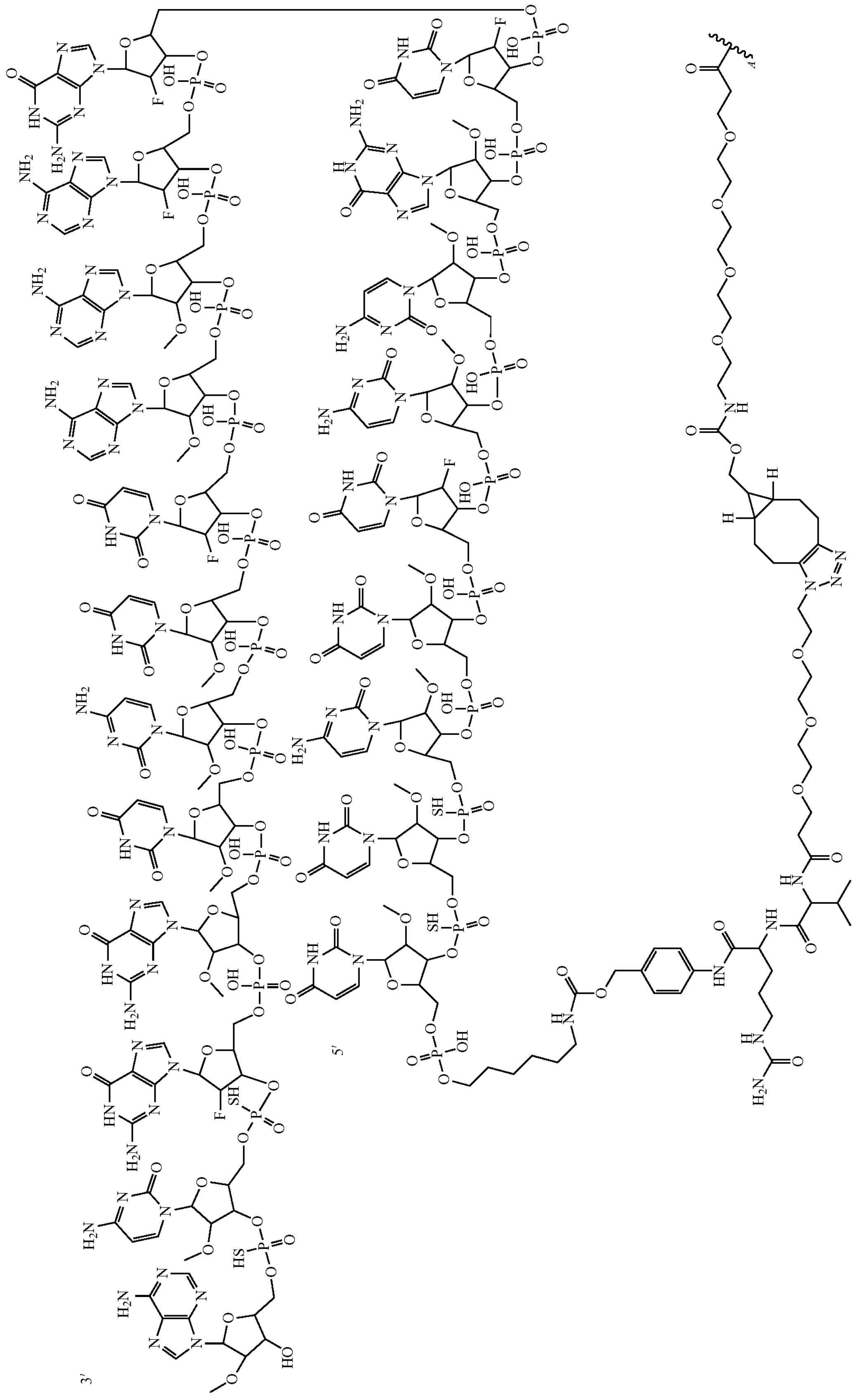
Sense Strand

-continued
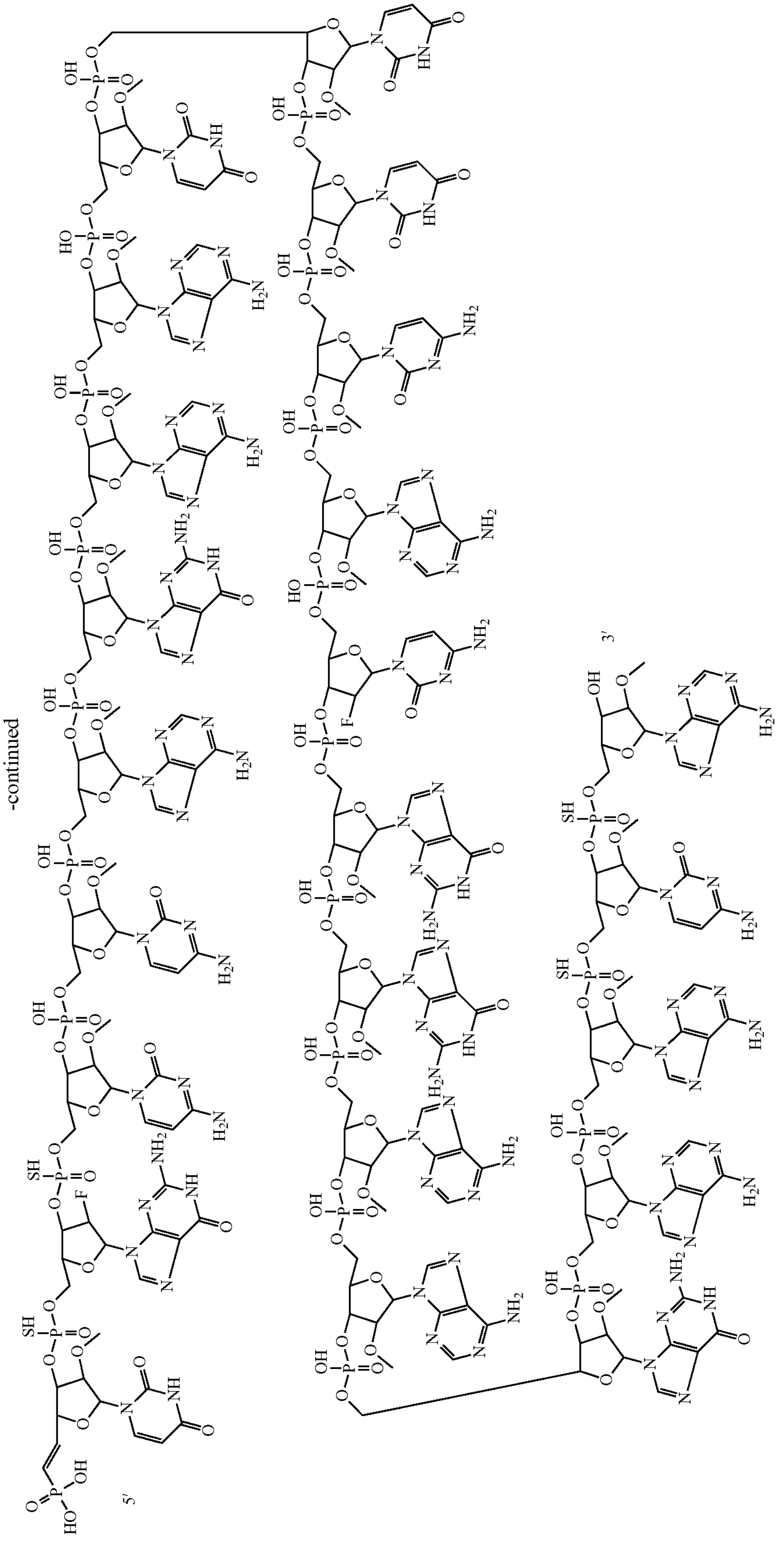
Antisense Strand or a pharmaceutically acceptable salt thereof.

28. The composition of any one of embodiments 1-27, wherein the complexes are present in the composition at a concentration in the range of 10 mg/mL to 200 mg/mL.

29. The composition of any one of embodiments 1-28, further comprising one or more antibodies that are not covalently linked to an oligonucleotide.

30. The composition of embodiment 29, wherein the average value of n1 of complexes in the composition is in the range of 0.5 to 5, optionally wherein the average value of n1 of complexes in the composition is 1.

31. A method of reducing DUX4 expression in a subject, the method comprising administering to the subject an effective amount of the composition of any one of embodiments 1-30.

32. A method of treating facioscapulohumeral muscular dystrophy (FSHD) in a subject, the method comprising administering to the subject an effective amount of the composition ofany one of embodiments 1-30.

33. The method of embodiment 31 or embodiment 32, wherein the subject has aberrant production of DUX4 protein.

34. The method of any one of embodiments 31-33, wherein the complexes reduce DUX4 expression in the subject.

35. The method of embodiment 34, wherein reducing DUX4 expression comprises reducing DUX4 protein and/or mRNA levels.

36. The method of any one of embodiments 31 to 35, wherein the antibody comprises a VH that comprises an N-terminal pyroglutamate.

37. A complex comprising a structure of formula (I): $[R^1]_{n1}$—$R^2$, wherein each $R^1$ comprises a group of the formula (Ia):

(Ia)

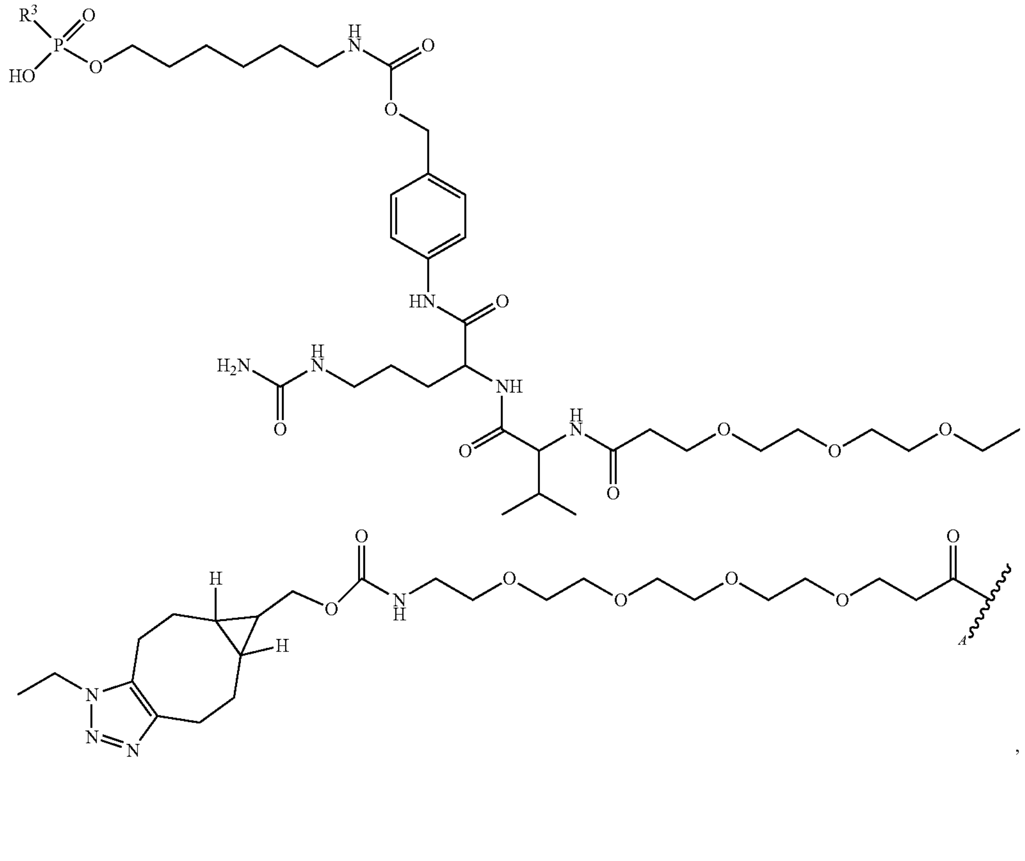

, or a pharmaceutically acceptable salt thereof, wherein $R^3$ comprises an RNAi oligonucleotide comprising an antisense strand comprising a nucleobase sequence of SEQ ID NO: 22 and a structure (5'→3') of VP-mU*fG*mCmCmAmGmAmAmUmUmUmCm AfCmGmGmAmAmGmAmA*mC*mA, and a sense strand comprising a nucleobase sequence of SEQ ID NO: 21 and a structure (5'→3') of mU*mU*mCmUfUmCmCmGfUfGfAmAmAfUm UmCmUmGfG*mC*mA, wherein: mA, mC, mG, and mU are 2'-O-methyl adenosine, 2'-O-methyl cytidine, 2'-O-methyl guanosine, and 2'-O-methyl uridine, respectively; fA, fC, fG, and fU are 2'-fluoro adenosine, 2'-fluoro cytidine, 2'-fluoro guanosine, and 2'-fluoro uridine, respectively; * between two nucleosides represents a phosphorothioate linkage; the absence of "*" between two nucleosides represents a phosphodiester internucleoside linkage; and "VP" represents 5'-(E)-Vinylphosphonate;

wherein $R^2$ comprises a Fab, and wherein the Fab comprises a CDR-H1, a CDR-H2, a CDR-H3, a CDR-L1, a CDR-L2, and a CDR-L3 selected from Table 2, optionally wherein the Fab comprises a VH comprising the amino acid sequence of SEQ ID NO: 17 and a VL comprising the amino acid sequence of SEQ ID NO: 18, further optionally wherein the Fab comprises a VH comprising an N-terminal pyroglutamate, further optionally wherein the Fab comprises a heavy chain comprising the amino acid sequence of SEQ ID NO: 19 and a light chain comprising the amino acid sequence of SEQ ID NO: 20;

wherein $R^1$ is covalently linked to $R^2$ at attachment point A; and wherein n1 is an integer representing the number of instances of $R^1$, wherein each instance of $R^1$ is covalently linked to a different amino acid residue of the Fab, optionally wherein each different amino acid residue is a lysine.

38. A complex comprising a structure of formula (I): $[R^1]_{n1}$—$R^2$, wherein each $R^1$ comprises a group of the formula (Ib):

(Ib)

3′-mA*mC*mAmAmGmAmAmGmGfCmAmCmUmUmUmAmAmGmAmCmC*fG*mU-5′-VP Antisense (SEQ ID NO: 22)

5′-mU*mU*mCmUfUmCmCmGfUfGfAmAmAfUmUmCmUmGfG*mC*mA-3′ Sense (SEQ ID NO: 21)

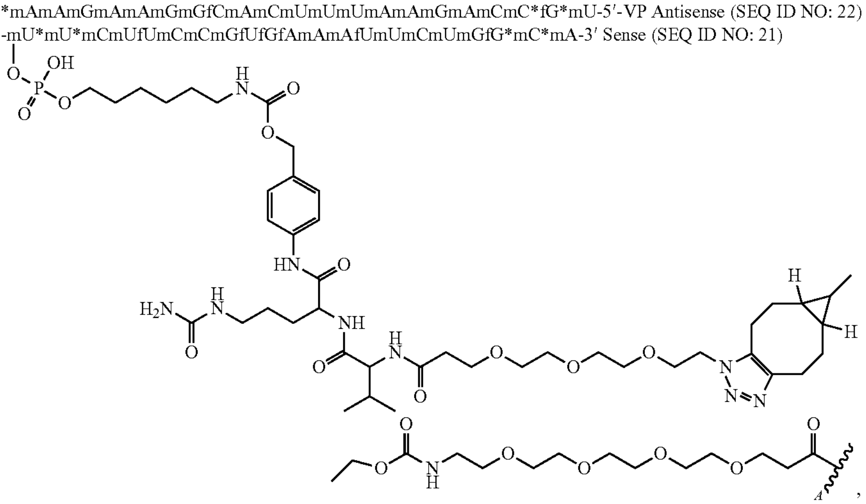

, or a pharmaceutically acceptable salt thereof, wherein: mA, mC, mG, and mU are 2'-O-methyl adenosine, 2'-O-methyl cytidine, 2'-O-methyl guanosine, and 2'-O-methyl uridine, respectively; fA, fC, fG, and fU are 2'-fluoro adenosine, 2'-fluoro cytidine, 2'-fluoro guanosine, and 2'-fluoro uridine, respectively; * between two nucleosides represents a phosphorothioate linkage; the absence of "*" between two nucleosides represents a phosphodiester internucleoside linkage; and "VP" represents 5'-(E)-Vinylphosphonate, such that the oligonucleotide is an RNAi oligonucleotide comprising an antisense strand comprising a nucleobase sequence of UGCCAGAAUUUCACGGAAGAACA (SEQ ID NO: 22) and a sense strand comprising a nucleobase sequence of UUCUUCCGUGAAAUUCUGGCA (SEQ ID NO: 21);

wherein $R^2$ comprises a Fab, and wherein the Fab comprises a CDR-H1, a CDR-H2, a CDR-H3, a CDR-L1, a CDR-L2, and a CDR-L3 selected from Table 2, optionally wherein the Fab comprises a VH comprising the amino acid sequence of SEQ ID NO: 17 and a VL comprising the amino acid sequence of SEQ ID NO: 18, further optionally wherein the Fab comprises a VH comprising an N-terminal pyroglutamate, further optionally wherein the Fab comprises a heavy chain comprising the amino acid sequence of SEQ ID NO: 19 and a light chain comprising the amino acid sequence of SEQ ID NO: 20;

wherein $R^1$ is covalently linked to $R^2$ at attachment point A; and wherein n1 is an integer representing the number of instances of $R^1$, wherein each instance of $R^1$ is covalently linked to a different amino acid residue of the Fab, optionally wherein each different amino acid residue is a lysine.

39. A complex comprising a structure of formula (I): $[R^1]_{n1}$—$R^2$, wherein $R^1$ comprises a group of the formula (Ic), in which the antisense strand and the sense strand form a double stranded oligonucleotide:

(Ic)
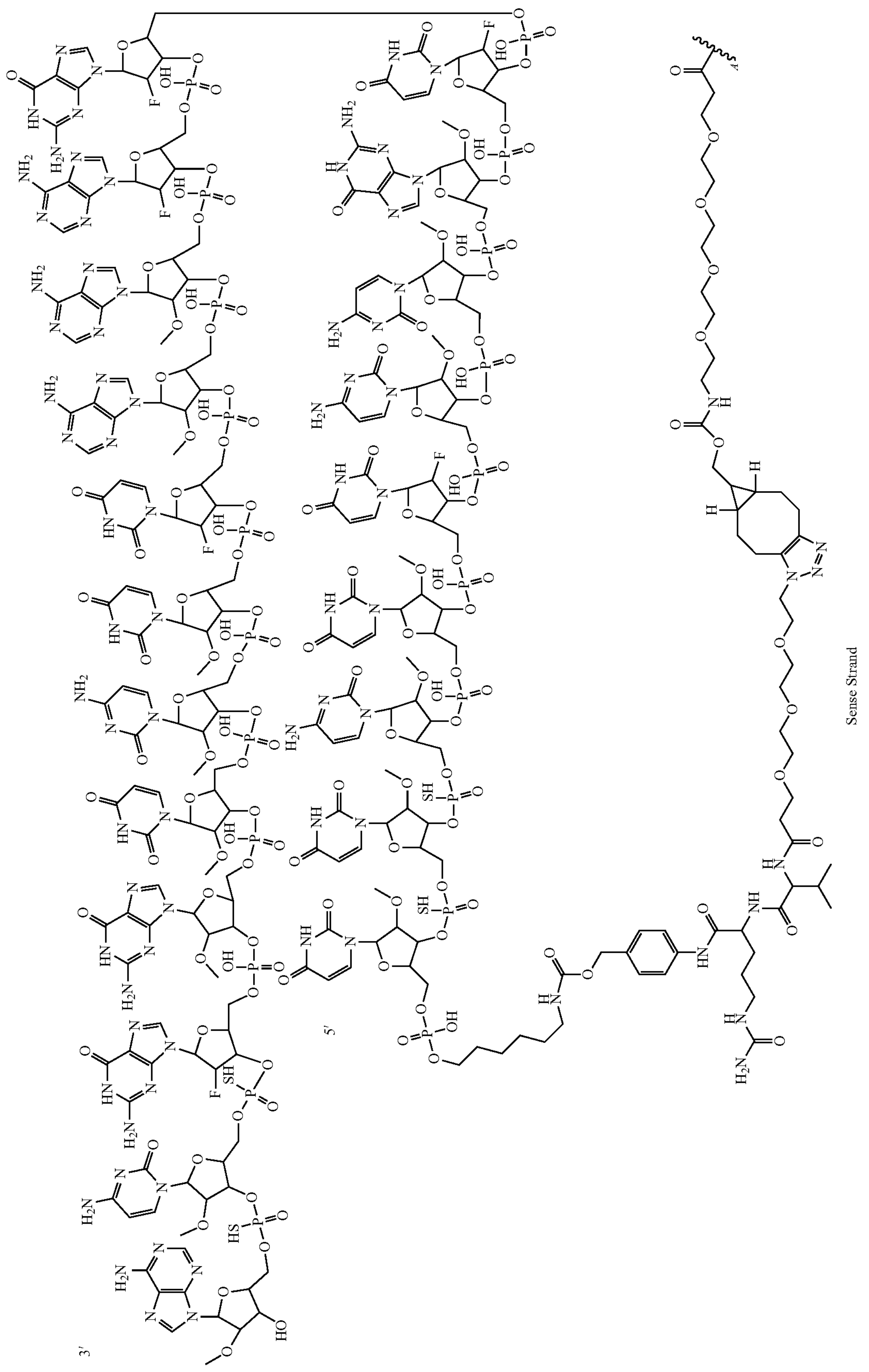

-continued
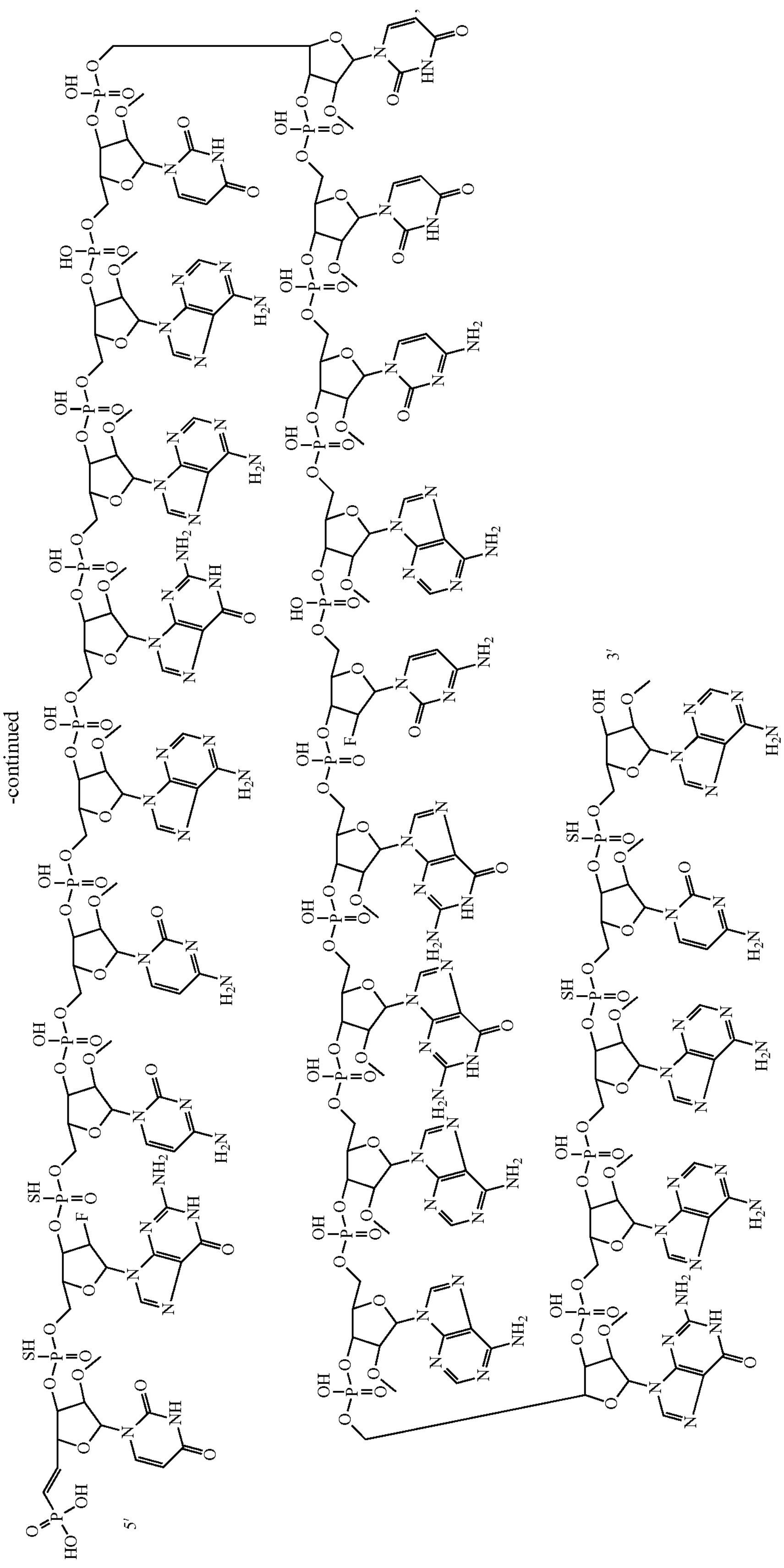
Antisense Strand or a pharmaceutically acceptable salt thereof, wherein $R^2$ comprises a Fab comprising a CDR-H1, a CDR-H2, a CDR-H3, a CDR-L1, a CDR-L2, and a CDR-L3 selected from Table 2, optionally wherein the Fab comprises a VH comprising the amino acid sequence of SEQ ID NO: 17 and a VL comprising the amino acid sequence of SEQ ID NO: 18, further optionally wherein the Fab comprises a VH comprising an N-terminal pyroglutamate, further optionally wherein the Fab comprises a heavy chain comprising the amino acid sequence of SEQ ID NO: 19 and a light chain comprising the amino acid sequence of SEQ ID NO: 20; wherein $R^1$ is covalently linked to $R^2$ at attachment point A;

wherein n1 is an integer representing the number of instances of $R^1$, wherein each instance of $R^1$ is covalently linked to a different amino acid residue of the Fab, optionally wherein each different amino acid residue is a lysine.

40. A complex comprising a structure of the formula (Id):

(Id)
3′-mA*mC*mAmAmGmAmAmGmGfCmAmCmUmUmUmAmAmGmAmCmC*fG*mU-5′-VP Antisense (SEQ ID NO: 22)
5′-mU*mU*mCmUfUmCmCmGfUfGfAmAmAfUmUmCmUmGfG*mC*mA-3′ Sense (SEQ ID NO: 21)
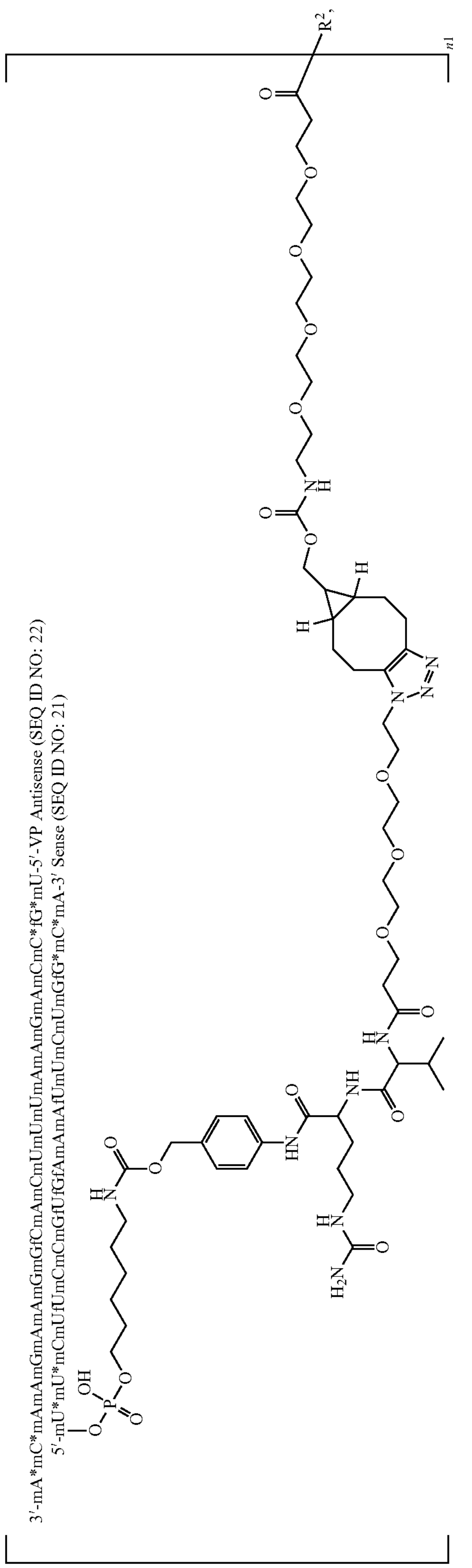

or a pharmaceutically acceptable salt thereof, wherein: mA, mC, mG, and mU are 2'-O-methyl adenosine, 2'-O-methyl cytidine, 2'-O-methyl guanosine, and 2'-O-methyl uridine, respectively;

fA, fC, fG, and fU are 2'-fluoro adenosine, 2'-fluoro cytidine, 2'-fluoro guanosine, and 2'-fluoro uridine, respectively; * between two nucleosides represents a phosphorothioate linkage; the absence of "*" between two nucleosides represents a phosphodiester internucleoside linkage; and "VP" represents 5'-(E)-Vinylphosphonate, such that the oligonucleotide is an RNAi oligonucleotide comprising an antisense strand comprising a nucleobase sequence of UGCCAGAAUUUCACGGAAGAACA (SEQ ID NO: 22) and a sense strand comprising a nucleobase sequence of UUCUUCCGUGAAAUUCUGGCA (SEQ ID NO: 21;

wherein $R^2$ comprises a Fab, and wherein the Fab comprises a CDR-H1, a CDR-H2, a CDR-H3, a CDR-L1, a CDR-L2, and a CDR-L3 selected from Table 2, optionally wherein the Fab comprises a VH comprising the amino acid sequence of SEQ ID NO: 17 and a VL comprising the amino acid sequence of SEQ ID NO: 18, further optionally wherein the Fab comprises a VH comprising an N-terminal pyroglutamate, further optionally wherein the Fab comprises a heavy chain comprising the amino acid sequence of SEQ ID NO: 19 and a light chain comprising the amino acid sequence of SEQ ID NO: 20;

wherein n1 is an integer representing the number of instances of the group enclosed by square brackets, wherein each instance of the group enclosed by square brackets is covalently linked to a different amino acid residue of the Fab, optionally wherein each different amino acid residue is a lysine.

41. A formulation comprising a plurality of complexes of any one of embodiments 37-40, and tris(hydroxymethyl) aminomethane at a concentration of 5 to 50 mM, and sucrose at a concentration of 2 w/v % to 15 w/v %, wherein the formulation is an aqueous solution and is at a pH of 6.5 to 8.5, optionally wherein the plurality of complexes are at a concentration of 10 mg/mL to 200 mg/mL.

42. A formulation comprising a plurality of complexes of any one of embodiments 37-40, and tris(hydroxymethyl) aminomethane at a concentration of 5 to 50 mM, and sucrose at a concentration of 3 w/v % to 10 w/v %, wherein the formulation is an aqueous solution and is at a pH of 6.5 to 8.5, optionally wherein the plurality of complexes are at a concentration of 10 mg/mL to 200 mg/mL.

43. A formulation comprising a plurality of complexes of any one of embodiments 37-40, and tris(hydroxymethyl) aminomethane at a concentration of 25 mM, and sucrose at a concentration of 10 w/v %, wherein the formulation is an aqueous solution and is at a pH of 7.5, optionally wherein the plurality of complexes are at a concentration of 10 mg/mL to 200 mg/mL.

44. The formulation of any one of embodiments 41-43, further comprising one or more antibodies that are not covalently linked to an oligonucleotide.

45. The formulation of embodiment 44, wherein the average value of n1 of complexes in the formulation is in the range of 0.5 to 5, optionally wherein the average value of n1 of complexes in the formulation is 1.

46. A lyophilized form of the formulation of any one of embodiments 41-45.

47. A product produced by a process comprising lyophilizing the formulation of any one of embodiments 41-45.

48. A frozen form of the formulation of any one of embodiments 41-45.

49. A product produced by a process comprising freezing the formulation of any one of embodiments 41-45.

50. A lyophilized cake comprising a plurality of complexes of any one of embodiments 37-40, tris(hydroxymethyl)aminomethane, and sucrose.

Equivalents and Terminology

The disclosure illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments, optional features, modification and variation of the concepts herein disclosed may be resorted to by those skilled in the art, and that such modifications and variations are considered to be within the scope of this disclosure.

In addition, where features or aspects of the disclosure are described in terms of Markush groups or other grouping of alternatives, those skilled in the art will recognize that the disclosure is also thereby described in terms of any individual member or subgroup of members of the Markush group or other group.

It should be appreciated that, in some embodiments, sequences presented in the sequence listing may be referred to in describing the structure of an oligonucleotide or other nucleic acid. In such embodiments, the actual oligonucleotide or other nucleic acid may have one or more alternative nucleosides (e.g., an RNA counterpart of a DNA nucleoside or a DNA counterpart of an RNA nucleoside) and/or (e.g., and) one or more modified nucleosides and/or (e.g., and) one or more modified internucleoside linkages and/or (e.g., and) one or more other modification compared with the specified sequence while retaining essentially same or similar complementary properties as the specified sequence.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. Unless otherwise indicated, ranges of values herein are inclusive of their endpoints (e.g., a range of X to Y is inclusive of the values X and Y). It should be understood that recitations herein of a value from X to Y indicates that the specified value falls in the range of X to Y. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein. Variations of those embodiments may become apparent to those of ordinary skill in the art upon reading the foregoing description.

The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. Those skilled in the art will recognize, or be able to ascertain using no more than routine experimentation, many equivalents to the specific embodiments of the invention described herein. Such equivalents are intended to be encompassed by the following claims.

What is claimed is:
1. A complex comprising a structure of formula (I): $[R^1]_{n1}—R^2$, wherein each $R^1$ comprises a group of the formula (Ic), in which the antisense strand and the sense strand form a double stranded oligonucleotide:
(Ic)
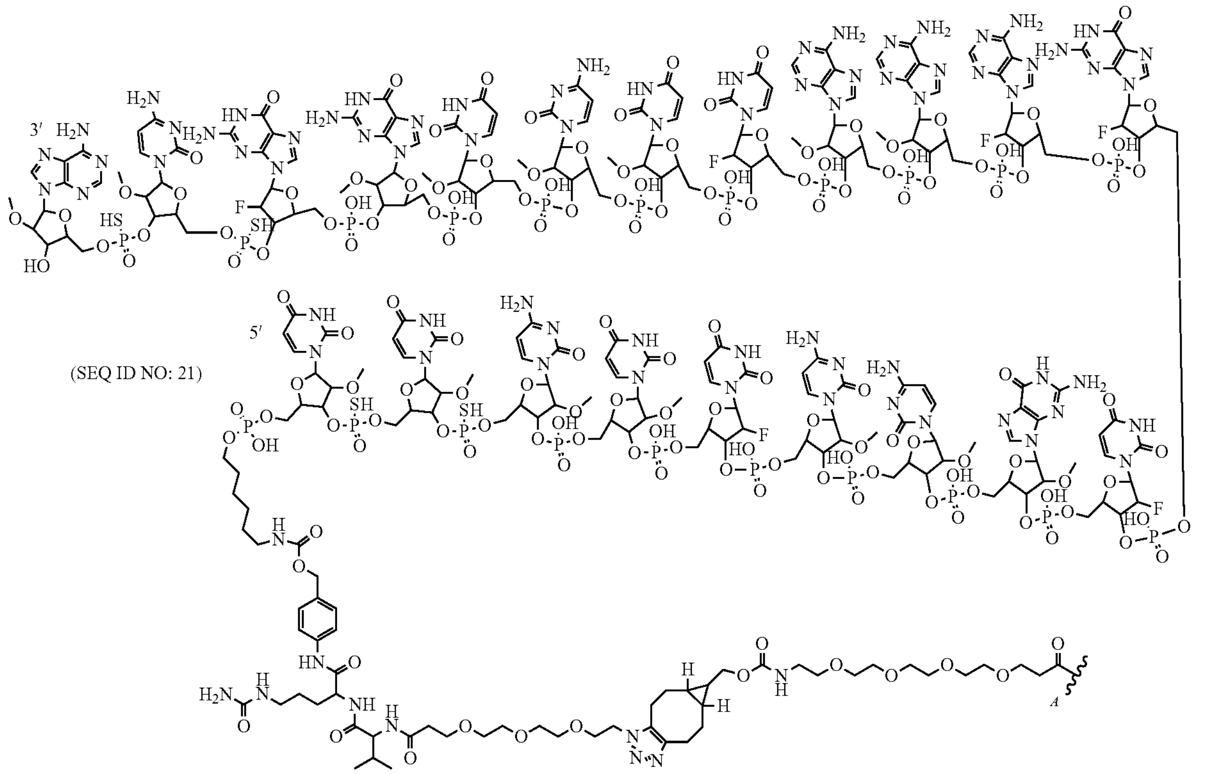
(SEQ ID NO: 21)
Sense Strand
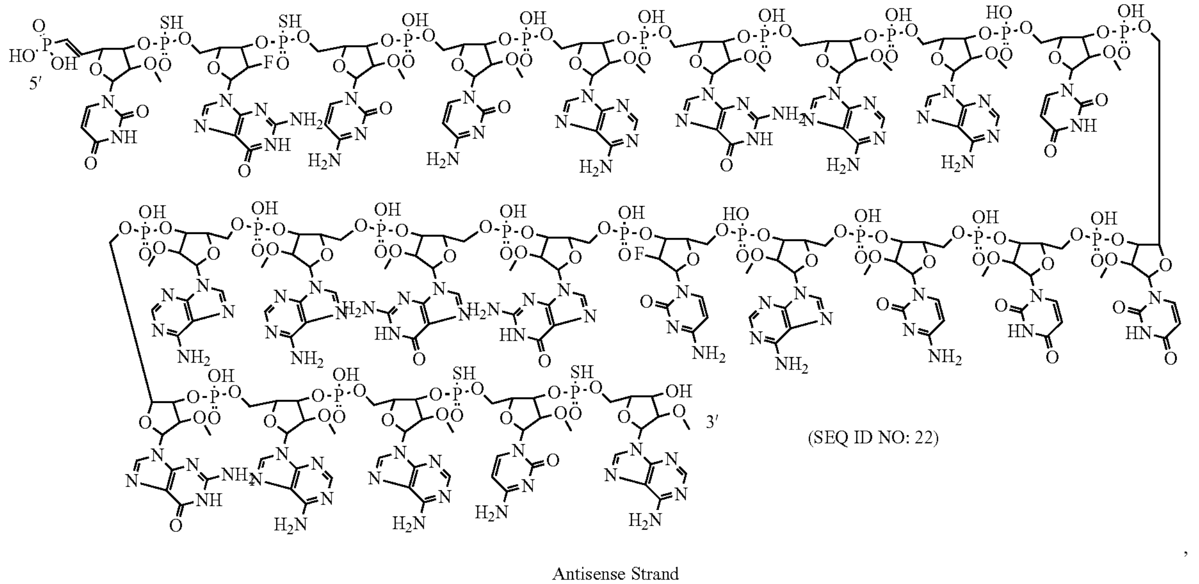
(SEQ ID NO: 22)
Antisense Strand
,
or a pharmaceutically acceptable salt thereof, wherein $R^2$ comprises a Fab comprising a heavy chain comprising the amino acid sequence of SEQ ID NO: 19 and a light chain comprising the amino acid sequence of SEQ ID NO: 20;

wherein $R^1$ is covalently linked at attachment point A to $R^2$; wherein n1 is an integer of 1-5 representing the number of instances of $R^1$, and wherein each instance of $R^1$ is covalently linked to a different amino acid residue of the Fab.

2. The complex of claim 1, wherein each of the different amino acid residue is a lysine.

3. The complex of claim 1, wherein the heavy chain of the Fab comprises an N-terminal pyroglutamate.

4. The complex of claim 3, wherein n1 is 1.

5. A composition comprising the complex of claim 1, wherein the average value of n1 of complexes in the composition is in the range of 0.5 to 1.5.

6. A composition comprising the complex of claim 5, wherein the average value of n1 of complexes in the composition is 1.

7. The composition of claim 6, wherein the composition is formulated for intravenous administration, and wherein the subject is human.

8. A complex comprising a structure of formula (I): $[R^1]_{n1}—R^2$, wherein each $R^1$ comprises a group of the formula (Ia):

mU*mU*mCmUfUmCmCmGfUfGfAmAmAfUmUm CmUmGfG*mC*mA, wherein: mA, mC, mG, and mU are 2'-O-methyl adenosine, 2'-O-methyl cytidine, 2'-O-methyl guanosine, and 2'-O-methyl uridine, respectively; fA, fC, fG, and fU are 2'-fluoro adenosine, 2'-fluoro cytidine, 2'-fluoro guanosine, and 2'-fluoro uridine, respectively; "*" between two nucleosides represents a phosphorothioate linkage; the absence of "*" between two nucleosides represents a phosphodiester internucleoside linkage; and "VP" represents 5'-(E)-Vinylphosphonate;

wherein $R^2$ comprises a Fab comprising a heavy chain comprising the amino acid sequence of SEQ ID NO: 19 and a light chain comprising the amino acid sequence of SEQ ID NO: 20;

wherein $R^1$ is covalently linked at attachment point A to $R^2$; wherein n1 is an integer of 1-5 representing the number of instances of $R^1$, and wherein each instance of $R^1$ is covalently linked to a different amino acid residue of the Fab.

9. The complex of claim 8, wherein each of the different amino acid residue is a lysine.

10. The complex of claim 8, wherein the heavy chain of the Fab comprises an N-terminal pyroglutamate.

(Ia)

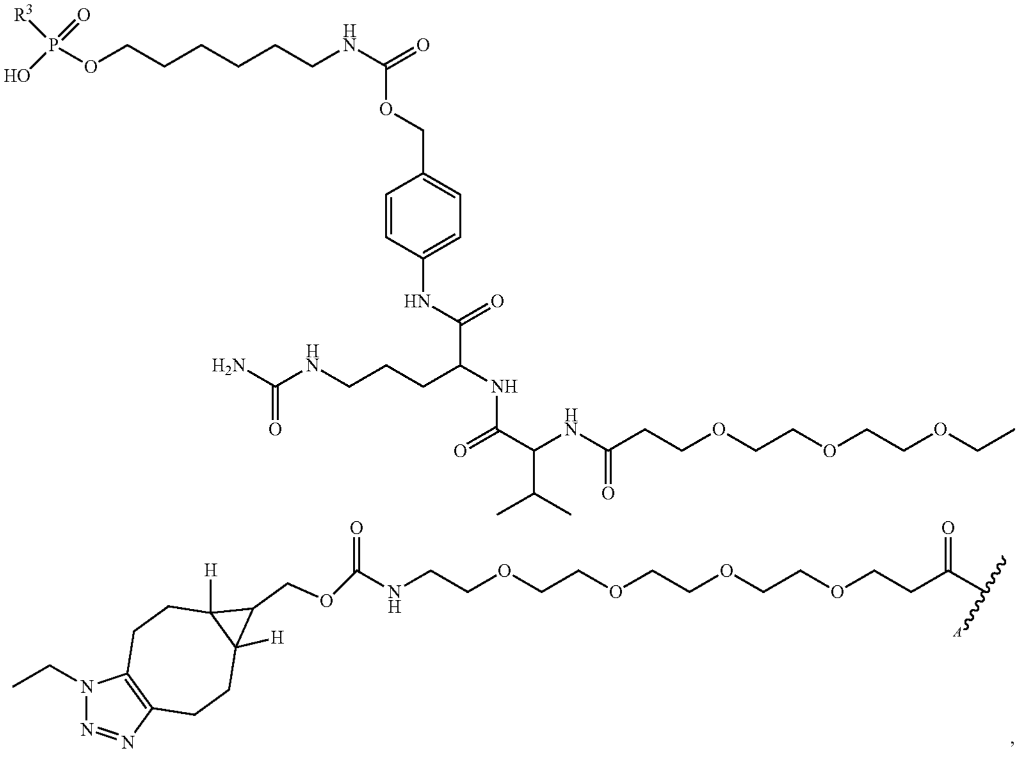

, or a pharmaceutically acceptable salt thereof, wherein $R^3$ comprises an RNAi oligonucleotide comprising an antisense strand comprising a nucleobase sequence of SEQ ID NO: 22 and a structure (5'→3') of VP-mU*fG*mCmCmAmGmAmAmUmUmCm AfCmGmGmAmAmGmAmA*mC*mA, and a sense strand comprising a nucleobase sequence of SEQ ID NO: 21 and a structure (5'→3') of

11. The complex of claim 10, wherein n1 is 1.

12. A composition comprising the complex of claim 8, wherein the average value of n1 of complexes in the composition is in the range of 0.5 to 1.5.

13. A composition comprising the complex of claim 12, wherein the average value of n1 of complexes in the composition is 1.

14. The composition of claim 13, wherein the composition is formulated for intravenous administration, and wherein the subject is human.

15. A complex comprising a structure of formula (I): $[R^1]_{n1}—R^2$, wherein each $R^1$ comprises a group of the formula (Ib):

(Ib)

3'-mA*mC*mAmAmGmAmAmGmGfCmAmCmUmUmUmAmAmGmAmCmC*fG*mU-5'-VP Antisense (SEQ ID NO: 22)
5'-mU*mU*mCmUfUmCmCmGfUfGfAmAmAfUmUmCmUmGfG*mC*mA-3' Sense (SEQ ID NO: 21)

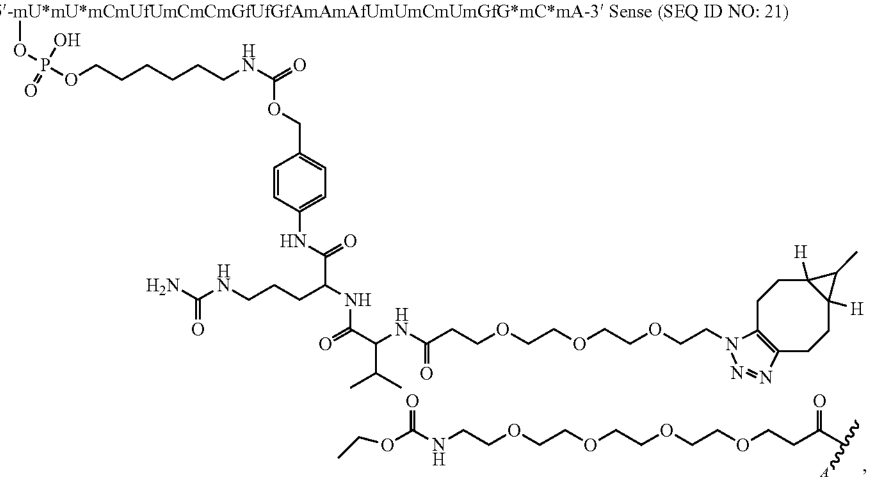

, or a pharmaceutically acceptable salt thereof, wherein: mA, mC, mG, and mU are 2'-O-methyl adenosine, 2'-O-methyl cytidine, 2'-O-methyl guanosine, and 2'-O-methyl uridine, respectively; fA, fC, fG, and fU are 2'-fluoro adenosine, 2'-fluoro cytidine, 2'-fluoro guanosine, and 2'-fluoro uridine, respectively; "*" between two nucleosides represents a phosphorothioate linkage; the absence of "*" between two nucleosides represents a phosphodiester internucleoside linkage; and "VP" represents 5'-(E)-Vinylphosphonate;

wherein $R^2$ comprises a Fab comprising a heavy chain comprising the amino acid sequence of SEQ ID NO: 19 and a light chain comprising the amino acid sequence of SEQ ID NO: 20;

wherein $R^1$ is covalently linked at attachment point A to $R^2$; wherein n1 is an integer of 1-5 representing the number of instances of $R^1$, and wherein each instance of $R^1$ is covalently linked to a different amino acid residue of the Fab.

16. The complex of claim 15, wherein each of the different amino acid residue is a lysine.

17. The complex of claim 15, wherein the heavy chain of the Fab comprises an N-terminal pyroglutamate.

18. The complex of claim 17, wherein n1 is 1.

19. A composition comprising the complex of claim 15, wherein the average value of n1 of complexes in the composition is in the range of 0.5 to 1.5.

20. A composition comprising the complex of claim 19, wherein the average value of n1 of complexes in the composition is 1.

21. The composition of claim 20, wherein the composition is formulated for intravenous administration, and wherein the subject is human.

22. A complex comprising a structure of the formula (Id):

(Id)
3′-mA*mC*mAmAmGmAmAmGmGfCmAmCmUmUmUmAmAmGmAmCmC*fG*mU-5′-VP Antisense (SEQ ID NO: 22)
5′-mU*mU*mCmUfUmCmCmGfUfGfAmAmAfUmUmCmUmGfG*mC*mA-3′ Sense (SEQ ID NO: 21)
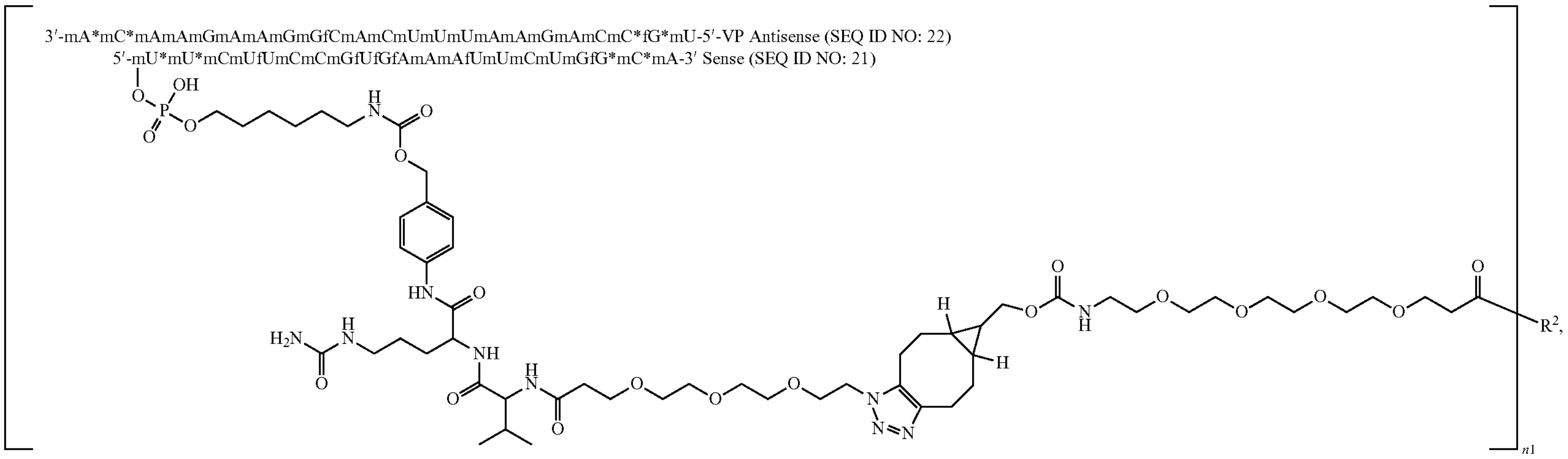

or a pharmaceutically acceptable salt thereof, wherein: mA, mC, mG, and mU are 2'-O-methyl adenosine, 2'-O-methyl cytidine, 2'-O-methyl guanosine, and 2'-O-methyl uridine, respectively;

fA, fC, fG, and fU are 2'-fluoro adenosine, 2'-fluoro cytidine, 2'-fluoro guanosine, and 2'-fluoro uridine, respectively; "*" between two nucleosides represents a phosphorothioate linkage; the absence of "*" between two nucleosides represents a phosphodiester internucleoside linkage; and "VP" represents 5'-(E)-Vinylphosphonate;

wherein $R^2$ comprises a Fab comprising a heavy chain comprising the amino acid sequence of SEQ ID NO: 19 and a light chain comprising the amino acid sequence of SEQ ID NO: 20;

wherein n1 is an integer of 1-5 representing the number of instances of the group enclosed by square brackets, and wherein each instance of the group enclosed by square brackets is covalently linked to a different amino acid residue of the Fab.

23. The complex of claim 22, wherein each of the different amino acid residue is a lysine.

24. The complex of claim 22, wherein the heavy chain of the Fab comprises an N-terminal pyroglutamate.

25. The complex of claim 24, wherein n1 is 1.

26. A composition comprising the complex of claim 22, wherein the average value of n1 of complexes in the composition is in the range of 0.5 to 1.5.

27. A composition comprising the complex of claim 26, wherein the average value of n1 of complexes in the composition is 1.

28. The composition of claim 27, wherein the composition is formulated for intravenous administration, and wherein the subject is human.

* * * * *

SEQUENCE LISTING

```
Sequence total quantity: 28
SEQ ID NO: 1            moltype = AA  length = 9
FEATURE                 Location/Qualifiers
REGION                  1..9
                        note = Synthetic
source                  1..9
                        mol_type = protein
                        organism = synthetic construct
SEQUENCE: 1
GYSITSGYY                                                         9

SEQ ID NO: 2            moltype = AA  length = 7
FEATURE                 Location/Qualifiers
REGION                  1..7
                        note = Synthetic
source                  1..7
                        mol_type = protein
                        organism = synthetic construct
SEQUENCE: 2
ITFDGAN                                                           7

SEQ ID NO: 3            moltype = AA  length = 12
FEATURE                 Location/Qualifiers
REGION                  1..12
                        note = Synthetic
source                  1..12
                        mol_type = protein
                        organism = synthetic construct
SEQUENCE: 3
TRSSYDYDVL DY                                                     12

SEQ ID NO: 4            moltype = AA  length = 6
FEATURE                 Location/Qualifiers
REGION                  1..6
                        note = Synthetic
source                  1..6
                        mol_type = protein
                        organism = synthetic construct
SEQUENCE: 4
QDISNF                                                            6

SEQ ID NO: 5            moltype =   length =
SEQUENCE: 5
000

SEQ ID NO: 6            moltype = AA  length = 9
FEATURE                 Location/Qualifiers
REGION                  1..9
                        note = Synthetic
source                  1..9
                        mol_type = protein
                        organism = synthetic construct
SEQUENCE: 6
QQGHTLPYT                                                         9

SEQ ID NO: 7            moltype = AA  length = 6
FEATURE                 Location/Qualifiers
REGION                  1..6
                        note = Synthetic
source                  1..6
```

-continued

```
                        mol_type = protein
                        organism = synthetic construct
SEQUENCE: 7
SGYYWN                                                                   6

SEQ ID NO: 8            moltype = AA  length = 16
FEATURE                 Location/Qualifiers
REGION                  1..16
                        note = Synthetic
source                  1..16
                        mol_type = protein
                        organism = synthetic construct
SEQUENCE: 8
YITFDGANNY NPSLKN                                                        16

SEQ ID NO: 9            moltype = AA  length = 10
FEATURE                 Location/Qualifiers
REGION                  1..10
                        note = Synthetic
source                  1..10
                        mol_type = protein
                        organism = synthetic construct
SEQUENCE: 9
SSYDYDVLDY                                                               10

SEQ ID NO: 10           moltype = AA  length = 11
FEATURE                 Location/Qualifiers
REGION                  1..11
                        note = Synthetic
source                  1..11
                        mol_type = protein
                        organism = synthetic construct
SEQUENCE: 10
RASQDISNFL N                                                             11

SEQ ID NO: 11           moltype = AA  length = 7
FEATURE                 Location/Qualifiers
REGION                  1..7
                        note = Synthetic
source                  1..7
                        mol_type = protein
                        organism = synthetic construct
SEQUENCE: 11
YTSRLHS                                                                  7

SEQ ID NO: 12           moltype = AA  length = 8
FEATURE                 Location/Qualifiers
REGION                  1..8
                        note = Synthetic
source                  1..8
                        mol_type = protein
                        organism = synthetic construct
SEQUENCE: 12
GYSITSGY                                                                 8

SEQ ID NO: 13           moltype =   length =
SEQUENCE: 13
000

SEQ ID NO: 14           moltype = AA  length = 8
FEATURE                 Location/Qualifiers
REGION                  1..8
                        note = Synthetic
source                  1..8
                        mol_type = protein
                        organism = synthetic construct
SEQUENCE: 14
SYDYDVLD                                                                 8

SEQ ID NO: 15           moltype = AA  length = 7
FEATURE                 Location/Qualifiers
REGION                  1..7
                        note = Synthetic
source                  1..7
                        mol_type = protein
                        organism = synthetic construct
SEQUENCE: 15
SQDISNF                                                                  7
```

-continued

```
SEQ ID NO: 16          moltype = AA  length = 6
FEATURE                Location/Qualifiers
REGION                 1..6
                       note = Synthetic
source                 1..6
                       mol_type = protein
                       organism = synthetic construct
SEQUENCE: 16
GHTLPY                                                               6

SEQ ID NO: 17          moltype = AA  length = 119
FEATURE                Location/Qualifiers
REGION                 1..119
                       note = Synthetic
source                 1..119
                       mol_type = protein
                       organism = synthetic construct
SEQUENCE: 17
QVQLQESGPG LVKPSQTLSL TCTVTGYSIT SGYYWNWIRQ PPGKGLEWIG YITFDGANNY  60
NPSLKNRVSI SRDTSKNQFS LKLSSVTAED TATYYCTRSS YDYDVLDYWG QGTTVTVSS   119

SEQ ID NO: 18          moltype = AA  length = 107
FEATURE                Location/Qualifiers
REGION                 1..107
                       note = Synthetic
source                 1..107
                       mol_type = protein
                       organism = synthetic construct
SEQUENCE: 18
DIQMTQSPSS LSASVGDRVT ITCRASQDIS NFLNWYQQKP GQPVKLLIYY TSRLHSGVPS  60
RFSGSGSGTD FTLTISSLQP EDFATYYCQQ GHTLPYTFGQ GTKLEIK                107

SEQ ID NO: 19          moltype = AA  length = 227
FEATURE                Location/Qualifiers
REGION                 1..227
                       note = Synthetic
source                 1..227
                       mol_type = protein
                       organism = synthetic construct
SEQUENCE: 19
QVQLQESGPG LVKPSQTLSL TCTVTGYSIT SGYYWNWIRQ PPGKGLEWIG YITFDGANNY  60
NPSLKNRVSI SRDTSKNQFS LKLSSVTAED TATYYCTRSS YDYDVLDYWG QGTTVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHT                227

SEQ ID NO: 20          moltype = AA  length = 214
FEATURE                Location/Qualifiers
REGION                 1..214
                       note = Synthetic
source                 1..214
                       mol_type = protein
                       organism = synthetic construct
SEQUENCE: 20
DIQMTQSPSS LSASVGDRVT ITCRASQDIS NFLNWYQQKP GQPVKLLIYY TSRLHSGVPS  60
RFSGSGSGTD FTLTISSLQP EDFATYYCQQ GHTLPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 21          moltype = RNA  length = 21
FEATURE                Location/Qualifiers
misc_feature           1..16
                       note = Synthetic
source                 1..21
                       mol_type = other RNA
                       organism = synthetic construct
SEQUENCE: 21
ttcttccgtg aaattctggc a                                              21

SEQ ID NO: 22          moltype = RNA  length = 23
FEATURE                Location/Qualifiers
source                 1..23
                       mol_type = other RNA
                       organism = synthetic construct
SEQUENCE: 22
tgccagaatt tcacggaaga aca                                            23

SEQ ID NO: 23          moltype = AA  length = 760
FEATURE                Location/Qualifiers
source                 1..760
```

```
                        mol_type = protein
                        organism = Homo sapiens
SEQUENCE: 23
MMDQARSAFS NLFGGEPLSY TRFSLARQVD GDNSHVEMKL AVDEEENADN NTKANVTKPK  60
RCSGSICYGT IAVIVFFLIG FMIGYLGYCK GVEPKTECER LAGTESPVRE EPGEDFPAAR  120
RLYWDDLKRK LSEKLDSTDF TGTIKLLNEN SYVPREAGSQ KDENLALYVE NQFREFKLSK  180
VWRDQHFVKI QVKDSAQNSV IIVDKNGRLV YLVENPGGYV AYSKAATVTG KLVHANFGTK  240
KDFEDLYTPV NGSIVIVRAG KITFAEKVAN AESLNAIGVL IYMDQTKFPI VNAELSFFGH  300
AHLGTGDPYT PGFPSFNHTQ FPPSRSSGLP NIPVQTISRA AAEKLFGNME GDCPSDWKTD  360
STCRMVTSES KNVKLTVSNV LKEIKILNIF GVIKGFVEPD HYVVVGAQRD AWGPGAAKSG  420
VGTALLLKLA QMFSDMVLKD GFQPSRSIIF ASWSAGDFGS VGATEWLEGY LSSLHLKAFT  480
YINLDKAVLG TSNFKVSASP LLYTLIEKTM QNVKHPVTGQ FLYQDSNWAS KVEKLTLDNA  540
AFPFLAYSGI PAVSFCFCED TDYPYLGTTM DTYKELIERI PELNKVARAA AEVAGQFVIK  600
LTHDVELNLD YERYNSQLLS FVRDLNQYRA DIKEMGLSLQ WLYSARGDFF RATSRLTTDF  660
GNAEKTDRFV MKKLNDRVMR VEYHFLSPYV SPKESPFRHV FWGSGSHTLP ALLENLKLRK  720
QNNGAFNETL FRNQLALATW TIQGAANALS GDVWDIDNEF                       760

SEQ ID NO: 24           moltype = RNA  length = 23
FEATURE                 Location/Qualifiers
source                  1..23
                        mol_type = other RNA
                        organism = synthetic construct
SEQUENCE: 24
tgttcttccg tgaaattctg gca                                         23

SEQ ID NO: 25           moltype = DNA  length = 1574
FEATURE                 Location/Qualifiers
source                  1..1574
                        mol_type = genomic DNA
                        organism = Homo sapiens
SEQUENCE: 25
atggccctcc cgacaccctc ggacagcacc ctccccgcgg aagcccgggg acgaggacgg  60
cgacggagac tcgtttggac cccgagccaa agcgaggccc tgcgagcctg ctttgagcgg  120
aacccgtacc cgggcatcgc caccagagaa cggctggccc aggccatcgg cattccggag  180
cccagggtcc agatttggtt tcagaatgag aggtcacgcc agctgaggca gcaccggcgg  240
gaatctcggc cctggcccgg gagacgcggc ccgccagaag gccggcgaaa gcggaccgcc  300
gtcaccggat cccagaccgc cctgctcctc cgagcctttg agaaggatcg ctttccaggc  360
atcgccgccc gggaggagct ggccagagag acgggcctcc cggagtccag gattcagatc  420
tggtttcaga atcgaagggc caggcacccg ggacagggtg gcagggcgcc cgcgcaggca  480
ggcggcctgt gcagcgcggc ccccggcggg ggtcaccctg ctccctcgtg ggtcgccttc  540
gcccacaccg gcgcgtgggg aacggggctt cccgcacccc acgtgccctg cgcgcctggg  600
gctctcccac agggggcttt cgtgagccag gcagcgaggg ccgcccccgc gctgcagccc  660
agccaggccg cgccggcaga ggggatctcc caacctgccc cggcgcgcgg ggatttcgcc  720
tacgccgccc cggctcctcc ggacggggcg ctctcccacc ctcaggctcc tcgctggcct  780
ccgcacccgg gcaaaagccg ggaggaccgg gacccgcagc gcgacggcct gccgggcccc  840
tgcgcggtgg cacagcctgg gcccgctcaa gcggggccgc agggccaagg ggtgcttgcg  900
ccacccacgt cccaggggag tccgtggtgg ggctggggcc ggggtcccca ggtcgccggg  960
gcggcgtggg aaccccaagc cggggcagct ccacctcccc agcccgcgcc cccggacgcc  1020
tccgcctccg cgcggcaggg gcagatgcaa ggcatcccgg cgccctccca ggcgctccag  1080
gagccggcgc cctggtctgc actcccctgc ggcctgctgc tggatgagct cctggcgagc  1140
ccggagtttc tgcagcaggc gcaacctctc ctagaaacgg aggccccggg ggagctggag  1200
gcctcggaag aggccgcctc gctggaagca cccctcagcg aggaagaata ccgggctctg  1260
ctggaggagc tttaggacgc ggggtctagg cccggtgaga gactccacac cgcggagaac  1320
tgccattctt tcctgggcat cccggggatc ccagagccgg cccaggtacc agcagacctg  1380
cgcgcagtgc gcaccccggc tgacgtgcaa gggagctcgc tggcctctct gtgcccttgt  1440
tcttccgtga aattctggct gaatgtctcc ccccaccttc cgacgctgtc taggcaaacc  1500
tggattagag ttacatctcc tggatgatta gttcagagat atattaaaat gccccctccc  1560
tgtggatcct atag                                                   1574

SEQ ID NO: 26           moltype = DNA  length = 1710
FEATURE                 Location/Qualifiers
source                  1..1710
                        mol_type = genomic DNA
                        organism = Homo sapiens
SEQUENCE: 26
atggccctcc cgacaccctc ggacagcacc ctccccgcgg aagcccgggg acgaggacgg  60
cgacggagac tcgtttggac cccgagccaa agcgaggccc tgcgagcctg ctttgagcgg  120
aacccgtacc cgggcatcgc caccagagaa cggctggccc aggccatcgg cattccggag  180
cccagggtcc agatttggtt tcagaatgag aggtcacgcc agctgaggca gcaccggcgg  240
gaatctcggc cctggcccgg gagacgcggc ccgccagaag gccggcgaaa gcggaccgcc  300
gtcaccggat cccagaccgc cctgctcctc cgagcctttg agaaggatcg ctttccaggc  360
atcgccgccc gggaggagct ggccagagag acgggcctcc cggagtccag gattcagatc  420
tggtttcaga atcgaagggc caggcacccg ggacagggtg gcagggcgcc cgcgcaggca  480
```

-continued

```
ggcggcctgt gcagcgcggc ccccggcggg ggtcaccctg ctccctcgtg ggtcgccttc  540
gcccacaccg gcgcgtgggg aacggggctt cccgcacccc acgtgccctg cgcgcctggg  600
gctctcccac agggggcttt cgtgagccag gcagcgaggg ccgcccccgc gctgcagccc  660
agccaggccg cgccggcaga ggggatctcc caacctgccc cggcgcgcgg ggatttcgcc  720
tacgccgccc cggctcctcc ggacggggcg ctctcccacc ctcaggctcc tcggtggcct  780
ccgcacccgg gcaaaagccg ggaggaccgg gacccgcagc gcgacggcct gccgggcccc  840
tgcgcggtgg cacagcctgg gcccgctcaa gcggggccgc agggccaagg ggtgcttgcg  900
ccacccacgt cccaggggag tccgtggtgg ggctggggcc ggggtcccca ggtcgccggg  960
gcggcgtggg aaccccaagc cggggcagct ccacctcccc agcccgcgcc cccggacgcc  1020
tccgcctccg cgcggcaggg gcagatgcaa ggcatcccgg cgccctccca ggcgctccag  1080
gagccggcgc cctggtctgc actcccctgc ggcctgctgc tggatgagct cctggcgagc  1140
ccggagtttc tgcagcaggc gcaacctctc ctagaaacgg aggccccggg ggagctggag  1200
gcctcggaag aggccgcctc gctggaagca cccctcagcg aggaagaata ccgggctctg  1260
ctggaggagc tttaggacgc ggggttggga cggggtcggg tggttcgggg cagggcggtg  1320
gcctctcttt cgcggggaac acctggctgg ctacggaggg gcgtgtctcc gccccgcccc  1380
ctccaccggg ctgaccggcc tgggattcct gccttctagg tctaggcccg gtgagagact  1440
ccactccgcg gagaactgcc tttctttcct gggcatcccg gggatcccag agccggccca  1500
ggtaccagca gacctgcgcg cagtgcgcac cccggctgac gtgcaaggga gctcgctggc  1560
ctctctgtgc ccttgttctt ccgtgaaatt ctggctgaat gtctcccccc accttccgac  1620
gctgtctagg caaacctgga ttagagttac atctcctgga tgattagttc agagatatat  1680
taaaatgccc cctccctgtg gatcctatag                                   1710

SEQ ID NO: 27          moltype = DNA  length = 2024
FEATURE                Location/Qualifiers
source                 1..2024
                       mol_type = genomic DNA
                       organism = Mus musculus
SEQUENCE: 27
atggcagaag ctggcagccc tgttggtggc agtggtgtgg cacgggaatc ccggcggcgc  60
aggaagacgg tttggcaggc ctggcaagag caggccctgc tatcaacttt caagaagaag  120
agatacctga gcttcaagga gaggaaggag ctggccaagc gaatgggggt ctcagattgc  180
cgcatccgcg tgtggtttca gaaccgcagg aatcgcagtg gagaggaggg gcatgcctca  240
aagaggtcca tcagaggctc caggcggcta gcctcgccac agctccagga agagcttgga  300
tccaggccac agggtagagg catgcgctca tctggcagaa ggcctcgcac tcgactcacc  360
tcgctacagc tcaggatcct agggcaagcc tttgagagga acccacgacc aggctttgct  420
accagggagg agctggcgcg tgacacaggg ttgcccgagg acacgatcca catatggttt  480
caaaaccgaa gagctcggcg gcgccacagg aggggcaggc ccacagctca agatcaagac  540
ttgctggcgt cacaagggtc ggatggggcc cctgcaggtc cggaaggcag agagcgtgaa  600
ggtgcccagg agaacttgtt gccacaggaa gaagcaggaa gtacgggcat ggatacctcg  660
agccctagcg acttgccctc cttctgcgga gagtcccagc ctttccaagt ggcacagccc  720
cgtggagcag gccaacaaga ggcccccact cgagcaggca acgcaggctc tctggaaccc  780
ctccttgatc agctgctgga tgaagtccaa gtagaagagc ctgctccagc ccctctgaat  840
ttggatggag accctggtgg cagggtgcat gaaggttccc aggagagctt ttggccacag  900
gaagaagcag gaagtacagg catggatact tctagcccca gcgactcaaa ctccttctgc  960
agagagtccc agccttccca agtggcacag ccctgtggag cgggccaaga agatgcccgc  1020
actcaagcag acagcacagg ccctctggaa ctcctcctcc ttgatcaact gctggacgaa  1080
gtccaaaagg aagagcatgt gccagtccca ctggattggg gtagaaatcc tggcagcagg  1140
gagcatgaag gttcccagga cagcttactg cccctggagg aagcagtaaa ttcgggcatg  1200
gatacctcga tccctagcat ctggccaacc ttctgcagag aatcccagcc tccccaagtg  1260
gcacagccct ctggaccagg ccaagcacag gcccccactc aaggtgggaa cacggacccc  1320
ctggagctct tcctctatca actgttggat gaagtccaag tagaagagca tgctccagcc  1380
cctctgaatt gggatgtaga tcctggtggc agggtgcatg aaggttcgtg ggagagcttt  1440
tggccacagg aagaagcagg aagtacaggc ctggatactt caagccccag cgactcaaac  1500
tccttcttca gagagtccaa gccttcccaa gtggcacagc gccgtggagc gggccaagaa  1560
gatgcccgca ctcaagcaga cagcacaggc cctctggaac tcctcctctt tgatcaactg  1620
ctggacgaag tccaaaagga agagcatgtg ccagccccac tggattgggg tagaaatcct  1680
ggcagcatgg agcatgaagg ttcccaggac agcttactgc ccctggagga agcagcaaat  1740
tcgggcaggg atacctcgat ccctagcatc tggccagcct tctgcagaaa atcccagcct  1800
ccccaagtgg cacagccctc tggaccaggc caagcacagg cccccattca aggtgggaac  1860
acggaccccc tggagctctt ccttgatcaa ctgctgaccg aagtccaact tgaggagcag  1920
gggcctgccc ctgtgaatgt ggaggaaaca tgggagcaaa tggacacaac acctatctgc  1980
ctctcacttc agaagaatat cagactcttc tagatatgct ctga                   2024

SEQ ID NO: 28          moltype = RNA  length = 23
FEATURE                Location/Qualifiers
source                 1..23
                       mol_type = other RNA
                       organism = synthetic construct
SEQUENCE: 28
tgttcttccg tgaaattctg gct                                          23
```